(12) United States Patent
Hueter et al.

(10) Patent No.: US 7,781,411 B2
(45) Date of Patent: Aug. 24, 2010

(54) DERIVATIVES OF AVERMECTIN, AVERMECTIN MONOSACCHARIDE AND AVERMECTIN AGLYCONE

(75) Inventors: Ottmar Franz Hueter, Basel (CH); Thomas Pitterna, Basel (CH); Pierre Jung, Basel (CH); Fiona Murphy Kessabi, Basel (CH); Laura Quaranta, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 199 days.

(21) Appl. No.: 11/574,588

(22) PCT Filed: Aug. 19, 2005

(86) PCT No.: PCT/EP2005/008981

§ 371 (c)(1),
(2), (4) Date: Sep. 4, 2007

(87) PCT Pub. No.: WO2006/024405

PCT Pub. Date: Mar. 9, 2006

(65) Prior Publication Data

US 2008/0300134 A1    Dec. 4, 2008

(30) Foreign Application Priority Data

Sep. 3, 2004 (EP) .................. 04020953

(51) Int. Cl.
*A61K 31/70* (2006.01)
*C07H 17/08* (2006.01)
(52) U.S. Cl. .................. 514/30; 536/7.1
(58) Field of Classification Search .............. 536/7.1
See application file for complete search history.

(56) References Cited

U.S. PATENT DOCUMENTS 4,134,973 A  1/1979  Fisher
4,203,976 A  5/1980  Fisher et al.

FOREIGN PATENT DOCUMENTS

EP    0481672    4/1992

*Primary Examiner*—Elli Peselev
(74) *Attorney, Agent, or Firm*—William Mulholland

(57) ABSTRACT

Certain derivatives of avermectin, avermectin monosaccharide and avermectin aglycone, having on the 4", 4' or 13 position, respectively, a 6-membered cyclic acetal with a substituent on position 2, that are useful in controlling pests, in particular pests that are harmful to crop plants and to its propagation material, such as representatives of the class insecta, the order acarina and the class nematode, are provided.

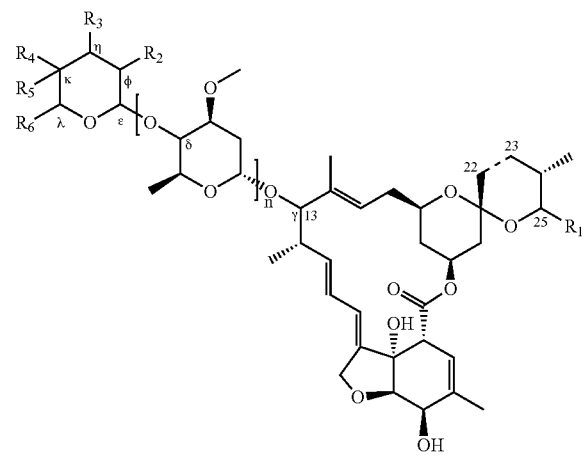

(I)

12 Claims, No Drawings

DERIVATIVES OF AVERMECTIN, AVERMECTIN MONOSACCHARIDE AND AVERMECTIN AGLYCONE

This application is a 371 of International Application No. PCT/EP2005/008981 filed Aug. 19, 2005, which claims priority to EP 04020953.8 filed Sep. 3, 2004, the contents of which are incorporated herein by reference.

The present invention relates in particular to certain avermectin, avermectin monosaccharide and avermectin aglycone derivatives, processes for preparing such derivatives, intermediates in the preparation of such derivatives, and the use of certain derivatives for controlling pests.

Certain macrolide compounds for controlling pests are known. However, the biological properties of these known compounds are not entirely satisfactory, and, as a consequence, there is still a need for providing further compounds having pesticidal properties.

It has been found that certain derivatives of avermectin, avermectin monosaccharide and avermectin aglycone, having on the 4", 4' or 13 position, respectively, a 6-membered cyclic acetal with a substituent on position 2, are useful in controlling pests, in particular pests that are harmful to crop plants and to its propagation material, such as representatives of the class insecta, the order acarina and the class nematoda.

Accordingly, in a first aspect, the present invention provides a compound of the formula (I)

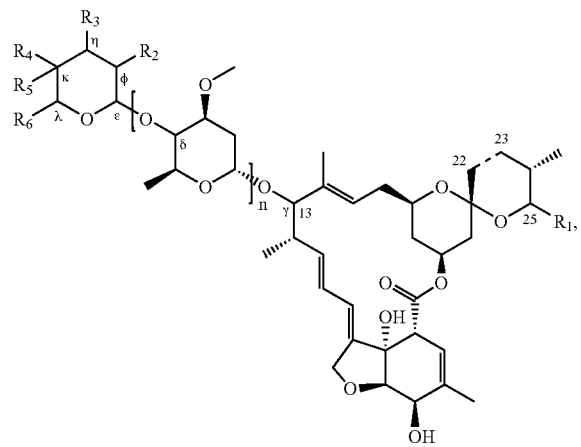

(I)

wherein the bond between carbon atoms 22 and 23 indicated with a broken line is a single or double bond, n is 0, 1 or 2, $R_1$ represents a $C_1$-$C_{12}$alkyl, $C_3$-$C_8$cycloalkyl or $C_2$-$C_{12}$alkenyl group, $R_2$ represents $R_{15}$, $R_{16}O$, $R_{16}C(=O)O$, $R_{15}OC(=O)O$, $R_{16}S$, $R_{16}C(=O)S$, $R_{16}R_{17}N$, $R_{16}(CN)N$, $R_{16}C(=O)R_{17}N$, $R_{15}OC(=O)R_{17}N$, $R_{15}SO_2R_{17}N$, $R_{18}R_{19}N-C(=O)-O$, $R_{18}R_{19}N-C(=O)R_{17}N$, or a $R_{18}R_{19}N-SO_2R_{17}N$ group, $R_3$ represents hydrogen or a $R_2$ group, or $R_2$ and $R_3$ together represent $-OCR_7R_8O-$, $-OC(O)O-$, or $-OC(S)O-$, $R_4$ represents a halogen, hydrogen or a chemical constituent, $R_5$ represents hydrogen, a hydrocarbyl or substituted hydrocarbyl group, or $R_4$ and $R_5$ together represent $=O$, $=NR_9$ or $=CR_{10}R_{11}$, and $R_6$ represents $R_{16}$, $R_{16}OCH_2$, $R_{16}C(=O)OCH_2$, $R_{15}OC(=O)OCH_2$, $R_{16}C(=S)OCH_2$, $R_{16}SCH_2$, $R_{16}C(=O)SCH_2$, $R_{16}C(=S)SCH_2$, $R_{16}R_{17}NCH_2$, $R_{16}(NC)NCH_2$, $R_{16}(R_{17}O)NCH_2$, $R_{16}C(=O)NR_{17}CH_2$, $R_{16}C(=O)N(OR_{17})CH_2$, $R_{15}OC(=O)NR_{17}CH_2$, $R_{15}C(=O)N(OR_{17})CH_2$, $R_{15}SO_2NR_{17}CH_2$, $R_{16}R_{17}NOCH_2$, $R_{16}(NC)NOCH_2$, $R_{16}(R_{17}O)NOCH_2$, $R_{16}C(=O)NR_{17}OCH_2$, $R_{18}R_{19}N-NR_{17}CH_2$, $R_{18}(NC)N-NR_{17}CH_2$, $R_{18}(R_{19}O)N-NR_{17}CH_2$, $R_{18}R_{19}N-C(=O)-OCH_2$, $R_{18}R_{19}N-C(=O)NR_{17}CH_2$, or a $R_{18}R_{19}N-SO_2NR_{17}CH_2$ group;

wherein $R_7$ and $R_8$ represent, independently of each other, hydrogen, or a $C_1$-$C_6$alkyl group, $R_9$ represents a hydrogen, or a $R_2$ group, $R_{10}$ and $R_{11}$, represent, independently of each other, hydrogen, halogen, cyano, formyl, $C(O)OR_{12}$, $C(O)NR_{13}R_{14}$, unsubstituted or mono- to pentasubstituted $C_1$-$C_6$alkyl, unsubstituted or mono- to pentasubstituted $C_2$-$C_6$alkenyl, unsubstituted or mono- to pentasubstituted $C_2$-$C_6$alkynyl, unsubstituted or mono- to pentasubstituted $C_3$-$C_6$cycloalkyl, unsubstituted or mono- to pentasubstituted aryl, or unsubstituted or mono- to pentasubstituted heteroaryl group, $R_{15}$ represents unsubstituted or mono- to pentasubstituted $C_1$-$C_6$alkyl, unsubstituted or mono- to pentasubstituted $C_2$-$C_6$alkenyl, unsubstituted or mono- to pentasubstituted $C_2$-$C_6$alkynyl, unsubstituted or mono- to pentasubstituted $C_3$-$C_6$cycloalkyl, unsubstituted or mono- to pentasubstituted aryl, or unsubstituted or mono- to pentasubstituted heteroaryl group, and $R_{12}$, $R_{13}$, $R_{14}$, $R_{16}$, $R_{17}$, $R_{18}$ and $R_{19}$ represent, independently of each other, hydrogen or $R_{15}$, or $R_{16}$ and $R_{17}$, or $R_{18}$ and $R_{19}$, together represent, independently of each other, a three- to ten-membered ring, optionally containing heteroatoms;

with the proviso that (i) the substituent $R_4$ is not a hydroxy, if $R_2$ and $R_3$ are hydroxy groups, $R_5$ is a hydrogen, and $R_6$ is a $CH_3$ or $CH_2OH$ group, or (ii) the substituent $R_4$ is not a $OCH_2C_6H_5$ or $OC(=O)C_6H_5$ group, if $R_2$ and $R_3$ are $OCH_2C_6H_5$ or $OC(=O)C_6H_5$ groups, $R_5$ is a hydrogen, and $R_6$ is a $CH_2OCH_2C_6H_5$ or $CH_2C(=O)C_6H_5$ group, or (iii) $R_4$ is not $OCH_3$, if $R_2$ and $R_3$ are $OCH_3$ groups, $R_5$ is a hydrogen, $R_6$ is $CH_2OCH_3$, and the carbon configurations of the cyclic acetal at 2-position ($\phi$) is (R), at 3-position ($\eta$) is (S), at 4-position ($\kappa$) is (S), and at 5-position ($\lambda$) is (R), or (iv) $R_4$ is not $OCH_3$, if $R_2$ and $R_3$ are $OCH_3$ groups, $R_5$ and $R_6$ are hydrogens, and the carbon configurations of the cyclic acetal at 2-position ($\phi$) is (S), at 3-position ($\eta$) is (R), and at 4-position ($\kappa$) is (R), and n is 1 or (v) $R_4$ is not $OCH_3$, if $R_2$ and $R_3$ are $OCH_3$ groups, $R_5$ is a hydrogen, $R_6$ is $CH_3$, and the carbon configurations of the cyclic acetal at 2-position ($\phi$) is (S), at 3-position ($\eta$) is (R), at 4-position ($\kappa$) is (R), and at 5-position ($\lambda$) is (S), and n is 1 or (vi) the substituent $R_4$ is not an unsubstituted acetyloxy group, if (a) $R_2$ and $R_3$ are an unsubstituted acetyloxy, or (b) $R_2$ is an unsubstituted acetylamino group and $R_3$ is an unsubstituted acetyloxy, and, for either (a) or (b), $R_5$ is hydrogen and $R_6$ is H, $CH_3$, $CH_2C(=O)CH_3$, or $CO_2H$ group;

and if appropriate, an E/Z isomer and/or diastereoisomer and/or tautomer of the compound of formula (I), in each case in free form or in salt form.

The symbols $\delta$, $\epsilon$, $\phi$, $\eta$, $\kappa$, $\lambda$ and $\gamma$ in formula (I) represent that the configuration of the corresponding carbon atom can be (S) or (R).

In a second aspect, the present invention provides a process for preparing a compound of formula (I)

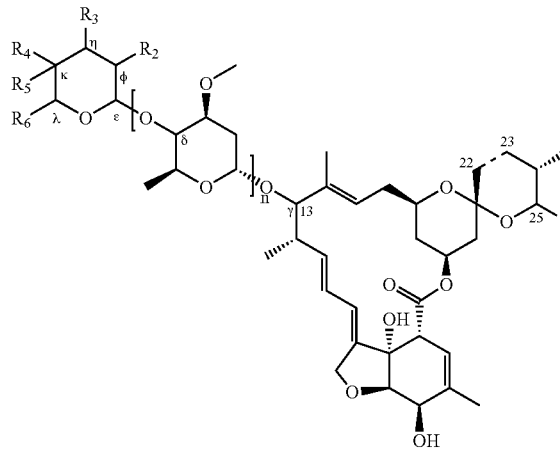

(I)

wherein $R_1$, $R_2$, $R_3$, $R_4$, $R_5$, $R_6$, the bond between the carbon atoms 22 and 23 and n are as defined above in the first aspect, comprising the steps of:

(i) carrying out a glycosylation reaction at the hydroxy group at the 13-, 4'-, or 4"-position (n is 0, 1 or 2 respectively) of the mectin scaffold using an activated tetrahydropyran with $R_2$, $R_3$, $R_4$, $R_5$ and $R_6$ substituents to yield a compound of formula (II)

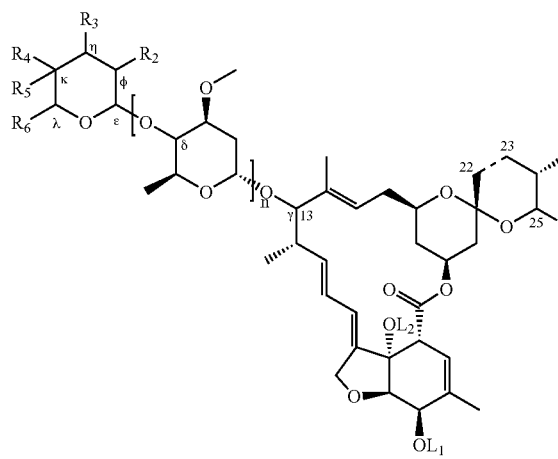

(II)

wherein $R_1$, $R_2$, $R_3$, $R_4$, $R_5$, $R_6$, the bond between the carbon atoms 22 and 23 and n are as defined above in the first aspect, $L_1$ is a protecting group and $L_2$ is hydrogen or a protecting group; and either (ii) removing the protecting group $L_1$ and $L_2$, if applicable, to yield a compound of formula (I), or (iii) carrying out reactions on one or more of $R_2$, $R_3$, $R_4$, $R_5$, $R_6$ groups to modify the group and then removing the protecting group $L_1$ and $L_2$, if applicable, to yield a compound of formula (I).

In a third aspect, the present invention provides a process for preparing a compound of formula (I)

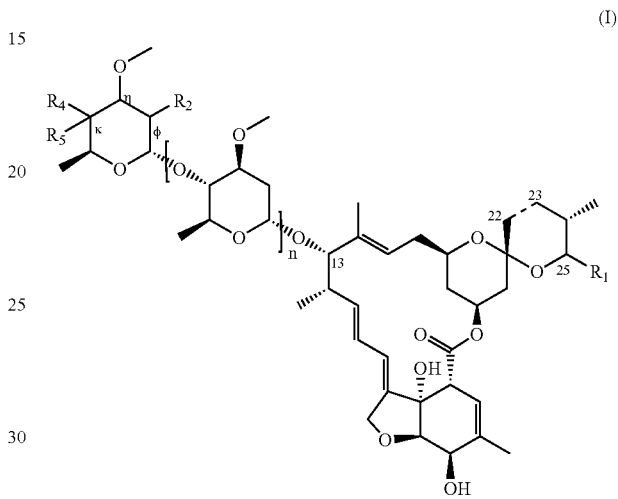

(I)

wherein $R_1$, $R_4$, $R_5$ and the bond between the carbon atoms 22 and 23 are as defined above the first aspect, n is 0 or 1, and $R_2$ is $R_{15}$ as defined in the first aspect, comprising the steps of:

(i) oxidising the hydroxy group at the 4'- or 4"-position to yield a oxo-compound of formula (III),

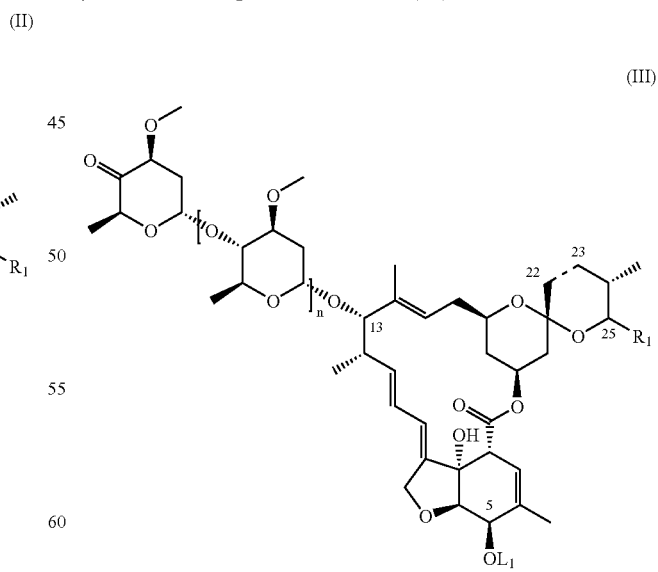

(III)

wherein $R_1$, and the bond between the carbon atoms 22 and 23 are as defined above in the first aspect, n is 0 or 1, and $L_1$ is a protecting group, and (iii) reacting the compound of formula (III) with a base and a trialkylsilyl compound to form an enolate, (iv) oxidizing the enolate to an enone of the formula (IV),

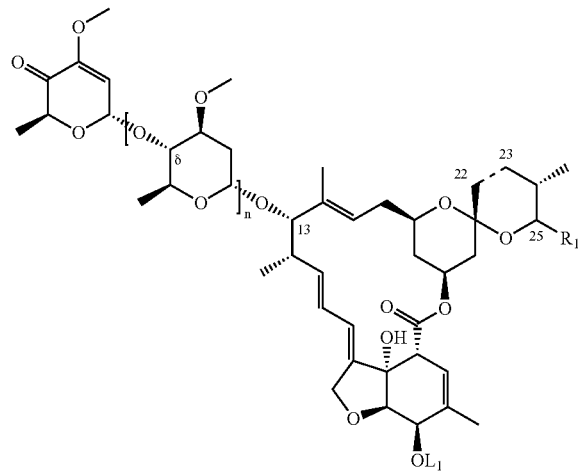

(IV)

wherein $R_1$, and the bond between the carbon atoms 22 and 23 are as defined above in the first aspect, n is 0 or 1, and $L_1$ is a protecting group (v) adding an organometallic reagent having a substituent $R_2$ to the enone, and (vi) carrying out reactions on one or more of $R_2$, $R_4$, $R_5$ groups to modify the group and then removing the protecting group $L_1$ to yield a compound of formula (I).

In a fourth aspect, the present invention provides a compound of the formula (II)

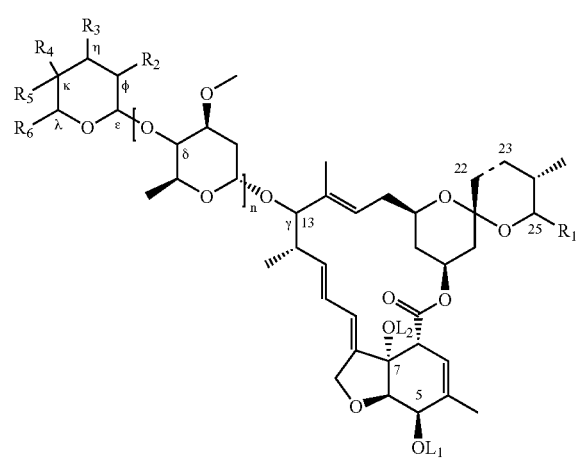

(II)

wherein $R_1$, $R_2$, $R_3$, $R_4$, $R_5$, $R_6$, the bond between the carbon atoms 22 and 23 and n are as defined above in the first aspect, $L_1$ is a protecting group, and $L_2$ is hydrogen or a protecting group.

In a fifth aspect, the present invention provides a pesticidal composition comprising at least one compound of the formula (I), or (II), as defined in the first or fourth aspect respectively, as active compound, and at least one auxiliary.

In a sixth aspect, the present invention provides a method for controlling pests, especially ecto- or endo-pests in animals and plant pests, comprising applying a composition defined in the fifth aspect to the pests or their habitat.

In a seventh aspect, the present invention provides a process for preparing a composition defined in the fifth aspect comprising mixing intimately and/or grinding at least one compound of the formula (I), or (II), as defined in the first, or fourth aspect respectively, as active compound, with at least one auxiliary.

In an eighth aspect, the present invention provides the use of a compound of the formula (I), or (II), as defined in the first, or fourth aspect respectively, for preparing a composition as defined in the fifth aspect.

In a ninth aspect, the present invention provides the use of a composition as defined in the fifth aspect for controlling pests.

In a tenth aspect, the present invention provides a method for protecting plant propagation material comprising treating the propagation material, or the location where the propagation material is planted, with a composition defined in the fifth aspect.

In an eleventh aspect, the present invention provides a pest resistant plant propagation material having adhered thereto at least one compound of the formula (I), or (II), as defined in the first, or fourth aspect respectively; preferably treated by the method of the tenth aspect.

A compound of the present invention is a certain substituted derivative of avermectin, avermectin monosaccharide, or avermectin aglycone.

Avermectins are known to the person skilled in the art. They are a group of structurally closely related pesticidally active compounds, which are obtained by fermenting a strain of the microorganism *Streptomyces avermitilis*. Also the derivatives where $R_1$ is not iso-propyl or sec-butyl, for example, where it is cyclohexyl or 1-methyl butyl, are obtained by fermentation. Derivatives of Avermectins can be obtained by conventional chemical syntheses. The present invention relates to a new series of compounds having a new carbohydrate unit attached to avermectin, avermectin monosaccharide, or avermectin aglycone.

The compounds of the present invention are derivatives of (i) avermectin when n is 2 in formula (I), (ii) avermectin monosaccharide when n is 1 in formula (I), and (iii) avermectin aglycone when n is 0 in formula (I), wherein the bond between carbon atoms 22 and 23 indicated with a broken line is a single or double bond. Accordingly, the mectin scaffold as used in the specification refers to any one of:

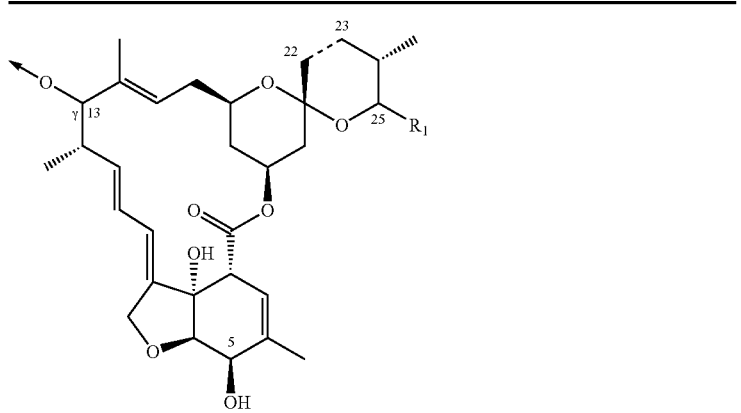
Avermectin aglycone
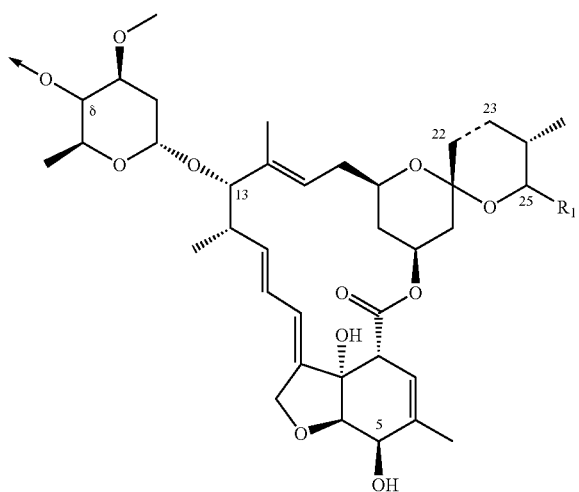
Avermectin monosaccharide
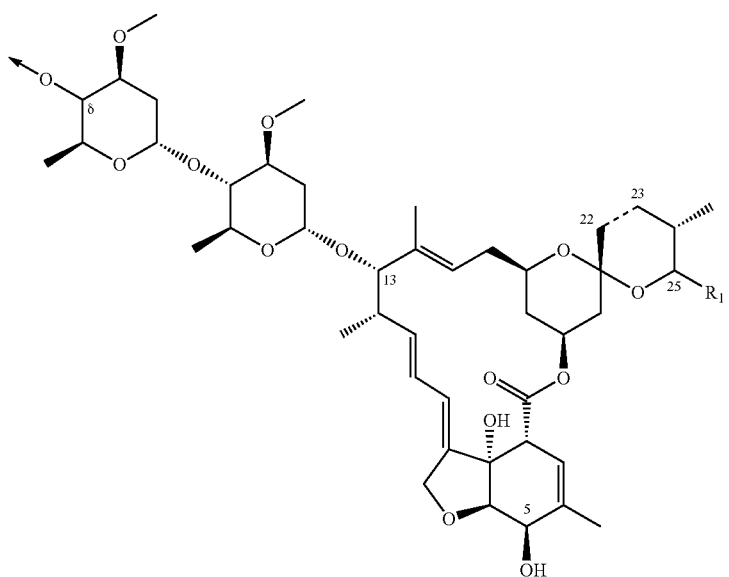
Avermectin
The arrows indicate the connection point to the newly introduced pyran derivative.

The avermectins, which can be obtained from *Streptomyces avermitilis*, are referred to as A1a, A1b, A2a, A2b, B1a, B1b, B2a and B2b. The compounds referred to as "A" and "B" have a methoxy radical and an OH group, respectively, in the 5-position. The "a" series and the "b" series are compounds in which the substituent $R_1$ (in position 25) is a sec-butyl radical and an isopropyl radical, respectively. The number 1 in the name of the compounds means that carbon atoms 22 and 23 are linked by a double bond; the number 2 means that they are linked by a single bond and that the carbon atom 23 carries an OH group. The above nomenclature is adhered to in the description of the present invention to denote the specific structure type in the not naturally occurring avermectin derivatives according to the invention, which corresponds to the naturally occurring avermectin. The compounds according to the invention are especially derivatives of avermectin compounds of the B1 series, advantageously B1a and B1b; derivatives having a single bond between carbon atoms 22 and 23; derivatives having substituents other than sec-butyl or isopropyl in position 25; and derivatives of the corresponding monosaccharides.

For a review of macrolide chemistries, see: Ivermectin Abamectin. Fisher, M. H.; Mrozik, H. Editor(s)—Campbell, William Cecil, (1989), 1-23; and Macrolide Antibiotics (2nd Edition), Sunazuka, Toshiaki, Omura, Sadafumi; Iwasaki, Shigeo, Omura, Satoshi. Editor(s)—Omura, Satoshi (2002), 99-180.

For a review on glycosylation chemistries, see: Demchenko, A. V., Synlett (2003), 1225-1240; Nicolaou, K. C., Mitchel H. J. Angewandte-Chemie (2001), 113, 1624-1672; Garegg, J. P., Advances in Carbohydrate Chemistry and Biochemistry (1997), 52, 179-205; and Toshima K., Tatsuta K., Chemical Reviews (1993), 1503-1531.

EP-A-7812 describes the synthesis of avermectin monosaccharide, or avermectin aglycone and the preparation of mono-, di- and triglycosyl derivatives, glycosylation of the mectin scaffolds with activated peracetylated saccharides, in which the acetyl groups can be cleaved after the glycosylation. See also U.S. Pat. No. 4,156,720.

For a preparation of cuprates and 1,4-addition of these cuprates to a conjugated enone see Clarke, P. D., Fitton A. O., Suschitzky H., Wallace, T. W., Tetrahydron Letters (1986), 27, 91-94.

The present invention describes the glycosylation of avermectin, avermectin monosaccharide, or avermectin aglycone at the hydroxy groups at position 4", 4' or 13 respectively with new sugar derivatives, modifying the substituents at the newly introduced sugar after glycosylation or introduction of new substituents at position 2" or 2' of desoxy sugar derivatives. Such compounds have been found to have pesticidal efficacy.

Each compound of the invention may be present as a single isomer, an E/Z isomer and/or diastereoisomer and/or tautomer. Accordingly, a compound, for example, of formula (I) is, if appropriate, also to be understood as including the corresponding E/Z isomer and/or diastereoisomer and/or tautomer, even if the latter are not specifically mentioned in each case.

Each compound of the invention, such as compound of formula (I), and, where applicable, its E/Z isomer and/or diastereoisomer and/or tautomer can form salts, for example acid addition salts. These acid addition salts are formed, for example, with strong inorganic acids, such as mineral acids, for example, sulfuric acid, a phosphoric acid or a hydrohalic acid, with strong organic carboxylic acids, such as unsubstituted or substituted, for example halo-substituted, $C_1$-$C_4$alkanecarboxylic acids, for example, acetic acid, unsaturated or saturated dicarboxylic acids, for example, oxalic acid, malonic acid, maleic acid, fumaric acid or phthalic acid, hydroxycarboxylic acids, for example, ascorbic acid, lactic acid, malic acid, tartaric acid or citric acid, or benzoic acid, or with organic sulfonic acids, such as unsubstituted or substituted, for example, halo-substituted, $C_1$-$C_4$alkane- or arylsulfonic acids, for example, methane- or p-toluene-sulfonic acid. Compound of formula (I) that have at least one acidic group can furthermore form salts with bases. Suitable salts with bases are, for example, metal salts, such as alkali metal salts or alkaline earth metal salts, for example, sodium, potassium or magnesium salts, or salts with ammonia or with an organic amine, such as morpholine, piperidine, pyrrolidine, a mono-, di- or tri-lower alkylamine, for example, ethylamine, diethylamine, triethylamine or dimethylpropylamine, or a mono-, di- or trihydroxy-lower alkylamine, for example, mono-, di- or tri-ethanolamine. Corresponding internal salts may also be formed where appropriate. Among the salts of the compound of formula (I), the agrochemically advantageous salts are preferred.

Any reference to the free compound of the invention, for example, of formula (I), or its salt, is to be understood as including, where appropriate, also the corresponding salt or the free compound of formula (I), respectively. The same applies to an E/Z isomer and/or diastereoisomer and/or tautomer of the compound of the invention, for example, of formula (I), and salt thereof.

The invention is described in detail below. Further, as described below each embodiment of a feature of the present invention is independent of an embodiment of another feature.

In the context of the first aspect of the invention, preference is given to following groups:

(2) a compound of the first aspect (also referred to as group (1)) in free form;

(3) a compound of the first aspect (also referred to as group (1)) in salt form;

(4) a compound according to any one of groups (1) to (3) wherein $R_4$ represents a halogen, $R_{16}$, $R_{16}O$, $R_{16}C(=O)O$, $R_{15}OC(=O)O$, $R_{16}C(=S)O$, $R_{16}S$, $R_{16}C(=O)S$, $R_{16}C(=S)$ S, $R_{16}R_{17}N$, $R_{16}(NC)N$, $R_{16}(R_{17}O)N$, $R_{16}C(=O)R_{17}N$, $R_{16}C(=O)(OR_{17})N$, $R_{15}OC(=O)R_{17}N$, $R_{15}OC(=O)$ $(OR_{17})N$, $R_{15}SO_2R_{17}N$, $R_{16}R_{17}NO$, $R_{16}(NC)NO$, $(R_{16}R_{17}C=)NO$, $R_{16}C(=O)R_{17}NO$, $R_{18}R_{19}N$—$R_{17}N$, $R_{18}$ $(NC)N$—$R_{17}N$, $R_{18}(R_{19}O)N$—$R_{17}N$, $R_{18}R_{19}N$—$C(=O)$— O, $R_{18}R_{19}N$—$C(=O)R_{17}N$, or a $R_{18}R_{19}N$—$SO_2R_{17}N$ group;

(5) a compound according to any one of groups (1) to (4) wherein $R_5$ represents a hydrogen, cyano, unsubstituted or mono- to pentasubstituted $C_1$-$C_6$alkyl, unsubstituted or mono- to pentasubstituted $C_2$-$C_6$alkenyl, unsubstituted or mono- to pentasubstituted $C_2$-$C_6$alkynyl group, unsubstituted or mono- to pentasubstituted $C_3$-$C_6$cycloalkyl group, or $R_4$ and $R_5$ together represent a group like =O, =$NR_9$ or =$CR_{10}R_{11}$.

(6) a compound according to any one of groups (1) to (5), wherein the substituents of the alkyl-, alkenyl-, alkynyl-, cycloalkyl, aryl or heteroaryl radicals mentioned, if applicable, under $R_5$, $R_{10}$, $R_{11}$, $R_{12}$, $R_{13}$, $R_{14}$, $R_{15}$, $R_{16}$, $R_{17}$, $R_{18}R_{17}$, $R_{18}$, $R_{19}$ are selected from the group consisting of OH, =O, SH, =S, halogen, CN, SCN, $N_3$, $NO_2$, aryl, $C_3$-$C_8$cycloalkyl, $C_1$-$C_{12}$haloalkyl, $C_3$-$C_8$halocycloalkyl, $C_1$-$C_{12}$alkoxy, $C_3$-$C_8$cycloalkoxy, $C_1$-$C_{12}$haloalkoxy, $C_1$-$C_{12}$alkylthio, $C_1$-$C_{12}$cycloalkylthio, $C_1$-$C_{12}$haloalkylthio, $C_1$-$C_6$alkoxy-$C_1$-$C_6$alkyl, $C_2$-$C_8$alkenyl, $C_2$-$C_6$alkenyloxy, $C_2$-$C_6$haloalkenyl, $C_2$-$C_6$haloalkenyloxy, $C_2$-$C_8$alkynyl, $C_2$-$C_6$haloalkynyl, $C_2$-$C_6$haloalkynyloxy, $C_2$-$C_6$alkenylthio, $C_2$-$C_6$haloalkenylthio, $C_1$-$C_6$alkylsulfinyl, $C_3$-$C_8$cycloalkylsulfinyl, $C_1$-$C_6$haloalkylsulfinyl, $C_3$-$C_8$halocycloalkylsulfinyl, $C_2$-$C_6$alkenylsulfinyl, $C_2$-$C_6$haloalkenylsulfinyl, $C_1$-$C_6$alkylsulfonyl, $C_3$-$C_8$cycloalkylsulfonyl, $C_1$-$C_6$haloalkylsulfonyl, $C_3$-$C_8$halocycloalkylsulfonyl $C_2$-$C_6$alkenylsulfonyl, $C_2$-$C_6$haloalkenylsulfonyl, phenoxy, phenyl-$C_1$-$C_6$alkyl, trialkylsilyl; —C(=O)$R_{20}$, —O—C(=O)—$R_{21}$, —NH—C(=O)—$R_{20}$ and —N($R_{22}$)$_2$ (wherein the two $R_{22}$ are independent of each other), aryl, benzyl, heterocyclyl, aryloxy, benzyloxy, heterocyclyloxy, arylthio, benzylthio and heterocyclylthio; wherein the aryl, heterocyclyl, aryloxy, benzyloxy, heterocyclyloxy, arylthio, benzylthio and heterocyclylthio substituents are unsubstituted or, depending on the possibilities of substitution on the ring, are mono- to pentasubstituted by substituents selected from the group consisting of OH, =O, halogen, CN, $NO_2$, $C_1$-$C_{12}$alkyl, $C_1$-$C_{12}$hydroxyalkyl, $C_3$-$C_8$cycloalkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$haloalkylthio, $C_1$-$C_6$alkoxy-$C_1$-$C_6$alkyl, dimethylamino-$C_1$-$C_6$alkoxy, $C_2$-$C_8$alkenyl, $C_2$-$C_8$alkynyl, phenoxy, phenyl-$C_1$-$C_6$alkyl; methylenedioxy, —C(=O)$R_{20}$, —O—C(=O)—$R_{21}$, —NH—C(=O)$R_{20}$, —N($R_{22}$)$_2$ (wherein the two $R_{22}$ are independent of each other), $C_1$-$C_6$alkylsulfinyl, $C_3$-$C_8$cycloalkylsulfinyl, $C_1$-$C_6$haloalkylsulfinyl, $C_3$-$C_8$halocycloalkylsulfinyl, $C_1$-$C_6$alkylsulfonyl, $C_3$-$C_8$cycloalkylsulfonyl, $C_1$-$C_6$haloalkylsulfonyl and $C_3$-$C_8$halocycloalkylsulfonyl; wherein $R_{20}$ is a H, OH, SH, —N($R_{22}$)$_2$ (wherein the two $R_{22}$ are independent of each other), $C_1$-$C_{24}$alkyl, $C_2$-$C_{12}$alkenyl, $C_1$-$C_8$hydroxyalkyl, $C_1$-$C_{12}$haloalkyl, $C_1$-$C_{12}$alkoxy, $C_1$-$C_{12}$haloalkoxy, $C_1$-$C_6$alkoxy-$C_1$-$C_6$alkyl, $C_1$-$C_6$alkoxy-$C_1$-$C_6$alkoxy, $C_1$-$C_6$alkoxy-$C_1$-$C_6$alkoxy-$C_1$-$C_6$alkyl, $C_1$-$C_{12}$alkylthio, $C_2$-$C_8$alkenyloxy, $C_2$-$C_8$alkynyloxy; aryl, benzyl, heterocyclyl, aryloxy, benzyloxy, or heterocyclyloxy; or aryl, benzyl, heterocyclyl, aryloxy, benzyloxy or heterocyclyloxy, which are mono- to trisubstituted in the ring independently of one another by halogen, nitro, $C_1$-$C_6$alkyl, $C_1$-$C_6$alkoxy, $C_1$-$C_6$haloalkyl or $C_1$-$C_6$haloalkoxy group;

$R_{21}$ is H, $C_1$-$C_6$alkyl, which is optionally substituted with one to five substituents selected from the group consisting of halogen, $C_1$-$C_6$alkoxy, hydroxy and cyano, $C_1$-$C_8$-cycloalkyl, aryl, benzyl, or heteroaryl; or aryl, benzyl or heteroaryl, which, depending on the possibilities of substitution on the ring, are mono- to trisubstituted by substituents selected from the group consisting of OH, halogen, CN, $NO_2$, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio and $C_1$-$C_{12}$haloalkylthio; and $R_{22}$ is H, $C_1$-$C_6$alkyl, which is optionally substituted with one to five substituents selected from the group consisting of halogen, $C_1$-$C_6$alkoxy, hydroxy and cyano, $C_1$-$C_8$-cycloalkyl, aryl, benzyl, or heteroaryl; or aryl, benzyl or heteroaryl, which, depending on the possibilities of substitution on the ring, are mono- to trisubstituted by substituents selected from the group consisting of OH, halogen, CN, $NO_2$, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio and $C_1$-$C_{12}$haloalkylthio;

(7) a compound according to any one of groups (1) to (6), wherein the configuration at the carbon atom at 13-position (γ) is (S);

(8) a compound according to any one of groups (1) to (6), wherein the configuration at the carbon atom at 13-position (γ) is (R);

(9) a compound according to any one of groups (1) to (8), wherein $R_2$ is not a hydroxy, a alkanoyloxy or an alkanoylamino group;

(10) a compound according to any one of groups (1) to (9), wherein $R_1$ is isopropyl, or sec-butyl;

(11) a compound according to any one of groups (1) to (9), wherein $R_1$ is cyclohexyl;

(12) a compound according to any one of groups (1) to (9), wherein $R_1$ is 1-methyl-butyl;

(13) a compound according to any one of groups (1) to (12), wherein the bond between carbon atoms 22 and 23 is a single bond;

(14) a compound according to any one of groups (1) to (12), wherein the bond between carbon atoms 22 and 23 is a double bond;

(15) a compound according to any one of groups (1) to (14), wherein n is 2;

(16) a compound according to any one of groups (1) to (14), wherein n is 1;

(17) a compound according to any one of groups (1) to (14), wherein n is 0;

(18) a compound according to any one of groups (1) to (16), wherein the configuration of the carbon atom at the 4'-position is (δ) (S);

(19) a compound according to any one of groups (1) to (16), wherein the configuration of the carbon atom at the 4'-position (δ) is (R);

(20) a compound according to any one of groups (1) to (15), wherein the configuration of the carbon atom at the 4"-position (δ) is (R)

(21) a compound according to any one of groups (1) to (15), wherein the configuration of the carbon atom at the 4"-position (δ) is (S)

(22) a compound according to any one of groups (1) to (21), wherein $R_2$ represents $R_{15}$, $R_{16}$O, or $R_{16}$OC(=O)O—;

(23) a compound according to any one of groups (1) to (22), wherein $R_3$ represents H, $R_{16}$O, or $R_{16}$OC(=O)O—;

(24) a compound according to any one of groups (1) to (23), wherein $R_4$ represents H, $R_{15}$O, $R_{16}$C(=O)O—, or $R_{16}R_{17}$N;

(25) a compound according to any one of groups (1) to (24), wherein $R_5$ represents H, or $R_{15}$;

(26) a compound according to any one of groups (1) to (23), wherein $R_4$ and $R_5$ together represent =O, or =NO$R_{16}$;

(27) a compound according to any one of groups (1) to (26), wherein $R_6$ represents H, $R_{15}$, or $R_{16}$OCH$_2$;

(28) a compound according to any one groups (22) to (25) and (27), wherein $R_{15}$ represents unsubstituted or mono- to pentasubstituted $C_1$-$C_6$alkyl, preferably an unsubstituted $C_1$-$C_3$alkyl;

(29) a compound according to any one groups (22), (23), (24), (26) and (27), wherein $R_{16}$ represents H or unsubstituted or mono- to penta-substituted $C_1$-$C_6$alkyl;

(30) a compound according to group (24) wherein $R_{17}$ represents H or unsubstituted or mono- to penta-substituted $C_1$-$C_6$alkyl;

(31) a compound according to any one of groups (1) to (30), wherein the configuration of the carbon atom at the 1-position (ε) of the cyclic acetal is (R);

(32) a compound according to any one of groups (1) to (30), wherein the configuration of the carbon atom at the 1-position (ε) of the cyclic acetal is (S);

(33) a compound according to any one of groups (1) to (32), wherein when $R_2$, $R_3$, and $R_4$ are $OCH_3$, preferably $OC_{1-4}$alkyl, the carbon configurations of the cyclic acetal at 3-position (η) and 4-position (κ) are opposite to each other;

(34) a compound according to any one of groups (1) to (33), wherein when $R_2$, $R_3$, and $R_4$ are $OCH_3$, preferably $OC_{1-4}$alkyl, the carbon configurations of the cyclic acetal at 2-position (Φ) and 3-position (η) are the same, preferably (R);

(35) a compound according to any one of groups (1) to (32), wherein when $R_2$, $R_3$, and $R_4$ are the same substituents, the carbon configurations of the cyclic acetal at 3-position (η) and 4-position (κ) are opposite to each other;

(36) a compound according to any one of groups (1) to (32) and (35), wherein when $R_2$, $R_3$, and $R_4$ are the same substituents, the carbon configurations of the cyclic acetal at 2-position (Φ) and 3-position (η) are the same, preferably (R);

(37) a compound according to any one of groups (1) to (32), (34) and (36), wherein the carbon configurations of the cyclic acetal at 2-position (Φ), 3-position (η) and 4-position (κ) are the same;

(38) a compound according to any one of groups (1) to (37), wherein the configuration of the carbon atom at the 2-position (Φ) of the cyclic acetal is (R);

(39) a compound according to any one of groups (1) to (37), wherein the configuration of the carbon atom at the 2-position (Φ) of the cyclic acetal is (S);

(40) a compound according to any one of groups (1) to (39), wherein the configuration of the carbon atom at the 3-position (η) of the cyclic acetal is (R);

(41) a compound according to any one of groups (1) to (39), wherein the configuration of the carbon atom at the 3-position (η) of the cyclic acetal is (S);

(42) a compound according to any one of groups (1) to (41), wherein the configuration of the carbon atom at the 4-position (κ) of the cyclic acetal is (R);

(43) a compound according to any one of groups (1) to (41), wherein the configuration of the carbon atom at the 4-position (κ) of the cyclic acetal is (S);

(44) a compound according to any one of groups (1) to (43), wherein the configuration of the carbon atom at the 5-position (λ) of the cyclic acetal is (R);

(45) a compound according to any one of groups (1) to (43), wherein the configuration of the carbon atom at the 5-position (λ) of the cyclic acetal is (S).

A preferred compound of formula (I) or formula (II) is an avermectin or avermectin monosaccharide derivative, wherein the bond between carbon atoms 22 and 23 is a double bond, n is 1 or 2, $R_1$ represents a $C_1$-$C_4$alkyl group (preferably isopropyl, or sec-butyl), $R_2$ represents $C_1$-$C_4$alkyl or $C_1$-$C_4$alkoxy, $R_3$ represents $C_1$-$C_4$alkoxy, $R_4$ represents H, OH, $C_1$-$C_4$alkoxy, $C_1$-$C_4$alkoxy$C_1$-$C_4$alkoxy, $C_1$-$C_4$alkanoyloxy, $C_1$-$C_4$alkoxycarbonyloxy, $C_2$-$C_4$alkenyloxycarbonyloxy, $C_1$-$C_4$alkylamino, di$C_1$-$C_4$alkylamino, $C_1$-$C_4$alkanoylamino, di$C_1$-$C_4$alkanoylamino, $C_1$-$C_4$alkanoyl-$C_1$-$C_4$alkyl-amino, $C_1$-$C_4$alkoxycarbonylamino, di$C_1$-$C_4$alkoxycarbonylamino, $C_1$-$C_4$alkoxycarbonyl-$C_1$-$C_4$alkyl-amino, or $C_2$-$C_4$alkenyloxycarbonyl-$C_1$-$C_4$alkyl-amino, $R_5$ represents H, $C_1$-$C_4$alkyl, $C_2$-$C_3$alkenyl, $C_2$-$C_3$alkynyl or CN, or $R_4$ and $R_5$ together represent =O, =NOH, =NO$C_1$-$C_4$alkyl, or =NO$C_1$-$C_4$alkanoyl, and $R_6$ represents H, methyl, $C_1$-$C_4$alkoxyCH$_2$, or $C_1$-$C_4$alkanoyloxyCH$_2$, wherein (a) the carbon configurations of the cyclic acetal at 3-position (η) and 4-position (κ) are opposite to each other, (b) the carbon configurations of the cyclic acetal at 2-position (Φ) and 3-position (η) are the same, preferably (R), or (c) the carbon configurations of the cyclic acetal at 2-position (Φ), 3-position (η) and 4-position (κ) are the same, and in any one of (a), (b) or (c) the carbon configurations at any one of the other carbons atoms, independently of each other, is (R) or (S).

Where the same general group (or radical or substituent) type is described as present in a compound in two or more positions, the specific groups may be the same or different. Further, where a number range of substitution is indicated, for example, mono-, to pentasubstituted $C_1$ to $C_{12}$alkyl, a skilled person would understand that extent of substitutions would depend on the availability of substitution sites. Unless defined otherwise, the general terms used in the present application have the meanings given below:

Chemical constituent, preferably an organic group, is a group of atoms attached via an atom selected from carbon, nitrogen, sulfur, oxygen, or phosphorus. Preferably the attaching atom is carbon, nitrogen, sulfur or oxygen. Examples include unsubstituted and substituted hydrocarbyl groups, carbonate and derivatives, nitrate and derivatives, phosphate and derivatives, sulfate and derivatives, OH and derivatives, amine and derivatives, thio groups and derivatives, sulfinyl groups and sulfonyl groups. Most preferred are OH, amine and derivatives thereof.

Hydrocarbyl group is a group of atoms attached via a carbon atom. The group contains one or more carbon atoms and one or more hydrogen atoms, which group can be aliphatic, alicyclic, bicyclic, spirocyclic (each saturated or unsaturated), aromatic, straight-chained, branched-chained, or a group with a combination thereof. Examples include methyl, ethyl, isopropyl, cyclohexyl, vinyl, ethynyl, allyl, phenyl, or benzyl. Preferably a hydrocarbyl group contains 1 to 15, more preferably 1 to 12, especially 1 to 4, such as 1 or 2, carbon atoms.

Substituted hydrocarbyl group is a group of atoms attached via a carbon atom. The group contains one or more carbon atoms, optionally one or more hydrogen atoms, and one or more hetero atoms, such as a halogen, boron, oxygen, nitrogen, sulfur, phosphorus, or a mixture thereof. Examples include cyano, halogen substituted carbon-containing groups, alkoxy groups, heterocyclic groups, such as pyridine and derivatives thereof, and carbonyl containing groups. Preferably a substituted hydrocarbyl group contains 1 to 15, more preferably 1 to 12, especially 1 to 4, such as 1 to 2, carbon atoms.

Unless defined otherwise, carbon-containing groups (for example, alkyl, alkenyl, cycloalkyl) contain 1 up to and including 6, preferably 1 up to and including 4, in particular 1 or 2, carbon atoms.

Halogen—as a group per se and also as a structural element of other groups and compounds, such as haloalkyl, haloalkoxy and haloalkylthio—is fluorine, chlorine, bromine or iodine, in particular fluorine, chlorine or bromine, especially fluorine or chlorine.

Alkyl—as a group per se and also as a structural element of other groups and compounds, such as haloalkyl, alkoxy and alkylthio—is, in each case taking into account the number of carbon atoms contained in each case in the group or compound in question, either straight-chain, i.e., methyl, ethyl, propyl, butyl, pentyl, hexyl, heptyl or octyl, or branched, for example, isopropyl, isobutyl, sec-butyl, tert-butyl, isopentyl, neopentyl or isohexyl. Preferred number of carbon atoms in an alkyl group is between 1 to 6, such as 1 to 4.

Cycloalkyl—as a group per se and also as a structural element of other groups and compounds, such as, for example, of halocycloalkyl, cycloalkoxy and cycloalkylthio—is, in each case taking into account the number of carbon atoms contained in each case in the group or compound in question, cyclopropyl, cyclobutyl, cyclopentyl, cyclohexyl, cycloheptyl or cyclooctyl. Preferred number of carbon atoms in a cycloalkyl group is between 3 to 6, such as 3 to 4.

Alkenyl—as a group per se and also as a structural element of other groups and compounds—is, taking into account the number of carbon atoms and conjugated or isolated double bonds contained in the group, either straight-chain, for example, vinyl, allyl, 2-butenyl, 3-pentenyl, 1-hexenyl, 1-heptenyl, 1,3-hexadienyl or 1,3-octadienyl, or branched, for example, isopropenyl, isobutenyl, isoprenyl, tert-pentenyl, isohexenyl, isoheptenyl or isooctenyl. Preference is given to alkenyl groups having 3 to 12, in particular 3 to 6, especially 3 or 4, carbon atoms.

Alkynyl—as a group per se and also as a structural element of other groups and compounds—is, in each case taking into account the number of carbon atoms and conjugated or isolated triple bonds contained in the group or compound in question, either straight-chain, for example, ethynyl, propargyl, 2-butynyl, 3-pentynyl, 1-hexynyl, 1-heptynyl, 3-hexen-1-ynyl or 1,5-heptadien-3-ynyl, or branched, for example, 3-methylbut-1-ynyl, 4-ethylpent-1-ynyl, 4-methylhex-2-ynyl or 2-methylhept-3-ynyl. Preference is given to alkynyl groups having 3 to 12, in particular 3 to 6, especially 3 or 4, carbon atoms.

Alkoxy—as a group per se and also as a structural element of other groups and compounds is, in each case taking into account the number of carbon atoms contained in each case in the group or compound in question, either straight-chain, e.g., methoxy, ethoxy or propoxy, or branched-chain, for example, isopropoxy, isobutyoxy, or sec-butoxy. One or more oxygen atoms can be present in the group. Preferred number of carbon atoms in an alkoxy group is between 1 to 6, such as 1 to 4. Similarly, the oxygen atom in the group alkenyloxy or alkynyloxy can be in any position and the preferred number of carbon atoms in either group is between 2 to 6, such as 2 to 4.

Halogen—substituted carbon—containing groups and compounds, such as, for example, halogen-substituted alkyl, alkenyl, alkynyl, cycloalkyl, alkoxy or alkylthio, can be partially halogenated or perhalogenated, where in the case of polyhalogenation the halogen substituents can be identical or different. Examples of haloalkyl—as a group per se and also as a structural element of other groups and compounds, such as haloalkoxy or haloalkylthio—are methyl which is mono- to trisubstituted by fluorine, chlorine and/or bromine, such as $CHF_2$ or $CF_3$; ethyl which is mono- to pentasubstituted by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl which is mono- to heptasubstituted by fluorine, chlorine and/or bromine, such as $CH_2CHBrCH_2Br$, $CF_2CHFCF_3$, $CH_2CF_2CF_3$, $CF(CF_3)_2$ or $CH(CF_3)_2$; butyl or one of its isomers, mono- to nonasubstituted by fluorine, chlorine and/or bromine, such as $CF(CF_3)CHFCF_3$ or $CH_2(CF_2)_2CF_3$; pentyl or one of its isomers, mono- to undecasubstituted by fluorine, chlorine and/or bromine, such as $CF(CF_3)(CHF_2)CF_3$ or $CH_2(CF_2)_3CF_3$; and hexyl or one of its isomers, mono- to tridecasubstituted by fluorine, chlorine and/or bromine, such as $(CH_2)_4CHBrCH_2Br$, $CF_2(CHF)_4CF_3$, $CH_2(CF_2)_4CF_3$ or $C(CF_3)_2(CHF)_2CF_3$.

Aryl is in particular phenyl, naphthyl, anthracenyl, phenanthrenyl, perylenyl or fluorenyl, preferably phenyl.

Heterocyclyl is understood as being a three- to seven-membered monocyclic ring, which may be saturated or unsaturated, and that contains from one to three hetero atoms selected from the group consisting of B, N, O and S, especially N and S; or a bicyclic ring system having from 8 to 14 ring atoms, which may be saturated or unsaturated, and that may contain either in only one ring or in both rings independently of one another, one or two hetero atoms selected from N, O and S; heterocyclyl is in particular piperidinyl, piperazinyl, oxiranyl, morpholinyl, thiomorpholinyl, pyridyl, N-oxidopyridinio, pyrimidyl, pyrazinyl, s-triazinyl, 1,2,4-triazinyl, thienyl, furanyl, dihydrofuranyl, tetrahydrofuranyl, pyranyl, tetrahydropyranyl, pyrrolyl, pyrrolinyl, pyrrolidinyl, pyrazolyl, imidazolyl, imidazolinyl, thiazolyl, isothiazolyl, triazolyl, oxazolyl, thiadiazolyl, thiazolinyl, thiazolidinyl, oxadiazolyl, dioxaborolanyl, phthalimidoyl, benzothienyl, quinolinyl, quinoxalinyl, benzofuranyl, benzimidazolyl, benzpyrrolyl, benzthiazolyl, indolinyl, isoindolinyl, cumarinyl, indazolyl, benzothiophenyl, benzofuranyl, pteridinyl or purinyl, which are preferably attached via a C atom; thienyl, benzofuranyl, benzothiazolyl, tetrahydropyranyl, dioxaborolanyl, or indolyl is preferred; in particular dioxaborolanyl, pyridyl or thiazolyl. The said heterocyclyl radicals may preferrably be unsubstituted or—depending on the substitution possibilities on the ring system—substituted by 1 to 3 substituents selected from the group consisting of halogen, =O, —OH, =S, SH, nitro, $C_1$-$C_6$alkyl, $C_1$-$C_6$hydroxyalkyl, $C_1$-$C_6$alkoxy, $C_1$-$C_6$haloalkyl, $C_1$-$C_6$haloalkoxy, phenyl and benzyl.

The invention also provides a process for preparing a compound of the formula (I) or formula (II) via a glycosylation and enolation routes.

Glycosylation (A) Advantageously, avermectin aglycone, avermectin monosaccharide, avermectin or their epimers at positions 13, 4' or 4" respectively with the oxygen protected at 5-carbon position and optionally the oxygen protected at 7-carbon position (formula (V) below) is used as a starting material.

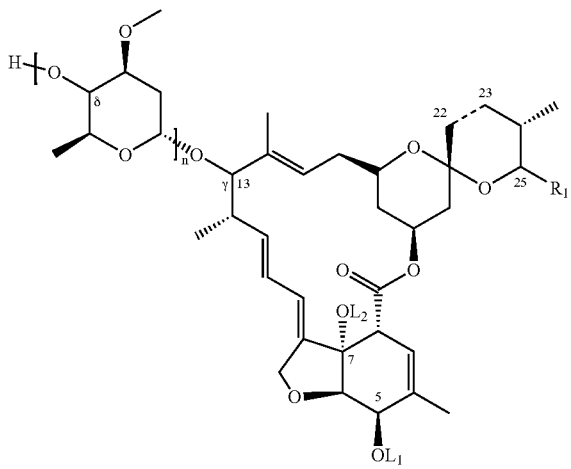

(V)

wherein $R_1$, n and the bond between carbon atoms 22 and 23 is as defined for a compound of formula (I) of the first aspect, $L_1$ and $L_2$ are suitable protecting groups to prevent reaction on the oxygen atom on the 5-carbon position, or 7-carbon position respectively.

The free hydroxy group at position 13, 4' or 4" (n is 0, 1 or 2 respectively) in formula (V) is reacted with activated agent and an activated tetrahydropyran of formula (α)

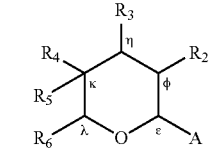

(α)

wherein $R_2$, $R_3$, $R_4$, $R_5$, $R_6$ are as defined above in the first aspect, wherein A is a suitable leaving group, to yield a compound of formula (II)

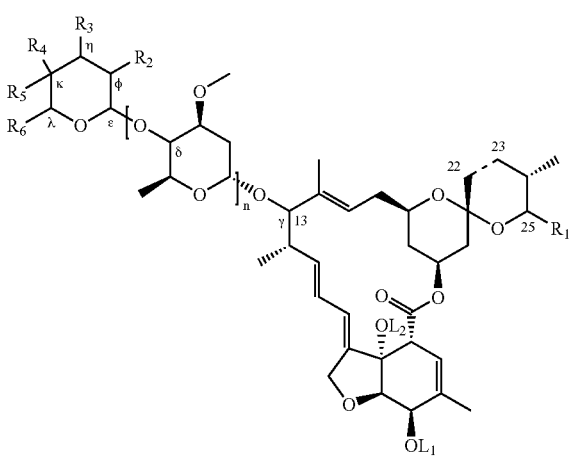

(II)

wherein $R_1$, $R_2$, $R_3$, $R_4$, $R_5$, $R_6$, the bond between the carbon atoms 22 and 23 and n are as defined above in the first aspect, $L_1$ is a protecting group and $L_2$ is hydrogen or a protecting group; and either (B) the protecting groups $L_1$ and $L_2$, if applicable, can be removed with a deprotection agent, for example an acidic and/or fluoride reagent, to yield a compound of formula (I), or (C) reactions can be carried out on one or more of $R_2$, $R_3$, $R_4$, $R_5$, $R_6$ groups to modify the group, and then the protecting groups $L_1$ and $L_2$, if applicable, can be removed with a deprotection agent, for example an acidic and/or fluoride reagent, to yield a compound of formula (I).

Enolation (D) Preferably, 4" or 4' oxo avermectin or avermectin monosaccharide respectively with the oxygen protected at 5-carbon position (formula (III)) is used as a starting material.

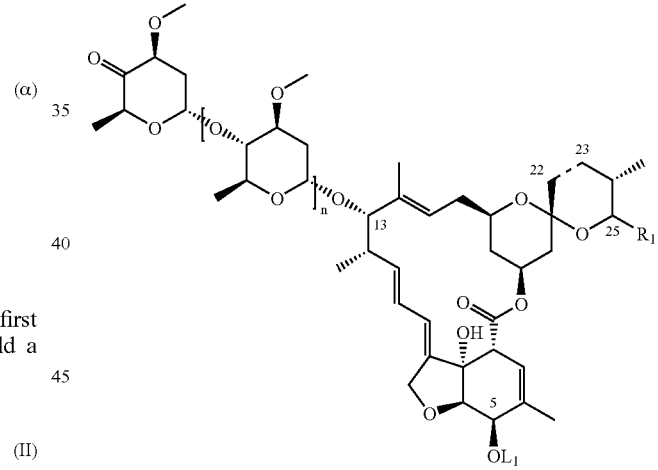

(III)

wherein $R_1$ and the bond between the carbon atoms 22 and 23 are as defined above in the first aspect, n is 0 or 1, and $L_1$ is a protecting group. The preparation of such a starting material is described in EP-A-0343708, and briefly involves oxidation of the 4" or 4' hydroxyl group of avermectin or avermectin monosaccharide, respectively, in which the oxygen at 5-carbon position is protected.

The compound of formula (III) is reacted with a base and an electrophile E-X, preferably a trialkylsilyl compound, to form a mixture of enolates of formula (VIa) and (VIb).

(VIa)

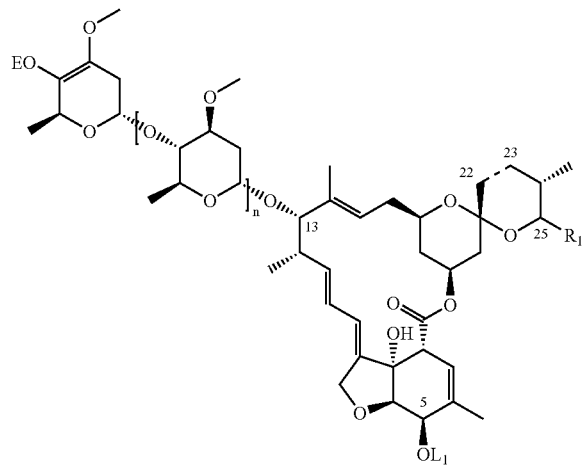

(VIb)

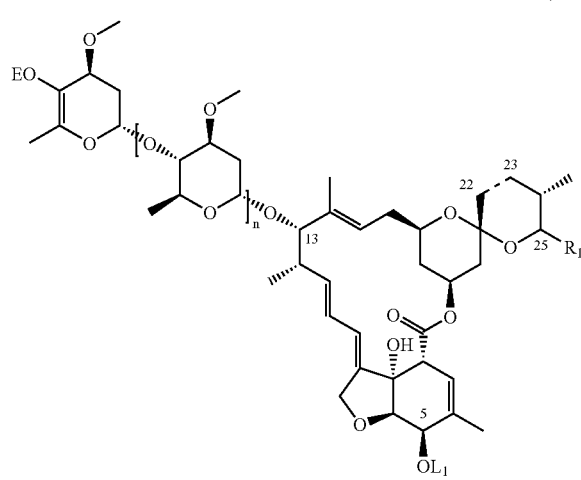

wherein $R_1$ and the bond between the carbon atoms 22 and 23 are as defined above in the first aspect, n is 0 or 1, $L_1$ is a protecting group, and E is silyl group for each formula above, (E) The compound of formula (VIa) is oxidised with a suitable oxidant to an enone of the formula (IV), (IV)

wherein $R_1$ and the bond between the carbon atoms 22 and 23 are as defined above in the first aspect, n is 0 or 1, and $L_1$ is a protecting group (F) the compound of formula (IV) is reacted with an organometallic reagent, for example, of formula (β)

$$(R_2)_r\text{-M-(Hal)}_s \qquad (\beta)$$

or adducts or solvates of varying composition, wherein $R_2$ is as defined for compound of formula (I), wherein it is hydrocarbyl or substituted hydrocarbyl group, and M is a metal atom or a group of metal atoms, preferably a lithium cuprate, and Hal is a halogen atom, preferably chlorine, bromine or iodine, r is 1 to 2 and s is 0 to 2 as function of the metal charge (such a reagent is known or can be prepared by methods known) to yield a compound of formula (VII), and (VII)

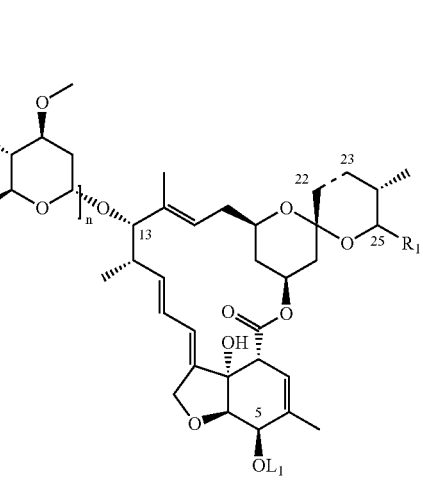

wherein $R_1$ and the bond between the carbon atoms 22 and 23 are as defined above in the first aspect, n is 0 or 1, and $L_1$ is a protecting group, (G) the compound (VII) can be used for further reaction sequences at the keto group in the 4" or 4' position; such reactions are known to the person skilled in the art, for example starting with reduction, addition of organometallics or reductive amination and then performing other transformations at the resulting hydroxy or amino group respectively, for example alkylation or acylation, and (H) the protecting group $L_1$ can be removed with a deprotection agent, for example an acidic and/or fluoride reagent, to yield a compound of formula (I).

It is believed that the process of the third aspect can in principle be applied to other 2-desoxy sugars and then coupled to a mectin scaffold or other 2-desoxy sugars can be coupled to a mectin scaffold and the reaction of the third aspect carried out.

The present invention, therefore, provides derivatives where the terminal pyran ring has the D or L configuration of rhamnopyranose, xylopyranose, arabinopyranose, allopyranose, idopyranose, gulopyranose, altropyranose, glucopyranose, galactopyranose, fucopyranose, lyxopyranose, ribopyranose, mannopyranose or talopyranose; preferred are rhamnopyranose, xylopyranose, allopyranose, idopyranose, gulopyranose, altropyranose, lyxopyranose, ribopyranose, mannopyranose or talopyranose. Especially preferred is the L configuration.

The conditions for reactions described are carried out in a manner known per se, for example in the absence or, customarily, in the presence of a suitable solvent or diluent or of a mixture thereof, the reactions being carried out, as required, with cooling, at room temperature or with heating, for example, in a temperature range of approximately from −80° C. to the boiling temperature of the reaction medium, preferably from approximately 0° C. to approximately +150° C., and, if necessary, in a closed vessel, under pressure, under an inert gas atmosphere and/or under anhydrous conditions. Especially advantageous reaction conditions can be found in the Example section.

The reaction time is not critical; a reaction time of from about 0.1 to about 24 hours, especially from about 0.5 to about 10 hours, is preferred.

The product is isolated by customary methods, for example by means of filtration, crystallization, distillation or chromatography, or any suitable combination of such methods.

It is generally useful to protect oxygen at the 5-carbon position with a protecting group $L_1$ to prevent reaction on that position when carrying out reactions with avermectin and avermectin monosaccharide. Preference is given to trialkylsilyl radicals, such as trimethylsilyl, triethylsilyl, dimethyl-tert-butylsilyl, diphenyl-tert-butylsilyl, esters, such as methoxyacetates and phenoxyacetates, and carbonates, such as allylcarbonates. Dimethyl-tert-butylsilyl ether is especially preferred. In some cases it might be useful to protect oxygen at the 7-carbon position with a protecting group $L_2$ to prevent reaction on that position when carrying out reactions with avermectin and avermectin monosaccharide. Preference is given to trialkylsilyl radicals, such as trimethylsilyl or triethylsilyl. Trimethylsilyl ether is especially preferred.

The starting materials mentioned that are used for the preparation of the compound of formula (I), the intermediates (e.g., the compound of formula (II), or (V)), and, where applicable, their E/Z isomer and/or diastereoisomer and/or tautomer are known or can be prepared by methods known per se.

The process steps (A) to (H) described above are detailed further below:

Process Step (A):

Examples of solvents and diluents include: aromatic, aliphatic and alicyclic hydrocarbons and halogenated hydrocarbons, such as benzene, toluene, xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; esters of carboxylic acids, such as ethyl acetate; amides, such as dimethylformamide, dimethylacetamide or 1-methyl-2-pyrrolidinones; nitriles, such as acetonitrile or propionitrile; sulfoxides, such as dimethyl sulfoxide; or mixtures of the mentioned solvents. Preference is given to halogenated hydrocarbons, such as dichloromethane, trichloromethane, tetrachloromethane, especially dichloromethane.

The reactions are advantageously carried out in a temperature range of approximately −70° C. to 50° C., preferably from −40° C. to 25° C.

The activated tetrahydropyran of formula (α) used in step (A)

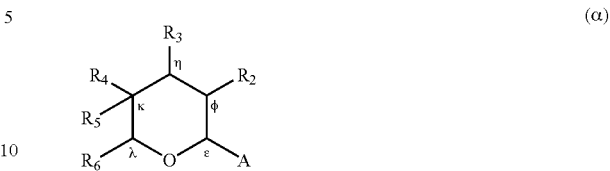

is known or can be prepared by methods known. The leaving group A can be, for example, a halogenide, like fluoride, chloride, bromide or iodide, or a alkylthiogroup, or a arylthiogroup. A preferred leaving group is the phenylthiogroup.

Suitable activating agents for halogenides as leaving groups are metal salts, such as silver, mercury and cadmium salts. Preferred salts are $Ag_2CO_3$ and $Ag_2O$.

Suitable activation agents for alkylthiogroups or arylthiogroups as leaving groups are oxidative reagents, such as bromine, N-Bromosuccinimide, Iodide, N-Iodosuccinimide, preferably in the presence of an acid, such as trifluorosulfonic acid or a Lewis acid, such as silver triflate or copper triflate.

Especially preferred conditions for the reaction are described in Example 1 (step A), Example 3 (step A), Example 5 (step A).

Process Step (B)

Examples of solvents and diluents are the same as those mentioned under Process step (A). In particular, cyclic ethers, such as tetrahydrofuran, or alcohols, such as methanol, are especially suitable.

The reactions are advantageously carried out in a temperature range of approximately 0° C. to 110° C., preferably from 0° C. to 50° C.

Once the desired reactions are completed, the reagents used for removing the protecting group $L_1$ are acids, such as hydrochloric acid, methanesulfonic acid, $BF_3.OEt_2$, HF in pyridine, $Zn(BF_4)_2.H_2O$, p-toluenesulfonic acid, $AlCl_3$, $HgCl_2$; ammonium fluoride, such as tetrabutylammonium fluoride; bases, such as ammonia, trialkylamine or heterocyclic bases; hydrogenolysis with a catalyst, such as palladium-on-carbon; reducing agents, such as sodium borohydride or tributyltin hydride with a catalyst, such as $Pd(PPh_3)_4$, or also zinc with acetic acid. Preference is given to acids, such as methanesulfonic acid or HF in pyridine; sodium borohydride with Pd(0); bases, such as ammonia, triethylamine or pyridine; especially acids, such as HF in pyridine or methanesulfonic acid. Generally, an acidic reagent, such as a mixture of methanesulfonic acid in methanol or a HF in a mixture of pydrine/THF, is effective in removing dimethyl-tert-butylsilyl ether group from oxygen at the 5-carbon position. Preferred conditions for removing the dimethyl-tert-butylsilyl ether group from oxygen at the 5-carbon position are described in Examples 1 (Step B), Example 2, Example 3 (Step C), Example 4 (Step B), Example 5 (Step B), Example 6 (Step B), Example 7 (Step B), Example 9, Example 11 (Step E), Example 12.

The alkylsilyl protecting group $L_2$ at the 7-carbon is removed by the same acidic reagents, mentioned above for removing the dimethyl-tert-butylsilyl ether group from oxygen at the 5-carbon.

Process Step (C):

The person skilled in the art can select several reaction conditions for organic group transformations from the literature or reviews, e.g. Synthetic Organic Methodology: Comprehensive Organic Transformations. A Guide to Functional Group Preparations. Larock, R. C. (1989), 1060 pp. Publisher: (VCH, Weinheim, Fed. Rep. Ger.); Protective Groups in Organic Synthesis. 2nd Ed., Greene, Theodora W.; Wuts, Peter G. M. (1991), 473 pp. Publisher: (John Wiley and Sons, Inc., New York, N.Y.). Examples are:

Cleavage of an Allylcarbonate or Allylcarbamate Group:

Examples of solvents and diluents are the same as those mentioned under Process step (A). In particular, cyclic ethers, such as teratrahydrofuran are especially suitable.

Cleavage agents are reducing agents, such as sodium borohydride or tributyltin hydride or formic acid/triphenylphosphine with a catalyst, such as $Pd(PPh_3)_4$.

The reactions are advantageously carried out in a temperature range of approximately 0° C. to 110° C., preferably at from 0° C. to 50° C.

Especially preferred conditions for the reaction are described in Example 3 (step B), Example 4 (step A), Example 8, Example 10.

Alkylation of an OH-Group:

Examples of solvents and diluents are the same as those mentioned under Process step (A). In particular, cyclic ethers, such as teratrahydrofuran or halogenated hydrocarbons, such as chloroform and dichloromethan are especially suitable.

Suitable bases are especially trialkylamines, such as triethylamine or ethyldiisopropylamine.

The reactions are advantageously carried out in a temperature range approximately 0° C. to 110° C., preferably at from 0° C. to 50° C.

Especially preferred conditions for the reaction are described in Example 5 (step A), Example 6 (step A).

Oxidation of an OH-Group to a Ketone:

Examples of solvents and diluents are the same as those mentioned under Process step (A). In particular, halogenated hydrocarbons, such as chloroform and dichloromethan are especially suitable.

Suitable oxidation reagents are especially DMSO in the presence of acid chlorides, such as oxalylchloride or acid anhydrides, such as acetic acid anhydride.

Suitable bases for quenching the reaction are especially trialkylamines, such as triethylamine or ethyldiisopropylamine.

The reactions are advantageously carried out in a temperature range of approximately −70° C. to 0° C., preferably from −50° C. to −10° C.

Reduction of a Keto Group to an Alcohol:

Examples of solvents and diluents are the same as those mentioned under Process step (A). In particular, alcohols, such as methanol and ethanol are especially suitable.

Suitable reduction reagents are especially metalhydrides, such as sodium borohydride.

The reactions are advantageously carried out in a temperature range of approximately −50° C. to 50° C., preferably from 0° C. to 50° C.

Especially preferred conditions for the reaction are described in Example 11 (step C).

Alkylation of a Keto Group:

Examples of solvents and diluents are the same as those mentioned under Process step (A). In particular, ethers, such as diethyl ether, dipropyl ether, diisopropyl ether, dibutyl ether, tert-butyl methyl ether, tetrahydrofuran or dioxane are especially suitable.

Suitable alkylation reagents are organometallic reagents, especially Grignard reagents, such as methylmagnesium chloride.

The reactions are advantageously carried out in a temperature range of approximately −50° C. to 50° C., preferably from 0° C. to 50° C.

Reductive Amination of a Keto Group:

Examples of solvents and diluents are the same as those mentioned under Process step (A). In particular, esters, such as ethylacetate and aromatic solvents, such as toluene, are especially suitable.

Suitable reagents for imine formation are alkylsilylamines, such as bis(trimethylsilyl)amine or heptamethyldisalazane in the presence of a Lewis acid, such as Zinc bromide or Zinc chloride.

Suitable reduction reagents are especially metalhydrides, such as sodium borohydride or sodium cyano borohydride.

The reactions are advantageously carried out in a temperature range of approximately −50° C. to 50° C., preferably from 0° C. to 50° C.

Especially preferred conditions for the reaction are described in Example 12.

Acylation of an Amino Group:

Examples of solvents and diluents are the same as those mentioned under Process step (A). In particular, esters, such as ethylacetate and aromatic solvents, such as toluene, are especially suitable. Preferred are biphasic systems consisting of the solvents mentioned above and aqueous sodium bicarbonate.

Suitable acylating agents are acyl chlorides.

Especially preferred conditions for the reaction are described in Example 13.

Once the desired reactions are completed, the protecting groups $L_1$ and $L_2$, if applicable, can be removed under the conditions described in Process step (B).

Process Step (D):

Examples of solvents and diluents are the same as those mentioned under Process step (A). In particular, aromatic hydrocarbons, such as benzene or toluene are especially suitable.

Suitable bases are especially trialkylamines, such as triethylamine or ethyldiisopropylamine.

Suitable electrophiles E-X are trialkylsilyl halogenides, such as trimethylsilyl chloride, triethylsilyl chloride, triisopropyl chloride, dimethyl-tert-butylsilyl chloride, diphenyl-tert-butylsilyl chloride, or trialkylsilyl trifluormethansulfonates, such as trimethylsilyl trifluormethansulfonates, triethylsilyl trifluormethansulfonates, triisopropyl trifluormethansulfonates, dimethyl-tert-butylsilyl trifluormethansulfonates, diphenyl-tert-butylsilyl trifluormethansulfonates.

The reactions are advantageously carried out in a temperature range of from approximately 0° C. to 110° C., preferably at from 50° C. to 110° C.

Especially preferred conditions for the reaction are described in Example 11 (step A).

Process Step (E):

Examples of solvents and diluents are the same as those mentioned under Process step (A). In particular, halogenated hydrocarbons, such as chloroform and dichloromethan or esters, such as ethylacetate and water are especially suitable.

The reactions are advantageously carried out in a temperature range of from approximately −70° C. to 50° C., preferably at from −10° C. to 25° C.

Preferably, a mixture of regioisomers (compounds of formulae (VIa) and (VIb)) are used for the source of enolate for the oxidation step to the cyclic conjugated enone of formula (IV); if desired the compound of formula (VIa) may be separated from the regioisomer mixture and used for the oxidation step.

Examples of oxidant suitable for oxidizing the enolate to a enone are hydrogen peroxide, arylperoxoic acid, alkyl hydroperoxide, dimethyldioxirane, potassium peroxymonosulfate sulfate, sodium periodate, bialkylperoxide, 2-iodylbenzoic acid, α-Cumene hydroperoxide, oxaziridine analogues; preferred is 3-chloroperbenzoic acid. The reaction is preferably carried out in biphasic system.

Especially preferred conditions for the reaction are described in Example 11 (step B).

Process Step (F):

Examples of solvents and diluents are the same as those mentioned under Process step (A). In particular, ethers, such as diethyl ether, dipropyl ether, diisopropyl ether, dibutyl ether, tert-butyl methyl ether, or tetrahydrofuran are especially suitable.

The reactions are advantageously carried out in a temperature range of from approximately −30° C. to 50° C., preferably at from −10° C. to 25° C.

The organometallic reagent of formula (β) used in step (F)

$(R_2)_r\text{-M-(Hal)}_s$ (β)

is known or can be prepared by methods known. A suitable example is an alkylcuprate. Especially preferred conditions for the reaction are described in Example 11 (step C).

Process Step (G):

The conditions for the organic group transformations described in Process step (C are also applicable.

Process Step (H):

Once the desired reactions are completed, the protecting groups $L_1$ and $L_2$, if applicable, can be removed under the conditions described in Process step (B).

The compound of the invention may be in the form of one of possible isomers. Therefore, a preparation can result in mixture of isomers, e.g., a diastereomeric mixture; the invention relates both to a pure isomer and to a diastereomeric mixture and is to be interpreted accordingly, even if stereochemical details are not mentioned specifically in every case.

A diastereomeric mixture can be resolved into the pure isomers by known methods, for example by recrystallisation from a solvent, by chromatography, for example, high pressure liquid chromatography (HPLC) on acetylcellulose, with the aid of suitable microorganisms, by cleavage with specific, immobilised enzymes, or via the formation of inclusion compounds, for example using crown ethers, only one isomer being complexed.

Apart from by separation of corresponding mixtures of isomers, pure diastereoisomers can be obtained according to the invention also by generally known methods of stereoselective synthesis, for example by carrying out the process according to the invention using starting materials having correspondingly suitable stereochemistry.

In each case it may be advantageous to isolate or synthesise the biologically more active isomer, where the individual components have different biological activity.

The compound of formulae (I) to (VII) may also be obtained in the form of their hydrates and/or may include other solvents, for example solvents that may have been used for the crystallisation of compounds in solid form.

The invention relates to all those embodiments of the process according to which a compound obtainable as an intermediate at any stage of the process is used as starting material for the remaining steps to prepare a compound of formula (I). For instance a compound of formula (I) can be used as a starting material for the preparation of another compound of formula (I). Such manipulation methods are known to those skilled in the art, such as alkylation, acylation, metathesis, addition of organometallics, reduction and oxidation.

In the processes of the present invention it is preferable to use those starting materials and intermediates, which result in a compound of formula (I).

The invention relates especially to the preparation processes described in Examples 1 to 13.

Also within the scope of the present invention is a compound of formula (I) having a protecting group $L_1$ on the oxygen atom at the 5-carbon position instead of being a hydroxy group or a compound of formula (I) having a protecting group $L_1$ on the oxygen atom at the 5-carbon position instead of being a hydroxy group and having a protecting group $L_2$ on the oxygen atom at the 7-carbon position instead of being a hydroxy group. In the event the protecting group is present, it is preferably hydrolysable under mild conditions. Preference is given to trialkylsilyl radicals, such as trimethylsilyl, triethylsilyl, dimethyl-tert-butylsilyl, diphenyl-tert-butylsilyl, esters, such as methoxyacetates and phenoxyacetates, and carbonates, such as allylcarbonates. Dimethyl-tert-butylsilyl ether is especially preferred.

The compounds of any one of the formulae (I) and (VII) can be intermediates for the synthesis of compounds of formula (I). The use, therefore, of compounds of formula (I) and (VII) for the synthesis of compounds of formula (I) is also a subject of this invention. The preferences for the substituent groups, as appropriate, are the same as defined for the compound of the formula (I) in groups (2) to (45).

In the context of the invention, a reference is made to compounds of formulae (I-1) to (1-120) of Table X and Tables 1 to 720 below; and in each case, if appropriate, to its E/Z isomer or a mixture thereof.

TABLE X

A compound of any one of the formulae (I-1) to (1-120) in which $Q_1$ and $Q_2$ represent the macrolide structures below, in which the arrow represents the connection point of the newly introduced pyran derivative:

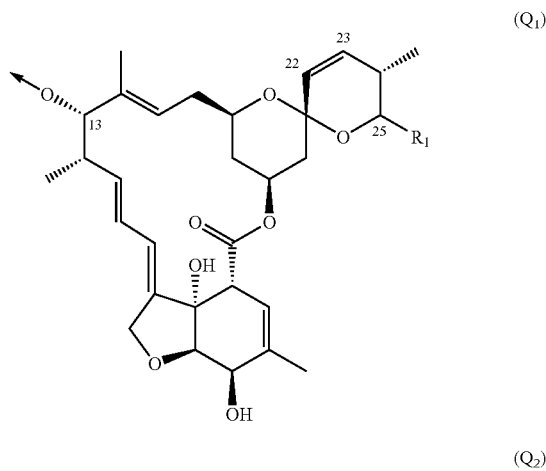

TABLE X-continued
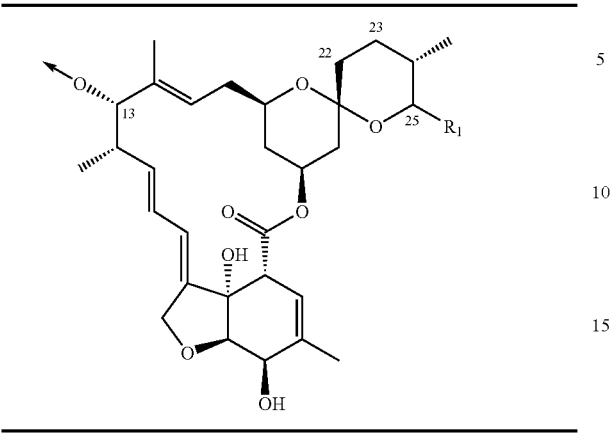
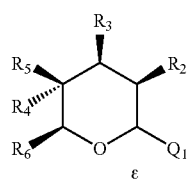
(I-1)
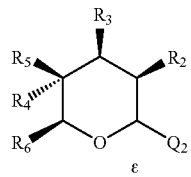
(I-2)
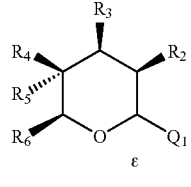
(I-3)
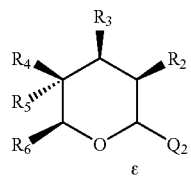
(I-4)
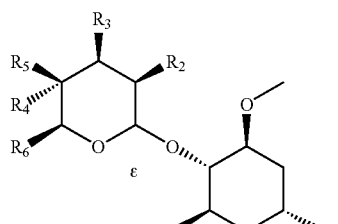
(I-5)
TABLE X-continued
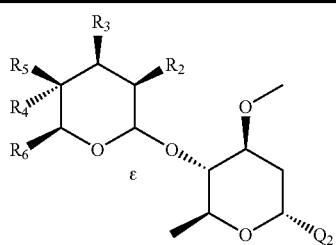
(I-6)
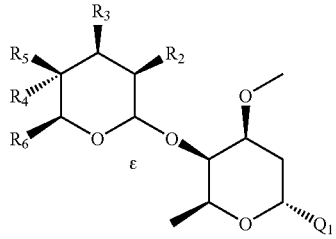
(I-7)
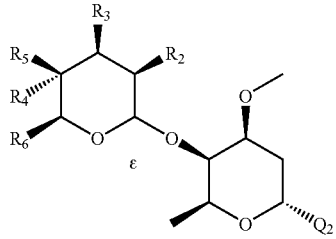
(I-8)
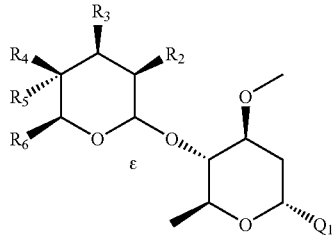
(I-9)
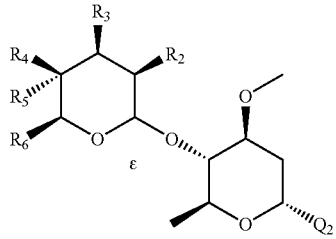
(I-10)
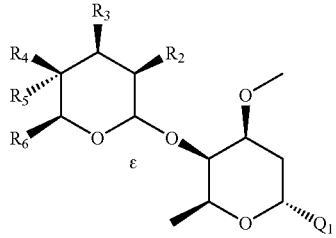
(I-11)

TABLE X-continued
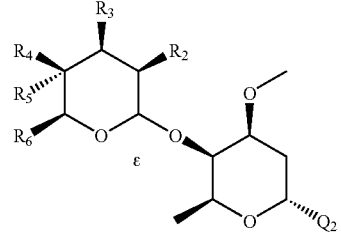
(I-13)
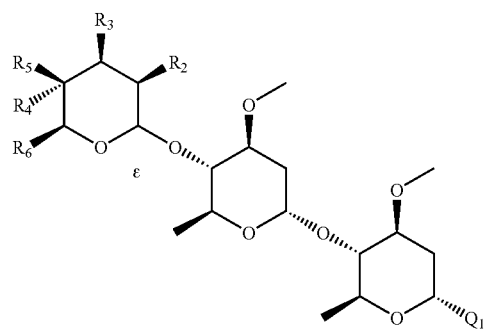
(I-14)
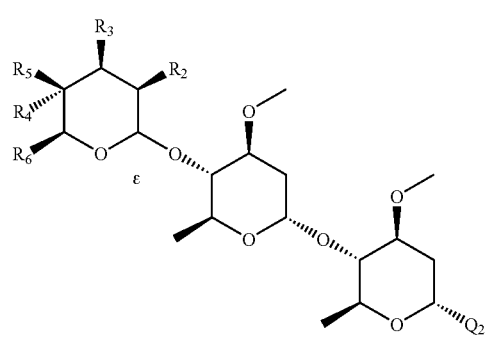
(I-15)
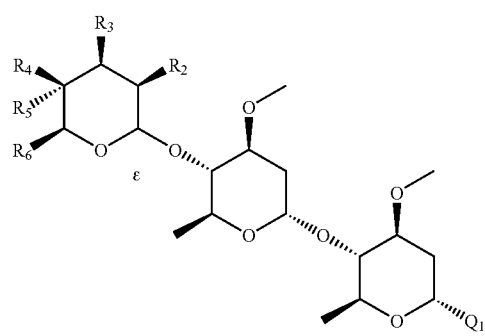
(I-16)
TABLE X-continued
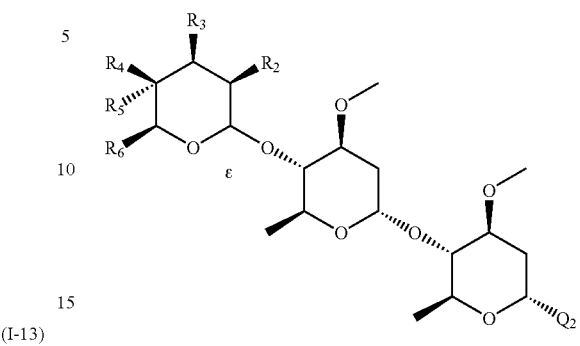
(I-17)
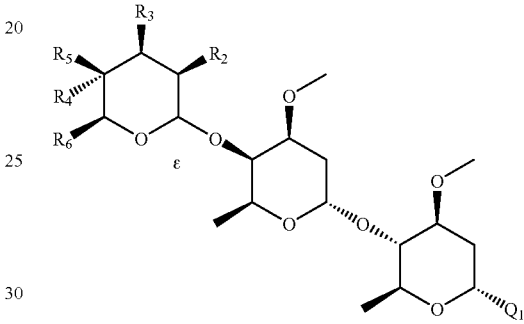
(I-18)
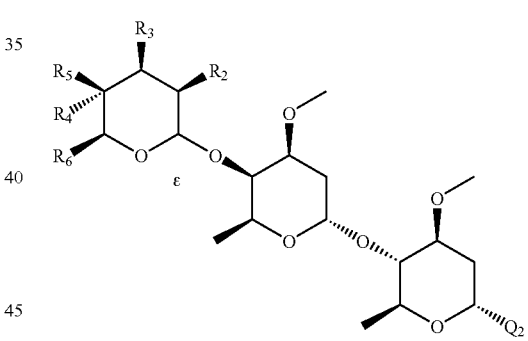
(I-19)
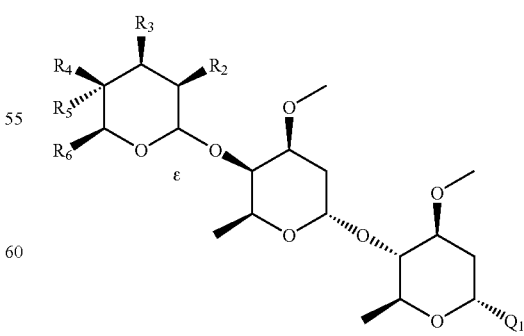
(I-20)

TABLE X-continued
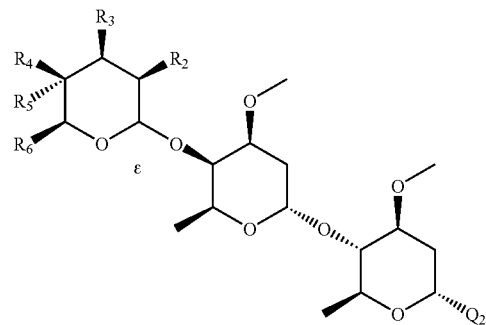
(I-21)
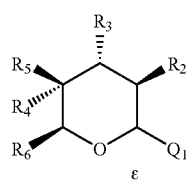
(I-22)
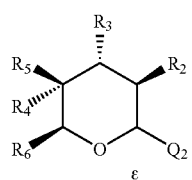
(I-23)
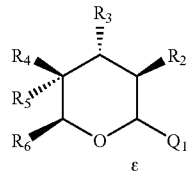
(I-24)
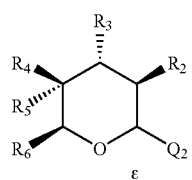
(I-25)
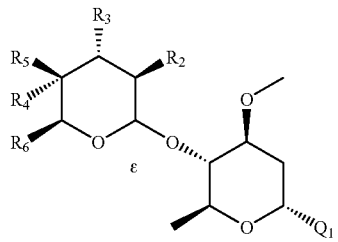
(I-26)
TABLE X-continued
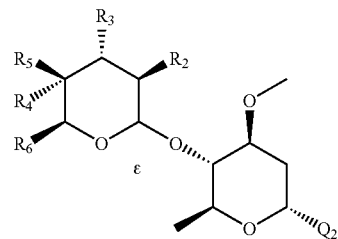
(I-27)
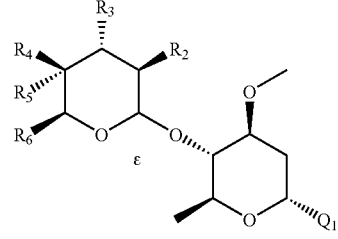
(I-28)
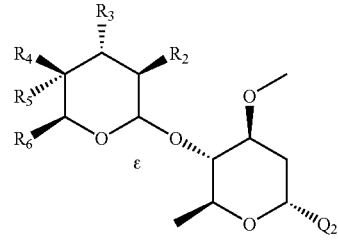
(I-29)
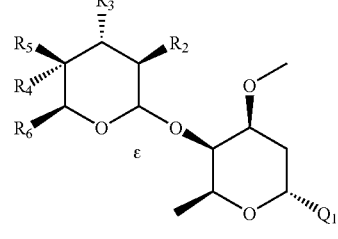
(I-30)
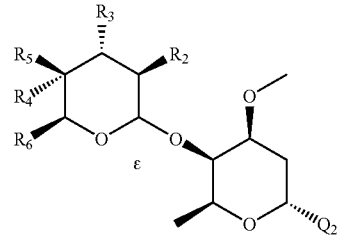
(I-31)
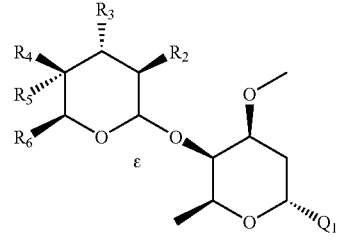
(I-32)

TABLE X-continued
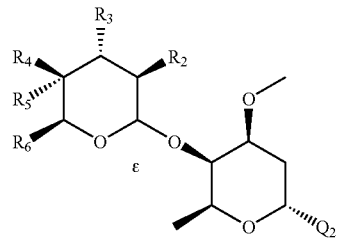
(I-33)
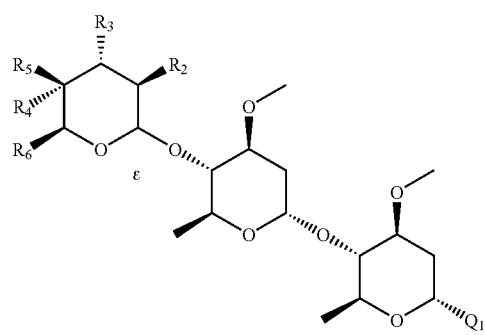
(I-34)
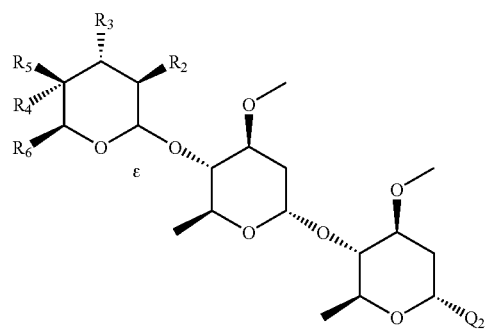
(I-35)
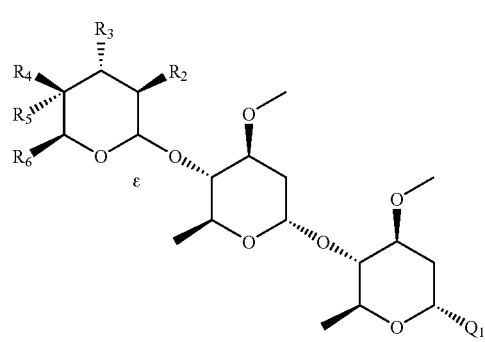
(I-36)
TABLE X-continued
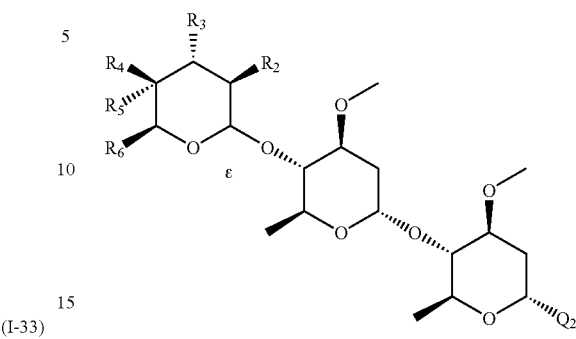
(I-37)
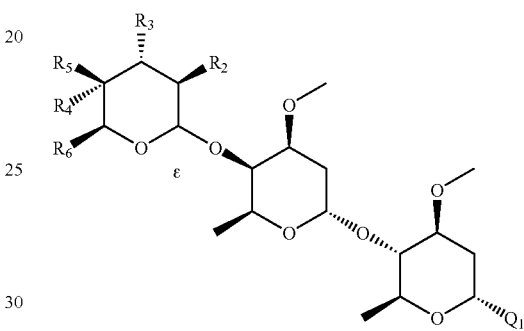
(I-38)
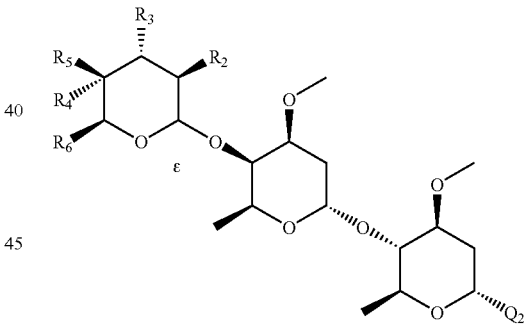
(I-39)
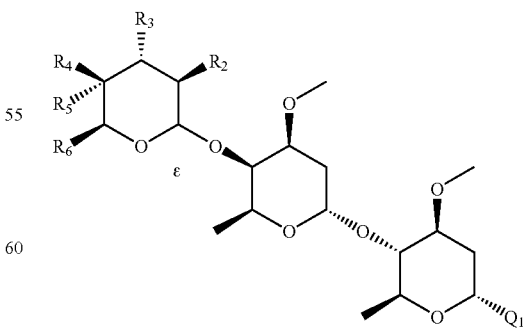
(I-40)

TABLE X-continued
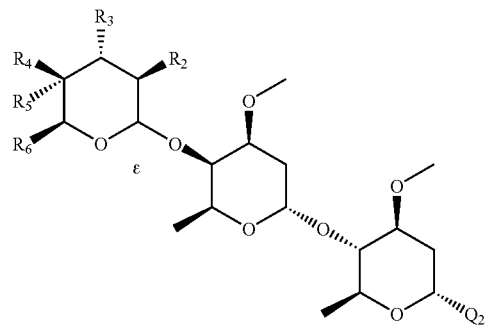
(I-41)
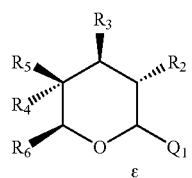
(I-42)
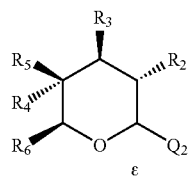
(I-43)
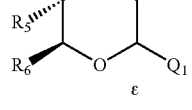
(I-44)
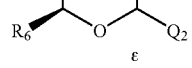
(I-45)
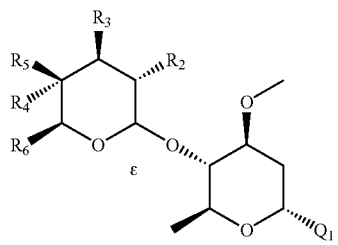
(I-46)
TABLE X-continued
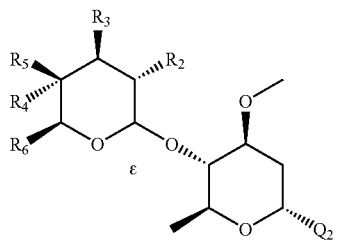
(I-47)
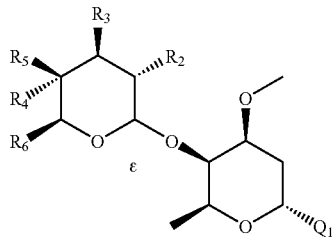
(I-48)
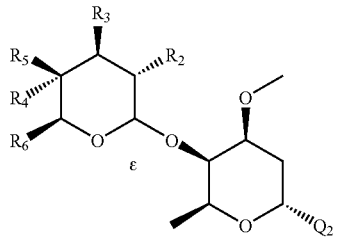
(I-49)
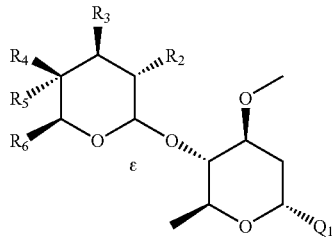
(I-50)
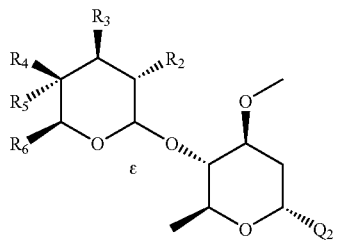
(I-51)
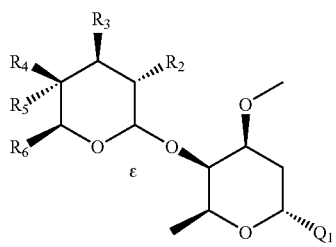
(I-52)

TABLE X-continued
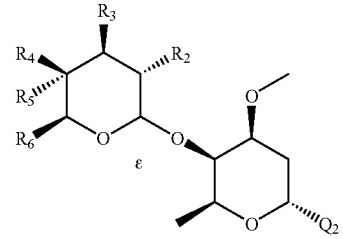
(I-53)
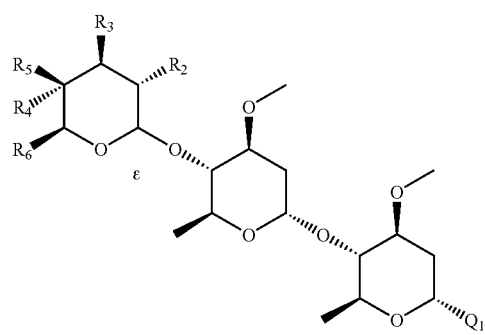
(I-54)
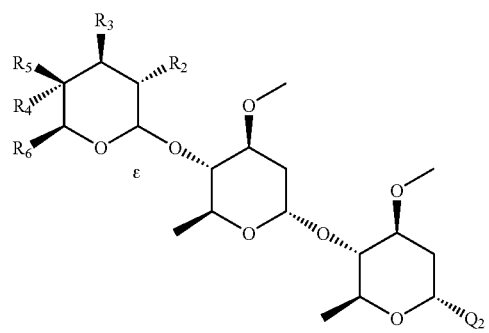
(I-55)
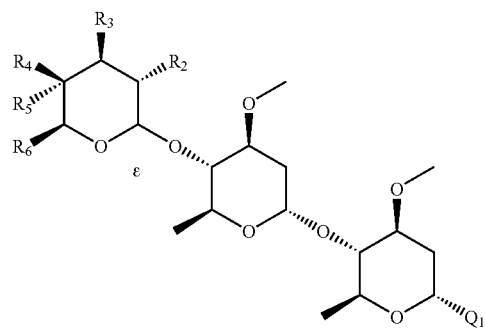
(I-56)
TABLE X-continued
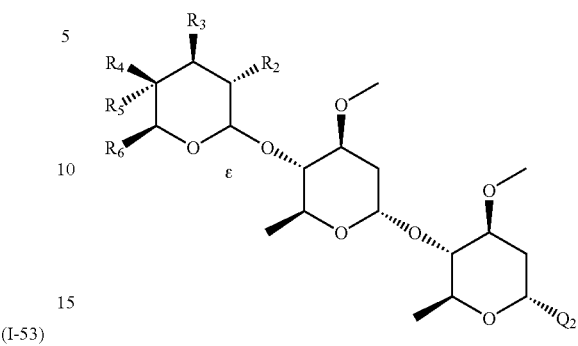
(I-57)
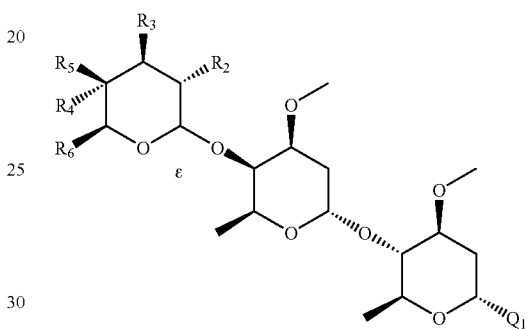
(I-58)
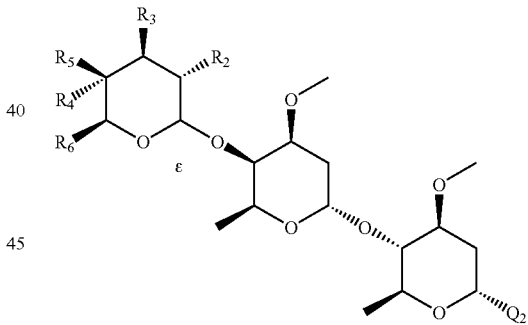
(I-59)
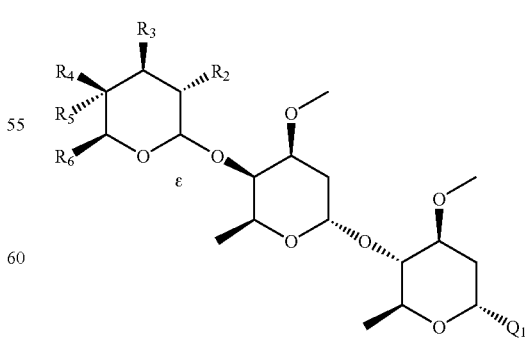
(I-60)

TABLE X-continued
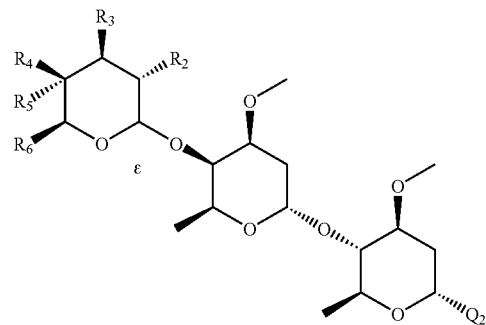
(I-61)
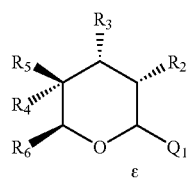
(I-62)
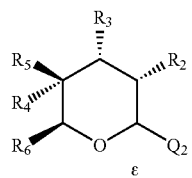
(I-63)
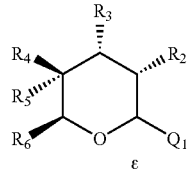
(I-64)
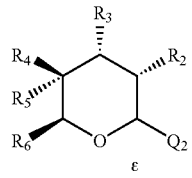
(I-65)
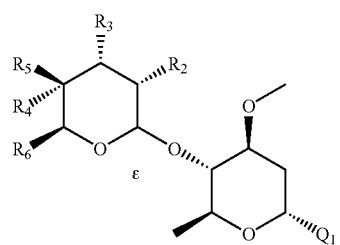
(I-66)
TABLE X-continued
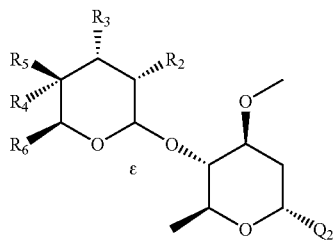
(I-67)
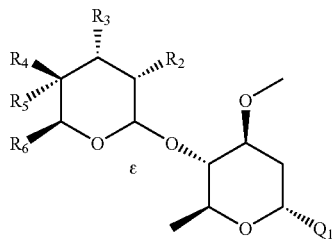
(I-68)
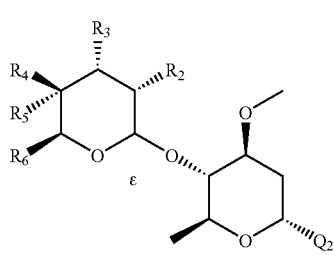
(I-69)
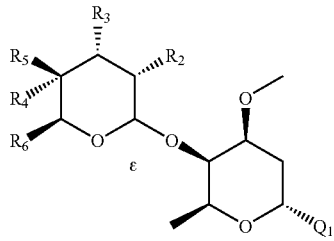
(I-70)
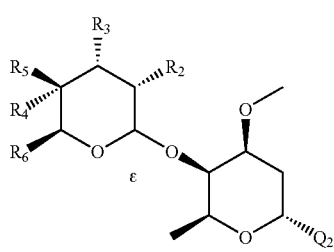
(I-71)
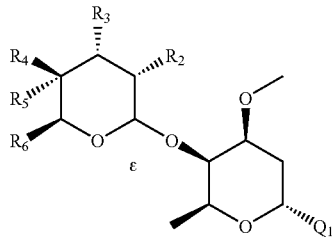
(I-72)

TABLE X-continued
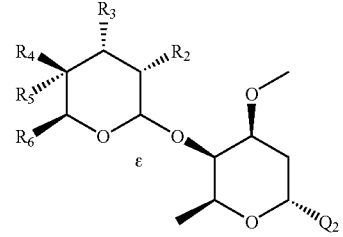
(I-73)
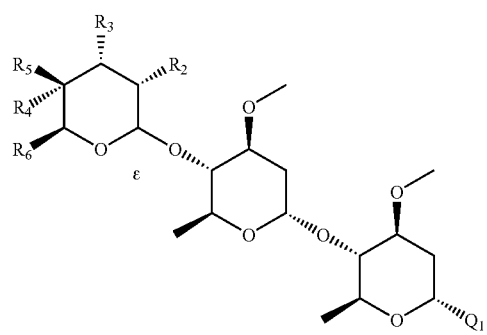
(I-74)
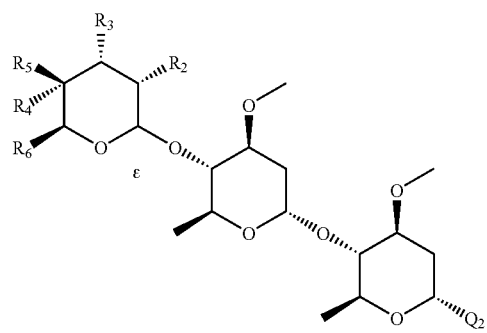
(I-75)
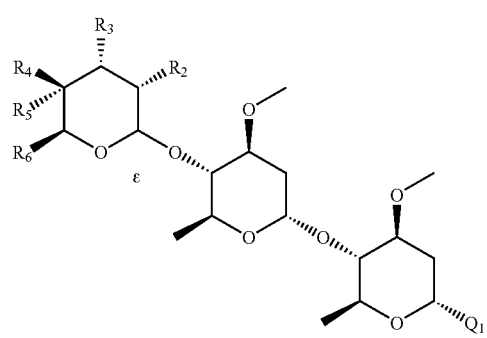
(I-76)
TABLE X-continued
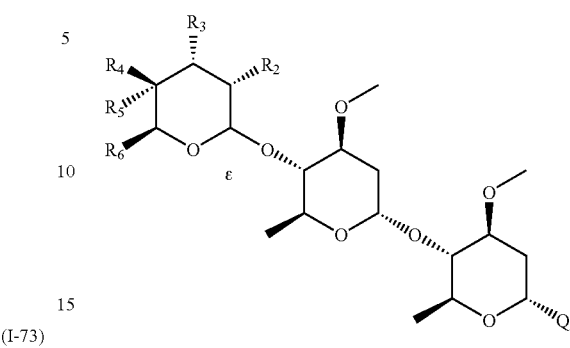
(I-77)
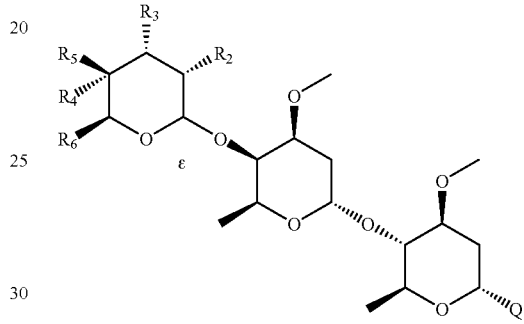
(I-78)
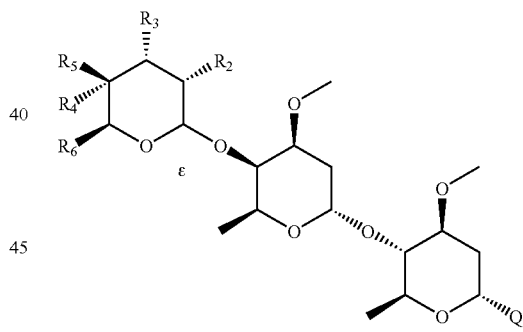
(I-79)
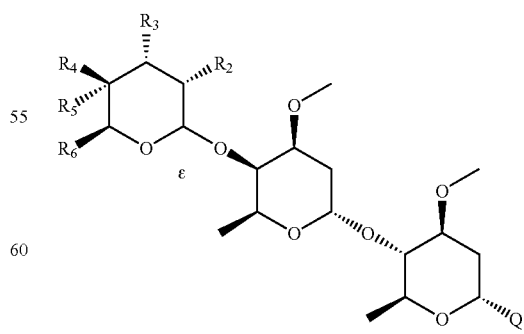
(I-80)

TABLE X-continued
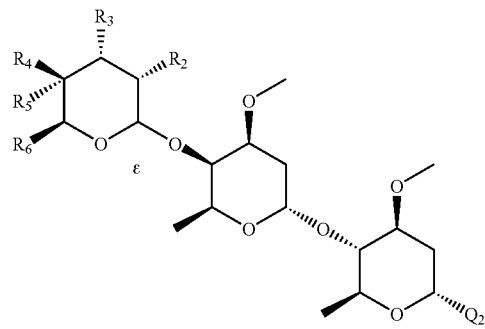
(I-81)
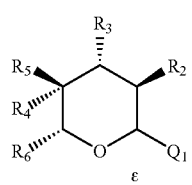
(I-82)
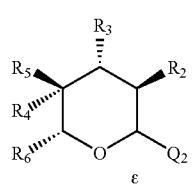
(I-83)
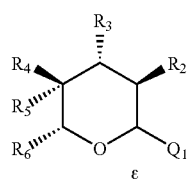
(I-84)
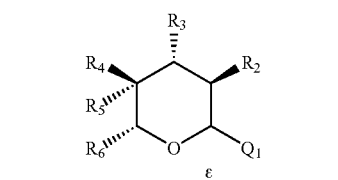
(I-85)
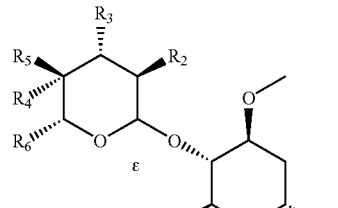
(I-86)
TABLE X-continued
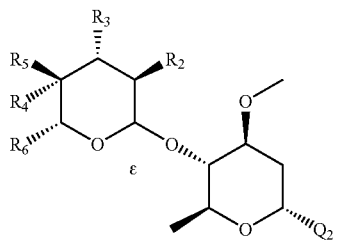
(I-87)
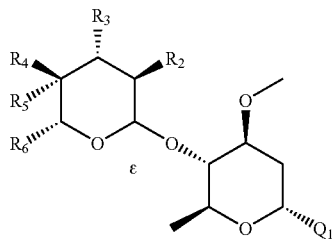
(I-88)
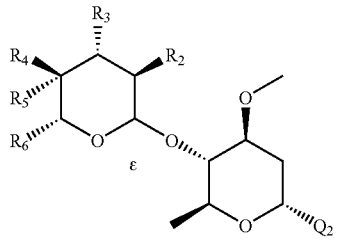
(I-89)
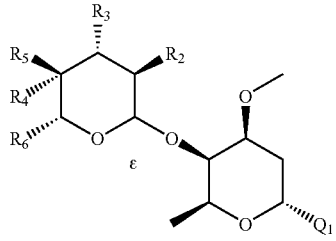
(I-90)
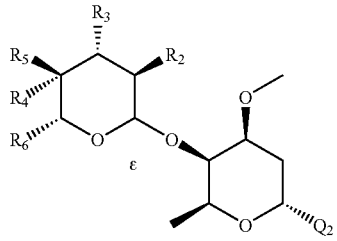
(I-91)
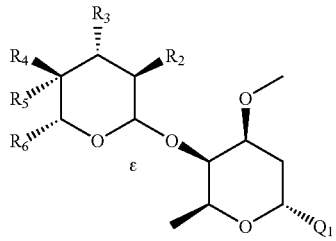

TABLE X-continued
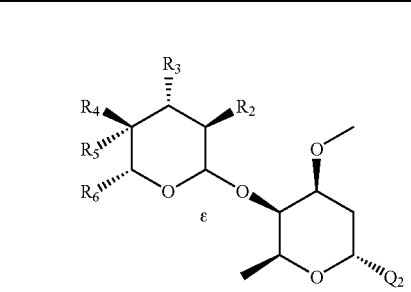
(I-92)
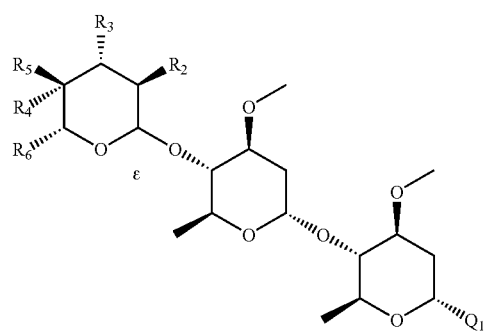
(I-93)
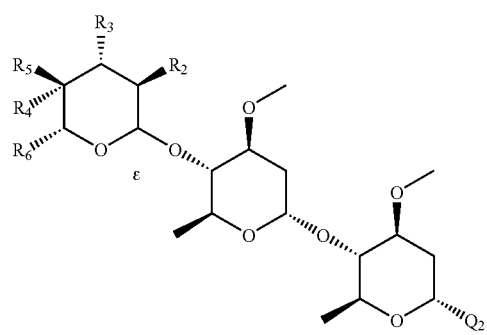
(I-94)
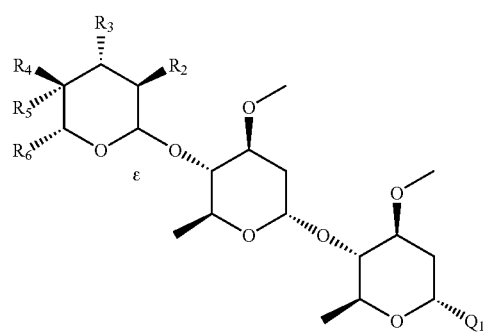
(I-95)
(I-96)
TABLE X-continued
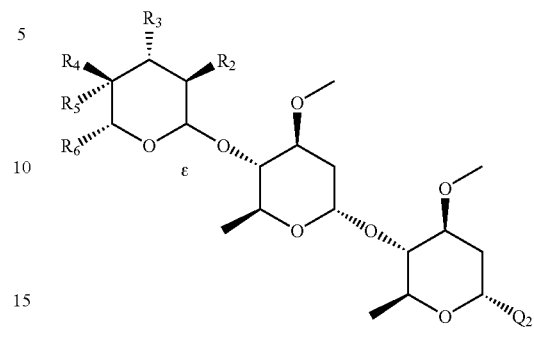
(I-96)
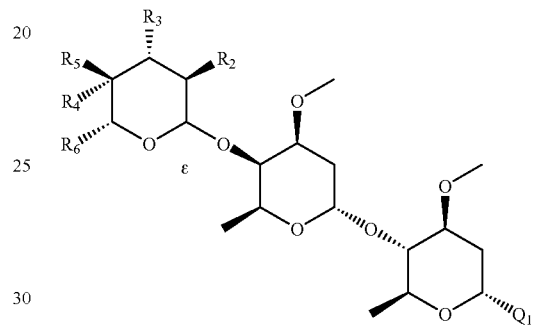
(I-97)
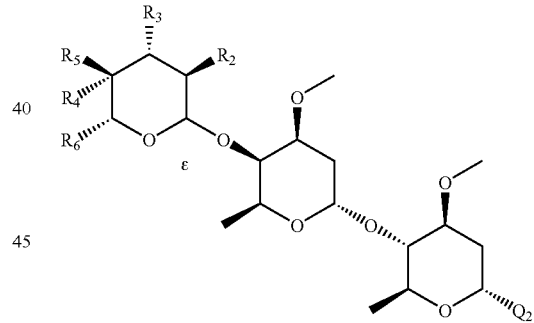
(I-98)
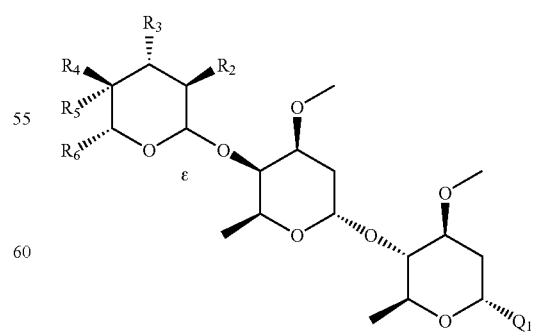
(I-99)
(I-100)

TABLE X-continued
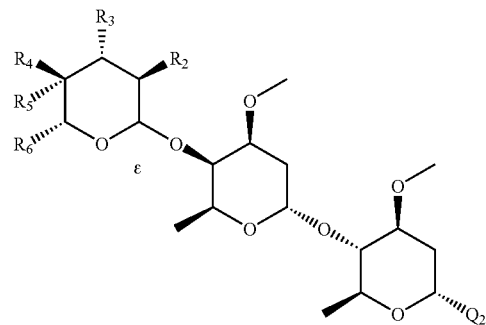
(I-101)
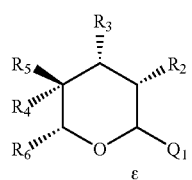
(I-102)
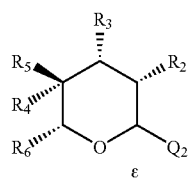
(I-103)
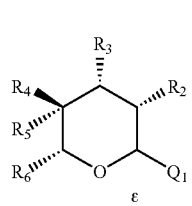
(I-104)
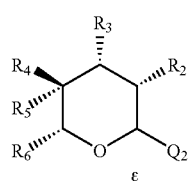
(I-105)
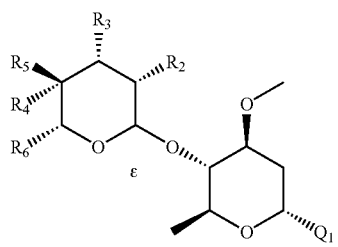
(I-106)
TABLE X-continued
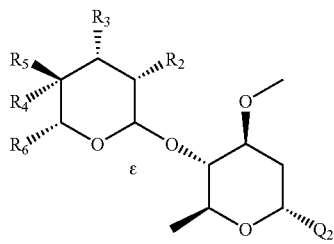
(I-107)
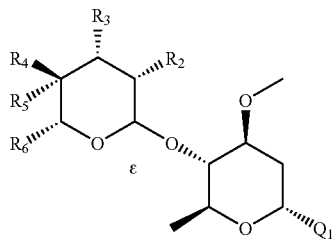
(I-108)
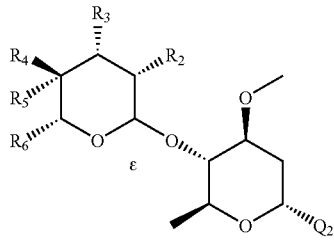
(I-109)
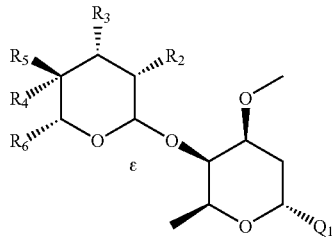
(I-110)
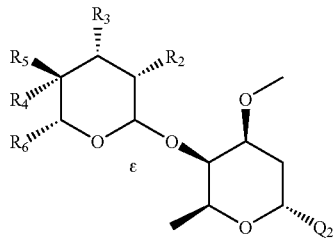
(I-111)
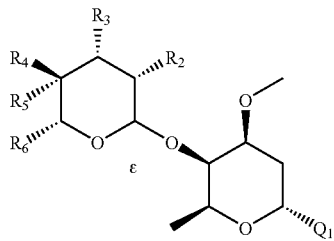
(I-112)

TABLE X-continued
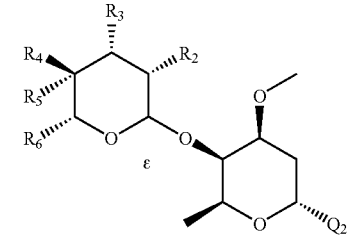
(I-113)
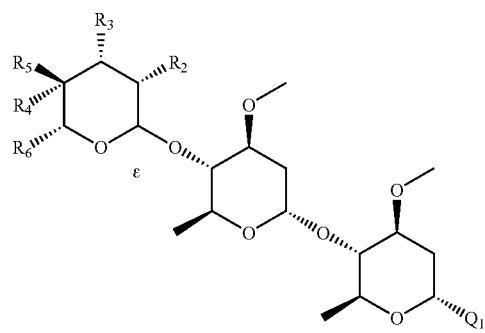
(I-114)
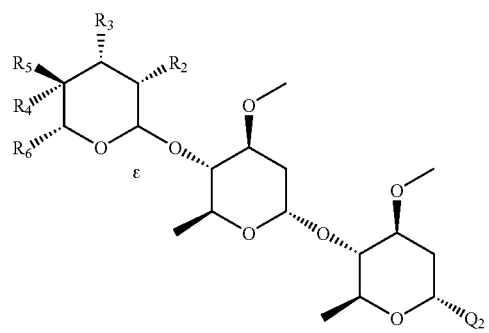
(I-115)
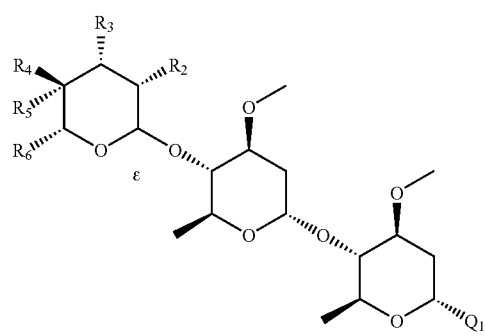
(I-116)
TABLE X-continued
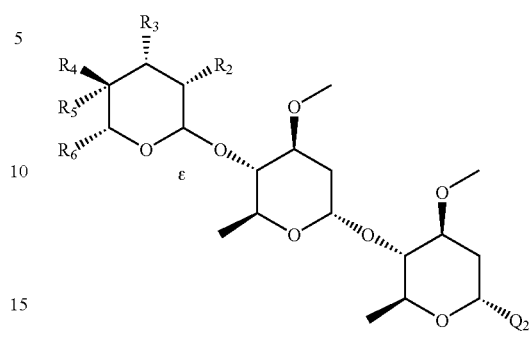
(I-117)
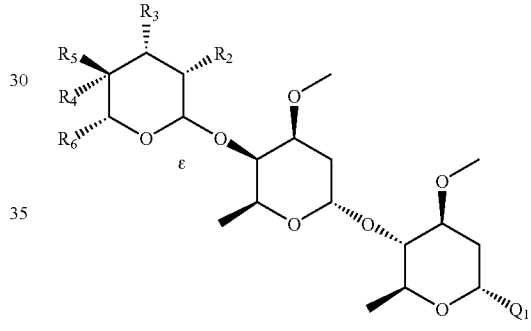
(I-118)
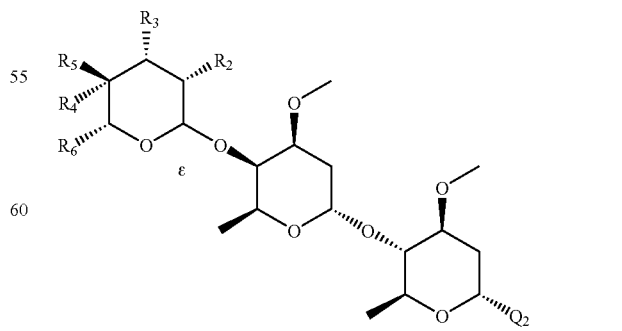
(I-119)

TABLE X-continued

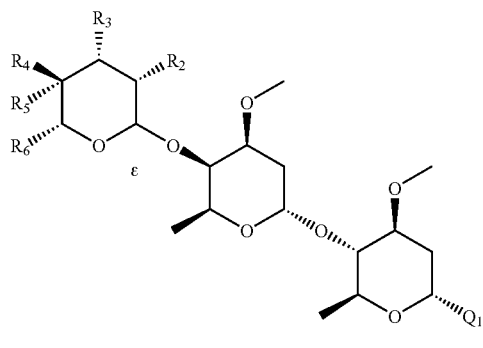

(I-120)

TABLE X-continued

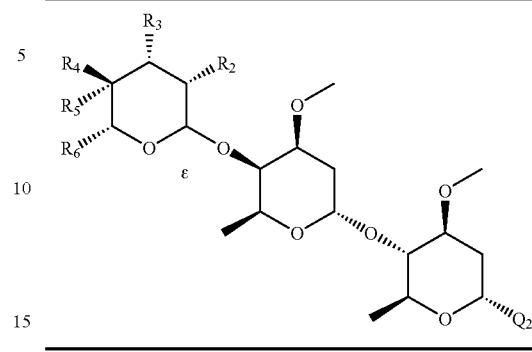

where, for each formula

| Line | $R_2$ | $R_3$ | $R_4$ | $R_5$ | $R_6$ |
|---|---|---|---|---|---|
| 1 | OCH$_3$ | OCH$_3$ | H | H | CH$_3$ |
| 2 | OCH$_2$CH$_3$ | OCH$_2$CH$_3$ | H | H | CH$_3$ |
| 3 | OCH$_3$ | OCH$_3$ | CH$_3$ | H | CH$_3$ |
| 4 | OCH$_2$CH$_3$ | OCH$_2$CH$_3$ | CH$_3$ | H | CH$_3$ |
| 5 | OCH$_3$ | OCH$_3$ | CH$_2$CH$_3$ | H | CH$_3$ |
| 6 | OCH$_2$CH$_3$ | OCH$_2$CH$_3$ | CH$_2$CH$_3$ | H | CH$_3$ |
| 7 | OCH$_3$ | OCH$_3$ | OH | H | CH$_3$ |
| 8 | OCH$_2$CH$_3$ | OCH$_2$CH$_3$ | OH | H | CH$_3$ |
| 9 | OCH$_3$ | OCH$_3$ | OH | CH$_3$ | CH$_3$ |
| 10 | OCH$_2$CH$_3$ | OCH$_2$CH$_3$ | OH | CH$_3$ | CH$_3$ |
| 11 | OCH$_3$ | OCH$_3$ | OCH$_3$ | H | CH$_3$ |
| 12 | OCH$_2$CH$_3$ | OCH$_2$CH$_3$ | OCH$_2$CH$_3$ | H | CH$_3$ |
| 13 | OCH$_3$ | OCH$_3$ | OCH$_2$OCH$_3$ | H | CH$_3$ |
| 14 | OCH$_3$ | OCH$_3$ | OCH$_2$OCH$_2$CH$_3$ | H | CH$_3$ |
| 15 | OCH$_3$ | OCH$_3$ | OCH$_2$C(O)CH$_3$ | H | CH$_3$ |
| 16 | OCH$_3$ | OCH$_3$ | OCH$_2$C(O)CH$_2$CH$_3$ | H | CH$_3$ |
| 17 | OCH$_3$ | OCH$_3$ | OC(O)CH$_3$ | H | CH$_3$ |
| 18 | OCH$_3$ | OCH$_3$ | OC(O)CH$_2$CH$_3$ | H | CH$_3$ |
| 19 | OCH$_3$ | OCH$_3$ | OC(S)(N-imidazole) | H | CH$_3$ |
| 20 | OCH$_3$ | OCH$_3$ | OC(O)OCH$_3$ | H | CH$_3$ |
| 21 | OCH$_3$ | OCH$_3$ | OC(O)OCH$_2$CH=CH$_2$ | H | CH$_3$ |
| 22 | OCH$_3$ | OCH$_3$ | OC(O)NHCH$_3$ | H | CH$_3$ |
| 23 | OCH$_3$ | OCH$_3$ | OC(O)NHCH$_2$CH$_3$ | H | CH$_3$ |
| 24 | OCH$_3$ | OCH$_3$ | OC(O)NHCH$_2$CH$_2$OCH$_3$ | H | CH$_3$ |
| 25 | OCH$_3$ | OCH$_3$ | ONH$_2$ | H | CH$_3$ |
| 26 | OCH$_3$ | OCH$_3$ | O—N=CH$_2$ | H | CH$_3$ |
| 27 | OCH$_3$ | OCH$_3$ | O—N=C(CH$_3$)CH$_2$OCH$_3$ | H | CH$_3$ |
| 28 | OCH$_3$ | OCH$_3$ | O—N=C(CH$_3$)CH$_2$SCH$_3$ | H | CH$_3$ |
| 29 | OCH$_3$ | OCH$_3$ | O—N=C(CH$_3$)CH$_2$N(CH$_3$)$_2$ | H | CH$_3$ |
| 30 | OCH$_3$ | OCH$_3$ | O—NHCH$_3$ | H | CH$_3$ |
| 31 | OCH$_3$ | OCH$_3$ | O—N(CH$_3$)C(O)H | H | CH$_3$ |
| 32 | OCH$_3$ | OCH$_3$ | O—N(CH$_3$)C(O)CH$_3$ | H | CH$_3$ |
| 33 | OCH$_3$ | OCH$_3$ | O—NHSO$_2$NH$_2$ | H | CH$_3$ |
| 34 | OCH$_3$ | OCH$_3$ | O—NHSO$_2$CH$_3$ | H | CH$_3$ |
| 35 | OCH$_3$ | OCH$_3$ | NH$_2$ | H | CH$_3$ |
| 36 | OCH$_3$ | OCH$_3$ | NH$_2$ | CH$_3$ | CH$_3$ |
| 37 | OCH$_3$ | OCH$_3$ | NH$_2$ | CN | CH$_3$ |
| 38 | OCH$_3$ | OCH$_3$ | NHCH$_3$ | H | CH$_3$ |
| 39 | OCH$_3$ | OCH$_3$ | NHCH$_3$ | CH$_3$ | CH$_3$ |
| 40 | OCH$_3$ | OCH$_3$ | NHCH$_3$ | CN | CH$_3$ |
| 41 | OCH$_3$ | OCH$_3$ | NHCH$_2$CH$_3$ | H | CH$_3$ |
| 42 | OCH$_3$ | OCH$_3$ | NHCH$_2$CH$_3$ | CH$_3$ | CH$_3$ |
| 43 | OCH$_3$ | OCH$_3$ | NHCH$_2$CH$_3$ | CN | CH$_3$ |
| 44 | OCH$_3$ | OCH$_3$ | N(CH$_3$)$_2$ | H | CH$_3$ |
| 45 | OCH$_3$ | OCH$_3$ | N(CH$_3$)$_2$ | CH$_3$ | CH$_3$ |
| 46 | OCH$_3$ | OCH$_3$ | N(CH$_3$)$_2$ | CN | CH$_3$ |
| 47 | OCH$_3$ | OCH$_3$ | N(CH$_3$)CH$_2$CH$_3$ | H | CH$_3$ |
| 48 | OCH$_3$ | OCH$_3$ | N(CH$_3$)CH$_2$CH$_3$ | CH$_3$ | CH$_3$ |
| 49 | OCH$_3$ | OCH$_3$ | N(CH$_3$)CH$_2$CH$_3$ | CN | CH$_3$ |
| 50 | OCH$_3$ | OCH$_3$ | NHOH | H | CH$_3$ |
| 51 | OCH$_3$ | OCH$_3$ | NHOH | CH$_3$ | CH$_3$ |
| 52 | OCH$_3$ | OCH$_3$ | NHOH | CN | CH$_3$ |
| 53 | OCH$_3$ | OCH$_3$ | NHC(O)H | H | CH$_3$ |

-continued

| Line | R₂ | R₃ | R₄ | R₅ | R₆ |
|---|---|---|---|---|---|
| 54 | OCH₃ | OCH₃ | NHC(O)H | CH₃ | CH₃ |
| 55 | OCH₃ | OCH₃ | NHC(O)H | CN | CH₃ |
| 56 | OCH₃ | OCH₃ | NHC(O)CH₃ | H | CH₃ |
| 57 | OCH₃ | OCH₃ | NHC(O)CH₃ | CH₃ | CH₃ |
| 58 | OCH₃ | OCH₃ | NHC(O)CH₃ | CN | CH₃ |
| 59 | OCH₃ | OCH₃ | NHC(O)CH₂CH₃ | H | CH₃ |
| 60 | OCH₃ | OCH₃ | NHC(O)CH₂CH₃ | CH₃ | CH₃ |
| 61 | OCH₃ | OCH₃ | NHC(O)CH₂CH₃ | CN | CH₃ |
| 62 | OCH₃ | OCH₃ | NHC(O)CH₂OCH₃ | H | CH₃ |
| 63 | OCH₃ | OCH₃ | NHC(O)CH₂OCH₃ | CH₃ | CH₃ |
| 64 | OCH₃ | OCH₃ | NHC(O)CH₂OCH₃ | CN | CH₃ |
| 65 | OCH₃ | OCH₃ | N(CH₃)OH | H | CH₃ |
| 66 | OCH₃ | OCH₃ | N(CH₃)OH | CH₃ | CH₃ |
| 67 | OCH₃ | OCH₃ | N(CH₃)C(O)H | H | CH₃ |
| 68 | OCH₃ | OCH₃ | N(CH₃)C(O)H | CH₃ | CH₃ |
| 69 | OCH₃ | OCH₃ | N(CH₃)C(O)CH₃ | H | CH₃ |
| 70 | OCH₃ | OCH₃ | N(CH₃)C(O)CH₃ | CH₃ | CH₃ |
| 71 | OCH₃ | OCH₃ | N(CH₃)C(O)CH₂CH₃ | H | CH₃ |
| 72 | OCH₃ | OCH₃ | N(CH₃)C(O)CH₂CH₃ | CH₃ | CH₃ |
| 73 | OCH₃ | OCH₃ | N(CH₃)C(O)CH₂OCH₃ | H | CH₃ |
| 74 | OCH₃ | OCH₃ | N(CH₃)C(O)CH₂OCH₃ | CH₃ | CH₃ |
| 75 | OCH₃ | OCH₃ | N(CH₃)C(O)OCH₃ | H | CH₃ |
| 76 | OCH₃ | OCH₃ | N(CH₃)C(O)OCH₃ | CH₃ | CH₃ |
| 77 | OCH₃ | OCH₃ | N(CH₃)C(O)OCH₂CH₃ | H | CH₃ |
| 78 | OCH₃ | OCH₃ | N(CH₃)C(O)OCH₂CH₃ | CH₃ | CH₃ |
| 79 | OCH₃ | OCH₃ | N(CH₃)C(O)OCH₂CH₂=CH₂ | H | CH₃ |
| 80 | OCH₃ | OCH₃ | N(CH₃)C(O)OCH₂CH₂=CH₂ | CH₃ | CH₃ |
| 81 | OC(O)OCH₂—CH₂=CH₂ | OC(O)OCH₂—CH₂=CH₂ | OCH₂OCH₃ | H | CH₃ |
| 82 | OC(O)OCH₂—CH₂=CH₂ | OC(O)OCH₂—CH₂=CH₂ | OCH₂OCH₂CH₃ | H | CH₃ |
| 83 | OH | OH | OCH₂OCH₃ | H | CH₃ |
| 84 | OH | OH | OCH₂OCH₂CH₃ | H | CH₃ |
| 85 | CH₃ | OCH₃ | H | H | CH₃ |
| 86 | CH₃ | OCH₃ | CH₃ | H | CH₃ |
| 87 | CH₃ | OCH₃ | CH₂CH₃ | H | CH₃ |
| 88 | CH₃ | OCH₃ | OH | H | CH₃ |
| 89 | CH₃ | OCH₃ | OH | CH₃ | CH₃ |
| 90 | CH₃ | OCH₃ | OCH₃ | H | CH₃ |
| 91 | CH₃ | OCH₃ | OCH₂OCH₃ | H | CH₃ |
| 92 | CH₃ | OCH₃ | OCH₂OCH₂CH₃ | H | CH₃ |
| 93 | CH₃ | OCH₃ | OCH₂C(O)CH₃ | H | CH₃ |
| 94 | CH₃ | OCH₃ | OCH₂C(O)CH₂CH₃ | H | CH₃ |
| 95 | CH₃ | OCH₃ | OC(O)CH₃ | H | CH₃ |
| 96 | CH₃ | OCH₃ | OC(O)CH₂CH₃ | H | CH₃ |
| 97 | CH₃ | OCH₃ | OC(S)(N-imidazole) | H | CH₃ |
| 98 | CH₃ | OCH₃ | OC(O)OCH₃ | H | CH₃ |
| 99 | CH₃ | OCH₃ | OC(O)OCH₂CH₂=CH₂ | H | CH₃ |
| 100 | CH₃ | OCH₃ | OC(O)NHCH₃ | H | CH₃ |
| 101 | CH₃ | OCH₃ | OC(O)NHCH₂CH₃ | H | CH₃ |
| 102 | CH₃ | OCH₃ | OC(O)NHCH₂CH₂OCH₃ | H | CH₃ |
| 103 | CH₃ | OCH₃ | ONH₂ | H | CH₃ |
| 104 | CH₃ | OCH₃ | O—N=CH₂ | H | CH₃ |
| 105 | CH₃ | OCH₃ | O—N=C(CH₃)CH₂OCH₃ | H | CH₃ |
| 106 | CH₃ | OCH₃ | O—N=C(CH₃)CH₂SCH₃ | H | CH₃ |
| 107 | CH₃ | OCH₃ | O—N=C(CH₃)CH₂N(CH₃)₂ | H | CH₃ |
| 108 | CH₃ | OCH₃ | O—NHCH₃ | H | CH₃ |
| 109 | CH₃ | OCH₃ | O—N(CH₃)C(O)H | H | CH₃ |
| 110 | CH₃ | OCH₃ | O—N(CH₃)C(O)CH₃ | H | CH₃ |
| 111 | CH₃ | OCH₃ | O—NHSO₂NH₂ | H | CH₃ |
| 112 | CH₃ | OCH₃ | O—NHSO₂CH₃ | H | CH₃ |
| 113 | CH₃ | OCH₃ | NH₂ | H | CH₃ |
| 114 | CH₃ | OCH₃ | NH₂ | CH₃ | CH₃ |
| 115 | CH₃ | OCH₃ | NH₂ | CN | CH₃ |
| 116 | CH₃ | OCH₃ | NHCH₃ | H | CH₃ |
| 117 | CH₃ | OCH₃ | NHCH₃ | CH₃ | CH₃ |
| 118 | CH₃ | OCH₃ | NHCH₃ | CN | CH₃ |
| 119 | CH₃ | OCH₃ | NHCH₂CH₃ | H | CH₃ |
| 120 | CH₃ | OCH₃ | NHCH₂CH₃ | CH₃ | CH₃ |
| 121 | CH₃ | OCH₃ | NHCH₂CH₃ | CN | CH₃ |
| 122 | CH₃ | OCH₃ | N(CH₃)₂ | H | CH₃ |
| 123 | CH₃ | OCH₃ | N(CH₃)₂ | CH₃ | CH₃ |
| 124 | CH₃ | OCH₃ | N(CH₃)₂ | CN | CH₃ |
| 125 | CH₃ | OCH₃ | N(CH₃)CH₂CH₃ | H | CH₃ |
| 126 | CH₃ | OCH₃ | N(CH₃)CH₂CH₃ | CH₃ | CH₃ |
| 127 | CH₃ | OCH₃ | N(CH₃)CH₂CH₃ | CN | CH₃ |
| 128 | CH₃ | OCH₃ | NHOH | H | CH₃ |
| 129 | CH₃ | OCH₃ | NHOH | CH₃ | CH₃ |
| 130 | CH₃ | OCH₃ | NHOH | CN | CH₃ |

-continued

| Line | R₂ | R₃ | R₄ | R₅ | R₆ |
|---|---|---|---|---|---|
| 131 | CH₃ | OCH₃ | NHC(O)H | H | CH₃ |
| 132 | CH₃ | OCH₃ | NHC(O)H | CH₃ | CH₃ |
| 133 | CH₃ | OCH₃ | NHC(O)H | CN | CH₃ |
| 134 | CH₃ | OCH₃ | NHC(O)CH₃ | H | CH₃ |
| 135 | CH₃ | OCH₃ | NHC(O)CH₃ | CH₃ | CH₃ |
| 136 | CH₃ | OCH₃ | NHC(O)CH₃ | CN | CH₃ |
| 137 | CH₃ | OCH₃ | NHC(O)CH₂CH₃ | H | CH₃ |
| 138 | CH₃ | OCH₃ | NHC(O)CH₂CH₃ | CH₃ | CH₃ |
| 139 | CH₃ | OCH₃ | NHC(O)CH₂CH₃ | CN | CH₃ |
| 140 | CH₃ | OCH₃ | NHC(O)CH₂OCH₃ | H | CH₃ |
| 141 | CH₃ | OCH₃ | NHC(O)CH₂OCH₃ | CH₃ | CH₃ |
| 142 | CH₃ | OCH₃ | NHC(O)CH₂OCH₃ | CN | CH₃ |
| 143 | CH₃ | OCH₃ | N(CH₃)OH | H | CH₃ |
| 144 | CH₃ | OCH₃ | N(CH₃)OH | CH₃ | CH₃ |
| 145 | CH₃ | OCH₃ | N(CH₃)C(O)H | H | CH₃ |
| 146 | CH₃ | OCH₃ | N(CH₃)C(O)H | CH₃ | CH₃ |
| 147 | CH₃ | OCH₃ | N(CH₃)C(O)CH₃ | H | CH₃ |
| 148 | CH₃ | OCH₃ | N(CH₃)C(O)CH₃ | CH₃ | CH₃ |
| 149 | CH₃ | OCH₃ | N(CH₃)C(O)CH₂CH₃ | H | CH₃ |
| 150 | CH₃ | OCH₃ | N(CH₃)C(O)CH₂CH₃ | CH₃ | CH₃ |
| 151 | CH₃ | OCH₃ | N(CH₃)C(O)CH₂OCH₃ | H | CH₃ |
| 152 | CH₃ | OCH₃ | N(CH₃)C(O)CH₂OCH₃ | CH₃ | CH₃ |
| 153 | CH₃ | OCH₃ | N(CH₃)C(O)OCH₃ | H | CH₃ |
| 154 | CH₃ | OCH₃ | N(CH₃)C(O)OCH₃ | CH₃ | CH₃ |
| 155 | CH₃ | OCH₃ | N(CH₃)C(O)OCH₂CH₃ | H | CH₃ |
| 156 | CH₃ | OCH₃ | N(CH₃)C(O)OCH₂CH₃ | CH₃ | CH₃ |
| 157 | CH₃ | OCH₃ | N(CH₃)C(O)OCH₂CH₂=CH₂ | H | CH₃ |
| 158 | CH₃ | OCH₃ | N(CH₃)C(O)OCH₂CH₂=CH₂ | CH₃ | CH₃ |
| 159 | CH₂CH₃ | OCH₃ | H | H | CH₃ |
| 160 | CH₂CH₃ | OCH₃ | CH₃ | H | CH₃ |
| 161 | CH₂CH₃ | OCH₃ | CH₂CH₃ | H | CH₃ |
| 162 | CH₂CH₃ | OCH₃ | OH | H | CH₃ |
| 163 | CH₂CH₃ | OCH₃ | OH | CH₃ | CH₃ |
| 164 | CH₂CH₃ | OCH₃ | OCH₃ | H | CH₃ |
| 165 | CH₂CH₃ | OCH₃ | OCH₂OCH₃ | H | CH₃ |
| 166 | CH₂CH₃ | OCH₃ | OCH₂OCH₂CH₃ | H | CH₃ |
| 167 | CH₂CH₃ | OCH₃ | OCH₂C(O)CH₃ | H | CH₃ |
| 168 | CH₂CH₃ | OCH₃ | OCH₂C(O)CH₂CH₃ | H | CH₃ |
| 169 | CH₂CH₃ | OCH₃ | OC(O)CH₃ | H | CH₃ |
| 170 | CH₂CH₃ | OCH₃ | OC(O)CH₂CH₃ | H | CH₃ |
| 171 | CH₂CH₃ | OCH₃ | OC(S)(N-imidazole) | H | CH₃ |
| 172 | CH₂CH₃ | OCH₃ | OC(O)OCH₃ | H | CH₃ |
| 173 | CH₂CH₃ | OCH₃ | OC(O)OCH₂CH₂=CH₂ | H | CH₃ |
| 174 | CH₂CH₃ | OCH₃ | OC(O)NHCH₃ | H | CH₃ |
| 175 | CH₂CH₃ | OCH₃ | OC(O)NHCH₂CH₃ | H | CH₃ |
| 176 | CH₂CH₃ | OCH₃ | OC(O)NHCH₂CH₂OCH₃ | H | CH₃ |
| 177 | CH₂CH₃ | OCH₃ | ONH₂ | H | CH₃ |
| 178 | CH₂CH₃ | OCH₃ | O—N=CH₂ | H | CH₃ |
| 179 | CH₂CH₃ | OCH₃ | O—N=C(CH₃)CH₂OCH₃ | H | CH₃ |
| 180 | CH₂CH₃ | OCH₃ | O—N=C(CH₃)CH₂SCH₃ | H | CH₃ |
| 181 | CH₂CH₃ | OCH₃ | O—N=C(CH₃)CH₂N(CH₃)₂ | H | CH₃ |
| 182 | CH₂CH₃ | OCH₃ | O—NHCH₃ | H | CH₃ |
| 183 | CH₂CH₃ | OCH₃ | O—N(CH₃)C(O)H | H | CH₃ |
| 184 | CH₂CH₃ | OCH₃ | O—N(CH₃)C(O)CH₃ | H | CH₃ |
| 185 | CH₂CH₃ | OCH₃ | O—NHSO₂NH₂ | H | CH₃ |
| 186 | CH₂CH₃ | OCH₃ | O—NHSO₂CH₃ | H | CH₃ |
| 187 | CH₂CH₃ | OCH₃ | NH₂ | H | CH₃ |
| 188 | CH₂CH₃ | OCH₃ | NH₂ | CH₃ | CH₃ |
| 189 | CH₂CH₃ | OCH₃ | NH₂ | CN | CH₃ |
| 190 | CH₂CH₃ | OCH₃ | NHCH₃ | H | CH₃ |
| 191 | CH₂CH₃ | OCH₃ | NHCH₃ | CH₃ | CH₃ |
| 192 | CH₂CH₃ | OCH₃ | NHCH₃ | CN | CH₃ |
| 193 | CH₂CH₃ | OCH₃ | NHCH₂CH₃ | H | CH₃ |
| 194 | CH₂CH₃ | OCH₃ | NHCH₂CH₃ | CH₃ | CH₃ |
| 195 | CH₂CH₃ | OCH₃ | NHCH₂CH₃ | CN | CH₃ |
| 196 | CH₂CH₃ | OCH₃ | N(CH₃)₂ | H | CH₃ |
| 197 | CH₂CH₃ | OCH₃ | N(CH₃)₂ | CH₃ | CH₃ |
| 198 | CH₂CH₃ | OCH₃ | N(CH₃)₂ | CN | CH₃ |
| 199 | CH₂CH₃ | OCH₃ | N(CH₃)CH₂CH₃ | H | CH₃ |
| 200 | CH₂CH₃ | OCH₃ | N(CH₃)CH₂CH₃ | CH₃ | CH₃ |
| 201 | CH₂CH₃ | OCH₃ | N(CH₃)CH₂CH₃ | CN | CH₃ |
| 202 | CH₂CH₃ | OCH₃ | NHOH | H | CH₃ |
| 203 | CH₂CH₃ | OCH₃ | NHOH | CH₃ | CH₃ |
| 204 | CH₂CH₃ | OCH₃ | NHOH | CN | CH₃ |
| 205 | CH₂CH₃ | OCH₃ | NHC(O)H | H | CH₃ |
| 206 | CH₂CH₃ | OCH₃ | NHC(O)H | CH₃ | CH₃ |
| 207 | CH₂CH₃ | OCH₃ | NHC(O)H | CN | CH₃ |

-continued

| Line | R₂ | R₃ | R₄ | R₅ | R₆ |
|---|---|---|---|---|---|
| 208 | CH₂CH₃ | OCH₃ | NHC(O)CH₃ | H | CH₃ |
| 209 | CH₂CH₃ | OCH₃ | NHC(O)CH₃ | CH₃ | CH₃ |
| 210 | CH₂CH₃ | OCH₃ | NHC(O)CH₃ | CN | CH₃ |
| 211 | CH₂CH₃ | OCH₃ | NHC(O)CH₂CH₃ | H | CH₃ |
| 212 | CH₂CH₃ | OCH₃ | NHC(O)CH₂CH₃ | CH₃ | CH₃ |
| 213 | CH₂CH₃ | OCH₃ | NHC(O)CH₂CH₃ | CN | CH₃ |
| 214 | CH₂CH₃ | OCH₃ | NHC(O)CH₂OCH₃ | H | CH₃ |
| 215 | CH₂CH₃ | OCH₃ | NHC(O)CH₂OCH₃ | CH₃ | CH₃ |
| 216 | CH₂CH₃ | OCH₃ | NHC(O)CH₂OCH₃ | CN | CH₃ |
| 217 | CH₂CH₃ | OCH₃ | N(CH₃)OH | H | CH₃ |
| 218 | CH₂CH₃ | OCH₃ | N(CH₃)OH | CH₃ | CH₃ |
| 219 | CH₂CH₃ | OCH₃ | N(CH₃)C(O)H | H | CH₃ |
| 220 | CH₂CH₃ | OCH₃ | N(CH₃)C(O)H | CH₃ | CH₃ |
| 221 | CH₂CH₃ | OCH₃ | N(CH₃)C(O)CH₃ | H | CH₃ |
| 222 | CH₂CH₃ | OCH₃ | N(CH₃)C(O)CH₃ | CH₃ | CH₃ |
| 223 | CH₂CH₃ | OCH₃ | N(CH₃)C(O)CH₂CH₃ | H | CH₃ |
| 224 | CH₂CH₃ | OCH₃ | N(CH₃)C(O)CH₂CH₃ | CH₃ | CH₃ |
| 225 | CH₂CH₃ | OCH₃ | N(CH₃)C(O)CH₂OCH₃ | H | CH₃ |
| 226 | CH₂CH₃ | OCH₃ | N(CH₃)C(O)CH₂OCH₃ | CH₃ | CH₃ |
| 227 | CH₂CH₃ | OCH₃ | N(CH₃)C(O)OCH₃ | H | CH₃ |
| 228 | CH₂CH₃ | OCH₃ | N(CH₃)C(O)OCH₃ | CH₃ | CH₃ |
| 229 | CH₂CH₃ | OCH₃ | N(CH₃)C(O)OCH₂CH₃ | H | CH₃ |
| 230 | CH₂CH₃ | OCH₃ | N(CH₃)C(O)OCH₂CH₃ | CH₃ | CH₃ |
| 231 | CH₂CH₃ | OCH₃ | N(CH₃)C(O)OCH₂CH₂=CH₂ | H | CH₃ |
| 232 | CH₂CH₃ | OCH₃ | N(CH₃)C(O)OCH₂CH₂=CH₂ | CH₃ | CH₃ |
| 233 | OCH₃ | OCH₃ | H | H | H |
| 234 | OCH₂CH₃ | OCH₂CH₃ | H | H | H |
| 235 | OCH₃ | OCH₃ | CH₃ | H | H |
| 236 | OCH₂CH₃ | OCH₂CH₃ | CH₃ | H | H |
| 237 | OCH₃ | OCH₃ | CH₂CH₃ | H | H |
| 238 | OCH₂CH₃ | OCH₂CH₃ | CH₂CH₃ | H | H |
| 239 | OCH₃ | OCH₃ | OH | H | H |
| 240 | OCH₂CH₃ | OCH₂CH₃ | OH | H | H |
| 241 | OCH₃ | OCH₃ | OH | CH₃ | H |
| 242 | OCH₂CH₃ | OCH₂CH₃ | OH | CH₃ | H |
| 243 | OCH₃ | OCH₃ | OCH₃ | H | H |
| 244 | OCH₂CH₃ | OCH₂CH₃ | OCH₂CH₃ | H | H |
| 245 | OCH₃ | OCH₃ | OCH₂OCH₃ | H | H |
| 246 | OCH₃ | OCH₃ | OCH₂OCH₂CH₃ | H | H |
| 247 | OCH₃ | OCH₃ | OCH₂C(O)CH₃ | H | H |
| 248 | OCH₃ | OCH₃ | OCH₂C(O)CH₂CH₃ | H | H |
| 249 | OCH₃ | OCH₃ | OC(O)CH₃ | H | H |
| 250 | OCH₃ | OCH₃ | OC(O)CH₂CH₃ | H | H |
| 251 | OCH₃ | OCH₃ | OC(S)(N-imidazole) | H | H |
| 252 | OCH₃ | OCH₃ | OC(O)OCH₃ | H | H |
| 253 | OCH₃ | OCH₃ | OC(O)OCH₂CH₂=CH₂ | H | H |
| 254 | OCH₃ | OCH₃ | OC(O)NHCH₃ | H | H |
| 255 | OCH₃ | OCH₃ | OC(O)NHCH₂CH₃ | H | H |
| 256 | OCH₃ | OCH₃ | OC(O)NHCH₂CH₂OCH₃ | H | H |
| 257 | OCH₃ | OCH₃ | ONH₂ | H | H |
| 258 | OCH₃ | OCH₃ | O—N=CH₂ | H | H |
| 259 | OCH₃ | OCH₃ | O—N=C(CH₃)CH₂OCH₃ | H | H |
| 260 | OCH₃ | OCH₃ | O—N=C(CH₃)CH₂SCH₃ | H | H |
| 261 | OCH₃ | OCH₃ | O—N=C(CH₃)CH₂N(CH₃)₂ | H | H |
| 262 | OCH₃ | OCH₃ | O—NHCH₃ | H | H |
| 263 | OCH₃ | OCH₃ | O—N(CH₃)C(O)H | H | H |
| 264 | OCH₃ | OCH₃ | O—N(CH₃)C(O)CH₃ | H | H |
| 265 | OCH₃ | OCH₃ | O—NHSO₂NH₂ | H | H |
| 266 | OCH₃ | OCH₃ | O—NHSO₂CH₃ | H | H |
| 267 | OCH₃ | OCH₃ | NH₂ | H | H |
| 268 | OCH₃ | OCH₃ | NH₂ | CH₃ | H |
| 269 | OCH₃ | OCH₃ | NH₂ | CN | H |
| 270 | OCH₃ | OCH₃ | NHCH₃ | H | H |
| 271 | OCH₃ | OCH₃ | NHCH₃ | CH₃ | H |
| 272 | OCH₃ | OCH₃ | NHCH₃ | CN | H |
| 273 | OCH₃ | OCH₃ | NHCH₂CH₃ | H | H |
| 274 | OCH₃ | OCH₃ | NHCH₂CH₃ | CH₃ | H |
| 275 | OCH₃ | OCH₃ | NHCH₂CH₃ | CN | H |
| 276 | OCH₃ | OCH₃ | N(CH₃)₂ | H | H |
| 277 | OCH₃ | OCH₃ | N(CH₃)₂ | CH₃ | H |
| 278 | OCH₃ | OCH₃ | N(CH₃)₂ | CN | H |
| 279 | OCH₃ | OCH₃ | N(CH₃)CH₂CH₃ | H | H |
| 280 | OCH₃ | OCH₃ | N(CH₃)CH₂CH₃ | CH₃ | H |
| 281 | OCH₃ | OCH₃ | N(CH₃)CH₂CH₃ | CN | H |
| 282 | OCH₃ | OCH₃ | NHOH | H | H |
| 283 | OCH₃ | OCH₃ | NHOH | CH₃ | H |
| 284 | OCH₃ | OCH₃ | NHOH | CN | H |

-continued

| Line | R₂ | R₃ | R₄ | R₅ | R₆ |
|---|---|---|---|---|---|
| 285 | OCH₃ | OCH₃ | NHC(O)H | H | H |
| 286 | OCH₃ | OCH₃ | NHC(O)H | CH₃ | H |
| 287 | OCH₃ | OCH₃ | NHC(O)H | CN | H |
| 288 | OCH₃ | OCH₃ | NHC(O)CH₃ | H | H |
| 289 | OCH₃ | OCH₃ | NHC(O)CH₃ | CH₃ | H |
| 290 | OCH₃ | OCH₃ | NHC(O)CH₃ | CN | H |
| 291 | OCH₃ | OCH₃ | NHC(O)CH₂CH₃ | H | H |
| 292 | OCH₃ | OCH₃ | NHC(O)CH₂CH₃ | CH₃ | H |
| 293 | OCH₃ | OCH₃ | NHC(O)CH₂CH₃ | CN | H |
| 294 | OCH₃ | OCH₃ | NHC(O)CH₂OCH₃ | H | H |
| 295 | OCH₃ | OCH₃ | NHC(O)CH₂OCH₃ | CH₃ | H |
| 296 | OCH₃ | OCH₃ | NHC(O)CH₂OCH₃ | CN | H |
| 297 | OCH₃ | OCH₃ | N(CH₃)OH | H | H |
| 298 | OCH₃ | OCH₃ | N(CH₃)OH | CH₃ | H |
| 299 | OCH₃ | OCH₃ | N(CH₃)C(O)H | H | H |
| 300 | OCH₃ | OCH₃ | N(CH₃)C(O)H | CH₃ | H |
| 301 | OCH₃ | OCH₃ | N(CH₃)C(O)CH₃ | H | H |
| 302 | OCH₃ | OCH₃ | N(CH₃)C(O)CH₃ | CH₃ | H |
| 303 | OCH₃ | OCH₃ | N(CH₃)C(O)CH₂CH₃ | H | H |
| 304 | OCH₃ | OCH₃ | N(CH₃)C(O)CH₂CH₃ | CH₃ | H |
| 305 | OCH₃ | OCH₃ | N(CH₃)C(O)CH₂OCH₃ | H | H |
| 306 | OCH₃ | OCH₃ | N(CH₃)C(O)CH₂OCH₃ | CH₃ | H |
| 307 | OCH₃ | OCH₃ | N(CH₃)C(O)OCH₃ | H | H |
| 308 | OCH₃ | OCH₃ | N(CH₃)C(O)OCH₃ | CH₃ | H |
| 309 | OCH₃ | OCH₃ | N(CH₃)C(O)OCH₂CH₃ | H | H |
| 310 | OCH₃ | OCH₃ | N(CH₃)C(O)OCH₂CH₃ | CH₃ | H |
| 311 | OCH₃ | OCH₃ | N(CH₃)C(O)OCH₂CH₂=CH₂ | H | H |
| 312 | OCH₃ | OCH₃ | N(CH₃)C(O)OCH₂CH₂=CH₂ | CH₃ | H |
| 313 | OCH₃ | OCH₃ | OCH₃ | H | CH₂OH |
| 314 | OCH₂CH₃ | OCH₂CH₃ | OCH₂CH₃ | H | CH₂OH |
| 315 | OCH₃ | OCH₃ | OCH₃ | H | CH₂OC(C₆H₅)₃ |
| 316 | OCH₂CH₃ | OCH₂CH₃ | OCH₂CH₃ | H | CH₂OC(C₆H₅)₃ |
| 317 | OCH₃ | OCH₃ | OCH₃ | H | CH₂OCH₃ |
| 318 | OCH₂CH₃ | OCH₂CH₃ | OCH₂CH₃ | H | CH₂OCH₂CH₃ |
| 319 | OCH₃ | OCH₃ | OCH₃ | H | CH₂OCH₂OCH₃ |
| 320 | OCH₃ | OCH₃ | OCH₃ | H | CH₂OCH₂OCH₂CH₃ |
| 321 | OCH₃ | OCH₃ | OCH₃ | H | CH₂OCH₂C(O)CH₃ |
| 322 | OCH₃ | OCH₃ | OCH₃ | H | CH₂OCH₂C(O)CH₂CH₃ |
| 323 | OCH₃ | OCH₃ | OCH₃ | H | CH₂OC(O)CH₃ |
| 324 | OCH₃ | OCH₃ | OCH₃ | H | CH₂OC(O)CH₂CH₃ |
| 325 | OCH₃ | OCH₃ | OCH₃ | H | CH₂OC(S)(N-imidazole) |
| 326 | OCH₃ | OCH₃ | OCH₃ | H | CH₂OC(O)OCH₃ |
| 327 | OCH₃ | OCH₃ | OCH₃ | H | CH₂OC(O)OCH₂CH₂=CH₂ |
| 328 | OCH₃ | OCH₃ | OCH₃ | H | CH₂OC(O)NHCH₃ |
| 329 | OCH₃ | OCH₃ | OCH₃ | H | CH₂OC(O)NHCH₂CH₃ |
| 330 | OCH₃ | OCH₃ | OCH₃ | H | CH₂ONH₂ |
| 331 | OCH₃ | OCH₃ | OCH₃ | H | CH₂O—N=CH₂ |
| 332 | OCH₃ | OCH₃ | OCH₃ | H | CH₂O—N=C(CH₃)CH₂OCH₃ |
| 333 | OCH₃ | OCH₃ | OCH₃ | H | CH₂O—N=C(CH₃)CH₂SCH₃ |
| 334 | OCH₃ | OCH₃ | OCH₃ | H | CH₂O—N=C(CH₃)CH₂N(CH₃)₂ |
| 335 | OCH₃ | OCH₃ | OCH₃ | H | CH₂O—NHCH₃ |
| 336 | OCH₃ | OCH₃ | OCH₃ | H | CH₂O—N(CH₃)C(O)H |
| 337 | OCH₃ | OCH₃ | OCH₃ | H | CH₂O—N(CH₃)C(O)CH₃ |
| 338 | OCH₃ | OCH₃ | OCH₃ | H | CH₂O—NHSO₂NH₂ |
| 339 | OCH₃ | OCH₃ | OCH₃ | H | CH₂O—NHSO₂CH₃ |
| 340 | OCH₃ | OCH₃ | OCH₃ | H | CH₂NH₂ |
| 341 | OCH₃ | OCH₃ | OCH₃ | H | CH₂NHCH₃ |
| 342 | OCH₃ | OCH₃ | OCH₃ | H | CH₂NHCH₂CH₃ |
| 343 | OCH₃ | OCH₃ | OCH₃ | H | CH₂N(CH₃)₂ |
| 344 | OCH₃ | OCH₃ | OCH₃ | H | CH₂N(CH₃)CH₂CH₃ |
| 345 | OCH₃ | OCH₃ | OCH₃ | H | CH₂NHOH |
| 346 | OCH₃ | OCH₃ | OCH₃ | H | CH₂NHC(O)H |
| 347 | OCH₃ | OCH₃ | OCH₃ | H | CH₂NHC(O)CH₃ |
| 348 | OCH₃ | OCH₃ | OCH₃ | H | CH₂NHC(O)CH₂CH₃ |
| 349 | OCH₃ | OCH₃ | OCH₃ | H | CH₂NHC(O)CH₂OCH₃ |
| 350 | OCH₃ | OCH₃ | OCH₃ | H | CH₂N(CH₃)OH |
| 351 | OCH₃ | OCH₃ | OCH₃ | H | CH₂N(CH₃)C(O)H |
| 352 | OCH₃ | OCH₃ | OCH₃ | H | CH₂N(CH₃)C(O)CH₃ |
| 353 | OCH₃ | OCH₃ | OCH₃ | H | CH₂N(CH₃)C(O)CH₂CH₃ |
| 354 | OCH₃ | OCH₃ | OCH₃ | H | CH₂N(CH₃)C(O)CH₂OCH₃ |
| 355 | OCH₃ | OCH₃ | OCH₃ | H | CH₂N(CH₃)C(O)OCH₃ |
| 356 | OCH₃ | OCH₃ | OCH₃ | H | CH₂N(CH₃)C(O)OCH₂CH₃ |
| 357 | OCH₃ | OCH₃ | OCH₃ | H | N(CH₃)C(O)OCH₂CH₃ |
| 358 | OCH₃ | OCH₃ | OCH₃ | H | N(CH₃)C(O)OCH₂CH₂=CH₂ |
| 359 | OCH₃ | OCH₃ | OCH₃ | H | CH₂N(CH₃)C(O)OCH₂CH₂=CH₂ |
| 360 | OCH₃ | OCH₃ | OCH₃ | H | CH=O |
| 361 | OCH₃ | OCH₃ | OCH₃ | H | CH=N—OH |

-continued

| Line | R₂ | R₃ | R₄ | R₅ | R₆ |
|---|---|---|---|---|---|
| 362 | OCH₃ | OCH₃ | OCH₃ | H | CH=N—OCH₃ |
| 363 | OCH₃ | OCH₃ | OCH₃ | H | CH=N—OCH₂CH₃ |
| 364 | OCH₃ | OCH₃ | OCH₃ | H | CH=N—OC(O)CH₃ |
| 365 | OCH₃ | OCH₃ | OCH₃ | H | CH=N—OC(O)CH₂OCH₃ |
| 366 | OCH₃ | OCH₃ | OCH₃ | H | CH=N—OSO₂NH₂ |
| 367 | OCH₃ | OCH₃ | OCH₃ | H | CH=N—NHC(O)CH₃ |
| 368 | OCH₃ | OCH₃ | OCH₃ | H | CH=N—NHC(O)C₆H₅ |
| 369 | OCH₃ | OCH₃ | OCH₃ | H | CH=N—NHC(O)OCH₃ |
| 370 | OCH₃ | OCH₃ | OCH₃ | H | CH=N—NHC(O)OC₆H₅ |
| 371 | OCH₃ | OCH₃ | OCH₃ | H | CH=N—NHC(O)NH₂ |
| 372 | OCH₃ | OCH₃ | OCH₃ | H | CH=N—NHSO₂CH₃ |
| 373 | OCH₃ | OCH₃ | OCH₃ | H | CH=CH₂ |
| 374 | OCH₃ | OCH₃ | OCH₃ | H | CH=CHCH₃ |
| 375 | OCH₃ | OCH₃ | OCH₃ | H | CH=CCl₂ |
| 376 | OCH₃ | OCH₃ | =O | | CH₃ |
| 377 | OCH₃ | OCH₃ | =N—OH | | CH₃ |
| 378 | OCH₃ | OCH₃ | =N—OCH₃ | | CH₃ |
| 379 | OCH₃ | OCH₃ | =N—OCH₂CH₃ | | CH₃ |
| 380 | OCH₃ | OCH₃ | =N—OC(O)CH₃ | | CH₃ |
| 381 | OCH₃ | OCH₃ | =N—OC(O)CH₂OCH₃ | | CH₃ |
| 382 | OCH₃ | OCH₃ | =N—OSO₂NH₂ | | CH₃ |
| 383 | OCH₃ | OCH₃ | =N—NHC(O)CH₃ | | CH₃ |
| 384 | OCH₃ | OCH₃ | =N—NHC(O)C₆H₅ | | CH₃ |
| 385 | OCH₃ | OCH₃ | =N—NHC(O)OCH₃ | | CH₃ |
| 386 | OCH₃ | OCH₃ | =N—NHC(O)OC₆H₅ | | CH₃ |
| 387 | OCH₃ | OCH₃ | =N—NHC(O)NH₂ | | CH₃ |
| 388 | OCH₃ | OCH₃ | =N—NHSO₂CH₃ | | CH₃ |
| 389 | OCH₃ | OCH₃ | =CH₂ | | CH₃ |
| 390 | OCH₃ | OCH₃ | =CHCH₃ | | CH₃ |
| 391 | OCH₃ | OCH₃ | =CCl₂ | | CH₃ |
| 392 | CH₃ | OCH₃ | =O | | CH₃ |
| 393 | CH₃ | OCH₃ | =N—OH | | CH₃ |
| 394 | CH₃ | OCH₃ | =N—OCH₃ | | CH₃ |
| 395 | CH₃ | OCH₃ | =N—OCH₂CH₃ | | CH₃ |
| 396 | CH₃ | OCH₃ | =N—OC(O)CH₃ | | CH₃ |
| 397 | CH₃ | OCH₃ | =N—OC(O)CH₂OCH₃ | | CH₃ |
| 398 | CH₃ | OCH₃ | =N—OSO₂NH₂ | | CH₃ |
| 399 | CH₃ | OCH₃ | =N—NHC(O)CH₃ | | CH₃ |
| 400 | CH₃ | OCH₃ | =N—NHC(O)C₆H₅ | | CH₃ |
| 401 | CH₃ | OCH₃ | =N—NHC(O)OCH₃ | | CH₃ |
| 402 | CH₃ | OCH₃ | =N—NHC(O)OC₆H₅ | | CH₃ |
| 403 | CH₃ | OCH₃ | =N—NHC(O)NH₂ | | CH₃ |
| 404 | CH₃ | OCH₃ | =N—NHSO₂CH₃ | | CH₃ |
| 405 | CH₃ | OCH₃ | =CH₂ | | CH₃ |
| 406 | CH₃ | OCH₃ | =CHCH₃ | | CH₃ |
| 407 | CH₃ | OCH₃ | =CCl₂ | | CH₃ |
| 408 | CH₂CH₃ | OCH₃ | =O | | CH₃ |
| 409 | CH₂CH₃ | OCH₃ | =N—OH | | CH₃ |
| 410 | CH₂CH₃ | OCH₃ | =N—OCH₃ | | CH₃ |
| 411 | CH₂CH₃ | OCH₃ | =N—OCH₂CH₃ | | CH₃ |
| 412 | CH₂CH₃ | OCH₃ | =N—OC(O)CH₃ | | CH₃ |
| 413 | CH₂CH₃ | OCH₃ | =N—OC(O)CH₂OCH₃ | | CH₃ |
| 414 | CH₂CH₃ | OCH₃ | =N—OSO₂NH₂ | | CH₃ |
| 415 | CH₂CH₃ | OCH₃ | =N—NHC(O)CH₃ | | CH₃ |
| 416 | CH₂CH₃ | OCH₃ | =N—NHC(O)C₆H₅ | | CH₃ |
| 417 | CH₂CH₃ | OCH₃ | =N—NHC(O)OCH₃ | | CH₃ |
| 418 | CH₂CH₃ | OCH₃ | =N—NHC(O)OC₆H₅ | | CH₃ |
| 419 | CH₂CH₃ | OCH₃ | =N—NHC(O)NH₂ | | CH₃ |
| 420 | CH₂CH₃ | OCH₃ | =N—NHSO₂CH₃ | | CH₃ |
| 421 | CH₂CH₃ | OCH₃ | =CH₂ | | CH₃ |
| 422 | CH₂CH₃ | OCH₃ | =CHCH₃ | | CH₃ |
| 423 | CH₂CH₃ | OCH₃ | =CCl₂ | | CH₃ |
| 424 | OCH₃ | OCH₃ | =O | | H |
| 425 | OCH₃ | OCH₃ | =N—OH | | H |
| 426 | OCH₃ | OCH₃ | =N—OCH₃ | | H |
| 427 | OCH₃ | OCH₃ | =N—OCH₂CH₃ | | H |
| 428 | OCH₃ | OCH₃ | =N—OC(O)CH₃ | | H |
| 429 | OCH₃ | OCH₃ | =N—OC(O)CH₂OCH₃ | | H |
| 430 | OCH₃ | OCH₃ | =N—OSO₂NH₂ | | H |
| 431 | OCH₃ | OCH₃ | =N—NHC(O)CH₃ | | H |
| 432 | OCH₃ | OCH₃ | =N—NHC(O)C₆H₅ | | H |
| 433 | OCH₃ | OCH₃ | =N—NHC(O)OCH₃ | | H |
| 434 | OCH₃ | OCH₃ | =N—NHC(O)OC₆H₅ | | H |
| 435 | OCH₃ | OCH₃ | =N—NHC(O)NH₂ | | H |
| 436 | OCH₃ | OCH₃ | =N—NHSO₂CH₃ | | H |

-continued

| Line | R₂ | R₃ | R₄ | R₅ | R₆ |
|---|---|---|---|---|---|
| 437 | OCH₃ | OCH₃ | =CH₂ | | H |
| 438 | OCH₃ | OCH₃ | =CHCH₃ | | H |
| 439 | OCH₃ | OCH₃ | =CCl₂ | | H | and

| | |
|---|---|
| Table 1 | A compound of the formula (I-1) wherein R₁ is sec-butyl or isopropyl, the configuration of the carbon atom at the ε position is (R), and the substituents R₂, R₃, R₄, R₅, and R₆ corresponds to a line 1 to 439 of Table X. |
| Table 2 | A compound of the formula (I-1) wherein R₁ is sec-butyl or isopropyl, the configuration of the carbon atom at the ε position is (S), and the substituents R₂, R₃, R₄, R₅, and R₆ corresponds to a line 1 to 439 of Table X. |
| Table 3 | A compound of the formula (I-1) wherein R₁ is cyclohexyl, the configuration of the carbon atom at the ε position is (R), and the substituents R₂, R₃, R₄, R₅, and R₆ corresponds to a line 1 to 439 of Table X. |
| Table 4 | A compound of the formula (I-1) wherein R₁ is cyclohexyl, the configuration of the carbon atom at the ε position is (S), and the substituents R₂, R₃, R₄, R₅, and R₆ corresponds to a line 1 to 439 of Table X. |
| Table 5 | A compound of the formula (I-1) wherein R₁ is 1-methyl butyl, the configuration of the carbon atom at the ε position is (R), and the substituents R₂, R₃, R₄, R₅, and R₆ corresponds to a line 1 to 439 of Table X. |
| Table 6 | A compound of the formula (I-1) wherein R₁ is 1-methyl butyl, the configuration of the carbon atom at the ε position is (S), and the substituents R₂, R₃, R₄, R₅, and R₆ corresponds to a line 1 to 439 of Table X. |
| Table 7 | A compound of the formula (I-2) wherein R₁ is sec-butyl or isopropyl, the configuration of the carbon atom at the ε position is (R), and the substituents R₂, R₃, R₄, R₅, and R₆ corresponds to a line 1 to 439 of Table X. |
| Table 8 | A compound of the formula (I-2) wherein R₁ is sec-butyl or isopropyl, the configuration of the carbon atom at the ε position is (S), and the substituents R₂, R₃, R₄, R₅, and R₆ corresponds to a line 1 to 439 of Table X. |
| Table 9 | A compound of the formula (I-2) wherein R₁ is cyclohexyl, the configuration of the carbon atom at the ε position is (R), and the substituents R₂, R₃, R₄, R₅, and R₆ corresponds to a line 1 to 439 of Table X. |
| Table 10 | A compound of the formula (I-2) wherein R₁ is cyclohexyl, the configuration of the carbon atom at the ε position is (S), and the substituents R₂, R₃, R₄, R₅, and R₆ corresponds to a line 1 to 439 of Table X. |
| Table 11 | A compound of the formula (I-2) wherein R₁ is 1-methyl butyl, the configuration of the carbon atom at the ε position is (R), and the substituents R₂, R₃, R₄, R₅, and R₆ corresponds to a line 1 to 439 of Table X. |
| Table 12 | A compound of the formula (I-2) wherein R₁ is 1-methyl butyl, the configuration of the carbon atom at the ε position is (S), and the substituents R₂, R₃, R₄, R₅, and R₆ corresponds to a line 1 to 439 of Table X. |
| Table 13 | A compound of the formula (I-3) wherein R₁ is sec-butyl or isopropyl, the configuration of the carbon atom at the ε position is (R), and the substituents R₂, R₃, R₄, R₅, and R₆ corresponds to a line 1 to 439 of Table X. |
| Table 14 | A compound of the formula (I-3) wherein R₁ is sec-butyl or isopropyl, the configuration of the carbon atom at the ε position is (S), and the substituents R₂, R₃, R₄, R₅, and R₆ corresponds to a line 1 to 439 of Table X. |
| Table 15 | A compound of the formula (I-3) wherein R₁ is cyclohexyl, the configuration of the carbon atom at the ε position is (R), and the substituents R₂, R₃, R₄, R₅, and R₆ corresponds to a line 1 to 439 of Table X. |
| Table 16 | A compound of the formula (I-3) wherein R₁ is cyclohexyl, the configuration of the carbon atom at the ε position is (S), and the substituents R₂, R₃, R₄, R₅, and R₆ corresponds to a line 1 to 439 of Table X. |
| Table 17 | A compound of the formula (I-3) wherein R₁ is 1-methyl butyl, the configuration of the carbon atom at the ε position is (R), and the substituents R₂, R₃, R₄, R₅, and R₆ corresponds to a line 1 to 439 of Table X. |
| Table 18 | A compound of the formula (I-3) wherein R₁ is 1-methyl butyl, the configuration of the carbon atom at the ε position is (S), and the substituents R₂, R₃, R₄, R₅, and R₆ corresponds to a line 1 to 439 of Table X. |
| Table 19 | A compound of the formula (I-4) wherein R₁ is sec-butyl or isopropyl, the configuration of the carbon atom at the ε position is (R), and the substituents R₂, R₃, R₄, R₅, and R₆ corresponds to a line 1 to 439 of Table X. |
| Table 20 | A compound of the formula (I-4) wherein R₁ is sec-butyl or isopropyl, the configuration of the carbon atom at the ε position is (S), and the substituents R₂, R₃, R₄, R₅, and R₆ corresponds to a line 1 to 439 of Table X. |
| Table 21 | A compound of the formula (I-4) wherein R₁ is cyclohexyl, the configuration of the carbon atom at the ε position is (R), and the substituents R₂, R₃, R₄, R₅, and R₆ corresponds to a line 1 to 439 of Table X. |
| Table 22 | A compound of the formula (I-4) wherein R₁ is cyclohexyl, the configuration of the carbon atom at the ε position is (S), and the substituents R₂, R₃, R₄, R₅, and R₆ corresponds to a line 1 to 439 of Table X. |

-continued

| | |
|---|---|
| Table 23 | A compound of the formula (I-4) wherein $R_1$ is 1-methyl butyl, the configuration of the carbon atom at the $\epsilon$ position is (R), and the substituents $R_2$, $R_3$, $R_4$, $R_5$, and $R_6$ corresponds to a line 1 to 439 of Table X. |
| Table 24 | A compound of the formula (I-4) wherein $R_1$ is 1-methyl butyl, the configuration of the carbon atom at the $\epsilon$ position is (S), and the substituents $R_2$, $R_3$, $R_4$, $R_5$, and $R_6$ corresponds to a line 1 to 439 of Table X. |
| Table 25 | A compound of the formula (I-5) wherein $R_1$ is sec-butyl or isopropyl, the configuration of the carbon atom at the $\epsilon$ position is (R), and the substituents $R_2$, $R_3$, $R_4$, $R_5$, and $R_6$ corresponds to a line 1 to 439 of Table X. |
| Table 26 | A compound of the formula (I-5) wherein $R_1$ is sec-butyl or isopropyl, the configuration of the carbon atom at the $\epsilon$ position is (S), and the substituents $R_2$, $R_3$, $R_4$, $R_5$, and $R_6$ corresponds to a line 1 to 439 of Table X. |
| Table 27 | A compound of the formula (I-5) wherein $R_1$ is cyclohexyl, the configuration of the carbon atom at the $\epsilon$ position is (R), and the substituents $R_2$, $R_3$, $R_4$, $R_5$, and $R_6$ corresponds to a line 1 to 439 of Table X. |
| Table 28 | A compound of the formula (I-5) wherein $R_1$ is cyclohexyl, the configuration of the carbon atom at the $\epsilon$ position is (S), and the substituents $R_2$, $R_3$, $R_4$, $R_5$, and $R_6$ corresponds to a line 1 to 439 of Table X. |
| Table 29 | A compound of the formula (I-5) wherein $R_1$ is 1-methyl butyl, the configuration of the carbon atom at the $\epsilon$ position is (R), and the substituents $R_2$, $R_3$, $R_4$, $R_5$, and $R_6$ corresponds to a line 1 to 439 of Table X. |
| Table 30 | A compound of the formula (I-5) wherein $R_1$ is 1-methyl butyl, the configuration of the carbon atom at the $\epsilon$ position is (S), and the substituents $R_2$, $R_3$, $R_4$, $R_5$, and $R_6$ corresponds to a line 1 to 439 of Table X. |
| Table 31 | A compound of the formula (I-6) wherein $R_1$ is sec-butyl or isopropyl, the configuration of the carbon atom at the $\epsilon$ position is (R), and the substituents $R_2$, $R_3$, $R_4$, $R_5$, and $R_6$ corresponds to a line 1 to 439 of Table X. |
| Table 32 | A compound of the formula (I-6) wherein $R_1$ is sec-butyl or isopropyl, the configuration of the carbon atom at the $\epsilon$ position is (S), and the substituents $R_2$, $R_3$, $R_4$, $R_5$, and $R_6$ corresponds to a line 1 to 439 of Table X. |
| Table 33 | A compound of the formula (I-6) wherein $R_1$ is cyclohexyl, the configuration of the carbon atom at the $\epsilon$ position is (R), and the substituents $R_2$, $R_3$, $R_4$, $R_5$, and $R_6$ corresponds to a line 1 to 439 of Table X. |
| Table 34 | A compound of the formula (I-6) wherein $R_1$ is cyclohexyl, the configuration of the carbon atom at the $\epsilon$ position is (S), and the substituents $R_2$, $R_3$, $R_4$, $R_5$, and $R_6$ corresponds to a line 1 to 439 of Table X. |
| Table 35 | A compound of the formula (I-6) wherein $R_1$ is 1-methyl butyl, the configuration of the carbon atom at the $\epsilon$ position is (R), and the substituents $R_2$, $R_3$, $R_4$, $R_5$, and $R_6$ corresponds to a line 1 to 439 of Table X. |
| Table 36 | A compound of the formula (I-6) wherein $R_1$ is 1-methyl butyl, the configuration of the carbon atom at the $\epsilon$ position is (S), and the substituents $R_2$, $R_3$, $R_4$, $R_5$, and $R_6$ corresponds to a line 1 to 439 of Table X. |
| Table 37 | A compound of the formula (I-7) wherein R1 is sec-butyl or isopropyl, the configuration of the carbon atom at the $\epsilon$ position is (R), and the substituents $R_2$, $R_3$, $R_4$, $R_5$, and $R_6$ corresponds to a line 1 to 439 of Table X. |
| Table 38 | A compound of the formula (I-7) wherein $R_1$ is sec-butyl or isopropyl, the configuration of the carbon atom at the $\epsilon$ position is (S), and the substituents $R_2$, $R_3$, $R_4$, $R_5$, and $R_6$ corresponds to a line 1 to 439 of Table X. |
| Table 39 | A compound of the formula (I-7) wherein $R_1$ is cyclohexyl, the configuration of the carbon atom at the $\epsilon$ position is (R), and the substituents $R_2$, $R_3$, $R_4$, $R_5$, and $R_6$ corresponds to a line 1 to 439 of Table X. |
| Table 40 | A compound of the formula (I-7) wherein $R_1$ is cyclohexyl, the configuration of the carbon atom at the $\epsilon$ position is (S), and the substituents $R_2$, $R_3$, $R_4$, $R_5$, and $R_6$ corresponds to a line 1 to 439 of Table X. |
| Table 41 | A compound of the formula (I-7) wherein $R_1$ is 1-methyl butyl, the configuration of the carbon atom at the $\epsilon$ position is (R), and the substituents $R_2$, $R_3$, $R_4$, $R_5$, and $R_6$ corresponds to a line 1 to 439 of Table X. |
| Table 42 | A compound of the formula (I-7) wherein $R_1$ is 1-methyl butyl, the configuration of the carbon atom at the $\epsilon$ position is (S), and the substituents $R_2$, $R_3$, $R_4$, $R_5$, and $R_6$ corresponds to a line 1 to 439 of Table X. |
| Table 43 | A compound of the formula (I-8) wherein $R_1$ is sec-butyl or isopropyl, the configuration of the carbon atom at the $\epsilon$ position is (R), and the substituents $R_2$, $R_3$, $R_4$, $R_5$, and $R_6$ corresponds to a line 1 to 439 of Table X. |
| Table 44 | A compound of the formula (I-8) wherein $R_1$ is sec-butyl or isopropyl, the configuration of the carbon atom at the $\epsilon$ position is (S), and the substituents $R_2$, $R_3$, $R_4$, $R_5$, and $R_6$ corresponds to a line 1 to 439 of Table X. |
| Table 45 | A compound of the formula (I-8) wherein $R_1$ is cyclohexyl, the configuration of the carbon atom at the $\epsilon$ position is (R), and the substituents $R_2$, $R_3$, $R_4$, $R_5$, and $R_6$ corresponds to a line 1 to 439 of Table X. |
| Table 46 | A compound of the formula (I-8) wherein $R_1$ is cyclohexyl, the configuration of the carbon atom at the $\epsilon$ position is (S), and the substituents $R_2$, $R_3$, $R_4$, $R_5$, and $R_6$ corresponds to a line 1 to 439 of Table X. |
| Table 47 | A compound of the formula (I-8) wherein $R_1$ is 1-methyl butyl, the configuration of the carbon atom at the $\epsilon$ position is (R), and the substituents $R_2$, $R_3$, $R_4$, $R_5$, and $R_6$ corresponds to a line 1 to 439 of Table X. |
| Table 48 | A compound of the formula (I-8) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |

-continued

| | |
|---|---|
| Table 49 | A compound of the formula (I-9) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 50 | A compound of the formula (I-9) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 51 | A compound of the formula (I-9) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 52 | A compound of the formula (I-9) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 53 | A compound of the formula (I-9) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 54 | A compound of the formula (I-9) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 55 | A compound of the formula (I-10) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 56 | A compound of the formula (I-10) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 57 | A compound of the formula (I-10) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 58 | A compound of the formula (I-10) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 59 | A compound of the formula (I-10) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 60 | A compound of the formula (I-10) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 61 | A compound of the formula (I-11) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 62 | A compound of the formula (I-11) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 63 | A compound of the formula (I-11) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 64 | A compound of the formula (I-11) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 65 | A compound of the formula (I-11) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 66 | A compound of the formula (I-11) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 67 | A compound of the formula (I-12) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 68 | A compound of the formula (I-12) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 69 | A compound of the formula (I-12) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 70 | A compound of the formula (I-12) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 71 | A compound of the formula (I-12) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 72 | A compound of the formula (I-12) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 73 | A compound of the formula (I-13) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 74 | A compound of the formula (I-13) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |

-continued

| | |
|---|---|
| Table 75 | A compound of the formula (I-13) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 76 | A compound of the formula (I-13) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 77 | A compound of the formula (I-13) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 78 | A compound of the formula (I-13) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 79 | A compound of the formula (I-14) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 80 | A compound of the formula (I-14) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 81 | A compound of the formula (I-14) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 82 | A compound of the formula (I-14) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 83 | A compound of the formula (I-14) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 84 | A compound of the formula (I-14) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 85 | A compound of the formula (I-15) wherein $R_1$ is sec-butyl or isopropyl, the configuration of the carbon atom at the $\epsilon$ position is (R), and the substituents $R_2$, $R_3$, $R_4$, $R_5$ and $R_6$ correspond to a line 1 to 439 of Table X. |
| Table 86 | A compound of the formula (I-15) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 87 | A compound of the formula (I-15) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 88 | A compound of the formula (I-15) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 89 | A compound of the formula (I-15) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 90 | A compound of the formula (I-15) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 91 | A compound of the formula (I-16) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 92 | A compound of the formula (I-16) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 93 | A compound of the formula (I-16) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 94 | A compound of the formula (I-16) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 95 | A compound of the formula (I-16) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 96 | A compound of the formula (I-16) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 97 | A compound of the formula (I-17) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 98 | A compound of the formula (I-17) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 99 | A compound of the formula (I-17) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 100 | A compound of the formula (I-17) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |

| | |
|---|---|
| Table 101 | A compound of the formula (I-17) wherein $R_1$ is 1-methyl butyl, the configuration of the carbon atom at the ε position is (R), and the substituents $R_2$, $R_3$, $R_4$, $R_5$, and $R_6$ correspond to a line 1 to 439 of Table X. |
| Table 102 | A compound of the formula (I-17) wherein $R_1$ is 1-methyl butyl, the configuration of the carbon atom at the ε position is (S), and the substituents $R_2$, $R_3$, $R_4$, $R_5$, and $R_6$ correspond to a line 1 to 439 of Table X. |
| Table 103 | A compound of the formula (I-18) wherein $R_1$ is sec-butyl or isopropyl, the configuration of the carbon atom at the ε position is (R), and the substituents $R_2$, $R_3$, $R_4$, $R_5$, and $R_6$ correspond to a line 1 to 439 of Table X. |
| Table 104 | A compound of the formula (I-18) wherein $R_1$ is sec-butyl or isopropyl, the configuration of the carbon atom at the ε position is (S), and the substituents $R_2$, $R_3$, $R_4$, $R_5$, and $R_6$ correspond to a line 1 to 439 of Table X. |
| Table 105 | A compound of the formula (I-18) wherein $R_1$ is cyclohexyl, the configuration of the carbon atom at the ε position is (R), and the substituents $R_2$, $R_3$, $R_4$, $R_5$, and $R_6$ correspond to a line 1 to 439 of Table X. |
| Table 106 | A compound of the formula (I-18) wherein $R_1$ is cyclohexyl, the configuration of the carbon atom at the ε position is (S), and the substituents $R_2$, $R_3$, $R_4$, $R_5$, and $R_6$ correspond to a line 1 to 439 of Table X. |
| Table 107 | A compound of the formula (I-18) wherein $R_1$ is 1-methyl butyl, the configuration of the carbon atom at the ε position is (R), and the substituents $R_2$, $R_3$, $R_4$, $R_5$, and $R_6$ correspond to a line 1 to 439 of Table X. |
| Table 108 | A compound of the formula (I-18) wherein $R_1$ is 1-methyl butyl, the configuration of the carbon atom at the ε position is (S), and the substituents $R_2$, $R_3$, $R_4$, $R_5$, and $R_6$ correspond to a line 1 to 439 of Table X. |
| Table 109 | A compound of the formula (I-19) wherein $R_1$ is sec-butyl or isopropyl, the configuration of the carbon atom at the ε position is (R), and the substituents $R_2$, $R_3$, $R_4$, $R_5$, and $R_6$ correspond to a line 1 to 439 of Table X. |
| Table 110 | A compound of the formula (I-19) wherein $R_1$ is sec-butyl or isopropyl, the configuration of the carbon atom at the ε position is (S), and the substituents $R_2$, $R_3$, $R_4$, $R_5$, and $R_6$ correspond to a line 1 to 439 of Table X. |
| Table 111 | A compound of the formula (I-19) wherein $R_1$ is cyclohexyl, the configuration of the carbon atom at the ε position is (R), and the substituents $R_2$, $R_3$, $R_4$, $R_5$, and $R_6$ correspond to a line 1 to 439 of Table X. |
| Table 112 | A compound of the formula (I-19) wherein $R_1$ is cyclohexyl, the configuration of the carbon atom at the ε position is (S), and the substituents $R_2$, $R_3$, $R_4$, $R_5$, and $R_6$ correspond to a line 1 to 439 of Table X. |
| Table 113 | A compound of the formula (I-19) wherein $R_1$ is 1-methyl butyl, the configuration of the carbon atom at the ε position is (R), and the substituents $R_2$, $R_3$, $R_4$, $R_5$, and $R_6$ correspond to a line 1 to 439 of Table X. |
| Table 114 | A compound of the formula (I-19) wherein $R_1$ is 1-methyl butyl, the configuration of the carbon atom at the ε position is (S), and the substituents $R_2$, $R_3$, $R_4$, $R_5$, and $R_6$ correspond to a line 1 to 439 of Table X. |
| Table 115 | A compound of the formula (I-20) wherein $R_1$ is sec-butyl or isopropyl, the configuration of the carbon atom at the ε position is (R), and the substituents $R_2$, $R_3$, $R_4$, $R_5$, and $R_6$ correspond to a line 1 to 439 of Table X. |
| Table 116 | A compound of the formula (I-20) wherein $R_1$ is sec-butyl or isopropyl, the configuration of the carbon atom at the ε position is (S), and the substituents $R_2$, $R_3$, $R_4$, $R_5$, and $R_6$ correspond to a line 1 to 439 of Table X. |
| Table 117 | A compound of the formula (I-20) wherein $R_1$ is cyclohexyl, the configuration of the carbon atom at the ε position is (R), and the substituents $R_2$, $R_3$, $R_4$, $R_5$, and $R_6$ correspond to a line 1 to 439 of Table X. |
| Table 118 | A compound of the formula (I-20) wherein $R_1$ is cyclohexyl, the configuration of the carbon atom at the ε position is (S), and the substituents $R_2$, $R_3$, $R_4$, $R_5$, and $R_6$ correspond to a line 1 to 439 of Table X. |
| Table 119 | A compound of the formula (I-20) wherein $R_1$ is 1-methyl butyl, the configuration of the carbon atom at the ε position is (R), and the substituents $R_2$, $R_3$, $R_4$, $R_5$, and $R_6$ correspond to a line 1 to 439 of Table X. |
| Table 120 | A compound of the formula (I-20) wherein $R_1$ is 1-methyl butyl, the configuration of the carbon atom at the ε position is (S), and the substituents $R_2$, $R_3$, $R_4$, $R_5$, and $R_6$ correspond to a line 1 to 439 of Table X. |
| Table 121 | A compound of the formula (I-21) wherein $R_1$ is sec-butyl or isopropyl, the configuration of the carbon atom at the ε position is (R), and the substituents $R_2$, $R_3$, $R_4$, $R_{5,\text{ and }R6}$ correspond to a line 1 to 439 of Table X. |
| Table 122 | A compound of the formula (I-21) wherein $R_1$ is sec-butyl or isopropyl, the configuration of the carbon atom at the ε position is (S), and the substituents $R_2$, $R_3$, $R_4$, $R_5$, and $R_6$ correspond to a line 1 to 439 of Table X. |
| Table 123 | A compound of the formula (I-21) wherein $R_1$ is cyclohexyl, the configuration of the carbon atom at the ε position is (R), and the substituents $R_2$, $R_3$, $R_4$, $R_5$, and $R_6$ correspond to a line 1 to 439 of Table X. |
| Table 124 | A compound of the formula (I-21) wherein $R_1$ is cyclohexyl, the configuration of the carbon atom at the ε position is (S), and the substituents $R_2$, $R_3$, $R_4$, $R_5$, and $R_6$ correspond to a line 1 to 439 of Table X. |
| Table 125 | A compound of the formula (I-21) wherein $R_1$ is 1-methyl butyl, the configuration of the carbon atom at the ε position is (R), and the substituents $R_2$, $R_3$, $R_4$, $R_5$, and $R_6$ correspond to a line 1 to 439 of Table X. |
| Table 126 | A compound of the formula (I-21) wherein $R_1$ is 1-methyl butyl, the configuration of the carbon atom at the ε position is (S), and the substituents $R_2$, $R_3$, $R_4$, $R_5$, and $R_6$ correspond to a line 1 to 439 of Table X. |

| | |
|---|---|
| Table 127 | A compound of the formula (I-22) wherein $R_1$ is sec-butyl or isopropyl, the configuration of the carbon atom at the ε position is (R), and the substituents $R_2$, $R_3$, $R_4$, $R_5$, and $R_6$ correspond to a line 1 to 439 of Table X. |
| Table 128 | A compound of the formula (I-22) wherein $R_1$ is sec-butyl or isopropyl, the configuration of the carbon atom at the ε position is (S), and the substituents $R_2$, $R_3$, $R_4$, $R_5$, and $R_6$ correspond to a line 1 to 439 of Table X. |
| Table 129 | A compound of the formula (I-22) wherein $R_1$ is cyclohexyl, the configuration of the carbon atom at the ε position is (R), and the substituents $R_2$, $R_3$, $R_4$, $R_5$, and $R_6$ correspond to a line 1 to 439 of Table X. |
| Table 130 | A compound of the formula (I-22) wherein $R_1$ is cyclohexyl, the configuration of the carbon atom at the ε position is (S), and the substituents $R_2$, $R_3$, $R_4$, $R_5$, and $R_6$ correspond to a line 1 to 439 of Table X. |
| Table 131 | A compound of the formula (I-22) wherein $R_1$ is 1-methyl butyl, the configuration of the carbon atom at the ε position is (R), and the substituents $R_2$, $R_3$, $R_4$, $R_5$, and $R_6$ correspond to a line 1 to 439 of Table X. |
| Table 132 | A compound of the formula (I-22) wherein $R_1$ is 1-methyl butyl, the configuration of the carbon atom at the ε position is (S), and the substituents $R_2$, $R_3$, $R_4$, $R_5$, and $R_6$ correspond to a line 1 to 439 of Table X. |
| Table 133 | A compound of the formula (I-23) wherein $R_1$ is sec-butyl or isopropyl, the configuration of the carbon atom at the ε position is (R), and the substituents $R_2$, $R_3$, $R_4$, $R_5$, and $R_6$ correspond to a line 1 to 439 of Table X. |
| Table 134 | A compound of the formula (I-23) wherein $R_1$ is sec-butyl or isopropyl, the configuration of the carbon atom at the ε position is (S), and the substituents $R_2$, $R_3$, $R_4$, $R_5$, and $R_6$ correspond to a line 1 to 439 of Table X. |
| Table 135 | A compound of the formula (I-23) wherein $R_1$ is cyclohexyl, the configuration of the carbon atom at the ε position is (R), and the substituents $R_2$, $R_3$, $R_4$, $R_5$, and $R_6$ correspond to a line 1 to 439 of Table X. |
| Table 136 | A compound of the formula (I-23) wherein $R_1$ is cyclohexyl, the configuration of the carbon atom at the ε position is (S), and the substituents $R_2$, $R_3$, $R_4$, $R_5$, and $R_6$ correspond to a line 1 to 439 of Table X. |
| Table 137 | A compound of the formula (I-23) wherein $R_1$ is 1-methyl butyl, the configuration of the carbon atom at the ε position is (R), and the substituents $R_2$, $R_3$, $R_4$, $R_5$, and $R_6$ correspond to a line 1 to 439 of Table X. |
| Table 138 | A compound of the formula (I-23) wherein $R_1$ is 1-methyl butyl, the configuration of the carbon atom at the ε position is (S), and the substituents $R_2$, $R_3$, $R_4$, $R_5$, and $R_6$ correspond to a line 1 to 439 of Table X. |
| Table 139 | A compound of the formula (I-24) wherein $R_1$ is sec-butyl or isopropyl, the configuration of the carbon atom at the ε position is (R), and the substituents $R_2$, $R_3$, $R_4$, $R_5$, and $R_6$ correspond to a line 1 to 439 of Table X. |
| Table 140 | A compound of the formula (I-24) wherein $R_1$ is sec-butyl or isopropyl, the configuration of the carbon atom at the ε position is (S), and the substituents $R_2$, $R_3$, $R_4$, $R_5$, and $R_6$ correspond to a line 1 to 439 of Table X. |
| Table 141 | A compound of the formula (I-24) wherein $R_1$ is cyclohexyl, the configuration of the carbon atom at the ε position is (R), and the substituents $R_2$, $R_3$, $R_4$, $R_5$, and $R_6$ correspond to a line 1 to 439 of Table X. |
| Table 142 | A compound of the formula (I-24) wherein $R_1$ is cyclohexyl, the configuration of the carbon atom at the ε position is (S), and the substituents $R_2$, $R_3$, $R_4$, $R_5$, and $R_6$ correspond to a line 1 to 439 of Table X. |
| Table 143 | A compound of the formula (I-24) wherein $R_1$ is 1-methyl butyl, the configuration of the carbon atom at the ε position is (R), and the substituents $R_2$, $R_3$, $R_4$, $R_5$, and $R_6$ correspond to a line 1 to 439 of Table X. |
| Table 144 | A compound of the formula (I-24) wherein $R_1$ is 1-methyl butyl, the configuration of the carbon atom at the ε position is (S), and the substituents $R_2$, $R_3$, $R_4$, $R_5$, and $R_6$ correspond to a line 1 to 439 of Table X. |
| Table 145 | A compound of the formula (I-25) wherein $R_1$ is sec-butyl or isopropyl, the configuration of the carbon atom at the ε position is (R), and the substituents $R_2$, $R_3$, $R_4$, $R_5$, and $R_6$ correspond to a line 1 to 439 of Table X. |
| Table 146 | A compound of the formula (I-25) wherein $R_1$ is sec-butyl or isopropyl, the configuration of the carbon atom at the ε position is (S), and the substituents $R_2$, $R_3$, $R_4$, $R_5$, and $R_6$ correspond to a line 1 to 439 of Table X. |
| Table 147 | A compound of the formula (I-25) wherein $R_1$ is cyclohexyl, the configuration of the carbon atom at the ε position is (R), and the substituents $R_2$, $R_3$, $R_4$, $R_5$, and $R_6$ correspond to a line 1 to 439 of Table X. |
| Table 148 | A compound of the formula (I-25) wherein $R_1$ is cyclohexyl, the configuration of the carbon atom at the ε position is (S), and the substituents $R_2$, $R_3$, $R_4$, $R_5$, and $R_6$ correspond to a line 1 to 439 of Table X. |
| Table 149 | A compound of the formula (I-25) wherein $R_1$ is 1-methyl butyl, the configuration of the carbon atom at the ε position is (R), and the substituents $R_2$, $R_3$, $R_4$, $R_5$, and $R_6$ correspond to a line 1 to 439 of Table X. |
| Table 150 | A compound of the formula (I-25) wherein $R_1$ is 1-methyl butyl, the configuration of the carbon atom at the ε position is (S), and the substituents $R_2$, $R_3$, $R_4$, $R_5$, and $R_6$ correspond to a line 1 to 439 of Table X. |
| Table 151 | A compound of the formula (I-26) wherein $R_1$ is sec-butyl or isopropyl, the configuration of the carbon atom at the ε position is (R), and the substituents $R_2$, $R_3$, $R_4$, $R_5$, and $R_6$ correspond to a line 1 to 439 of Table X. |
| Table 152 | A compound of the formula (I-26) wherein $R_1$ is sec-butyl or isopropyl, the configuration of the carbon atom at the ε position is (S), and the substituents $R_2$, $R_3$, $R_4$, $R_5$, and $R_6$ correspond to a line 1 to 439 of Table X. |

-continued

| | |
|---|---|
| Table 153 | A compound of the formula (I-26) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 154 | A compound of the formula (I-26) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 155 | A compound of the formula (I-26) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 156 | A compound of the formula (I-26) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 157 | A compound of the formula (I-27) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 158 | A compound of the formula (I-27) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 159 | A compound of the formula (I-27) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 160 | A compound of the formula (I-27) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 161 | A compound of the formula (I-27) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 162 | A compound of the formula (I-27) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 163 | A compound of the formula (I-28) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 164 | A compound of the formula (I-28) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 165 | A compound of the formula (I-28) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 166 | A compound of the formula (I-28) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 167 | A compound of the formula (I-28) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 168 | A compound of the formula (I-28) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 169 | A compound of the formula (I-29) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 170 | A compound of the formula (I-29) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 171 | A compound of the formula (I-29) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 172 | A compound of the formula (I-29) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 173 | A compound of the formula (I-29) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 174 | A compound of the formula (I-29) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 175 | A compound of the formula (I-30) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 176 | A compound of the formula (I-30) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 177 | A compound of the formula (I-30) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 178 | A compound of the formula (I-30) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |

-continued

| | |
|---|---|
| Table 179 | A compound of the formula (I-30) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 180 | A compound of the formula (I-30) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 181 | A compound of the formula (I-31) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 182 | A compound of the formula (I-31) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 183 | A compound of the formula (I-31) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 184 | A compound of the formula (I-31) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 185 | A compound of the formula (I-31) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 186 | A compound of the formula (I-31) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 187 | A compound of the formula (I-32) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 188 | A compound of the formula (I-32) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 189 | A compound of the formula (i-32) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 190 | A compound of the formula (I-32) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 191 | A compound of the formula (I-32) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 192 | A compound of the formula (I-32) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 193 | A compound of the formula (I-33) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 194 | A compound of the formula (I-33) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 195 | A compound of the formula (I-33) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 196 | A compound of the formula (I-33) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 197 | A compound of the formula (I-33) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 198 | A compound of the formula (I-33) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 199 | A compound of the formula (I-34) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 200 | A compound of the formula (I-34) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 201 | A compound of the formula (I-34) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 202 | A compound of the formula (I-34) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 203 | A compound of the formula (I-34) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 204 | A compound of the formula (I-34) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |

| | |
|---|---|
| Table 205 | A compound of the formula (I-35) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 206 | A compound of the formula (I-35) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 207 | A compound of the formula (I-35) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 208 | A compound of the formula (I-35) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 209 | A compound of the formula (I-35) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 210 | A compound of the formula (I-35) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 211 | A compound of the formula (I-36) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 212 | A compound of the formula (I-36) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 213 | A compound of the formula (I-36) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 214 | A compound of the formula (I-36) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 215 | A compound of the formula (I-36) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 216 | A compound of the formula (I-36) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 217 | A compound of the formula (I-37) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 218 | A compound of the formula (I-37) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 219 | A compound of the formula (I-37) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 220 | A compound of the formula (I-37) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 221 | A compound of the formula (I-37) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 222 | A compound of the formula (I-37) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 223 | A compound of the formula (I-38) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 224 | A compound of the formula (I-38) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 225 | A compound of the formula (I-38) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 226 | A compound of the formula (I-38) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 227 | A compound of the formula (I-38) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 228 | A compound of the formula (I-38) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 229 | A compound of the formula (I-39) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 230 | A compound of the formula (I-39) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |

| | |
|---|---|
| Table 231 | A compound of the formula (I-39) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 232 | A compound of the formula (I-39) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 233 | A compound of the formula (I-39) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 234 | A compound of the formula (I-39) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 235 | A compound of the formula (I-40) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 236 | A compound of the formula (I-40) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 237 | A compound of the formula (I-40) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 238 | A compound of the formula (I-40) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 239 | A compound of the formula (I-40) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 240 | A compound of the formula (I-40) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 241 | A compound of the formula (I-41) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 242 | A compound of the formula (I-41) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 243 | A compound of the formula (I-41) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 244 | A compound of the formula (I-41) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 245 | A compound of the formula (I-41) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 246 | A compound of the formula (I-41) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 247 | A compound of the formula (I-42) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 248 | A compound of the formula (I-42) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 249 | A compound of the formula (I-42) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 250 | A compound of the formula (I-42) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 251 | A compound of the formula (I-42) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 252 | A compound of the formula (I-42) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 253 | A compound of the formula (I-43) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 254 | A compound of the formula (I-43) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 255 | A compound of the formula (I-43) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 256 | A compound of the formula (I-43) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |

-continued

| | |
|---|---|
| Table 257 | A compound of the formula (I-43) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 258 | A compound of the formula (I-43) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 259 | A compound of the formula (I-44) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 260 | A compound of the formula (I-44) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 261 | A compound of the formula (I-44) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 262 | A compound of the formula (I-44) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 263 | A compound of the formula (I-44) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 264 | A compound of the formula (I-44) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 265 | A compound of the formula (I-45) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 266 | A compound of the formula (I-45) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 267 | A compound of the formula (I-45) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 268 | A compound of the formula (I-45) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 269 | A compound of the formula (I-45) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 270 | A compound of the formula (I-45) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 271 | A compound of the formula (I-46) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 272 | A compound of the formula (I-46) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 273 | A compound of the formula (I-46) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 274 | A compound of the formula (I-46) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 275 | A compound of the formula (I-46) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 276 | A compound of the formula (I-46) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 277 | A compound of the formula (I-47) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 278 | A compound of the formula (I-47) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 279 | A compound of the formula (I-47) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 280 | A compound of the formula (I-47) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 281 | A compound of the formula (I-47) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 282 | A compound of the formula (I-47) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |

| | |
|---|---|
| Table 283 | A compound of the formula (I-48) wherein $R_1$ is sec-butyl or isopropyl, the configuration of the carbon atom at the ε position is (R), and the substituents $R_2$, $R_3$, $R_4$, $R_5$, and $R_6$ correspond to a line 1 to 439 of Table X. |
| Table 284 | A compound of the formula (I-48) wherein $R_1$ is sec-butyl or isopropyl, the configuration of the carbon atom at the ε position is (S), and the substituents $R_2$, $R_3$, $R_4$, $R_5$, and $R_6$ correspond to a line 1 to 439 of Table X. |
| Table 285 | A compound of the formula (I-48) wherein $R_1$ is cyclohexyl, the configuration of the carbon atom at the ε position is (R), and the substituents $R_2$, $R_3$, $R_4$, $R_5$, and $R_6$ correspond to a line 1 to 439 of Table X. |
| Table 286 | A compound of the formula (I-48) wherein $R_1$ is cyclohexyl, the configuration of the carbon atom at the ε position is (S), and the substituents $R_2$, $R_3$, $R_4$, $R_5$, and $R_6$ correspond to a line 1 to 439 of Table X. |
| Table 287 | A compound of the formula (I-48) wherein $R_1$ is 1-methyl butyl, the configuration of the carbon atom at the ε position is (R), and the substituents $R_2$, $R_3$, $R_4$, $R_5$, and $R_6$ correspond to a line 1 to 439 of Table X. |
| Table 288 | A compound of the formula (I-48) wherein $R_1$ is 1-methyl butyl, the configuration of the carbon atom at the ε position is (S), and the substituents $R_2$, $R_3$, $R_4$, $R_5$, and $R_6$ correspond to a line 1 to 439 of Table X. |
| Table 289 | A compound of the formula (I-49) wherein $R_1$ is sec-butyl or isopropyl, the configuration of the carbon atom at the ε position is (R), and the substituents $R_2$, $R_3$, $R_4$, $R_5$, and $R_6$ correspond to a line 1 to 439 of Table X. |
| Table 290 | A compound of the formula (I-49) wherein $R_1$ is sec-butyl or isopropyl, the configuration of the carbon atom at the ε position is (S), and the substituents $R_2$, $R_3$, $R_4$, $R_5$, and $R_6$ correspond to a line 1 to 439 of Table X. |
| Table 291 | A compound of the formula (I-49) wherein $R_1$ is cyclohexyl, the configuration of the carbon atom at the ε position is (R), and the substituents $R_2$, $R_3$, $R_4$, $R_5$, and $R_6$ correspond to a line 1 to 439 of Table X. |
| Table 292 | A compound of the formula (I-49) wherein $R_1$ is cyclohexyl, the configuration of the carbon atom at the ε position is (S), and the substituents $R_2$, $R_3$, $R_4$, $R_5$, and $R_6$ correspond to a line 1 to 439 of Table X. |
| Table 293 | A compound of the formula (I-49) wherein $R_1$ is 1-methyl butyl, the configuration of the carbon atom at the ε position is (R), and the substituents $R_2$, $R_3$, $R_4$, $R_5$, and $R_6$ correspond to a line 1 to 439 of Table X. |
| Table 294 | A compound of the formula (I-49) wherein $R_1$ is 1-methyl butyl, the configuration of the carbon atom at the ε position is (S), and the substituents $R_2$, $R_3$, $R_4$, $R_5$, and $R_6$ correspond to a line 1 to 439 of Table X. |
| Table 295 | A compound of the formula (I-50) wherein $R_1$ is sec-butyl or isopropyl, the configuration of the carbon atom at the ε position is (R), and the substituents $R_2$, $R_3$, $R_4$, $R_5$, and $R_6$ correspond to a line 1 to 439 of Table X. |
| Table 296 | A compound of the formula (I-50) wherein $R_1$ is sec-butyl or isopropyl, the configuration of the carbon atom at the ε position is (S), and the substituents $R_2$, $R_3$, $R_4$, $R_5$, and $R_6$ correspond to a line 1 to 439 of Table X. |
| Table 297 | A compound of the formula (I-50) wherein $R_1$ is cyclohexyl, the configuration of the carbon atom at the ε position is (R), and the substituents $R_2$, $R_3$, $R_4$, $R_5$, and $R_6$ correspond to a line 1 to 439 of Table X. |
| Table 298 | A compound of the formula (I-50) wherein $R_1$ is cyclohexyl, the configuration of the carbon atom at the ε position is (S), and the substituents $R_2$, $R_3$, $R_4$, $R_5$, and $R_6$ correspond to a line 1 to 439 of Table X. |
| Table 299 | A compound of the formula (I-50) wherein $R_1$ is 1-methyl butyl, the configuration of the carbon atom at the ε position is (R), and the substituents $R_2$, $R_3$, $R_4$, $R_5$, and $R_6$ correspond to a line 1 to 439 of Table X. |
| Table 300 | A compound of the formula (I-50) wherein $R_1$ is 1-methyl butyl, the configuration of the carbon atom at the ε position is (S), and the substituents $R_2$, $R_3$, $R_4$, $R_5$, and $R_6$ correspond to a line 1 to 439 of Table X. |
| Table 301 | A compound of the formula (I-51) wherein $R_1$ is sec-butyl or isopropyl, the configuration of the carbon atom at the ε position is (R), and the substituents $R_2$, $R_3$, $R_4$, $R_5$, and $R_6$ correspond to a line 1 to 439 of Table X. |
| Table 302 | A compound of the formula (I-51) wherein $R_1$ is sec-butyl or isopropyl, the configuration of the carbon atom at the ε position is (S), and the substituents $R_2$, $R_3$, $R_4$, $R_5$, and $R_6$ correspond to a line 1 to 439 of Table X. |
| Table 303 | A compound of the formula (I-51) wherein $R_1$ is cyclohexyl, the configuration of the carbon atom at the ε position is (R), and the substituents $R_2$, $R_3$, $R_4$, $R_5$, and $R_6$ correspond to a line 1 to 439 of Table X. |
| Table 304 | A compound of the formula (I-51) wherein $R_1$ is cyclohexyl, the configuration of the carbon atom at the ε position is (S), and the substituents $R_2$, $R_3$, $R_4$, $R_5$, and $R_6$ correspond to a line 1 to 439 of Table X. |
| Table 305 | A compound of the formula (I-51) wherein $R_1$ is 1-methyl butyl, the configuration of the carbon atom at the ε position is (R), and the substituents $R_2$, $R_3$, $R_4$, $R_5$, and $R_6$ correspond to a line 1 to 439 of Table X. |
| Table 306 | A compound of the formula (I-51) wherein $R_1$ is 1-methyl butyl, the configuration of the carbon atom at the ε position is (S), and the substituents $R_2$, $R_3$, $R_4$, $R_5$, and $R_6$ correspond to a line 1 to 439 of Table X. |
| Table 307 | A compound of the formula (I-52) wherein $R_1$ is sec-butyl or isopropyl, the configuration of the carbon atom at the ε position is (R), and the substituents $R_2$, $R_3$, $R_4$, $R_5$, and $R_6$ correspond to a line 1 to 439 of Table X. |
| Table 308 | A compound of the formula (I-52) wherein $R_1$ is sec-butyl or isopropyl, the configuration of the carbon atom at the ε position is (S), and the substituents $R_2$, $R_3$, $R_4$, $R_5$, and $R_6$ correspond to a line 1 to 439 of Table X. |

-continued

| | |
|---|---|
| Table 309 | A compound of the formula (I-52) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 310 | A compound of the formula (I-52) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 311 | A compound of the formula (I-52) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 312 | A compound of the formula (I-52) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 313 | A compound of the formula (I-53) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 314 | A compound of the formula (I-53) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 315 | A compound of the formula (I-53) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 316 | A compound of the formula (I-53) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 317 | A compound of the formula (I-53) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 318 | A compound of the formula (I-53) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 319 | A compound of the formula (I-54) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 320 | A compound of the formula (I-54) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 321 | A compound of the formula (I-54) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 322 | A compound of the formula (I-54) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 323 | A compound of the formula (I-54) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 324 | A compound of the formula (I-54) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 325 | A compound of the formula (I-55) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 326 | A compound of the formula (I-55) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 327 | A compound of the formula (I-55) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 328 | A compound of the formula (I-55) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 329 | A compound of the formula (I-55) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 330 | A compound of the formula (I-55) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 331 | A compound of the formula (I-56) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 332 | A compound of the formula (I-56) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 333 | A compound of the formula (I-56) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 334 | A compound of the formula (I-56) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |

| | |
|---|---|
| Table 335 | A compound of the formula (I-56) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 336 | A compound of the formula (I-56) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 337 | A compound of the formula (I-57) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 338 | A compound of the formula (I-57) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 339 | A compound of the formula (I-57) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 340 | A compound of the formula (I-57) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 341 | A compound of the formula (I-57) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 342 | A compound of the formula (I-57) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 343 | A compound of the formula (I-58) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 344 | A compound of the formula (I-58) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 345 | A compound of the formula (I-58) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 346 | A compound of the formula (I-58) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 347 | A compound of the formula (I-58) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 348 | A compound of the formula (I-58) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 349 | A compound of the formula (I-59) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 350 | A compound of the formula (I-59) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 351 | A compound of the formula (I-59) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 352 | A compound of the formula (I-59) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 353 | A compound of the formula (I-59) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 354 | A compound of the formula (I-59) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 355 | A compound of the formula (I-60) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 356 | A compound of the formula (I-60) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 357 | A compound of the formula (I-60) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 358 | A compound of the formula (I-60) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 359 | A compound of the formula (I-60) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 360 | A compound of the formula (I-60) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |

| | |
|---|---|
| Table 361 | A compound of the formula (I-61) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 362 | A compound of the formula (I-61) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 363 | A compound of the formula (I-61) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 364 | A compound of the formula (I-61) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 365 | A compound of the formula (I-61) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 366 | A compound of the formula (I-61) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 367 | A compound of the formula (I-62) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 368 | A compound of the formula (I-62) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 369 | A compound of the formula (I-62) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 370 | A compound of the formula (I-62) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 371 | A compound of the formula (I-62) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 372 | A compound of the formula (I-62) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 373 | A compound of the formula (I-63) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 374 | A compound of the formula (I-63) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 375 | A compound of the formula (I-63) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 376 | A compound of the formula (I-63) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 377 | A compound of the formula (I-63) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 378 | A compound of the formula (I-63) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 379 | A compound of the formula (I-64) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 380 | A compound of the formula (I-64) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 381 | A compound of the formula (I-64) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 382 | A compound of the formula (I-64) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 383 | A compound of the formula (I-64) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 384 | A compound of the formula (I-64) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 385 | A compound of the formula (I-65) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 386 | A compound of the formula (I-65) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |

| | |
|---|---|
| Table 387 | A compound of the formula (I-65) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 388 | A compound of the formula (I-65) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 389 | A compound of the formula (I-65) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 390 | A compound of the formula (I-65) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 391 | A compound of the formula (I-66) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 392 | A compound of the formula (I-66) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 393 | A compound of the formula (I-66) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 394 | A compound of the formula (I-66) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 395 | A compound of the formula (I-66) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 396 | A compound of the formula (I-66) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 397 | A compound of the formula (I-67) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 398 | A compound of the formula (I-67) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 399 | A compound of the formula (I-67) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 400 | A compound of the formula (I-67) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 401 | A compound of the formula (I-67) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 402 | A compound of the formula (I-67) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 403 | A compound of the formula (I-68) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 404 | A compound of the formula (I-68) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 405 | A compound of the formula (I-68) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 406 | A compound of the formula (I-68) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 407 | A compound of the formula (I-68) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 408 | A compound of the formula (I-68) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 409 | A compound of the formula (I-69) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 410 | A compound of the formula (I-69) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 411 | A compound of the formula (I-69) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 412 | A compound of the formula (I-69) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |

| | |
|---|---|
| Table 413 | A compound of the formula (I-69) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 414 | A compound of the formula (I-69) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 415 | A compound of the formula (I-70) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 416 | A compound of the formula (I-70) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 417 | A compound of the formula (I-70) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 418 | A compound of the formula (I-70) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 419 | A compound of the formula (I-70) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 420 | A compound of the formula (I-70) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 421 | A compound of the formula (I-71) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 422 | A compound of the formula (I-71) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 423 | A compound of the formula (I-71) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 424 | A compound of the formula (I-71) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 425 | A compound of the formula (I-71) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 426 | A compound of the formula (I-71) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 427 | A compound of the formula (I-72) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 428 | A compound of the formula (I-72) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 429 | A compound of the formula (I-72) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 430 | A compound of the formula (I-72) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 431 | A compound of the formula (I-72) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 432 | A compound of the formula (I-72) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 433 | A compound of the formula (I-73) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 434 | A compound of the formula (I-73) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 435 | A compound of the formula (I-73) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 436 | A compound of the formula (I-73) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 437 | A compound of the formula (I-73) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 438 | A compound of the formula (I-73) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |

-continued

| | |
|---|---|
| Table 439 | A compound of the formula (I-74) wherein $R_1$ is sec-butyl or isopropyl, the configuration of the carbon atom at the ϵ position is (R), and the substituents $R_2$, $R_3$, $R_4$, $R_5$, and $R_6$ correspond to a line 1 to 439 of Table X. |
| Table 440 | A compound of the formula (I-74) wherein $R_1$ is sec-butyl or isopropyl, the configuration of the carbon atom at the ϵ position is (S), and the substituents $R_2$, $R_3$, $R_4$, $R_5$, and $R_6$ correspond to a line 1 to 439 of Table X. |
| Table 441 | A compound of the formula (I-74) wherein $R_1$ is cyclohexyl, the configuration of the carbon atom at the ϵ position is (R), and the substituents $R_2$, $R_3$, $R_4$, $R_5$, and $R_6$ correspond to a line 1 to 439 of Table X. |
| Table 442 | A compound of the formula (I-74) wherein $R_1$ is cyclohexyl, the configuration of the carbon atom at the ϵ position is (S), and the substituents $R_2$, $R_3$, $R_4$, $R_5$, and $R_6$ correspond to a line 1 to 439 of Table X. |
| Table 443 | A compound of the formula (I-74) wherein $R_1$ is 1-methyl butyl, the configuration of the carbon atom at the ϵ position is (R), and the substituents $R_2$, $R_3$, $R_4$, $R_5$, and $R_6$ correspond to a line 1 to 439 of Table X. |
| Table 444 | A compound of the formula (I-74) wherein $R_1$ is 1-methyl butyl, the configuration of the carbon atom at the ϵ position is (S), and the substituents $R_2$, $R_3$, $R_4$, $R_5$, and $R_6$ correspond to a line 1 to 439 of Table X. |
| Table 445 | A compound of the formula (I-75) wherein $R_1$ is sec-butyl or isopropyl, the configuration of the carbon atom at the ϵ position is (R), and the substituents $R_2$, $R_3$, $R_4$, $R_5$, and $R_6$ correspond to a line 1 to 439 of Table X. |
| Table 446 | A compound of the formula (I-75) wherein $R_1$ is sec-butyl or isopropyl, the configuration of the carbon atom at the ϵ position is (S), and the substituents $R_2$, $R_3$, $R_4$, $R_5$, and $R_6$ correspond to a line 1 to 439 of Table X. |
| Table 447 | A compound of the formula (I-75) wherein $R_1$ is cyclohexyl, the configuration of the carbon atom at the ϵ position is (R), and the substituents $R_2$, $R_3$, $R_4$, $R_5$, and $R_6$ correspond to a line 1 to 439 of Table X. |
| Table 448 | A compound of the formula (I-75) wherein $R_1$ is cyclohexyl, the configuration of the carbon atom at the ϵ position is (S), and the substituents $R_2$, $R_3$, $R_4$, $R_5$, and $R_6$ correspond to a line 1 to 439 of Table X. |
| Table 449 | A compound of the formula (I-75) wherein $R_1$ is 1-methyl butyl, the configuration of the carbon atom at the ϵ position is (R), and the substituents $R_2$, $R_3$, $R_4$, $R_5$, and $R_6$ correspond to a line 1 to 439 of Table X. |
| Table 450 | A compound of the formula (I-75) wherein $R_1$ is 1-methyl butyl, the configuration of the carbon atom at the ϵ position is (S), and the substituents $R_2$, $R_3$, $R_4$, $R_5$, and $R_6$ correspond to a line 1 to 439 of Table X. |
| Table 451 | A compound of the formula (I-76) wherein $R_1$ is sec-butyl or isopropyl, the configuration of the carbon atom at the ϵ position is (R), and the substituents $R_2$, $R_3$, $R_4$, $R_5$, and $R_6$ correspond to a line 1 to 439 of Table X. |
| Table 452 | A compound of the formula (I-76) wherein $R_1$ is sec-butyl or isopropyl, the configuration of the carbon atom at the ϵ position is (S), and the substituents $R_2$, $R_3$, $R_4$, $R_5$, and $R_6$ correspond to a line 1 to 439 of Table X. |
| Table 453 | A compound of the formula (I-76) wherein $R_1$ is cyclohexyl, the configuration of the carbon atom at the ϵ position is (R), and the substituents $R_2$, $R_3$, $R_4$, $R_5$, and $R_6$ correspond to a line 1 to 439 of Table X. |
| Table 454 | A compound of the formula (I-76) wherein $R_1$ is cyclohexyl, the configuration of the carbon atom at the ϵ position is (S), and the substituents $R_2$, $R_3$, $R_4$, $R_5$, and $R_6$ correspond to a line 1 to 439 of Table X. |
| Table 455 | A compound of the formula (I-76) wherein $R_1$ is 1-methyl butyl, the configuration of the carbon atom at the ϵ position is (R), and the substituents $R_2$, $R_3$, $R_4$, $R_5$, and $R_6$ correspond to a line 1 to 439 of Table X. |
| Table 456 | A compound of the formula (I-76) wherein $R_1$ is 1-methyl butyl, the configuration of the carbon atom at the ϵ position is (S), and the substituents $R_2$, $R_3$, $R_4$, $R_5$, and $R_6$ correspond to a line 1 to 439 of Table X. |
| Table 457 | A compound of the formula (I-77) wherein $R_1$ is sec-butyl or isopropyl, the configuration of the carbon atom at the ϵ position is (R), and the substituents $R_2$, $R_3$, $R_4$, $R_5$, and $R_6$ correspond to a line 1 to 439 of Table X. |
| Table 458 | A compound of the formula (I-77) wherein $R_1$ is sec-butyl or isopropyl, the configuration of the carbon atom at the ϵ position is (S), and the substituents $R_2$, $R_3$, $R_4$, $R_5$, and $R_6$ correspond to a line 1 to 439 of Table X. |
| Table 459 | A compound of the formula (I-77) wherein $R_1$ is cyclohexyl, the configuration of the carbon atom at the ϵ position is (R), and the substituents $R_2$, $R_3$, $R_4$, $R_5$, and $R_6$ correspond to a line 1 to 439 of Table X. |
| Table 460 | A compound of the formula (I-77) wherein $R_1$ is cyclohexyl, the configuration of the carbon atom at the ϵ position is (S), and the substituents $R_2$, $R_3$, $R_4$, $R_5$, and $R_6$ correspond to a line 1 to 439 of Table X. |
| Table 461 | A compound of the formula (I-77) wherein $R_1$ is 1-methyl butyl, the configuration of the carbon atom at the ϵ position is (R), and the substituents $R_2$, $R_3$, $R_4$, $R_5$, and $R_6$ correspond to a line 1 to 439 of Table X. |
| Table 462 | A compound of the formula (I-77) wherein $R_1$ is 1-methyl butyl, the configuration of the carbon atom at the ϵ position is (S), and the substituents $R_2$, $R_3$, $R_4$, $R_5$, and $R_6$ correspond to a line 1 to 439 of Table X. |
| Table 463 | A compound of the formula (I-78) wherein $R_1$ is sec-butyl or isopropyl, the configuration of the carbon atom at the ϵ position is (R), and the substituents $R_2$, $R_3$, $R_4$, $R_5$, and $R_6$ correspond to a line 1 to 439 of Table X. |
| Table 464 | A compound of the formula (I-78) wherein $R_1$ is sec-butyl or isopropyl, the configuration of the carbon atom at the ϵ position is (S), and the substituents $R_2$, $R_3$, $R_4$, $R_5$, and $R_6$ correspond to a line 1 to 439 of Table X. |

| | |
|---|---|
| Table 465 | A compound of the formula (I-78) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 466 | A compound of the formula (I-78) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 467 | A compound of the formula (I-78) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 468 | A compound of the formula (I-78) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 469 | A compound of the formula (I-79) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 470 | A compound of the formula (I-79) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 471 | A compound of the formula (I-79) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 472 | A compound of the formula (I-79) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 473 | A compound of the formula (I-79) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 474 | A compound of the formula (I-79) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 475 | A compound of the formula (I-80) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 476 | A compound of the formula (I-80) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 477 | A compound of the formula (I-80) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 478 | A compound of the formula (I-80) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 479 | A compound of the formula (I-80) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 480 | A compound of the formula (I-80) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 481 | A compound of the formula (I-81) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 482 | A compound of the formula (I-81) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 483 | A compound of the formula (I-81) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 484 | A compound of the formula (I-81) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 485 | A compound of the formula (I-81) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 486 | A compound of the formula (I-81) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 487 | A compound of the formula (I-82) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 488 | A compound of the formula (I-82) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 489 | A compound of the formula (I-82) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 490 | A compound of the formula (I-82) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |

| | |
|---|---|
| Table 491 | A compound of the formula (I-82) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 492 | A compound of the formula (I-82) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 493 | A compound of the formula (I-83) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 494 | A compound of the formula (I-83) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 495 | A compound of the formula (I-83) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 496 | A compound of the formula (I-83) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 497 | A compound of the formula (I-83) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 498 | A compound of the formula (I-83) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 499 | A compound of the formula (I-84) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 500 | A compound of the formula (I-84) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 501 | A compound of the formula (I-84) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 502 | A compound of the formula (I-84) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 503 | A compound of the formula (I-84) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 504 | A compound of the formula (I-84) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 505 | A compound of the formula (I-85) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 506 | A compound of the formula (I-85) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 507 | A compound of the formula (I-85) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 508 | A compound of the formula (I-85) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 509 | A compound of the formula (I-85) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 510 | A compound of the formula (I-85) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 511 | A compound of the formula (I-86) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 512 | A compound of the formula (I-86) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 513 | A compound of the formula (I-86) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 514 | A compound of the formula (I-86) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 515 | A compound of the formula (I-86) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 516 | A compound of the formula (I-86) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |

-continued

| | |
|---|---|
| Table 517 | A compound of the formula (I-87) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 518 | A compound of the formula (I-87) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 519 | A compound of the formula (I-87) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 520 | A compound of the formula (I-87) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 521 | A compound of the formula (I-87) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 522 | A compound of the formula (I-87) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 523 | A compound of the formula (I-88) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 524 | A compound of the formula (I-88) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 525 | A compound of the formula (I-88) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 526 | A compound of the formula (I-88) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 527 | A compound of the formula (I-88) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 528 | A compound of the formula (I-88) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 529 | A compound of the formula (I-89) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 530 | A compound of the formula (I-89) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 531 | A compound of the formula (I-89) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 532 | A compound of the formula (I-89) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 533 | A compound of the formula (I-89) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 534 | A compound of the formula (I-89) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 535 | A compound of the formula (I-90) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 536 | A compound of the formula (I-90) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 537 | A compound of the formula (I-90) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 538 | A compound of the formula (I-90) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 539 | A compound of the formula (I-90) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 540 | A compound of the formula (I-90) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 541 | A compound of the formula (I-91) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 542 | A compound of the formula (I-91) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |

| | |
|---|---|
| Table 543 | A compound of the formula (I-91) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 544 | A compound of the formula (I-91) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 545 | A compound of the formula (I-91) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 546 | A compound of the formula (I-91) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 547 | A compound of the formula (I-92) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 548 | A compound of the formula (I-92) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 549 | A compound of the formula (I-92) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 550 | A compound of the formula (I-92) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 551 | A compound of the formula (I-92) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 552 | A compound of the formula (I-92) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 553 | A compound of the formula (I-93) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 554 | A compound of the formula (I-93) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 555 | A compound of the formula (I-93) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 556 | A compound of the formula (I-93) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 557 | A compound of the formula (I-93) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 558 | A compound of the formula (I-93) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 559 | A compound of the formula (I-94) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 560 | A compound of the formula (I-94) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 561 | A compound of the formula (I-94) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 562 | A compound of the formula (I-94) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 563 | A compound of the formula (I-94) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 564 | A compound of the formula (I-94) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 565 | A compound of the formula (I-95) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 566 | A compound of the formula (I-95) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 567 | A compound of the formula (I-95) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 568 | A compound of the formula (I-95) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |

| | |
|---|---|
| Table 569 | A compound of the formula (I-95) wherein $R_1$ is 1-methyl butyl, the configuration of the carbon atom at the ε position is (R), and the substituents $R_2$, $R_3$, $R_4$, $R_5$, and $R_6$ correspond to a line 1 to 439 of Table X. |
| Table 570 | A compound of the formula (I-95) wherein $R_1$ is 1-methyl butyl, the configuration of the carbon atom at the ε position is (S), and the substituents $R_2$, $R_3$, $R_4$, $R_5$, and $R_6$ correspond to a line 1 to 439 of Table X. |
| Table 571 | A compound of the formula (I-96) wherein $R_1$ is sec-butyl or isopropyl, the configuration of the carbon atom at the ε position is (R), and the substituents $R_2$, $R_3$, $R_4$, $R_5$, and $R_6$ correspond to a line 1 to 439 of Table X. |
| Table 572 | A compound of the formula (I-96) wherein $R_1$ is sec-butyl or isopropyl, the configuration of the carbon atom at the ε position is (S), and the substituents $R_2$, $R_3$, $R_4$, $R_5$, and $R_6$ correspond to a line 1 to 439 of Table X. |
| Table 573 | A compound of the formula (I-96) wherein $R_1$ is cyclohexyl, the configuration of the carbon atom at the ε position is (R), and the substituents $R_2$, $R_3$, $R_4$, $R_5$, and $R_6$ correspond to a line 1 to 439 of Table X. |
| Table 574 | A compound of the formula (I-96) wherein $R_1$ is cyclohexyl, the configuration of the carbon atom at the ε position is (S), and the substituents $R_2$, $R_3$, $R_4$, $R_5$, and $R_6$ correspond to a line 1 to 439 of Table X. |
| Table 575 | A compound of the formula (I-96) wherein $R_1$ is 1-methyl butyl, the configuration of the carbon atom at the ε position is (R), and the substituents $R_2$, $R_3$, $R_4$, $R_5$, and $R_6$ correspond to a line 1 to 439 of Table X. |
| Table 576 | A compound of the formula (I-96) wherein $R_1$ is 1-methyl butyl, the configuration of the carbon atom at the ε position is (S), and the substituents $R_2$, $R_3$, $R_4$, $R_5$, and $R_6$ correspond to a line 1 to 439 of Table X. |
| Table 577 | A compound of the formula (I-97) wherein $R_1$ is sec-butyl or isopropyl, the configuration of the carbon atom at the ε position is (R), and the substituents $R_2$, $R_3$, $R_4$, $R_5$, and $R_6$ correspond to a line 1 to 439 of Table X. |
| Table 578 | A compound of the formula (I-97) wherein $R_1$ is sec-butyl or isopropyl, the configuration of the carbon atom at the ε position is (S), and the substituents $R_2$, $R_3$, $R_4$, $R_5$, and $R_6$ correspond to a line 1 to 439 of Table X. |
| Table 579 | A compound of the formula (I-97) wherein $R_1$ is cyclohexyl, the configuration of the carbon atom at the ε position is (R), and the substituents $R_2$, $R_3$, $R_4$, $R_5$, and $R_6$ correspond to a line 1 to 439 of Table X. |
| Table 580 | A compound of the formula (I-97) wherein $R_1$ is cyclohexyl, the configuration of the carbon atom at the ε position is (S), and the substituents $R_2$, $R_3$, $R_4$, $R_5$, and $R_6$ correspond to a line 1 to 439 of Table X. |
| Table 581 | A compound of the formula (I-97) wherein $R_1$ is 1-methyl butyl, the configuration of the carbon atom at the ε position is (R), and the substituents $R_2$, $R_3$, $R_4$, $R_5$, and $R_6$ correspond to a line 1 to 439 of Table X. |
| Table 582 | A compound of the formula (I-97) wherein $R_1$ is 1-methyl butyl, the configuration of the carbon atom at the ε position is (S), and the substituents $R_2$, $R_3$, $R_4$, $R_5$, and $R_6$ correspond to a line 1 to 439 of Table X. |
| Table 583 | A compound of the formula (I-98) wherein $R_1$ is sec-butyl or isopropyl, the configuration of the carbon atom at the ε position is (R), and the substituents $R_2$, $R_3$, $R_4$, $R_5$, and $R_6$ correspond to a line 1 to 439 of Table X. |
| Table 584 | A compound of the formula (I-98) wherein $R_1$ is sec-butyl or isopropyl, the configuration of the carbon atom at the ε position is (S), and the substituents $R_2$, $R_3$, $R_4$, $R_5$, and $R_6$ correspond to a line 1 to 439 of Table X. |
| Table 585 | A compound of the formula (I-98) wherein $R_1$ is cyclohexyl, the configuration of the carbon atom at the ε position is (R), and the substituents $R_2$, $R_3$, $R_4$, $R_5$, and $R_6$ correspond to a line 1 to 439 of Table X. |
| Table 586 | A compound of the formula (I-98) wherein $R_1$ is cyclohexyl, the configuration of the carbon atom at the ε position is (S), and the substituents $R_2$, $R_3$, $R_4$, $R_5$, and $R_6$ correspond to a line 1 to 439 of Table X. |
| Table 587 | A compound of the formula (I-98) wherein $R_1$ is 1-methyl butyl, the configuration of the carbon atom at the ε position is (R), and the substituents $R_2$, $R_3$, $R_4$, $R_5$, and $R_6$ correspond to a line 1 to 439 of Table X. |
| Table 588 | A compound of the formula (I-98) wherein $R_1$ is 1-methyl butyl, the configuration of the carbon atom at the ε position is (S), and the substituents $R_2$, $R_3$, $R_4$, $R_5$, and $R_6$ correspond to a line 1 to 439 of Table X. |
| Table 589 | A compound of the formula (I-99) wherein $R_1$ is sec-butyl or isopropyl, the configuration of the carbon atom at the ε position is (R), and the substituents $R_2$, $R_3$, $R_4$, $R_5$, and $R_6$ correspond to a line 1 to 439 of Table X. |
| Table 590 | A compound of the formula (I-99) wherein $R_1$ is sec-butyl or isopropyl, the configuration of the carbon atom at the ε position is (S), and the substituents $R_2$, $R_3$, $R_4$, $R_5$, and $R_6$ correspond to a line 1 to 439 of Table X. |
| Table 591 | A compound of the formula (I-99) wherein $R_1$ is cyclohexyl, the configuration of the carbon atom at the ε position is (R), and the substituents $R_2$, $R_3$, $R_4$, $R_5$, and $R_6$ correspond to a line 1 to 439 of Table X. |
| Table 592 | A compound of the formula (I-99) wherein $R_1$ is cyclohexyl, the configuration of the carbon atom at the ε position is (S), and the substituents $R_2$, $R_3$, $R_4$, $R_5$, and $R_6$ correspond to a line 1 to 439 of Table X. |
| Table 593 | A compound of the formula (I-99) wherein $R_1$ is 1-methyl butyl, the configuration of the carbon atom at the ε position is (R), and the substituents $R_2$, $R_3$, $R_4$, $R_5$, and $R_6$ correspond to a line 1 to 439 of Table X. |
| Table 594 | A compound of the formula (I-99) wherein $R_1$ is 1-methyl butyl, the configuration of the carbon atom at the ε position is (S), and the substituents $R_2$, $R_3$, $R_4$, $R_5$, and $R_6$ correspond to a line 1 to 439 of Table X. |

-continued

| | |
|---|---|
| Table 595 | A compound of the formula (I-100) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 596 | A compound of the formula (I-100) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 597 | A compound of the formula (I-100) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 598 | A compound of the formula (I-100) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 599 | A compound of the formula (I-100) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 600 | A compound of the formula (I-100) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 601 | A compound of the formula (I-101) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 602 | A compound of the formula (I-101) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 603 | A compound of the formula (I-101) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 604 | A compound of the formula (I-101) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 605 | A compound of the formula (I-101) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 606 | A compound of the formula (I-101) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 607 | A compound of the formula (I-102) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 608 | A compound of the formula (I-102) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 609 | A compound of the formula (I-102) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 610 | A compound of the formula (I-102) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 611 | A compound of the formula (I-102) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 612 | A compound of the formula (I-102) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 613 | A compound of the formula (I-103) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 614 | A compound of the formula (I-103) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 615 | A compound of the formula (I-103) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 616 | A compound of the formula (I-103) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 617 | A compound of the formula (I-103) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 618 | A compound of the formula (I-103) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 619 | A compound of the formula (I-104) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 620 | A compound of the formula (I-104) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |

| | |
|---|---|
| Table 621 | A compound of the formula (I-104) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 622 | A compound of the formula (I-104) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 623 | A compound of the formula (I-104) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 624 | A compound of the formula (I-104) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 625 | A compound of the formula (I-105) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 626 | A compound of the formula (I-105) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 627 | A compound of the formula (I-105) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 628 | A compound of the formula (I-105) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 629 | A compound of the formula (I-105) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 630 | A compound of the formula (I-105) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 631 | A compound of the formula (I-106) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 632 | A compound of the formula (I-106) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 633 | A compound of the formula (I-106) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 634 | A compound of the formula (I-106) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 635 | A compound of the formula (I-106) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 636 | A compound of the formula (I-106) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 637 | A compound of the formula (I-107) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 638 | A compound of the formula (I-107) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 639 | A compound of the formula (I-107) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 640 | A compound of the formula (I-107) wherein $R_1$ is cyclohexyl, the configuration of the carbon atom at the $\epsilon$ position is (S), and the substituents $R_2$, $R_3$, $R_4$, $R_5$, and $R_6$ corresponds to a line 1 to 439 of Table X. |
| Table 641 | A compound of the formula (I-107) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 642 | A compound of the formula (I-107) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 643 | A compound of the formula (I-108) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 644 | A compound of the formula (I-108) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 645 | A compound of the formula (I-108) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 646 | A compound of the formula (I-108) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |

-continued

| | |
|---|---|
| Table 647 | A compound of the formula (I-108) wherein $R_1$ is 1-methyl butyl, the configuration of the carbon atom at the ε position is (R), and the substituents $R_2$, $R_3$, $R_4$, $R_5$, and $R_6$ correspond to a line 1 to 439 of Table X. |
| Table 648 | A compound of the formula (I-108) wherein $R_1$ is 1-methyl butyl, the configuration of the carbon atom at the ε position is (S), and the substituents $R_2$, $R_3$, $R_4$, $R_5$, and $R_6$ correspond to a line 1 to 439 of Table X. |
| Table 649 | A compound of the formula (I-109) wherein $R_1$ is sec-butyl or isopropyl, the configuration of the carbon atom at the ε position is (R), and the substituents $R_2$, $R_3$, $R_4$, $R_5$, and $R_6$ correspond to a line 1 to 439 of Table X. |
| Table 650 | A compound of the formula (I-109) wherein $R_1$ is sec-butyl or isopropyl, the configuration of the carbon atom at the ε position is (S), and the substituents $R_2$, $R_3$, $R_4$, $R_5$, and $R_6$ correspond to a line 1 to 439 of Table X. |
| Table 651 | A compound of the formula (I-109) wherein $R_1$ is cyclohexyl, the configuration of the carbon atom at the ε position is (R), and the substituents $R_2$, $R_3$, $R_4$, $R_5$, and $R_6$ correspond to a line 1 to 439 of Table X. |
| Table 652 | A compound of the formula (I-109) wherein $R_1$ is cyclohexyl, the configuration of the carbon atom at the ε position is (S), and the substituents $R_2$, $R_3$, $R_4$, $R_5$, and $R_6$ correspond to a line 1 to 439 of Table X. |
| Table 653 | A compound of the formula (I-109) wherein $R_1$ is 1-methyl butyl, the configuration of the carbon atom at the ε position is (R), and the substituents $R_2$, $R_3$, $R_4$, $R_5$, and $R_6$ correspond to a line 1 to 439 of Table X. |
| Table 654 | A compound of the formula (I-109) wherein $R_1$ is 1-methyl butyl, the configuration of the carbon atom at the ε position is (S), and the substituents $R_2$, $R_3$, $R_4$, $R_5$, and $R_6$ correspond to a line 1 to 439 of Table X. |
| Table 655 | A compound of the formula (I-110) wherein $R_1$ is sec-butyl or isopropyl, the configuration of the carbon atom at the ε position is (R), and the substituents $R_2$, $R_3$, $R_4$, $R_5$, and $R_6$ correspond to a line 1 to 439 of Table X. |
| Table 656 | A compound of the formula (I-110) wherein $R_1$ is sec-butyl or isopropyl, the configuration of the carbon atom at the ε position is (S), and the substituents $R_2$, $R_3$, $R_4$, $R_5$, and $R_6$ correspond to a line 1 to 439 of Table X. |
| Table 657 | A compound of the formula (I-110) wherein $R_1$ is cyclohexyl, the configuration of the carbon atom at the ε position is (R), and the substituents $R_2$, $R_3$, $R_4$, $R_5$, and $R_6$ correspond to a line 1 to 439 of Table X. |
| Table 658 | A compound of the formula (I-110) wherein $R_1$ is cyclohexyl, the configuration of the carbon atom at the ε position is (S), and the substituents $R_2$, $R_3$, $R_4$, $R_5$, and $R_6$ correspond to a line 1 to 439 of Table X. |
| Table 659 | A compound of the formula (I-110) wherein $R_1$ is 1-methyl butyl, the configuration of the carbon atom at the ε position is (R), and the substituents $R_2$, $R_3$, $R_4$, $R_5$, and $R_6$ correspond to a line 1 to 439 of Table X. |
| Table 660 | A compound of the formula (I-110) wherein $R_1$ is 1-methyl butyl, the configuration of the carbon atom at the ε position is (S), and the substituents $R_2$, $R_3$, $R_4$, $R_5$, and $R_6$ correspond to a line 1 to 439 of Table X. |
| Table 661 | A compound of the formula (I-111) wherein $R_1$ is sec-butyl or isopropyl, the configuration of the carbon atom at the ε position is (R), and the substituents $R_2$, $R_3$, $R_4$, $R_5$, and $R_6$ correspond to a line 1 to 439 of Table X. |
| Table 662 | A compound of the formula (I-111) wherein $R_1$ is sec-butyl or isopropyl, the configuration of the carbon atom at the ε position is (S), and the substituents $R_2$, $R_3$, $R_4$, $R_5$, and $R_6$ correspond to a line 1 to 439 of Table X. |
| Table 663 | A compound of the formula (I-111) wherein $R_1$ is cyclohexyl, the configuration of the carbon atom at the ε position is (R), and the substituents $R_2$, $R_3$, $R_4$, $R_5$, and $R_6$ correspond to a line 1 to 439 of Table X. |
| Table 664 | A compound of the formula (I-111) wherein $R_1$ is cyclohexyl, the configuration of the carbon atom at the ε position is (S), and the substituents $R_2$, $R_3$, $R_4$, $R_5$, and $R_6$ correspond to a line 1 to 439 of Table X. |
| Table 665 | A compound of the formula (I-111) wherein $R_1$ is 1-methyl butyl, the configuration of the carbon atom at the ε position is (R), and the substituents $R_2$, $R_3$, $R_4$, $R_5$, and $R_6$ correspond to a line 1 to 439 of Table X. |
| Table 666 | A compound of the formula (I-111) wherein $R_1$ is 1-methyl butyl, the configuration of the carbon atom at the ε position is (S), and the substituents $R_2$, $R_3$, $R_4$, $R_5$, and $R_6$ correspond to a line 1 to 439 of Table X. |
| Table 667 | A compound of the formula (I-112) wherein $R_1$ is sec-butyl or isopropyl, the configuration of the carbon atom at the ε position is (R), and the substituents $R_2$, $R_3$, $R_4$, $R_5$, and $R_6$ correspond to a line 1 to 439 of Table X. |
| Table 668 | A compound of the formula (I-112) wherein $R_1$ is sec-butyl or isopropyl, the configuration of the carbon atom at the ε position is (S), and the substituents $R_2$, $R_3$, $R_4$, $R_5$, and $R_6$ correspond to a line 1 to 439 of Table X. |
| Table 669 | A compound of the formula (I-112) wherein $R_1$ is cyclohexyl, the configuration of the carbon atom at the ε position is (R), and the substituents $R_2$, $R_3$, $R_4$, $R_5$, and $R_6$ correspond to a line 1 to 439 of Table X. |
| Table 670 | A compound of the formula (I-112) wherein $R_1$ is cyclohexyl, the configuration of the carbon atom at the ε position is (S), and the substituents $R_2$, $R_3$, $R_4$, $R_5$, and $R_6$ correspond to a line 1 to 439 of Table X. |
| Table 671 | A compound of the formula (I-112) wherein $R_1$ is 1-methyl butyl, the configuration of the carbon atom at the ε position is (R), and the substituents $R_2$, $R_3$, $R_4$, $R_5$, and $R_6$ correspond to a line 1 to 439 of Table X. |
| Table 672 | A compound of the formula (I-112) wherein $R_1$ is 1-methyl butyl, the configuration of the carbon atom at the ε position is (S), and the substituents $R_2$, $R_3$, $R_4$, $R_5$, and $R_6$ correspond to a line 1 to 439 of Table X. |

| Table 673 | A compound of the formula (I-113) wherein $R_1$ is sec-butyl or isopropyl, the configuration of the carbon atom at the ε position is (R), and the substituents $R_2$, $R_3$, $R_4$, $R_5$, and $R_6$ correspond to a line 1 to 439 of Table X. |
|---|---|
| Table 674 | A compound of the formula (I-113) wherein $R_1$ is sec-butyl or isopropyl, the configuration of the carbon atom at the ε position is (S), and the substituents $R_2$, $R_3$, $R_4$, $R_5$, and $R_6$ correspond to a line 1 to 439 of Table X. |
| Table 675 | A compound of the formula (I-110) wherein $R_1$ is cyclohexyl, the configuration of the carbon atom at the ε position is (R), and the substituents $R_2$, $R_3$, $R_4$, $R_5$, and $R_6$ correspond to a line 1 to 439 of Table X. |
| Table 676 | A compound of the formula (I-113) wherein $R_1$ is cyclohexyl, the configuration of the carbon atom at the ε position is (S), and the substituents $R_2$, $R_3$, $R_4$, $R_5$, and $R_6$ correspond to a line 1 to 439 of Table X. |
| Table 677 | A compound of the formula (I-113) wherein $R_1$ is 1-methyl butyl, the configuration of the carbon atom at the ε position is (R), and the substituents $R_2$, $R_3$, $R_4$, $R_5$, and $R_6$ correspond to a line 1 to 439 of Table X. |
| Table 678 | A compound of the formula (I-113) wherein $R_1$ is 1-methyl butyl, the configuration of the carbon atom at the ε position is (S), and the substituents $R_2$, $R_3$, $R_4$, $R_5$, and $R_6$ correspond to a line 1 to 439 of Table X. |
| Table 679 | A compound of the formula (I-114) wherein $R_1$ is sec-butyl or isopropyl, the configuration of the carbon atom at the ε position is (R), and the substituents $R_2$, $R_3$, $R_4$, $R_5$, and $R_6$ correspond to a line 1 to 439 of Table X. |
| Table 680 | A compound of the formula (I-114) wherein $R_1$ is sec-butyl or isopropyl, the configuration of the carbon atom at the ε position is (S), and the substituents $R_2$, $R_3$, $R_4$, $R_5$, and $R_6$ correspond to a line 1 to 439 of Table X. |
| Table 681 | A compound of the formula (I-114) wherein $R_1$ is cyclohexyl, the configuration of the carbon atom at the ε position is (R), and the substituents $R_2$, $R_3$, $R_4$, $R_5$, and $R_6$ correspond to a line 1 to 439 of Table X. |
| Table 682 | A compound of the formula (I-114) wherein $R_1$ is cyclohexyl, the configuration of the carbon atom at the ε position is (S), and the substituents $R_2$, $R_3$, $R_4$, $R_5$, and $R_6$ correspond to a line 1 to 439 of Table X. |
| Table 683 | A compound of the formula (I-114) wherein $R_1$ is 1-methyl butyl, the configuration of the carbon atom at the ε position is (R), and the substituents $R_2$, $R_3$, $R_4$, $R_5$, and $R_6$ correspond to a line 1 to 439 of Table X. |
| Table 684 | A compound of the formula (I-114) wherein $R_1$ is 1-methyl butyl, the configuration of the carbon atom at the ε position is (S), and the substituents $R_2$, $R_3$, $R_4$, $R_5$, and $R_6$ correspond to a line 1 to 439 of Table X. |
| Table 685 | A compound of the formula (I-115) wherein $R_1$ is sec-butyl or isopropyl, the configuration of the carbon atom at the ε position is (R), and the substituents $R_2$, $R_3$, $R_4$, $R_5$, and $R_6$ correspond to a line 1 to 439 of Table X. |
| Table 686 | A compound of the formula (I-115) wherein $R_1$ is sec-butyl or isopropyl, the configuration of the carbon atom at the ε position is (S), and the substituents $R_2$, $R_3$, $R_4$, $R_5$, and $R_6$ correspond to a line 1 to 439 of Table X. |
| Table 687 | A compound of the formula (I-115) wherein $R_1$ is cyclohexyl, the configuration of the carbon atom at the ε position is (R), and the substituents $R_2$, $R_3$, $R_4$, $R_5$, and $R_6$ correspond to a line 1 to 439 of Table X. |
| Table 688 | A compound of the formula (I-115) wherein $R_1$ is cyclohexyl, the configuration of the carbon atom at the ε position is (S), and the substituents $R_2$, $R_3$, $R_4$, $R_5$, and $R_6$ correspond to a line 1 to 439 of Table X. |
| Table 689 | A compound of the formula (I-115) wherein $R_1$ is 1-methyl butyl, the configuration of the carbon atom at the ε position is (R), and the substituents $R_2$, $R_3$, $R_4$, $R_5$, and $R_6$ correspond to a line 1 to 439 of Table X. |
| Table 690 | A compound of the formula (I-115) wherein $R_1$ is 1-methyl butyl, the configuration of the carbon atom at the ε position is (S), and the substituents $R_2$, $R_3$, $R_4$, $R_5$, and $R_6$ correspond to a line 1 to 439 of Table X. |
| Table 691 | A compound of the formula (I-116) wherein $R_1$ is sec-butyl or isopropyl, the configuration of the carbon atom at the ε position is (R), and the substituents $R_2$, $R_3$, $R_4$, $R_5$, and $R_6$ correspond to a line 1 to 439 of Table X. |
| Table 692 | A compound of the formula (I-116) wherein $R_1$ is sec-butyl or isopropyl, the configuration of the carbon atom at the ε position is (S), and the substituents $R_2$, $R_3$, $R_4$, $R_5$, and $R_6$ corresponds to a line 1 to 439 of Table X. |
| Table 693 | A compound of the formula (I-116) wherein $R_1$ is cyclohexyl, the configuration of the carbon atom at the ε position is (R), and the substituents $R_2$, $R_3$, $R_4$, $R_5$, and $R_6$ correspond to a line 1 to 439 of Table X. |
| Table 694 | A compound of the formula (I-116) wherein $R_1$ is cyclohexyl, the configuration of the carbon atom at the ε position is (S), and the substituents $R_2$, $R_3$, $R_4$, $R_5$, and $R_6$ correspond to a line 1 to 439 of Table X. |
| Table 695 | A compound of the formula (I-116) wherein $R_1$ is 1-methyl butyl, the configuration of the carbon atom at the ε position is (R), and the substituents $R_2$, $R_3$, $R_4$, $R_5$, and $R_6$ correspond to a line 1 to 439 of Table X. |
| Table 696 | A compound of the formula (I-116) wherein $R_1$ is 1-methyl butyl, the configuration of the carbon atom at the ε position is (S), and the substituents $R_2$, $R_3$, $R_4$, $R_5$, and $R_6$ correspond to a line 1 to 439 of Table X. |
| Table 697 | A compound of the formula (I-117) wherein $R_1$ is sec-butyl or isopropyl, the configuration of the carbon atom at the ε position is (R), and the substituents $R_2$, $R_3$, $R_4$, $R_5$, and $R_6$ correspond to a line 1 to 439 of Table X. |
| Table 698 | A compound of the formula (I-117) wherein $R_1$ is sec-butyl or isopropyl, the configuration of the carbon atom at the ε position is (S), and the substituents $R_2$, $R_3$, $R_4$, $R_5$, and $R_6$ correspond to a line 1 to 439 of Table X. |

| | |
|---|---|
| Table 699 | A compound of the formula (I-117) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 700 | A compound of the formula (I-117) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 701 | A compound of the formula (I-117) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 702 | A compound of the formula (I-117) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 703 | A compound of the formula (I-118) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 704 | A compound of the formula (I-118) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 705 | A compound of the formula (I-118) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 706 | A compound of the formula (I-118) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 707 | A compound of the formula (I-118) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 708 | A compound of the formula (I-118) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 709 | A compound of the formula (I-119) wherein $R_1$ is sec-butyl or isopropyl, the configuration of the carbon atom at the $\epsilon$ position is (R), and the substituents $R_2$, $R_3$, $R_4$, $R_5$, and $R_6$ corresponds to a line 1 to 439 of Table X. |
| Table 710 | A compound of the formula (I-119) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 711 | A compound of the formula (I-119) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 712 | A compound of the formula (I-119) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 713 | A compound of the formula (I-119) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 714 | A compound of the formula (I-119) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |
| Table 715 | A compound of the formula (I-120) wherein $R_1$ is sec-butyl or isopropyl, the configuration of the carbon atom at the $\epsilon$ position is (R), and the substituents $R_2$, $R_3$, $R_4$, $R_5$, and $R_6$ correspond to a line 1 to 439 of Table X. |
| Table 716 | A compound of the formula (I-120) wherein $R_1$ is sec-butyl or isopropyl, the configuration of the carbon atom at the $\epsilon$ position is (S), and the substituents $R_2$, $R_3$, $R_4$, $R_5$, and $R_6$ correspond to a line 1 to 439 of Table X. |
| Table 717 | A compound of the formula (I-120) wherein $R_1$ is cyclohexyl, the configuration of the carbon atom at the $\epsilon$ position is (R), and the substituents $R_2$, $R_3$, $R_4$, $R_5$, and $R_6$ correspond to a line 1 to 439 of Table X. |
| Table 718 | A compound of the formula (I-120) wherein $R_1$ is cyclohexyl, the configuration of the carbon atom at the $\epsilon$ position is (S), and the substituents $R_2$, $R_3$, $R_4$, $R_5$, and $R_6$ correspond to a line 1 to 439 of Table X. |
| Table 719 | A compound of the formula (I-120) wherein $R_1$ is 1-methyl butyl, the configuration of the carbon atom at the $\epsilon$ position is (R), and the substituents $R_2$, $R_3$, $R_4$, $R_5$, and $R_6$ correspond to a line 1 to 439 of Table X. |
| Table 720 | A compound of the formula (I-120) wherein $R_1$ is 1-methyl butyl, the configuration of the carbon atom at the $\epsilon$ position is (S), and the substituents $R_2$, $R_3$, $R_4$, $R_5$, and $R_6$ correspond to a line 1 to 439 of Table X. |

In the area of pest control, especially for non-therapeutic applications, a compound of formula (I), or (II), is an active compound (also referred to as active ingredient) exhibiting valuable preventive and/or curative activity with a very advantageous biocidal spectrum and a very broad spectrum, even at low rates of concentration, while being well tolerated by warm-blooded animals, fish and plants. They are, surprisingly, equally suitable for controlling plant pests, and ecto- and endo-parasites in humans, in productive livestock, and domestic animals and pets. They are effective against all or individual development stages of normally sensitive animal pests, but also of resistant animal pests, such as representatives of the class insecta, order Acarina, class nematoda, cestodes and trematodes, while at the same time protecting useful organisms. The insecticidal, acaricidal or nematicidal activity of the active ingredients according to the invention may manifest itself directly, i.e., in the mortality of the pests, which occurs immediately or only after some time, for example during moulting, or indirectly, for example in reduced oviposition and/or hatching rate, good activity corresponding to a mortality of at least 50 to 60

Successful control within the scope of the subject of the invention is possible, in particular, of pests from the orders Lepidoptera, Coleoptera, Orthoptera, Isoptera, Psocoptera, Anoplura, Mallophaga, Thysanoptera, Heteroptera, Homoptera, Hymenoptera, Diptera, Siphonaptera, Thysanura and Acarina, mainly Acarina, Thysanura, Diptera, Lepidoptera and Coleoptera. Very especially good control is possible of the following pests:

*Abagrotis* spp., *Abraxas* spp., *Acantholeucania* spp., *Acanthoplusia* spp., *Acarus* spp., *Acarus siro*, *Aceria* spp., *Aceria sheldoni*, *Acleris* spp., *Acoloithus* spp., *Acompsia* spp., *Acossus* spp., *Acria* spp., *Acrobasis* spp., *Acrocercops* spp., *Acrolepia* spp., *Acrolepiopsis* spp., *Acronicta* spp., *Acropolitis* spp., *Actebia* spp., *Aculus* spp., *Aculus schlechtendali*, *Adoxophyes* spp., *Adoxophyes reticulana*, *Aedes* spp., *Aegeria* spp., *Aethes* spp., *Agapeta* spp., *Agonopterix* spp., *Agriopis* spp., *Agriotes* spp., *Agriphila* spp., *Agrochola* spp., *Agroperina* spp., *Alabama* ssp., *Alabama argillaceae*, *Agrotis* spp., *Albuna* spp., *Alcathoe* spp., *Alcis* spp., *Aleimma* spp., *Aletia* spp., *Aleurothrixus* spp., *Aleurothrixus floccosus*, *Aleyrodes* spp., *Aleyrodes brassicae*, *Allophyes* spp., *Alsophila* spp., *Amata* spp., *Amathes* spp., *Amblyomma* spp., *Amblyptilia* spp., *Ammoconia* spp., *Amorbia* spp., *Amphion* spp., *Amphipoea* spp., *Amphipyra* spp., *Amyelois* spp., *Anacampstodes* spp., *Anagrapha* spp., *Anarsia* spp., *Anatrychyntis* spp., *Anavitrinella* spp., *Ancylis* spp., *Andropolia* spp., *Anhimella* spp., *Antheraea* spp., *Antherigona* spp., *Antherigona soccata*, *Anthonomus* ssp., *Anthonomus grandis*, *Anticarsia* spp., *Anticarsia gemmatalis*, *Aonidiella* spp., *Apamea* spp., *Aphania* spp., *Aphelia* spp., *Aphididae*, *Aphis* spp., *Apotomis* spp., *Aproaerema* spp., *Archippus* spp., *Archips* spp., *Acromyrmex*, *Arctia* spp., *Argas* spp., *Argolamprotes* spp., *Argyresthia* spp., *Argyrogramma* spp., *Argyroploce* spp., *Argyrotaenia* spp., *Arotrophora* spp., *Ascotis* spp., *Aspidiotus* spp., *Aspilapteryx* spp., *Asthenoptycha* spp., *Aterpia* spp., *Athetis* spp., *Atomaria* spp., *Atomaria linearis*, *Atta* spp., *Atypha* spp., *Autographa* spp., *Axylia* spp., *Bactra* spp., *Barbara* spp., *Batrachedra* spp., *Battaristis* spp., *Bembecia* spp., *Bemisia* spp., *Bemisia tabaci*, *Bibio* spp., *Bibio hortulanis*, *Bisigna* spp., *Blastesthia* spp., *Blatta* spp., *Blatella* spp., *Blepharosis* spp., *Bleptina* spp., *Boarmia* spp., *Bombyx* spp., *Bomolocha* spp., *Boophilus* spp., *Brachmia* spp., *Bradina* spp., *Brevipalpus* spp., *Brithys* spp., *Bryobia* spp., *Bryobia praetiosa*, *Bryotropha* spp., *Bupalus* spp., *Busseola* spp., *Busseola fusca*, *Cabera* spp., *Cacoecimorpha* spp., *Cadra* spp., *Cadra cautella*, *Caenurgina* spp., *Calipitrimerus* spp., *Callierges* spp., *Callophpora* spp., *Callophpora erythrocephala*, *Calophasia* spp., *Caloptilia* spp., *Calybites* spp., *Capnoptycha* spp., *Capua* spp., *Caradrina* spp., *Caripeta* spp., *Carmenta* spp., *Carposina* spp., *Carposina nipponensis*, *Catamacta* spp., *Catelaphris* spp., *Catoptria* spp., *Caustoloma* spp., *Celaena* spp., *Celypha* spp., *Cenopis* spp., *Cephus* spp., *Ceramica* spp., *Cerapteryx* spp., *Ceratitis* spp, *Ceratophyllus* spp., *Ceroplaster* spp., *Chaetocnema* spp., *Chaetocnema tibialis*, *Chamaesphecia* spp., *Charanvca* spp., *Chemophila* spp., *Chersotis* spp., *Chiasmia* spp., *Chilo* spp., *Chionodes* spp., *Chorioptes* spp., *Choristoneura* spp., *Chrysaspidia* spp., *Chrysodeixis* spp., *Chrysomya* spp., *Chrysomphalus* spp., *Chrysomphalus dictyospermi*, *Chrysomphalus aonidium*, *Chrysoteuchia* spp., *Cilix* spp., *Cimex* spp., *Clysia* spp., *Clysia ambiguella*, *Clepsis* spp., *Cnaemidophorus* spp., *Cnaphalocrocis* spp., *Cnephasia* spp., *Coccus* spp., *Coccus hesperidum*, *Cochylis* spp., *Coleophora* spp., *Colotois* spp., *Commophila* spp., *Conistra* spp., *Conopomorpha* spp., *Corcyra* spp., *Cornutiplusia* spp., *Cosmia* spp., *Cosmopolites* spp., *Cosmopterix* spp., *Cossus* spp., *Costaeonvexa* spp., *Crambus* spp., *Creatonotos* spp., *Crocidolomia* spp., *Crocidolomia binotalis*, *Croesia* spp., *Crymodes* spp., *Cryptaspasma* spp., *Cryptoblabes* spp., *Cryptocala* spp., *Cryptophlebia* spp., *Cryptophlebia leucotreta*, *Cryptoptila* spp., *Ctenopseustis* spp., *Cucullia* spp., *Curculio* spp., *Culex* spp., *Cuterebra* spp., *Cydia* spp., *Cydia pomonella*, *Cymbalophora* spp., *Dactylethra* spp., *Dacus* spp., *Dadica* spp., *Damalinea* spp., *Dasychira* spp., *Decadarchis* spp., *Decodes* spp., *Deilephila* spp., *Deltodes* spp., *Dendrolimus* spp., *Depressaria* spp., *Dermestes* spp., *Dermanyssus* spp., *Dermanyssus gallinae*, *Diabrotica* spp., *Diachrysia* spp., *Diaphania* spp., *Diarsia* spp., *Diasemia* spp., *Diatraea* spp., *Diceratura* spp., *Dichomeris* spp., *Dichrocrocis* spp., *Dichrorampha* spp., *Dicycla* spp., *Dioryctria* spp., *Diparopsis* spp., *Diparopsis castanea*, *Dipleurina* spp., *Diprion* spp., *Diprionidae*, *Discestra* spp., *Distantiella* spp., *Distantiella theobroma*, *Ditula* spp., *Diurnea* spp., *Doratopteryx* spp., *Drepana* spp., *Drosphila* spp., *Drosphila melanogaster*, *Dysauxes* spp., *Dysdercus* spp., *Dysstroma* spp., *Eana* spp., *Earias* spp., *Ecclitica* spp., *Ecdytolopha* spp., *Ecpyrrhorrhoe* spp., *Ectomyelois* spp., *Eetropis* spp., *Egira* spp., *Elasmopalpus* spp., *Emmelia* spp., *mpoasca* spp., *Empyreuma* spp., *Enargia* spp., *Enarmonia* spp., *Endopiza* spp., *Endothenia* spp., *Endotricha* spp., *Eoreuma* spp., *Eotetranychus* spp., *Eotetranychus carpini*, *Epagoge* spp., *Epelis* spp., *Ephestia* spp., *Ephestiodes* spp., *Epiblema* spp., *Epiehoristodes* spp., *Epinotia* spp., *Epiphyas* spp., *Epiplema* spp., *Epipsestis* spp., *Epirrhoe* spp., *Episimus* spp., *Epitymbia* spp., *Epllachna* spp., *Erannis* spp., *Erastria* spp., *Eremnus* spp., *Ereunetis* spp., *Eriophyes* spp., *Eriosoma* spp., *Eriosoma lanigerum*, *Erythroneura* spp., *Estigmene* spp., *Ethmia* spp., *Etiella* spp., *Euagrotis* spp., *Eucosma* spp., *Euehlaena* spp., *Euelidia* spp., *Eueosma* spp., *Euchistus* spp., *Eucosmomorpha* spp., *Eudonia* spp., *Eufidonia* spp., *Euhyponomeutoides* spp., *Eulepitodes* spp., *Eulia* spp., *Eulithis* spp., *Eupithecia* spp., *Euplexia* spp., *Eupoecilia* spp., *Eupoecilia ambiguella*, *Euproctis* spp., *Eupsilia* spp., *Eurhodope* spp., *Eurois* spp., *Eurygaster* spp., *Eurythmia* spp., *Eustrotia* spp., *Euxoa* spp., *Euzophera* spp., *Evergestis* spp., *Evippe* spp., *Exartema* spp., *Fannia* spp., *Faronta* spp., *Feltia* spp., *Filatima* spp., *Fishia* spp., *Frankliniella* spp., *Fumibotys* spp., *Gaesa* spp., *Gasgardia* spp., *Gastrophilus* spp., *Gelechia* spp., *Gilpinia* spp., *Gilpinia polytoma*, *Glossina* spp., *Glyphipterix* spp., *Glyphodes* spp., *Gnorimoschemini* spp., *Gonodonta* spp., *Gortyna* spp., *Gracillaria* spp., *Graphania* spp., *Grapholita* spp., *Grapholitha* spp., *Gravitarmata* spp., *Gretchena* spp., *Griselda* spp., *Gryllotalpa* spp., *Gynaephora* spp., *Gyp-* sonoma spp., *Hada* spp., *Haematopinus* spp., *Halisidota* spp., *Harpipteryx* spp., *Harrisina* spp., *Hedya* spp., *Helicoverpa* spp., *Heliophobus* spp., *Heliothis* spp., *Hellula* spp., *Helotropa* spp., *Hemaris* spp., *Hercinothrips* spp., *Herculia* spp., *Hermonassa* spp., *Heterogenea* spp., *Holomelina* spp., *Homadaula* spp., *Homoeosoma* spp., *Homoglaea* spp., *Homohadena* spp., *Homona* spp., *Homonopsis* spp., *Hoplocampa* spp., *Hoplodrina* spp., *Hoshinoa* spp., *Hxalomma* spp., *Hydraecia* spp., *Hydriomena* spp., *Hyles* spp., *Hyloicus* spp., *Hypagyrtis* spp., *Hypatima* spp., *Hyphantria* spp., *Hyphantria cunea*, *Hypocala* spp., *Hypocoena* spp., *Hypodema* spp., *Hyppobosca* spp., *Hypsipyla* spp., *Hyssia* spp., *Hysterosia* spp., *Idaea* spp., *Idia* spp., *Ipimorpha* spp., *Isia* spp., *Isochorista* spp., *Isophrictis* spp., *Isopolia* spp., *Isotrias* spp., *Ixodes* spp., *Itame* spp., *Jodia* spp., *Jodis* spp., *Kawabea* spp., *Keiferia* spp., *Keiferia lycopersicella*, *Labdia* spp., *Lacinipolia* spp., *Lambdina* spp., *Lamprothritpa* spp., *Laodelphax* spp., *Lasius* spp., *Laspeyresia* spp., *Leptinotarsa* spp., *Leptinotarsa decemlineata*, *Leptocorisa* spp., *Leptostales* spp., *Lecanium* spp., *Lecanium corni*, *Lepidosaphes* spp., *Lepisma* spp., *Lepisma saccharina*, *Lesmone* spp., *Leucania* spp., *Leucinodes* spp., *Leucophaea* spp., *Leucophaea maderae*, *Leucoptera* spp., *Leucoptera scitella*, *Linognathus* spp., *Liposcelis* spp., *Lissorhoptrus* spp., *Lithacodia* spp., *Lithocolletis* spp., *Lithomoia* spp., *Lithophane* spp., *Lixodessa* spp., *Lobesia* spp., *Lobesia botrana*, *Lobophora* spp., *Locusta* spp., *Lomanaltes* spp., *Lomographa* spp., *Loxagrotis* spp., *Loxostege* spp., *Lucilia* spp., *Lymantria* spp., *Lymnaecia* spp., *Lyonetia* spp., *Lyriomyza* spp., *Macdonnoughia* spp., *Macrauzata* spp., *Macronoctua* spp., *Macrosiphus* spp., *Malacosoma* spp., *Maliarpha* spp., *Mamestra* spp., *Mamestra brassicae*, *Manduca* spp., *Manduca sexta*, *Marasmia* spp., *Margaritia* spp., *Matratinea* spp., *Matsumuraeses* spp., *Melanagromyza* spp., *Melipotes* spp., *Melissopus* spp., *Melittia* spp., *Melolontha* spp., *Meristis* spp., *Meritastis* spp., *Merophyas* spp., *Mesapamea* spp., *Mesogona* spp., *Mesoleuca* spp., *Metanema* spp., *Metendothenia* spp., *Metzneria* spp., *Micardia* spp., *Microcorses* spp., *Microleon* spp., *Mnesictena* spp., *Mocis* spp., *Monima* spp., *Monochroa* spp., *Monomorium* spp., *Monomorium pharaonis*, *Monopsis* spp., *Morrisonia* spp., *Musca* spp., *Mutuuraia* spp., *Myelois* spp., *Mythimna* spp., *Myzus* spp., *Naranga* spp., *Nedra* spp., *Nemapogon* spp., *Neodiprion* spp., *Neosphaleroptera* spp., *Nephelodes* spp., *Nephotettix* spp., *Nezara* spp., *Nilaparvata* spp., *Niphonympha* spp., *Nippoptilia* spp., *Noctua* spp., *Nola* spp., *Notocelia* spp., *Notodonta* spp., *Nudaurelia* spp., *Ochropleura* spp., *Ocnerostoma* spp., *Oestrus* spp., *Olethreutes* spp., *Oligia* spp., *Olindia* spp., *Olygonychus* spp., *Olygonychus gallinae*, *Oncocnemis* spp., *Operophtera* spp., *Ophisma* spp., *Opogona* spp., *Oraesia* spp., *Orniodoros* spp., *Orgyia* spp., *Oria* spp., *Orseolia* spp., *Orthodes* spp., *Orthogonia* spp., *Orthosia* spp., *Oryzaephilus* spp., *Oscinella* spp., *Oscinella frit*, *Osminia* spp., *Ostrinia* spp., *Ostrinia nubilalis*, *Otiorhynchus* spp., *Ourapteryx* spp., *Pachetra* spp., *Pachysphinx* spp., *Pagyda* spp., *Paleacrita* spp., *Paliga* spp., *Palthis* spp., *Pammene* spp., *Pandemis* spp., *Panemeria* spp., *Panolis* spp., *Panolis flammea*, *Panonychus* spp., *Parargyresthia* spp., *Paradiarsia* spp., *Paralobesia* spp., *Paranthrene* spp., *Parapandemis* spp., *Parapediasia* spp., *Parastichtis* spp., *Parasyndemis* spp., *Paratoria* spp., *Pareromene* spp., *Pectinophora* spp., *Pectinophora gossypiella*, *Pediculus* spp., *Pegomyia* spp., *Pegomyia hyoscyami*, *Pelochrista* spp., *Pennisetia* spp., *Penstemonia* spp., *Pemphigus* spp., *Peribatodes* spp., *Peridroma* spp., *Perileucoptera* spp., *Periplaneta* spp., *Perizoma* spp., *Petrova* spp., *Pexicopia* spp., *Phalonia* spp., *Phalonidia* spp., *Phaneta* spp., *Phlyctaenia* spp., *Phlyctinus* spp., *Phorbia* spp., *Phragmatobia* spp., *Phricanthes* spp., *Phthorimaea* spp., *Phthorimaea operculella*, *Phyllocnistis* spp., *Phyllocoptruta* spp., *Phyllocoptruta oleivora*, *Phyllonorycter* spp., *Phyllophila* spp., *Phylloxera* spp., *Pieris* spp., *Pieris rapae*, *Piesma* spp., *Planococus* spp., *Planotortrix* spp., *Platyedra* spp., *Platynota* spp., *Platyptilia* spp., *Platysenta* spp., *Plodia* spp., *Plusia* spp., *Plutella* spp., *Plutella xylostelia*, *Podosesia* spp., *Polia* spp., *Popillia* spp., *Polymixis* spp., *Polyphagotarsonemus* spp., *Polyphagotarsonemus latus*, *Prays* spp., *Prionoxystus* spp., *Probole* spp., *Proceras* spp., *Prochoerodes* spp., *Proeulia* spp., *Proschistis* spp., *Proselena* spp., *Proserpinus* spp., *Protagrotis* spp., *Proteoteras* spp., *Protobathra* spp., *Protoschinia* spp., *Pselnophorus* spp., *Pseudaletia* spp., *Pseudanthonomus* spp., *Pseudaternelia* spp., *Pseudaulacaspis* spp., *Pseudexentera* spp., *Pseudococus* spp., *Pseudohermenias* spp., *Pseudoplusia* spp., *Psoroptes* spp., *Psylla* spp., *Psylliodes* spp., *Pterophorus* spp., *Ptycholoma* spp., *Pulvinaria* spp., *Pulvinaria aethiopica*, *Pyralis* spp., *Pyrausta* spp., *Pyrgotis* spp., *Pyrreferra* spp., *Pyrrharctia* spp., *Quadraspidiotus* spp., *Rancora* spp., *Raphia* spp., *Reticultermes* spp., *Retinia* spp., *Rhagoletis* spp, *Rhagoletis pomonella*, *Rhipicephalus* spp., *Rhizoglyphus* spp., *Rhizopertha* spp., *Rhodnius* spp., *Rhophalosiphum* spp., *Rhopobota* spp., *Rhyacia* spp., *Rhyacionia* spp., *Rhynchopacha* spp., *Rhyzosthenes* spp., *Rivula* spp., *Rondotia* spp., *Rusidrina* spp., *Rynchaglaea* spp., *Sabulodes* spp., *Sahlbergella* spp., *Sahlbergella singularis*, *Saissetia* spp., *Samia* spp., *Sannina* spp., *Sanninoidea* spp., *Saphoideus* spp., *Sarcoptes* spp., *Sathrobrota* spp., *Scarabeidae*, *Sceliodes* spp., *Schinia* spp., *Schistocerca* spp., *Schizaphis* spp., *Schizura* spp., *Schreckensteinia* spp., *Sciara* spp., *Scirpophaga* spp., *Scirthrips auranti*, *Scoparia* spp., *Scopula* spp., *Scotia* spp., *Scotinophara* spp., *Scotogramma* spp., *Scrobipalpa* spp., *Scrobipalpopsis* spp., *Semiothisa* spp., *Sereda* spp., *Sesamia* spp., *Sesia* spp., *Sicya* spp., *Sideridis* spp., *Simyra* spp., *Sineugraphe* spp., *Sitochroa* spp., *Sitobion* spp., *Sitophilus* spp., *Sitotroga* spp., *Solenopsis* spp., *Smerinthus* spp., *Sophronia* spp., *Spaelotis* spp., *Spargaloma* spp., *Sparganothis* spp., *Spatalistis* spp., *Sperchia* spp., *Sphecia* spp., *Sphinx* spp., *Spilonota* spp., *Spodoptera* spp., *Spodoptera littoralis*, *Stagmatophora* spp., *Staphylinochrous* spp., *Stathmopoda* spp., *Stenodes* spp., *Sterrha* spp., *Stomoxys* spp., *Strophedra* spp., *Sunira* spp., *Sutyna* spp., *Swammerdamia* spp., *Syllomatia* spp., *Sympistis* spp., *Synanthedon* spp., *Synaxis* spp., *Syncopacma* spp., *Syndemis* spp., *Syngrapha* spp., *Synthomeida* spp., *Tabanus* spp., *Taeniarchis* spp., *Taeniothrips* spp., *Tannia* spp., *Tarsonemus* spp., *Tegulifera* spp., *Tehama* spp., *Teleiodes* spp., *Telorta* spp., *Tenebrio* spp., *Tephrina* spp., *Teratoglaea* spp., *Terricula* spp., *Tethea* spp., *Tetranychus* spp., *Thalpophila* spp., *Thaumetopoea* spp., *Thiodia* spp., *Thrips* spp., *Thrips palmi*, *Thrips tabaci*, *Thyridopteryx* spp., *Thyris* spp., *Tineola* spp., *Tipula* spp., *Tortricidia* spp., *Tortrix* spp., *Trachea* spp., *Trialeurodes* spp., *Trialeurodes vaporariorum*, *Triatoma* spp., *Triaxomera* spp., *Tribolium* spp., *Tricodectes* spp., *Trichoplusia* spp., *Trichoplusia ni*, *Trichoptilus* spp., *Trioza* spp., *Trioza erytreae*, *Triphaenia* spp., *Triphosa* spp., *Trogoderma* spp., *Tyria* spp., *Udea* spp., *Unaspis* spp., *Unaspis citri*, *Utetheisa* spp., *Valeriodes* spp., *Vespa* spp., *Vespamima* spp., *Vitacea* spp., *Vitula* spp., *Witlesia* spp., *Xanthia* spp., *Xanthorhoe* spp., *Xanthotype* spp., *Xenomicta* spp., *Xenopsylla* spp., *Xenopsylla cheopsis*, *Xestia* spp., *Xylena* spp., *Xylomyges* spp., *Xyrosaris* spp., *Yponomeuta* spp., *Ypsolopha* spp., *Zale* spp., *Zanclognathus* spp., *Zeiraphera* spp., *Zenodoxus* spp., *Zeuzera* spp., *Zygaena* spp., It is also possible to control pests of the class Nematoda using the compounds according to the invention. Such pests include, for example, root knot nematodes, cyst-forming nematodes and also stem and leaf nematodes; especially of *Heterodera* spp., e.g., *Heterodera schachtii, Heterodera avenae* and *Heterodora trifolii; Globodera* spp., e.g. *Globodera rostochiensis; Meloidogyne* spp., e.g., *Meloidogyne incognita* and *Meloidogyne javanica; Radopholus* spp., e.g., *Radopholus similis; Pratylenchus*, e.g., *Pratylenchus neglectans* and *Pratylenchus penetrans; Tylenchulus*, e.g., *Tylenchulus semipenetrans; Longidorus, Trichodorus, Xiphinema, Ditylenchus, Apheenchoides* and *Anguina*; especially *Meloidogyne*, e.g., *Meloidogyne incognita*, and *Heterodera*, e.g., *Heterodera glycines.*

An especially important aspect of the present invention is the use of the compound of formula (I), or (II) in the protection of plants against parasitic feeding pests.

The action of the compound of formula (I), or (II), and the compositions comprising the said compound against animal pests can be significantly broadened and adapted to the given circumstances by the addition of other insecticides, acaricides or nematicides. Suitable additives include, for example, representatives of the following classes of active ingredient: organophosphorus compounds, nitrophenols and derivatives, formamidines, ureas, carbamates, pyrethroids, chlorinated hydrocarbons, neonicotinoids and *Bacillus thuringiensis* preparations.

Examples of especially suitable mixing partners include: azamethiphos; chlorfenvinphos; cypermethrin, cypermethrin high-cis; cyromazine; diafenthiuron; diazinon; dichlorvos; dicrotophos; dicyclanil; fenoxycarb; fluazuron; furathiocarb; isazofos; iodfenphos; kinoprene; lufenuron; methacriphos; methidathion; monocrotophos; phosphamidon; profenofos; diofenolan; a compound obtainable from the *Bacillus thuringiensis* strain GC91 or from strain NCTC11821; pymetrozine; bromopropylate; methoprene; disulfoton; quinalphos; tau-fluvalinate; thiocyclam; thiometon; aldicarb; azinphos-methyl; benfuracarb; bifenthrin; buprofezin; carbofuran; dibutylaminothio; cartap; chlorfluazuron; chlorpyrifos; cyfluthrin; lambda-cyhalothrin; alpha-cypermethrin; zeta-cypermethrin; deltamethrin; diflubenzuron; endosulfan; ethiofencarb; fenitrothion; fenobucarb; fenvalerate; formothion; methiocarb; heptenophos; imidacloprid; thiamethoxam; clothianidine; isoprocarb; methamidophos; methomyl; mevinphos; parathion; parathion-methyl; phosalone; pirimicarb; propoxur; teflubenzuron; terbufos; triazamate; fenobucarb; tebufenozide; fipronil; beta-cyfluthrin; silafluofen; fenpyroximate; pyridaben; fenazaquin; pyriproxyfen; pyrimidifen; nitenpyram; acetamiprid; abamectin; emamectin; emamectin-benzoate; spinosad; a plant extract that is active against insects; a preparation that comprises nematodes and is active against insects; a preparation obtainable from *Bacillus subtilis*; a preparation that comprises fungi and is active against insects; a preparation that comprises viruses and is active against insects; chlorfenapyr; acephate; acrinathrin; alanycarb; alphamethrin; amitraz; AZ 60541; azinphos A; azinphos M; azocyclotin; bendiocarb; bensultap; beta-cyfluthrin; BPMC; brofenprox; bromophos A; bufencarb; butocarboxin; butylpyridaben; cadusafos; carbaryl; carbophenothion; chloethocarb; chlorethoxyfos; chlormephos; cis-resmethrin; clocythrin; clofentezine; cyanophos; cycloprothrin; cyhexatin; demeton M; demeton S; demeton-S-methyl; dichlofenthion; dicliphos; diethion; dimethoate; dimethylvinphos; dioxathion; edifenphos; esfenvalerate; ethion; ethofenprox; ethoprophos; etrimphos; fenamiphos; fenbutatin oxide; fenothiocarb; fenpropathrin; fenpyrad; fenthion; fluazinam; flucycloxuron; flucythrinate; flufenoxuron; flufenprox; fonophos; fosthiazate; fubfenprox; HCH; hexaflumuron; hexythiazox; IKI-220; iprobenfos; isofenphos; isoxathion; ivermectin; malathion; mecarbam; mesulfenphos; metaldehyde; metolcarb; milbemectin; moxidectin; naled; NC 184; omethoate; oxamyl; oxydemethon M; oxydeprofos; permethrin; phenthoate; phorate; phosmet; phoxim; pirimiphos M; pirimiphos E; promecarb; propaphos; prothiofos; prothoate; pyrachlophos; pyradaphenthion; pyresmethrin; pyrethrum; tebufenozide; salithion; sebufos; sulfotep; sulprofos; tebufenpyrad; tebupirimphos; tefluthrin; temephos; terbam; tetrachlorvinphos; thiacloprid; thiafenox; thiodicarb; thiofanox; thionazin; thuringiensin; tralomethrin; triarthene; triazophos; triazuron; trichlorfon; triflumuron; trimethacarb; vamidothion; xylylcarb; YI 5301/5302; zetamethrin; DPX-MP062-indoxacarb; methoxyfenozide; bifenazate; XMC (3,5-xylyl methylcarbamate); or the fungus pathogen *Metarhizium anisopliae.*

A compound of formula (I), or (II) can be used to control, i.e., to inhibit or destroy, pests of the mentioned type occurring on plants, especially on useful plants and ornamentals in agriculture, in horticulture and in forestry, or on parts of such plants, such as the fruits, blossoms, leaves, stems, tubers or roots, while in some cases plant parts that grow later are still protected against those pests.

Target crops include especially cereals, such as wheat, barley, rye, oats, rice, maize and sorghum; beet, such as sugar beet and fodder beet; fruit, e.g., pomes, stone fruit and soft fruit, such as apples, pears, plums, peaches, almonds, cherries and berries, e.g., strawberries, raspberries and blackberries; leguminous plants, such as beans, lentils, peas and soybeans; oil plants, such as rape, mustard, poppy, olives, sunflowers, coconut, castor oil, cocoa and groundnuts; cucurbitaceae, such as marrows, cucumbers and melons; fibre plants, such as cotton, flax, hemp and jute; citrus fruits, such as oranges, lemons, grapefruit and mandarins; vegetables, such as spinach, lettuce, asparagus, cabbages, carrots, onions, tomatoes, potatoes and paprika; lauraceae, such as avocado, cinnamon and camphor; and tobacco, nuts, coffee, aubergines, sugar cane, tea, pepper, vines, hops, bananas, natural rubber plants and ornamentals.

Further areas of use of a compound of formula (I), or (II) is the protection of stored goods and storerooms and the protection of raw materials, and also in the hygiene sector, especially the protection of domestic animals and productive livestock against pests of the mentioned type, more especially the protection of domestic animals, especially cats and dogs, from infestation by fleas, ticks and nematodes.

The invention therefore relates also to a pesticidal composition, such as emulsifiable concentrates, suspension concentrates, directly sprayable or dilutable solutions, spreadable pastes, dilute emulsions, wettable powders, soluble powders, dispersible powders, wettable powders, dusts, granules and encapsulations of polymer substances, that comprises at least one compound of formula (I), or (II), the choice of formulation being made in accordance with the intended objectives and the prevailing circumstances. Furthermore, the pesticidal composition is often diluted, and optionally combined with other pesticidal compositions, before its use as a pesticide. The invention, therefore, also relates to a tank mix composition (sometimes referred to as a slurry in the event the composition is a suspension), which comprises the pesticidal composition and a liquid carrier, generally water, and optionally one or more other pesticidal compositions, each other pesticidal composition comprising a further pesticide as active compound.

The active ingredient is used in those compositions in pure form, a solid active ingredient, for example, in a specific particle size, or preferably together with at least one of the auxiliary (also known as adjuvants) customary in formulation technology, such as extenders, e.g., solvents or solid carriers, or surface-active compounds (surfactants). In the area of parasite control in humans, domestic animals, productive livestock and pets it will be self-evident that only physiologically tolerable additives are used.

Solvents are, for example: non-hydrogenated or partly hydrogenated aromatic hydrocarbons, preferably fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols, such as ethanol, propanol or butanol, glycols and ethers and esters thereof, such as propylene glycol, dipropylene glycol ether, ethylene glycol or ethylene glycol monomethyl or -ethyl ether, ketones, such as cyclohexanone, isophorone or diacetone alcohol, strongly polar solvents, such as N-methylpyrrolid-2-one, dimethyl sulfoxide or N,N-dimethylformamide, water, non-epoxidized or epoxidized plant oils, such as non-epoxidized or epoxidized rapeseed, castor, coconut or soya oil, and silicone oils.

The solid carriers used, for example, for dusts and dispersible powders, are as a rule natural rock powders, such as calcite, talc, kaolin, montmorillonite or attapulgite. Highly disperse silicic acids or highly disperse absorbent polymers can also be added to improve the physical properties. Granular adsorptive granule carriers are porous types, such as pumice, crushed brick, sepiolite or bentonite, and non-sorbent carrier materials are calcite or sand. A large number of granular materials of inorganic or organic nature can furthermore be used, in particular dolomite or comminuted plant residues.

Surface-active compounds are, depending on the nature of the active compound to be formulated, nonionic, cationic and/or anionic surfactants or surfactant mixtures with good emulsifying, dispersing and wetting properties. The surfactants listed below are to be regarded only as examples; many other surfactants that are customary in formulation technology are suitable and are described in the relevant literature.

Nonionic surfactants are, in particular, polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl radical of the alkylphenols. Substances which are furthermore suitable are water-soluble polyethylene oxide adducts, containing 20 to 250 ethylene glycol ether and 10 to 100 propylene glycol ether groups, on propylene glycol, ethylene diaminopolypropylene glycol and alkyl polypropylene glycol having 1 to 10 carbon atoms in the alkyl chain. The compounds mentioned usually contain 1 to 5 ethylene glycol units per propylene glycol unit. Examples are nonylphenol-polyethoxyethanols, castor oil polyglycol ethers, polypropylene-polyethylene oxide adducts, tributylphenoxypolyethoxyethanol, polyethylene glycol and octylphenoxypolyethoxyethanol. Other substances are fatty acid esters of polyoxyethylene sorbitan, such as polyoxyethylene sorbitan trioleate.

The cationic surfactants are, in particular, quaternary ammonium salts which contain, as substituents, at least one alkyl radical having 8 to 22 C atoms and, as further substituents, lower, non-halogenated or halogenated alkyl, benzyl or lower hydroxyalkyl radicals. The salts are preferably in the form of halides, methyl-sulfates or ethyl-sulfates. Examples are stearyl-trimethyl-ammonium chloride and benzyl-di-(2-chloroethyl)-ethyl-ammonium bromide.

Suitable anionic surfactants can be both water-soluble soaps and water-soluble synthetic surface-active compounds. Suitable soaps are the alkali metal, alkaline earth metal and substituted or unsubstituted ammonium salts of higher fatty acids ($C_{10}$-$C_{22}$), such as the sodium or potassium salts of oleic or stearic acid, or of naturally occurring fatty acid mixtures, which can be obtained, for example, from coconut oil or tall oil; and furthermore also the fatty acid methyl-taurine salts. However, synthetic surfactants are more frequently used, in particular fatty sulfonates, fatty sulfates, sulfonated benzimidazole derivatives or alkylarylsulfonates. The fatty sulfonates and sulfates are as a rule in the form of alkali metal, alkaline earth metal or substituted or unsubstituted ammonium salts and in general have an alkyl radical of 8 to 22 C atoms, alkyl also including the alkyl moiety of acyl radicals; examples are the sodium or calcium salt of ligninsulfonic acid, of dodecylsulfuric acid ester or of a fatty alcohol sulfate mixture prepared from naturally occurring fatty acids. These also include the salts of sulfuric acid esters and sulfonic acids of fatty alcohol-ethylene oxide adducts. The sulfonated benzimidazole derivatives preferably contain 2 sulfonic acid groups and a fatty acid radical having about 8 to 22 C atoms. Alkylarylsulfonates are, for example, the sodium, calcium or triethanolammonium salts of dodecylbenzenesulfonic acid, of dibutylnaphthalenesulfonic acid or of a naphthalenesulfonic acid-formaldehyde condensation product. Corresponding phosphates, such as salts of the phosphoric acid ester of a p-nonylphenol-(4-14)-ethylene oxide adduct or phospholipids, can further also be used.

The compositions as a rule comprise 0.1 to 99%, in particular 0.1 to 95%, of active compound and 1 to 99.9%, in particular 5 to 99.9%, of at least one solid or liquid auxiliary, it being possible as a rule for 0 to 25%, in particular 0.1 to 20%, of the composition to be surfactants (% is in each case percent by weight). While concentrated compositions are more preferred as commercial goods, the end user as a rule uses dilute compositions which comprise considerably lower concentrations of active compound. Preferred compositions are composed, in particular, as follows (%=percent by weight):

Emulsifiable concentrates:

| | |
|---|---|
| active ingredient: | 1 to 90%, preferably 5 to 20% |
| surfactant: | 1 to 30%, preferably 10 to 20% |
| solvent: | balance |

Dusts:

| | |
|---|---|
| active ingredient: | 0.1 to 10%, preferably 0.1 to 1% |
| solid carrier: | 99.9 to 90%, preferably 99.9 to 99% |

Suspension concentrates:

| | |
|---|---|
| active ingredient: | 5 to 75%, preferably 10 to 50% |
| surfactant: | 1 to 40%, preferably 2 to 30% |
| water: | balance |

Wettable powders:

| | |
|---|---|
| active ingredient: | 0.5 to 90%, preferably 1 to 80% |
| surfactant: | 0.5 to 20%, preferably 1 to 15% |
| solid carrier: | balance |

Granules:

| | |
|---|---|
| active ingredient: | 0.5 to 30%, preferably 3 to 15% |
| solid carrier: | 99.5 to 70%, preferably 97 to 85% |

Specific formulation examples for use in crop protection are given below (%=percent by weight):

EXAMPLE F1

Emulsifiable Concentrates

|  | a) | b) | c) |
|---|---|---|---|
| Active compound | 25% | 40% | 50% |
| Calcium dodecylbenzenesulphonate | 5% | 8% | 6% |
| Castor oil polyethylene glycol ether (36 mol of EO) | 5% | — | — |
| Tributylphenol polyethylene glycol ether (30 mol of EO) | — | 12% | 4% |
| Cyclohexanone | — | 15% | 20% |
| Xylene mixture | 65% | 25% | 20% |

Mixing of finely ground active compound and additives gives an emulsion concentrate which, by dilution with water, affords emulsions of the desired concentration.

EXAMPLE F2

Solutions

|  | a) | b) | c) | d) |
|---|---|---|---|---|
| Active compound | 80% | 10% | 5% | 95% |
| Ethylene glycol monomethyl ether | — | 20% | — | — |
| Polyethylene glycol (MW 400) | — | 70% | — | — |
| N-methylpyrrolid-2-one | 20% | — | — | — |
| Epoxidized coconut oil | — | — | 1% | — |
| Aliphatic hydrocarbon (boiling range: 160-190°) | — | — | 94% | 5% |

Mixing of finely ground active compound and additives gives a solution suitable for use in the form of microdrops.

EXAMPLE F3

Granules

|  | a) | b) | c) | d) |
|---|---|---|---|---|
| Active compound | 5% | 10% | 8% | 21% |
| Kaolin | 94% | — | 79% | 54% |
| Finely divided silicic acid | 1% | — | 13% | 7% |
| Attapulgite | — | 90% | — | 18% |

The active compound is dissolved in dichlorometnane, the solution is sprayed onto the mixture of carriers and the solvent is evaporated under reduced pressure.

EXAMPLE F4

Wettable Powder

|  | a) | b) | c) |
|---|---|---|---|
| Active compound | 25% | 50% | 75% |
| Sodium lignosulphonate | 5% | 5% | — |
| Sodium lauryl sulphate | 3% | — | 5% |
| Sodium diisobutylnaphthalene sulphonate | — | 6% | 10% |
| Octylphenol polyethylene glycol ether (7-8 mol of EO) | — | 2% | — |
| Finely divided silicic acid | 5% | 10% | 10% |
| Kaolin | 62% | 27% | — |

Active compound and additives are mixed and the mixture is ground in a suitable mill. This gives wettable powders which can be diluted with water to give suspensions of the desired concentration.

EXAMPLE F5

Emulsifiable Concentrate

| | |
|---|---|
| Active compound | 10% |
| Octylphenol polyethylene glycol ether (4-5 mol of EO) | 3% |
| Calcium dodecylbenzenesulphonate | 3% |
| Castor oil polyethylene glycol ether (36 mol of EO) | 4% |
| Cyclohexanone | 30% |
| Xylene mixture | 50% |

Mixing of finely ground active compound and additives gives an emulsion concentrate which, by dilution with water, affords emulsions of the desired concentration.

EXAMPLE F6

Extruder Granules

| | |
|---|---|
| Active compound | 10% |
| Sodium lignosulphonate | 2% |
| Carboxymethylcellulose | 1% |
| Kaolin | 87% |

Active compound and additives are mixed, the mixture is ground, moistened with water, extruded and granulated, and the granules are dried in a stream of air.

EXAMPLE F7

Coated Granules

| | |
|---|---|
| Active compound | 3% |
| Polyethylene glycol (MW 200) | 3% |
| Kaolin | 94% |

In a mixer, the finely ground active compound is applied uniformly to the kaolin which has been moistened with polyethylene glycol. This gives dust-free coated granules.

EXAMPLE F8

Suspension Concentrate

| | |
|---|---|
| Active compound | 40% |
| Ethylene glycol | 10% |
| Nonylphenol polyethylene glycol ether (15 mol of EO) | 6% |
| Sodium lignosulphonate | 10% |
| Carboxymethylcellulose | 1% |
| Aqueous formaldehyde solution (37%) | 0.2% |
| Aqueous silicone oil emulsion (75%) | 0.8% |
| Water | 32% |

Mixing of finely ground active compound and additives gives a suspension concentrate which, by dilution with water, affords suspensions of the desired concentration.

The compositions according to the invention may also comprise further solid or liquid adjuvants, such as stabilisers, e.g., vegetable oils or epoxidised vegetable oils (e.g., epoxidised coconut oil, rapeseed oil or soybean oil), antifoams, e.g. silicone oil, preservatives, viscosity regulators, binders and/or tackifiers as well as fertilisers or other active ingredients for obtaining special effects, e.g., acaricides, bactericides, fungicides, nematicides, molluscicides or selective herbicides.

The pesticidal composition according to the invention, particularly for use as a crop protection product, is prepared in the absence of adjuvants, e.g., by grinding, sieving and/or compressing the compound of formula (I), or (II) (as active ingredient) or mixture thereof, for example, to a certain particle size, and in the presence of at least one adjuvant, for example, by intimately mixing and/or grinding the compound of formula (I), or (II) (as active ingredient) or mixture thereof with the adjuvant(s). The invention relates likewise to those processes for the preparation of the pesticidal composition according to the invention and to the use of a compound of formula (I), or (II), in the preparation of the composition.

The invention relates also to the methods of application of the pesticidal and tank mix compositions, i.e., the methods of controlling pests of the mentioned type, such as spraying, atomising, dusting, coating, dressing, scattering or pouring, which are selected in accordance with the intended objectives and the prevailing circumstances, and to the use of the compositions for controlling pests of the mentioned type. Typical rates of concentration are from 0.1 to 1000 ppm, preferably from 0.1 to 500 ppm, of active ingredient. The rates of application per hectare are generally from 1 to 2000 g of active ingredient per hectare, especially from 10 to 1000 g/ha, preferably from 20 to 600 g/ha, most preferably from 20 to 100 g/ha.

A preferred method of application in the area of crop protection is application to the foliage of the plants (foliar application), the frequency and the rate of application being dependent upon the risk of infestation by the pest in question. However, the active ingredient can also penetrate the plants through the roots (systemic action) when the locus of the plants is impregnated with a liquid formulation or when the active ingredient is incorporated in solid form into the locus of the plants, for example, into the soil, e.g., in granular form (soil application). In the case of paddy rice crops, such granules may be applied in metered amounts to the flooded rice field.

The pesticidal and tank mix compositions are also suitable for protecting plant propagation material, e.g., seed, such as fruits, tubers or grains, or plant cuttings, against animal pests. The propagation material can be treated with the composition before planting: seed, for example, can be dressed before being sown. The active ingredients according to the invention can also be applied to grains (coating), either by impregnating the seeds in a liquid formulation or by coating them with a solid formulation. The composition can also be applied to the planting site when the propagation material is being planted, for example, to the seed furrow during sowing. The invention relates also to such methods of treating plant propagation material and to the plant propagation material so treated.

PREPARATION EXAMPLES

Since in most cases the compounds are present as mixtures of the avermectin derivatives B1a and B1b, characterization by customary physical data such as melting point or refractive index is not applicable. For this reason, the compounds are characterized by their HPLC retention times which are determined during a LC/MS analysis (liquid chromatography/mass spectrometry) using electrospray ionization in the positive ion mode. Here, the term B1a refers to the main component in which $R_1$ is sec-butyl, with a content of usually more than 80%. B1b denotes the minor component in which $R_1$ is isopropyl. The compounds where two retention times are given both for the B1a and for the B1b derivative are mixtures of diastereomers that can be separated chromatographically. In the case of compounds where a retention time is given only in column B1a or only in column B1b, the pure B1a or B1b component, respectively, can be obtained during work-up. The molecular masses of the B1a and B1b components are confirmed by mass spectrometry.

The following methods are used for the chromatographic separation:

| Method A (Agilent HP1100) HPLC gradient conditions | | | |
|---|---|---|---|
| Solvent A: | 0.01% of trifluoroacetic acid in $H_2O$ | | |
| Solvent B: | 0.01% of trifluoroacetic acid in $CH_3CN$ | | |
| Time [min] | A [%] | B [%] | Flow rate [ml/min] |
| 0 | 80 | 20 | 0.5 |
| 0.1 | 60 | 40 | 0.5 |
| 6 | 40 | 60 | 0.5 |
| 11 | 15 | 85 | 0.5 |
| 15 | 15 | 85 | 0.5 |
| 17 | 0 | 100 | 0.5 |
| 20 | 0 | 100 | 0.5 |
| Type of column | Zorbax Bonus-RP | | |
| Column length | 50 mm | | |
| Internal diameter of column: | 2.1 mm | | |
| Particle Size: | 3.5 micron | | |
| Temperature | 40° C. | | |

| Method B (Agilent HP1100) HPLC gradient conditions | | | |
|---|---|---|---|
| Solvent A: | 0.01% of trifluoroacetic acid in $H_2O$ | | |
| Solvent B: | 0.01% of trifluoroacetic acid in $CH_3CN$ | | |
| Time [min] | A [%] | B [%] | Flow rate [ml/min] |
| 0 | 80 | 20 | 0.5 |
| 0.1 | 70 | 30 | 0.5 |

| Method B (Agilent HP1100) HPLC gradient conditions | | | |
|---|---|---|---|
| 10 | 40 | 60 | 0.5 |
| 14 | 0 | 100 | 0.5 |
| 17 | 0 | 100 | 0.5 |
| Type of column | Zorbax Bonus-RP | | |
| Column length | 50 mm | | |
| Internal diameter of column: | 2.1 mm | | |
| Particle Size: | 3.5 micron | | |
| Temperature | 40° C. | | |

| Method C (Waters Alliance 2690) HPLC gradient conditions | | | |
|---|---|---|---|
| Solvent A: | 0.01% of trifluoroacetic acid in $H_2O$ | | |
| Solvent B: | 0.01% of trifluoroacetic acid in $CH_3CN$ | | |
| Time [min] | A [%] | B [%] | Flow rate [ml/min] |
| 0 | 80 | 20 | 0.5 |
| 0.1 | 50 | 50 | 0.5 |
| 10 | 5 | 95 | 0.5 |
| 14 | 0 | 100 | 0.5 |
| 17 | 0 | 100 | 0.5 |
| Type of column | YMC-Pack ODS-AQ | | |
| Column length | 125 mm | | |
| Internal diameter of column: | 2.0 mm | | |
| Particle Size: | 5 micron | | |
| Temperature | 40° C. | | |

| Method D (Waters Alliance 2690, HP1100) HPLC gradient conditions | | | |
|---|---|---|---|
| Solvent A: | 0.01% of trifluoroacetic acid in $H_2O$ | | |
| Solvent B: | 0.01% of trifluoroacetic acid in $CH_3CN$ | | |
| Time [min] | A [%] | B [%] | Flow rate [ml/min] |
| 0 | 80 | 20 | 0.5 |
| 0.1 | 70 | 30 | 0.5 |
| 10 | 40 | 60 | 0.5 |
| 14 | 0 | 100 | 0.5 |
| 17 | 0 | 100 | 0.5 |
| Type of column | YMC-Pack ODS-AQ | | |
| Column length | 125 mm | | |
| Internal diameter of column: | 2.0 mm | | |
| Particle Size: | 5 micron | | |
| Temperature | 40° C. | | |

| Method E (Waters Alliance 2690) HPLC gradient conditions | | | |
|---|---|---|---|
| Solvent A: | 0.01% of trifluoroacetic acid in $H_2O$ | | |
| Solvent B: | 0.01% of trifluoroacetic acid in $CH_3CN$ | | |
| Time [min] | A [%] | B [%] | Flow rate [ml/min] |
| 0 | 80 | 20 | 0.5 |
| 0.1 | 70 | 30 | 0.5 |
| 10 | 40 | 60 | 0.5 |
| 14 | 0 | 100 | 0.5 |
| 17 | 0 | 100 | 0.5 |
| Type of column | Zorbax Bonus-RP | | |
| Column length | 50 mm | | |
| Internal diameter of column: | 2.1 mm | | |
| Particle Size: | 3.5 micron | | |
| Temperature | 40° C. | | |

| Method F (Agilent HP1100) HPLC gradient conditions | | | |
|---|---|---|---|
| Solvent A: | 0.01% of trifluoroacetic acid in $H_2O$ | | |
| Solvent B: | 0.01% of trifluoroacetic acid in $CH_3CN$ | | |
| Time [min] | A [%] | B [%] | Flow rate [ml/min] |
| 0 | 90 | 10 | 0.5 |
| 1 | 90 | 10 | 0.5 |
| 12 | 0 | 100 | 0.5 |
| 17 | 0 | 100 | 0.5 |
| Type of column | Zorbax Bonus-RP | | |
| Column length | 50 mm | | |
| Internal diameter of column: | 2.1 mm | | |
| Particle Size: | 3.5 micron | | |
| Temperature | 40° C. | | |

The YMC-Pack ODS-AQ column used for the chromatography of the compounds is manufactured by YMC, Alte Raesfelderstrasse 6, 46514 Schermbeck, Germany. The Zorbax Bonus-RP column is manufactured by Agilent Technologies, CH-4052 Basel, Switzerland.

In the following examples, the mixing ratios of the eluents are given as volume/volume, and the temperatures in ° C. TBDMS means tert-butyldimethysilyl, TIPS means tri-isopropylsilyl, TMS means trimethysilyl.

Example 1

13-O-(2',3',4'-tri-O-methyl-β-L-rhamnopyranosyl)-avermectin $B_1$ Aglycone (Table P1.1)

Step A: A solution of 1 g of 5-OTBDMS-7-OTMS-avermectin B1 aglycone, 542 mg of 1-S-phenyl-2,3,4-tri-O-methyl-α-L-rhamnopyranosid and 1 g crushed molecular sieves (4 Å) in 15 ml anhydrous dichloromethane under argon atmosphere is stirred at room temperature for 2 hours. The mixture is cooled to −30° C., 583 mg of N-iodo-succinimide and 11.3 µl of trifluorosulfonic acid are added and the mixture is stirred for 5 h at −30° C. The reaction mixture is quenched by addition of 65 µl Hünig's base and diluted with 20 ml of dichloromethane. The dichloromethane solution is filtered, washed with a saturated aqueous solution of sodium thiosulfate, a saturated aqueous solution of sodium hydrogencarbonate, and with water. The organic phase is dried over $Na_2SO_4$, filtered, and concentrated in vacuo. The residue is purified by chromatography on silica gel with hexane/ethylacetate to afford 5-OTBDMS-13-O-(2',3',4'-tri-O-methyl-α-L-rhamnopyranosyl)-avermectin $B_1$ aglycone and 5-OTBDMS-13-O-(2',3',4'-tri-O-methyl-β-L-rhamnopyranosyl)-avermectin $B_1$ aglycone.

Step B: To a solution of 45 mg 5-OTBDMS-13-O-(2',3',4'-tri-O-methyl-β-L-rhamnopyranosyl)-avermectin $B_1$ aglycone in 1.25 ml of tetrahydrofuran under argon atmosphere at room temperature are added 0.25 ml of a stock solution, which is prepared from 250 g 70% HF-Pyridine, 275 ml tetrahydrofuran and 125 ml pyridine. The mixture is stirred at room temperature for 19 hours, poured into a saturated aqueous solution of sodium hydrogencarbonate, and extracted with ethylacetate. Then the phases are separated and the aqueous phase is extracted with ethylacetate. The combined organic phases are dried over sodium sulfate, filtered, and the solvents are distilled off. The residue is purified by chromatography on silica gel with hexane/ethylacetate, yielding 13-O-(2,3,4-tri-O-methyl-β-L-rhamnopyranosyl)-avermectin $B_1$ aglycone.

Example 2

13-O-(2',3',4'-tri-O-methyl-α-L-rhamnopyranosyl)-avermectin $B_1$ Aglycone (Table P2. 1)

To a solution of 24 mg 5-OTBDMS-13-O-(2',3',4'-tri-O-methyl-α-L-rhamnopyranosyl)-avermectin $B_1$ aglycone (product of Step A of Example 1) in 0.65 ml of tetrahydrofuran under argon atmosphere at room temperature are added 0.13 ml of a stock solution, which is prepared from 250 g 70% HF-Pyridine, 275 ml tetrahydrofuran and 125 ml pyridine. The mixture is stirred at room temperature for 20 hours, poured into a saturated aqueous solution of sodium hydrogencarbonate, and extracted with ethylacetate. Then the phases are separated and the aqueous phase is extracted with ethylacetate. The combined organic phases are dried over sodium sulfate and the solvents are distilled off. The residue is purified by chromatography on silica gel with hexane/ethylacetate, yielding 13-O-(2',3',4'-tri-O-methyl-α-L-rhamnopyranosyl)-avermectin $B_1$ aglycone.

Example 3

4'-O-(2",3"-di-O-methyl-β-L-rhamnopyranosyl)-avermectin $B_1$ Monosaccharide (Table P3. 1)

Step A: A solution of 5.89 g of 5-OTBDMS-avermectin B1 monosaccharide, 2.83 g of 1-S-phenyl-4-O-allyloxycarbonyl-2,3-di-O-methyl-α-L-rhamnopyranosid and 10 g crushed molecular sieves (4 Å) in 100 ml anhydrous dichloromethane under argon atmosphere is stirred at room temperature for 1 hour. The mixture is cooled to −40° C., 3.14 g of N-iodosuccinimide and 0.13 ml of trifluorosulfonic acid are added and the mixture is stirred for 5 h at −30° C. The reaction mixture is allowed to warm up to −10° C. and is quenched after stirring for 1 h by addition of 1.54 ml of Hünig's base and diluted with 100 ml of dichloromethane. The dichloromethane solution is filtered, washed with a saturated aqueous solution of sodium thiosulfate, a saturated aqueous solution of sodium hydrogencarbonate, and with brine. The organic phase is dried over $Na_2SO_4$, filtered, and concentrated in vacuo. The residue is purified by chromatography on silica gel with hexane/ethylacetate to afford 5-OTBDMS-4'-O-(4"-O-allyloxycarbonyl-2",3"-di-O-methyl-α-L-rhamnopyranosyl)-avermectin B1 monosaccharide and 5-OTBDMS-4'-O-(4"-O-allyloxycarbonyl-2",3"-di-O-methyl-β-L-rhamnopyranosyl)-avermectin B1 monosaccharide.

Step B: To a solution of 1.59 g of 5-OTBDMS-4'-O-(4"-O-allyloxycarbonyl-2",3"-di-O-methyl-β-L-rhamnopyranosyl)-avermectin B1 monosaccharide in 100 ml of tetrahydrofuran are added under argon atmosphere 155 mg of triphenylphosphine, 0.29 ml of formic acid 232 mg of tetrakis(triphenylphosphine)palladium and the mixture is stirred at room temperature for 21 hours. The mixture is diluted with ethylacetate, washed with a saturated aqueous solution of sodium hydrogencarbonate, the phases are separated and the aqueous phase is extracted with ethylacetate. The combined organic phases are dried over sodium sulfate, filtered, and the solvents are distilled off. The residue is purified by chromatography on silica gel with hexane/ethylacetate to afford 5-OTBDMS-4'-O-(2",3"-di-O-methyl-α-L-rhamnopyranosyl)-avermectin B1 monosaccharide.

Step C: To a solution of 65 mg 5-OTBDMS-4'-O-(2",3"-di-O-methyl-β-L-rhamnopyranosyl)-avermectin B1 monosaccharide in 2 ml of tetrahydrofuran under argon atmosphere at room temperature are added 0.34 ml of a stock solution, which is prepared from 250 g 70% HF-Pyridine, 275 ml tetrahydrofuran and 125 ml pyridine. The mixture is stirred at room temperature for 24 hours, poured into a saturated aqueous solution of sodium hydrogencarbonate and extracted with ethylacetate. Then the aqueous phase is extracted again with ethylacetate. The combined organic phases are dried over sodium sulfate, filtered, and the solvents are distilled off. The residue is purified by chromatography on silica gel with hexane/ethylacetate, yielding 4'-O-(2",3"-di-O-methyl-β-L-rhamnopyranosyl)-avermectin B1 monosaccharide.

Example 4

4'-O-(2",3"-di-O-methyl-α-L-rhamnopyranosyl)-avermectin $B_1$ Monosaccharide (Table P4. 1)

Step A: To a solution of 184 mg of 5-OTBDMS-4'-O-(4"-O-allyloxycarbonyl-2",3"-di-O-methyl-α-L-rhamnopyranosyl)-avermectin B1 monosaccharide (product of Step A of Example 3) in 16 ml of tetrahydrofuran are added under argon atmosphere 17.4 mg of triphenylphosphine, 32 μl of formic acid and 26.2 mg of tetrakis(triphenylphosphine)palladium and the mixture is stirred at room temperature for 19 hours. The mixture is diluted with ethylacetate, washed with a saturated aqueous solution of sodium hydrogencarbonate, the phases are separated and the aqueous phase is extracted with ethylacetate. The combined organic phases are dried over sodium sulfate, filtered, and the solvents are distilled off. The residue is purified by chromatography on silica gel with hexane/ethylacetate to afford 5-OTBDMS-4'-O-(2",3"-di-O-methyl-α-L-rhamnopyranosyl)-avermectin B1 monosaccharide.

Step B: To a solution of 61 mg 5-OTBDMS-4'-O-(2",3"-di-O-methyl-α-L-rhamnopyranosyl)-avermectin B1 monosaccharide in 2 ml of tetrahydrofuran under argon atmosphere at room temperature are added 0.32 ml of a stock solution, which is prepared from 250 g 70% HF-Pyridine, 275 ml tetrahydrofuran and 125 ml pyridine. The mixture is stirred at room temperature for 16 hours, poured into a saturated aqueous solution of sodium hydrogencarbonate and extracted with ethylacetate. Then the aqueous phase is extracted again with ethylacetate. The combined organic phases are dried over sodium sulfate, filtered, and the solvents are distilled off. The residue is purified by chromatography on silica gel with hexane/ethylacetate, yielding 4'-O-(2",3"-di-O-methyl-β-L-rhamnopyranosyl)-avermectin B1 monosaccharide.

Example 5

4'-O-(4"-O-methoxymethyl-2",3"-di-O-methyl-β-L-rhamnopyranosyl)-avermectin $B_1$ Monosaccharide (Table P3. 6)

Step A: To a solution of 100 mg of 5-OTBDMS-4'-O-(2",3"-di-O-methyl-β-L-rhamnopyranosyl)-avermectin B1 monosaccharide (product of Step B of Example 3) in 2.7 ml of dichloromethane are added under argon atmosphere 23 μl of chloromethylether and 207 μl of Hünig's base and the mixture is stirred at 35° C. for 20 hours. Then 14 μl of chloromethylether and 123 μl of Hünig's base are added and the mixture is stirred at 35° C. for additional 5 hours. The mixture is poured into ice water, and extracted three times with dichloromethane. The combined organic phases are dried over sodium sulfate, filtered, and the solvents are distilled off. The residue is purified by chromatography on silica gel with hexane/ethylacetate to afford 5-OTBDMS-4'-O-(4"-O-methoxymethyl-2",3"-di-O-methyl-β-L-rhamnopyranosyl)-avermectin B1 monosaccharide.

Step B: To a solution of 80 mg 5-OTBDMS-4'-O-(4"-O-methoxymethyl-2",3"-di-O-methyl-β-L-rhamnopyranosyl)-avermectin B1 monosaccharide in 2.5 ml of tetrahydrofuran under argon atmosphere at room temperature are added 0.40 ml of a stock solution, which is prepared from 250 g 70% HF-Pyridine, 275 ml tetrahydrofuran and 125 ml pyridine. The mixture is stirred at room temperature for 18 hours, poured into a saturated aqueous solution of sodium hydrogencarbonate and extracted with ethylacetate. Then the aqueous phase is extracted again with ethylacetate. The combined organic phases are dried over sodium sulfate, filtered, and the solvents are distilled off. The residue is purified by chromatography on silica gel with hexane/ethylacetate, yielding 4'-O-(4"-O-methoxymethyl-2",3"-di-O-methyl-β-L-rhamnopyranosyl)-avermectin B1 monosaccharide.

Example 6

4'-O-(4"-O-methoxymethyl-2",3"-di-O-methyl-α-L-rhamnopyranosyl)-avermectin $B_1$ Monosaccharide (Table P4. 6)

Step A: To a solution of 100 mg of 5-OTBDMS-4'-O-(2",3"-di-O-methyl-α-L-rhamnopyranosyl)-avermectin B1 monosaccharide (product of Step A of Example 4) in 2.7 ml of dichloromethane are added under argon atmosphere 11 μl of chloromethylether and 103 μl of Hünig's base and the mixture is stirred at 35° C. for 15 hours. Then 11 μl of chloromethylether and 103 μl of Hünig's base are added and the mixture is stirred at 35° C. for additional 5 hours. The mixture is poured into ice water, and extracted three times with dichloromethane. The combined organic phases are dried over sodium sulfate, filtered, and the solvents are distilled off. The residue is purified by chromatography on silica gel with hexane/ethylacetate to afford 5-OTBDMS-4'-O-(4"-O-methoxymethyl-2",3"-di-O-methyl-α-L-rhamnopyranosyl)-avermectin B1 monosaccharide.

Step B: To a solution of 78 mg 5-OTBDMS-4'-O-(4"-O-methoxymethyl-2",3"-di-O-methyl-α-L-rhamnopyranosyl)-avermectin B1 monosaccharide in 2.5 ml of tetrahydrofuran under argon atmosphere at room temperature are added 0.39 ml of a stock solution, which is prepared from 250 g 70% HF-Pyridine, 275 ml tetrahydrofuran and 125 ml pyridine. The mixture is stirred at room temperature for 18 hours, poured into a saturated aqueous solution of sodium hydrogencarbonate and extracted with ethylacetate. Then the aqueous phase is extracted again with ethylacetate. The combined organic phases are dried over sodium sulfate, filtered, and the solvents are distilled off. The residue is purified by chromatography on silica gel with hexane/ethylacetate, yielding 4'-O-(4"-O-methoxymethyl-2",3"-di-O-methyl-α-L-rhamnopyranosyl)-avermectin B1 monosaccharide.

Example 7

4'-O-(4",6"-dideoxy-4"-allyloxycarbonyl(methyl)amino-2",3"-di-O-methyl-β-L-talopyranosyl)-avermectin $B_1$ Monosaccharide (Table P9. 4)

Step A: A solution of 1.61 g of 5-OTBDMS-avermectin B1 monosaccharide, 801 mg of 1-S-phenyl-4,6-dideoxy-4-allyloxycarbonyl(methyl)amino-2,3-di-O-methyl-β-L-talopyranosid and 2 g crushed molecular sieves (4 Å) in 35 ml anhydrous dichloromethane under argon atmosphere is stirred at room temperature for 1 hour. The mixture is cooled to −40° C., 860 mg of N-iodo-succinimide and 36 μl of trifluorosulfonic acid are added. The reaction mixture is allowed to warm up to −10° C. and is quenched after stirring for 5 h by addition of 0.42 ml of Hünig's base and diluted with 50 ml of dichloromethane. The dichloromethane solution is filtered, washed with a saturated aqueous solution of sodium thiosulfate, a saturated aqueous solution of sodium hydrogencarbonate, and with brine. The organic phase is dried over $Na_2SO_4$, filtered, and concentrated in vacuo. The residue is purified by chromatography on silica gel with hexane/ethylacetate to afford 5-OTBDMS-4'-O-(4",6"-dideoxy-4"-allyloxycarbonyl(methyl)amino-2",3"-di-O-methyl-α-L-talopyranosyl)-avermectin B1 monosaccharide and 5-OTBDMS-4'-O-(4",6"-dideoxy-4"-allyloxycarbonyl(methyl)amino-2",3"-di-O-methyl-β-L-talopyranosyl)-avermectin B1 monosaccharide.

Step B: To a solution of 58 mg 5-OTBDMS-4'-O-(4",6"-dideoxy-4"-allyloxycarbonyl(methyl)amino-2",3"-di-O-methyl-β-L-talopyranosyl)-avermectin B1 monosaccharide in 2 ml of tetrahydrofuran under argon atmosphere at room temperature are added 0.34 ml of a stock solution, which is prepared from 250 g 70% HF-Pyridine, 275 ml tetrahydrofuran and 125 ml pyridine. The mixture is stirred at room temperature for 24 hours, poured into a saturated aqueous solution of sodium hydrogencarbonate and extracted with ethylacetate. Then the aqueous phase is extracted again with ethylacetate. The combined organic phases are dried over sodium sulfate, filtered, and the solvents are distilled off. The residue is purified by chromatography on silica gel with hexane/ethylacetate, yielding 4'-O-(4",6"-dideoxy-4"-allyloxycarbonyl(methyl)amino-2",3"-di-O-methyl-β-L-talopyranosyl)-avermectin B1 monosaccharide.

Example 8

4'-O-(4",6"-dideoxy-4"-methylamino-2",3"-di-O-methyl-β-L-talopyranosyl)-avermectin $B_1$ Monosaccharide (Table P9. 2)

To a solution of 58 mg of 4'-O-(4",6"-dideoxy-4"-allyloxycarbonyl(methyl)amino-2",3"-di-O-methyl-β-L-talopyranosyl)-avermectin B1 monosaccharide (product of Step B of Example 7) in 7 ml of tetrahydrofuran are added under argon atmosphere in 3 portions each time 6.7 mg of triphenylphosphine, 12 μl of formic acid 10 mg of tetrakis(triphenylphosphine)palladium and the mixture is stirred at room temperature for 69 hours. The mixture is diluted with ethylacetate, washed with a saturated aqueous solution of sodium hydrogencarbonate, the phases are separated and the aqueous phase is extracted with ethylacetate. The combined organic phases are dried over sodium sulfate, filtered, and the solvents are distilled off. The residue is purified by chromatography on silica gel with hexane/ethylacetate to afford 4'-O-(4",6"-dideoxy-4"-methylamino-2",3"-di-O-methyl-β-L-talopyranosyl)-avermectin $B_1$ monosaccharide.

Example 9

4'-O-(4",6"-dideoxy-4"-allyloxycarbonyl(methyl)amino-2",3"-di-O-methyl-α-L-talopyranosyl)-avermectin $B_1$ Monosaccharide (Table P10. 8)

To a solution of 240 mg 5-OTBDMS-4'-O-(4",6"-dideoxy-4"-allyloxycarbonyl(methyl)amino-2",3"-di-O-methyl-α-L-talopyranosyl)-avermectin B1 monosaccharide (product of Step A of Example 7) in 7.5 ml of tetrahydrofuran under argon atmosphere at room temperature are added 1.15 ml of a stock solution, which is prepared from 250 g 70% HF-Pyridine, 275 ml tetrahydrofuran and 125 ml pyridine. The mixture is stirred at room temperature for 18 hours. Then 0.23 ml of the HF-pyridine stock solution is added and the mixture is stirred at room temperature for additional 3 hours poured into a saturated aqueous solution of sodium hydrogencarbonate and extracted with ethylacetate. Then the aqueous phase is extracted again with ethylacetate. The combined organic phases are dried over sodium sulfate, filtered, and the solvents are distilled off. The residue is purified by chromatography on silica gel with hexane/ethylacetate, yielding 4'-O-(4",6"-dideoxy-4"-allyloxycarbonyl(methyl)amino-2",3"-di-O-methyl-α-L-talopyranosyl)-avermectin B1 monosaccharide.

Example 10

4'-O-(4",6"-dideoxy-4"-methylamino-2",3"-di-O-methyl-α-L-talopyranosyl)-avermectin $B_1$ Monosaccharide (Table P10. 2)

To a solution of 232 mg of 4'-O-(4",6"-dideoxy-4"-allyloxycarbonyl(methyl)amino-2",3"-di-O-methyl-α-L-talopyranosyl)-avermectin B1 monosaccharide (product of Example 9) in 26 ml of tetrahydrofuran are added under argon atmosphere in 3 portions each time 26.8 mg of triphenylphosphine, 50 µl of formic acid 40.4 mg of tetrakis(triphenylphosphine)palladium and the mixture is stirred at room temperature for 66 hours. The mixture is diluted with ethylacetate, washed with a saturated aqueous solution of sodium hydrogencarbonate, the phases are separated and the aqueous phase is extracted with ethylacetate. The combined organic phases are dried over sodium sulfate, filtered, and the solvents are distilled off. The residue is purified by chromatography on silica gel with hexane/ethylacetate to afford 4'-O-(4",6"-dideoxy-4"-methylamino-2",3"-di-O-methyl-α-L-talopyranosyl)-avermectin $B_1$ monosaccharide.

Example 11

2"-(R)-methyl-3"-epi-avermectin $B_1$ (Table P13.1)

Step A: To a solution of 400 mg 4"-oxo-5-O-TBDMS-avermectin $B_1$ in 2.6 ml toluene are added 420 µl ethyldiisopropylamine and 500 µl triisopropylsilyl trifluoromethanesulfonate. The reaction mixture is stirred at 80° C. for three days, then allowed to cool to room temperature, washed with 1 N aqueous citric acid and, subsequently, with 1 N aqueous sodium bicarbonate, dried over sodium sulfate and the solvent evaporated. The residue can be purified by flash chromatography on silica gel with ethyl acetate and hexane to afford pure 4"-O-TIPS-3",4"-dehydro-5-O-TBDMS-avermectin $B_1$. Alternatively, the crude product can be used for Step B without chromatographic purification.

Step B: The crude product containing 4"-O-TIPS-3",4"-dehydro-5-O-TBDMS-avermectin B, from Step A is dissolved in a mixture of 3 ml ethyl acetate and 3 ml 1 N aqueous sodium bicarbonate. 100 mg 3-chloro-perbenzoic acid are added, and the mixture is stirred at room temperature for two days. Then the phases are separated, the organic phase is dried over sodium sulfate and the solvent evaporated. Purification by chromatography on silica gel with ethyl acetate and hexane affords 4"-oxo-2",3"-dehydro-5-O-TBDMS-avermectin $B_1$.

Step C: To a suspension of 83 mg copper(I)bromide dimethylsulfide complex in 3 ml anhydrous ether are added 500 µl of a 1.6 M solution of methyllithium in ether at room temperature. After 5 minutes, a solution of 200 mg 4"-oxo-2",3"-dehydro-5-O-TBDMS-avermectin $B_1$ in 2 ml ether is added. After 30 minutes, the reaction mixture is poured on a 2 M aqueous solution of ammonium chloride, the pH of which has been adjusted to 8 by addition of 2 M ammonium hydroxide. The phases are separated, the organic phase is dried over sodium sulfate and the solvent evaporated. Purification by chromatography on silica gel with ethyl acetate and hexane affords 2"-(R)-methyl-3"-epi-4"-oxo-5-O-TBDMS-avermectin $B_1$.

Step D: 300 mg 2"-(R)-methyl-3"-epi-4"-oxo-5-O-TBDMS-avermectin $B_1$ are dissolved in 10 ml ethanol and 34 mg sodium borohydride are added. The mixture is stirred at room temperature for 90 minutes. Then aqueous ammonium chloride is added, and the mixture is extracted with ethyl acetate, the organic phase is dried over sodium sulfate and the solvent evaporated. The residue can be purified to afford pure 2"-(R)-methyl-3"-epi-5-O-TBDMS-avermectin $B_1$. Alternatively, the crude product can be used for Step E without chromatographic purification.

Step E: The crude product containing 2"-(R)-methyl-3"-epi-5-O-TBDMS-avermectin $B_1$ from Step D is dissolved in 10 ml tetrahydrofuran. 3 ml of a stock solution are added, which is prepared from 250 g 70% HF-Pyridine, 275 ml tetrahydrofuran and 125 ml pyridine. The mixture is stirred at room temperature for 24 hours, poured into a saturated aqueous solution of sodium hydrogencarbonate and extracted with ethylacetate. Then the aqueous phase is extracted again with ethylacetate. The combined organic phases are dried over sodium sulfate, filtered, and the solvents are distilled off. The residue is purified by chromatography on silica gel with ethyl acetate and hexane to afford 2"-(R)-methyl-3"-epi-avermectin $B_1$ (Table P13.1).

Example 12

2"-(R)-methyl-3"-epi-4"-desoxy-4"-(S)-methylamino-avermectin $B_1$ (Table P13.4)

1.25 g 2"-(R)-methyl-3"-epi-4"-oxo-5-O-TBDMS-avermectin $B_1$ (product of Step C of Example 11) are dissolved in 8 ml ethyl acetate. 1 ml heptamethyldisilazane and 180 mg zinc chloride are added, and the mixture is stirred at 50° C. for 4 hours. The reaction mixture is cooled to 0° C., then 150 mg sodium borohydride in 2 ml ethanol are added. Then the mixture is allowed to warm to room temperature. After 40 minutes, 4 ml of 10% aqueous acetic acid are added. After stirring for another 5 minutes, the mixture is extracted with ethyl acetate, the organic phase is dried over sodium sulfate and the solvent evaporated. The residue is dissolved in 25 ml tetrahydrofuran. 6.5 ml of a stock solution are added, which is prepared from 250 g 70% HF-Pyridine, 275 ml tetrahydrofuran and 125 ml pyridine. The mixture is stirred at room temperature for 24 hours, poured into a saturated aqueous solution of sodium hydrogencarbonate and extracted with ethylacetate. Then the aqueous phase is extracted again with ethylacetate. The combined organic phases are dried over sodium sulfate, filtered, and the solvents are distilled off. The residue is purified by chromatography on silica gel with ethyl acetate and hexane to afford 2"-(R)-methyl-3"-epi-4"-desoxy-4"-(S)-methylamino-avermectin $B_1$ (Table P13.4).

Example 13

2"-(R)-methyl-3"-epi-4"-desoxy-4"-(S)-(acetyl-methyl-amino)-avermectin $B_1$ (Table P13.12)

225 mg 2"-(R)-methyl-3"-epi-4"-desoxy-4"-(S)-methylamino-avermectin $B_1$ (Example 12) is dissolved in a mixture of 2.5 ml ethyl acetate and 2.5 ml 1 N aqueous sodium bicarbonate. 50 µl acetyl chloride are added, and the mixture is stirred at room temperature for 16 hours. Then the phases are separated, the organic phase is dried over sodium sulfate and the solvent evaporated. Purification by chromatography on silica gel with ethyl acetate and hexane affords 2"-(R)-methyl-3"-epi-4"-desoxy-4"-(S)-(acetyl-methyl-amino)-avermectin $B_1$ (Table P13.12).

The other compounds in tables P1-P19 can be prepared as described in the examples above or by general procedures published in the literature known to the person skilled in the art. The numbers after the retention times in tables P1-P19 indicate which of the methods described above is used for the chromatographic separation:

1) Method A, 2) Method B, 3) Method C, 4) Method D, 5) Method E, 6) Method F

TABLE P1

A compound of formula

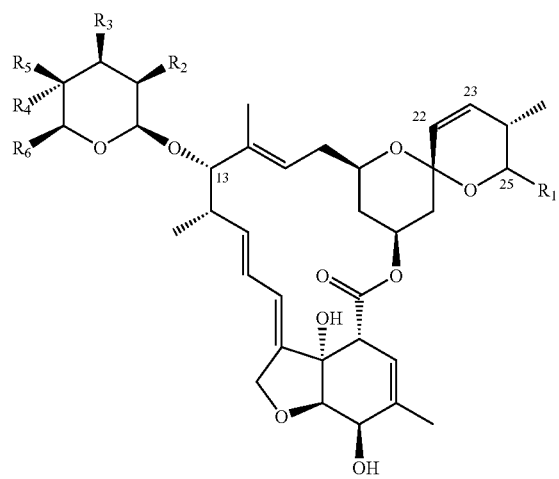

(I-1a)

wherein $R_1$ is sec-butyl or isopropyl, and

| | $R_2$ | $R_3$ | $R_4$ | $R_5$ | $R_6$ | Retention time (min) B1a | B1b |
|---|---|---|---|---|---|---|---|
| P1.1 | $OCH_3$ | $OCH_3$ | $OCH_3$ | H | $CH_3$ | 8.14[3] | — |
| P1.2 | $OCH_3$ | $OCH_3$ | OH | H | $CH_3$ | 11.39[4] | — |

TABLE P1-continued

A compound of formula

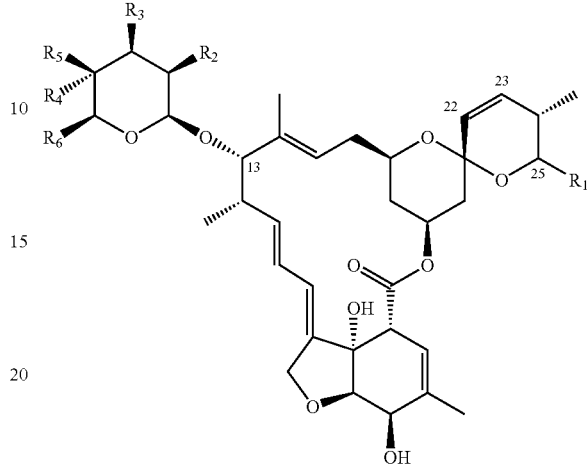

(I-1a)

wherein $R_1$ is sec-butyl or isopropyl, and

| | $R_2$ | $R_3$ | $R_4$ | $R_5$ | $R_6$ | Retention time (min) B1a | B1b |
|---|---|---|---|---|---|---|---|
| P1.3 | $OCH_3$ | $OCH_3$ | $OC(O)CH_3$ | H | $CH_3$ | 9.92[5] | — |
| P1.4 | $OCH_3$ | $OCH_3$ | $OCH_2OCH_3$ | H | $CH_3$ | 9.83[5] | — |

TABLE P2

A compound of formula

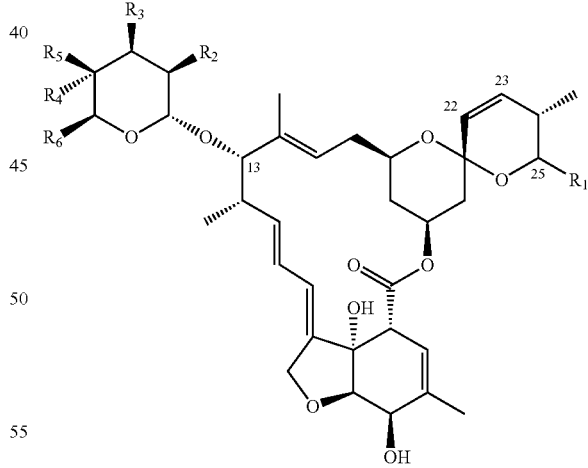

(I-1b)

wherein $R_1$ is sec-butyl or isopropyl, and

| | $R_2$ | $R_3$ | $R_4$ | $R_5$ | $R_6$ | Retention time (min) B1a | B1b |
|---|---|---|---|---|---|---|---|
| P2.1 | $OCH_3$ | $OCH_3$ | $OCH_3$ | H | $CH_3$ | 10.13[5] | — |
| P2.2 | $OCH_3$ | $OCH_3$ | OH | H | $CH_3$ | 12.81[4] | — |
| P2.3 | $OCH_3$ | $OCH_3$ | $OCH_2OCH_3$ | H | $CH_3$ | 9.39[6] | — |

TABLE P3

A compound of formula

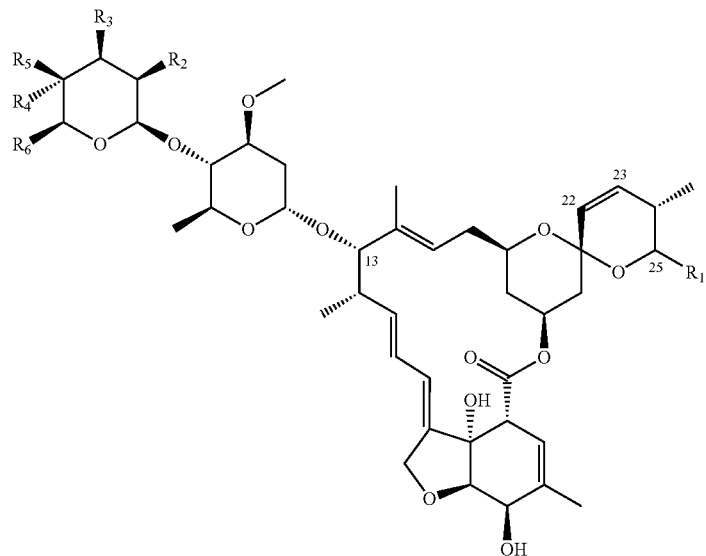

(I-5a)

wherein $R_1$ is sec-butyl or isopropyl, and

| | $R_2$ | $R_3$ | $R_4$ | $R_5$ | $R_6$ | Retention time (min) B1a | B1b |
|---|---|---|---|---|---|---|---|
| P3.1 | $OCH_3$ | $OCH_3$ | OH | H | $CH_3$ | $9.30^{2)}$ | — |
| P3.2 | $OCH_3$ | $OCH_3$ | H | H | $CH_3$ | $11.56^{2)}$ | — |
| P3.3 | $OCH_3$ | $OCH_3$ | $OCH_3$ | H | $CH_3$ | $11.51^{2)}$ | 10.68 |
| P3.4 | $OCH_2CH_3$ | $OCH_2CH_3$ | $OCH_2CH_3$ | H | $CH_3$ | $13.36^{2)}$ | — |
| P3.5 | $OCH_3$ | $OCH_3$ | $OC(O)CH_3$ | H | $CH_3$ | $11.09^{3)}$ | — |
| P3.6 | $OCH_3$ | $OCH_3$ | $OCH_2OCH_3$ | H | $CH_3$ | $11.76^{2)}$ | — |
| P3.7 | $OCH_3$ | $OCH_3$ | $OCH_3$ | H | H | $10.39^{2)}$ | — |
| P3.8 | $OCH_3$ | $OCH_3$ | =N—$OCH_2CH_3$ | | $CH_3$ | $9.65^{1)}$ | — |
| P3.9 | $OCH_3$ | $OCH_3$ | =N—OH | | $CH_3$ | $7.60^{1)}$ | — |

TABLE P4

A compound of formula

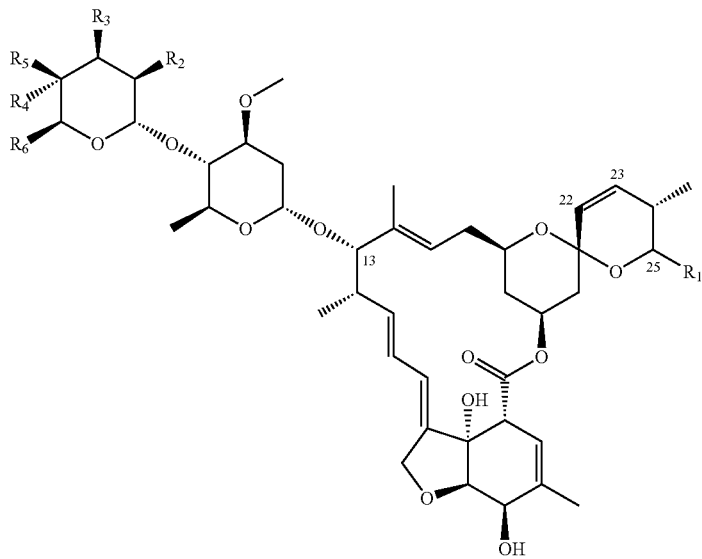

(I-5b)

wherein $R_1$ is sec-butyl or isopropyl, and

| | $R_2$ | $R_3$ | $R_4$ | $R_5$ | $R_6$ | Retention time (min) B1a | B1b |
|---|---|---|---|---|---|---|---|
| P4.1 | $OCH_3$ | $OCH_3$ | OH | H | $CH_3$ | $10.20^{4)}$ | — |
| P4.2 | $OCH_3$ | $OCH_3$ | H | H | $CH_3$ | $12.28^{2)}$ | — |
| P4.3 | $OCH_3$ | $OCH_3$ | $OCH_3$ | H | $CH_3$ | $12.32^{5)}$ | — |
| P4.4 | $OCH_2CH_3$ | $OCH_2CH_3$ | $OCH_2CH_3$ | H | $CH_3$ | $13.79^{2)}$ | — |
| P4.5 | $OCH_3$ | $OCH_3$ | $OC(O)CH_3$ | H | $CH_3$ | $11.63^{5)}$ | — |
| P4.6 | $OCH_3$ | $OCH_3$ | $OCH_2OCH_3$ | H | $CH_3$ | $12.51^{2)}$ | — |
| P4.7 | $OC(O)OCH_2$—$CH$=$CH_2$ | $OC(O)OCH_2$—$CH$=$CH_2$ | $OCH_2OCH_2CH_3$ | H | $CH_3$ | $14.24^{4)}$ | — |
| P4.8 | OH | OH | $OCH_2OCH_2CH_3$ | H | $CH_3$ | $9.01^{3)}$ | — |
| P4.9 | $OCH_3$ | $OCH_3$ | $OCH_2OCH_2CH_3$ | H | $CH_3$ | $12.86^{4)}$ | $12.34^{4)}$ |
| P4.10 | $OCH_3$ | $OCH_3$ | $OCH_3$ | H | H | $11.50^{2)}$ | — |
| P4.11 | $OCH_3$ | $OCH_3$ | =N—OH | | $CH_3$ | $8.43^{1)}$ | — |
| P4.12 | $OCH_3$ | $OCH_3$ | =N—$OCH_2CH_3$ | | $CH_3$ | $10.22^{1)}$ $10.33^{1)}$ | — |
| P4.13 | $OCH_3$ | $OCH_3$ | =N—$OC(O)CH_3$ | | $CH_3$ | $8.74^{1)}$ | — |
| P4.14 | $CH_3$ | $OCH_3$ | =N—OH | | $OH_3$ | $10.41^{3)}$ $10.73^{3)}$ | |

TABLE P5
A compound of formula
(I-6a)
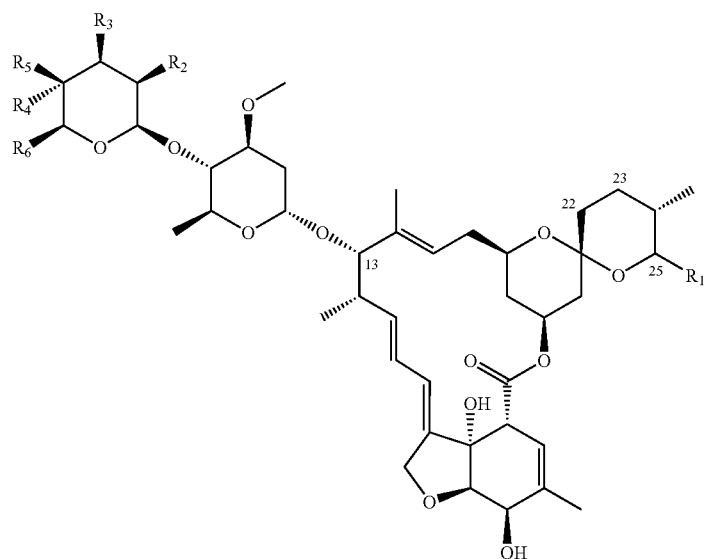
wherein $R_1$ is sec-butyl or isopropyl, and
| | $R_2$ | $R_3$ | $R_4$ | $R_5$ | $R_6$ | Retention time (min) B1a | B1b |
|---|---|---|---|---|---|---|---|
| P5.1 | $OCH_3$ | $OCH_3$ | $OCH_3$ | H | $CH_3$ | 12.84[2)] | — |
TABLE P6
A compound of formula
(I-6b)
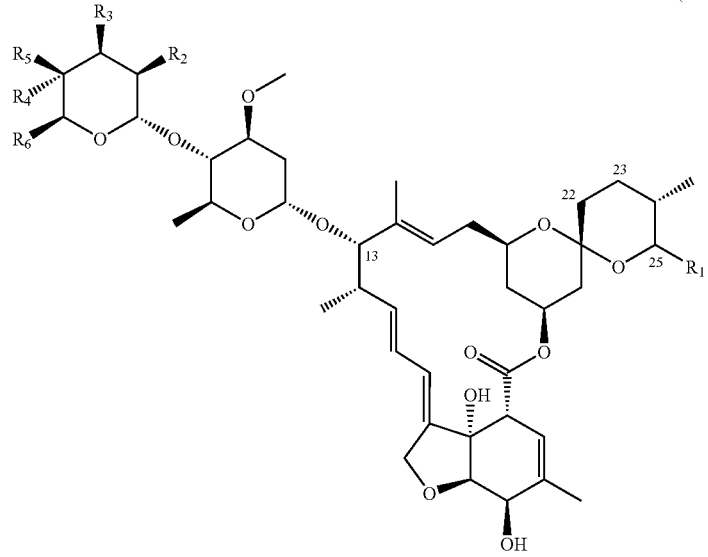
wherein $R_1$ is sec-butyl or isopropyl, and
| | $R_2$ | $R_3$ | $R_4$ | $R_5$ | $R_6$ | Retention time (min) B1a | B1b |
|---|---|---|---|---|---|---|---|
| P6.1 | $OCH_3$ | $OCH_3$ | $OCH_3$ | H | $CH_3$ | 13.43[2)] | — |

TABLE P7
A compound of formula
(I-7a)
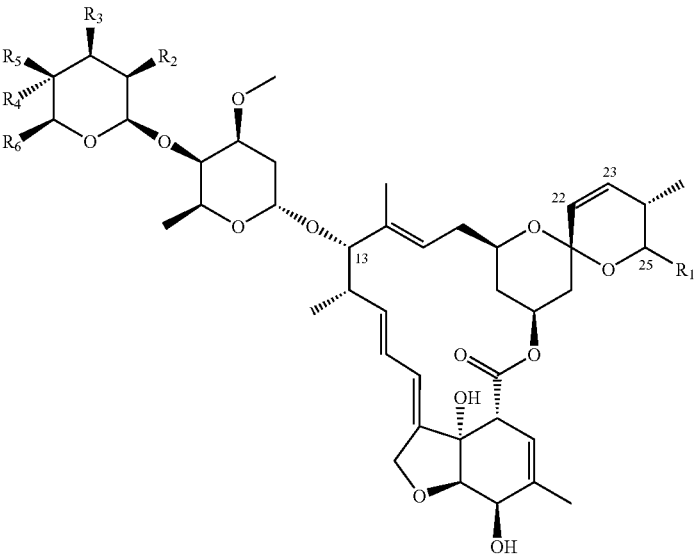
wherein $R_1$ is sec-butyl or isopropyl, and
| | $R_2$ | $R_3$ | $R_4$ | $R_5$ | $R_6$ | Retention time (min) B1a | B1b |
|---|---|---|---|---|---|---|---|
| P7.1 | OCH$_3$ | OCH$_3$ | OCH$_3$ | H | CH$_3$ | 11.04[4)] | — |
TABLE P8
A compound of formula
(I-7b)
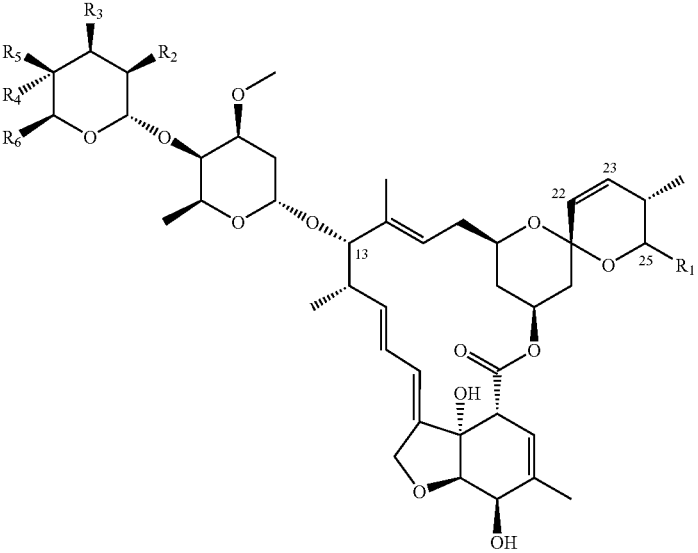
wherein $R_1$ is sec-butyl or isopropyl, and
| | $R_2$ | $R_3$ | $R_4$ | $R_5$ | $R_6$ | Retention time (min) B1a | B1b |
|---|---|---|---|---|---|---|---|
| P8.1 | OCH$_3$ | OCH$_3$ | OCH$_3$ | H | CH$_3$ | 10.88[4)] | — |

TABLE P9

A compound of formula

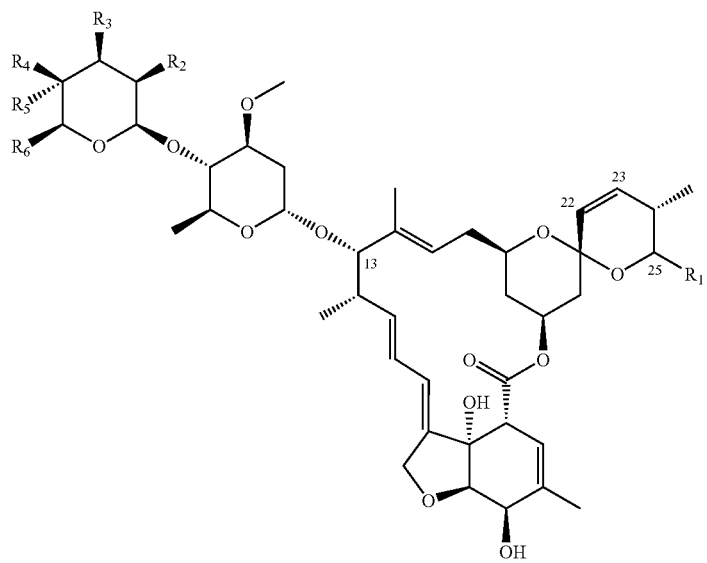

(I-9a)

wherein $R_1$ is sec-butyl or isopropyl, and

| | $R_2$ | $R_3$ | $R_4$ | $R_5$ | $R_6$ | Retention time (min) B1a | B1b |
|---|---|---|---|---|---|---|---|
| P9.1 | OCH$_3$ | OCH$_3$ | OH | CH$_3$ | CH$_3$ | 7.85[4] | — |
| P9.2 | OCH$_3$ | OCH$_3$ | NHCH$_3$ | H | CH$_3$ | 4.53[2] | — |
| P9.3 | OCH$_3$ | OCH$_3$ | N(CH$_3$)C(O)CH$_3$ | H | CH$_3$ | 6.85[1] | — |
| P9.4 | OCH$_3$ | OCH$_3$ | N(CH$_3$)C(O)OCH$_3$ | H | CH$_3$ | 8.21[1] | — |
| P9.5 | OCH$_3$ | OCH$_3$ | N(CH$_3$)C(O)OCH$_2$CH=CH$_2$ | H | CH$_3$ | 12.77[2] | — |

TABLE P10

A compound of formula

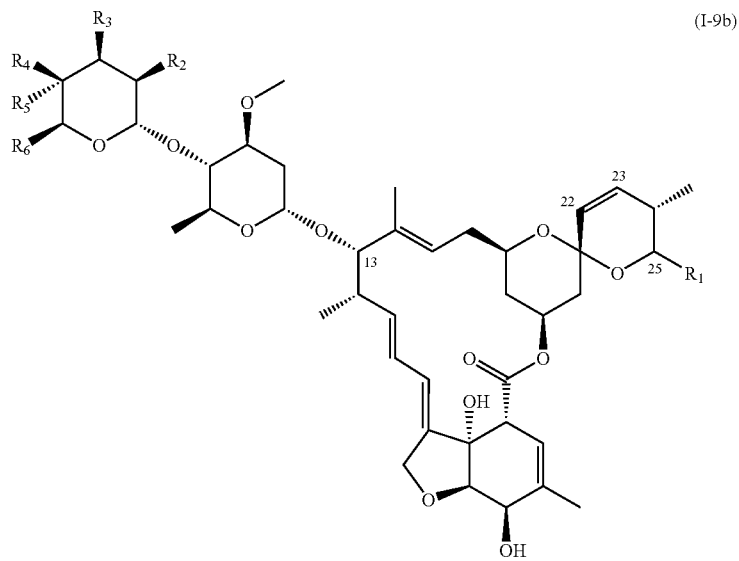

(I-9b)

wherein $R_1$ is sec-butyl or isopropyl, and

| | $R_2$ | $R_3$ | $R_4$ | $R_5$ | $R_6$ | Retention time (min) B1a | B1b |
|---|---|---|---|---|---|---|---|
| P10.1 | OCH$_3$ | OCH$_3$ | OH | CH$_3$ | CH$_3$ | 8.42[1] | — |

TABLE P10-continued

A compound of formula

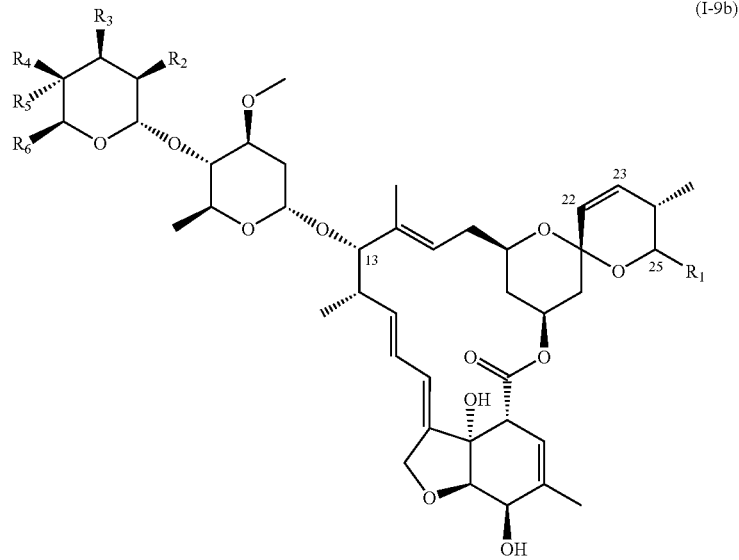

(I-9b)

wherein $R_1$ is sec-butyl or isopropyl, and

| | $R_2$ | $R_3$ | $R_4$ | $R_5$ | $R_6$ | Retention time (min) B1a | B1b |
|---|---|---|---|---|---|---|---|
| P10.2 | $OCH_3$ | $OCH_3$ | $NHCH_3$ | H | $CH_3$ | $10.81^{2)}$ | — |
| P10.3 | $OCH_3$ | $OCH_3$ | $N(CH_3)_2$ | H | $CH_3$ | $3.47^{1)}$ | — |
| P10.4 | $OCH_3$ | $OCH_3$ | $N(CH_3)C_2H_5$ | H | $CH_3$ | $3.75^{1)}$ | — |
| P10.5 | $OCH_3$ | $OCH_3$ | $N(CH_3)C(O)CH_3$ | H | $CH_3$ | $11.28^{2)}$ | — |
| P10.6 | $OCH_3$ | $OCH_3$ | $N(CH_3)C(O)CH_2OCH_3$ | H | $CH_3$ | $11.27^{2)}$ | — |
| P10.7 | $OCH_3$ | $OCH_3$ | $N(CH_3)C(O)OCH_3$ | H | $CH_3$ | $12.80^{2)}$ | — |
| P10.8 | $OCH_3$ | $OCH_3$ | $N(CH_3)C(O)OCH_2CH=CH_2$ | H | $CH_3$ | $13.48^{2)}$ | — |
| P10.9 | $CH_2CH_3$ | $OCH_3$ | OH | H | $CH_3$ | $12.07^{5)}$ | 11.79 |
| P10.10 | $CH_3$ | $OCH_3$ | OH | $CH_3$ | $CH_3$ | $12.35^{5)}$ | 11.79 |
| P10.11 | $OCH_3$ | $OCH_3$ | $NH_2$ | $CH_3$ | $CH_3$ | $5.89^{2)}$ | |
| P10.12 | $OCH_3$ | $OCH_3$ | $NHC(O)CH_3$ | $CH_3$ | $CH_3$ | $11.41^{2)}$ | |

TABLE P11
A compound of formula
(I-13a)
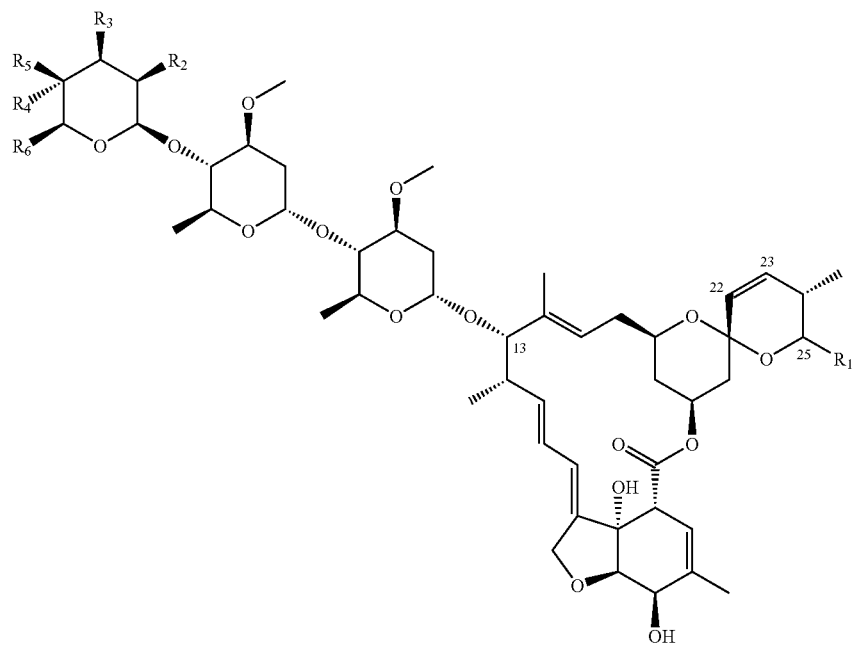
wherein $R_1$ is sec-butyl or isopropyl, and
| | $R_2$ | $R_3$ | $R_4$ | $R_5$ | $R_6$ | Retention time (min) B1a | B1b |
|---|---|---|---|---|---|---|---|
| P11.1 | OCH$_3$ | OCH$_3$ | OCH$_3$ | H | CH$_3$ | 9.11[1) | 8.54 |
| P11.2 | OCH$_3$ | OCH$_3$ | OC(O)CH$_3$ | H | CH$_3$ | 12.66[5) | — |

TABLE P12
A compound of formula
(I-13b)
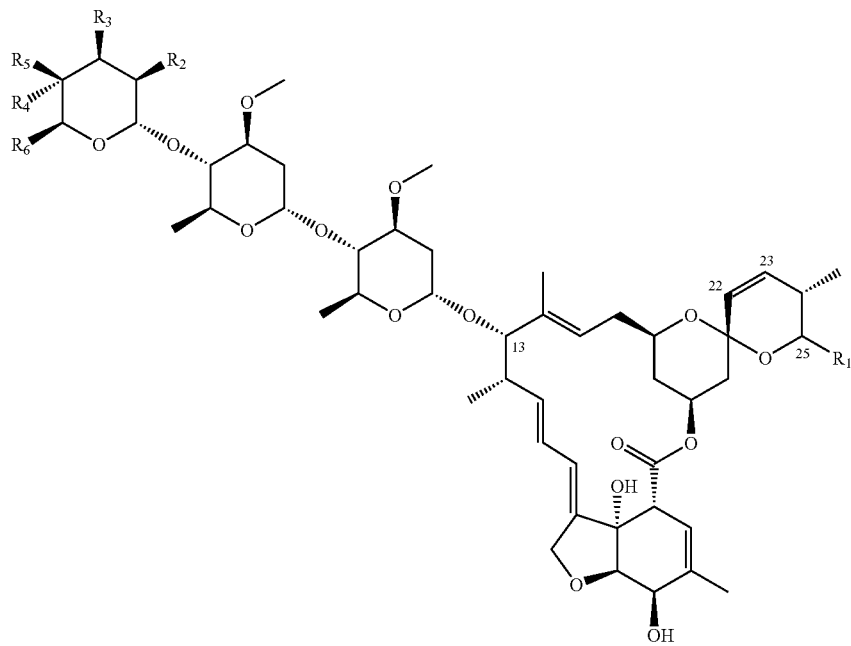
wherein $R_1$ is sec-butyl or isopropyl, and
|  | $R_2$ | $R_3$ | $R_4$ | $R_5$ | $R_6$ | Retention time (min) B1a | B1b |
|---|---|---|---|---|---|---|---|
| P12.1 | OCH$_3$ | OCH$_3$ | OCH$_3$ | H | CH$_3$ | 13.39[5)] | — |
| P12.2 | OCH$_3$ | OCH$_3$ | OC(O)CH$_3$ | H | CH$_3$ | 13.37[5)] | — |
| P12.3 | OC(O)OCH$_2$CH=CH$_2$ | OC(O)OCH$_2$CH=CH$_2$ | OCH$_2$OCH$_2$CH$_3$ | H | CH$_3$ | 14.76[5)] | — |

TABLE P13

A compound of formula

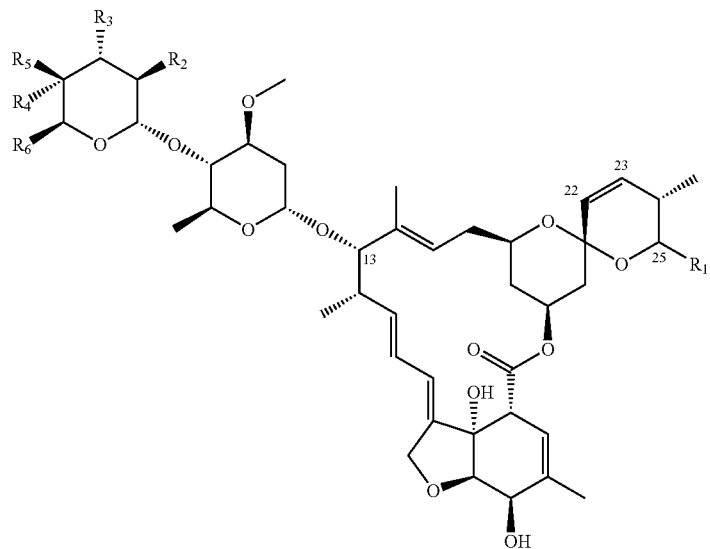

(I-25B)

wherein $R_1$ is sec-butyl or isopropyl, and

| | $R_2$ | $R_3$ | $R_4$ | $R_5$ | $R_6$ | Retention time (min) B1a | B1b |
|---|---|---|---|---|---|---|---|
| P13.1 | $CH_3$ | $OCH_3$ | OH | H | $CH_3$ | 9.54[3)] | — |
| P13.2 | $CH_3$ | $OCH_3$ | OH | $CH_3$ | $CH_3$ | 10.41[3)] | — |
| P13.3 | $CH_3$ | $OCH_3$ | $NH_2$ | H | $CH_3$ | 5.15[3)] | — |
| P13.4 | $CH_3$ | $OCH_3$ | $NHCH_3$ | H | $CH_3$ | 5.19[2)] | 4.78[2)] |
| P13.5 | $CH_3$ | $OCH_3$ | NHOH | H | $CH_3$ | 6.24[3)] | — |
| P13.6 | $CH_3$ | $OCH_3$ | $N(CH_3)_2$ | H | $CH_3$ | 4.99[5)] | — |
| P13.7 | $CH_3$ | $OCH_3$ | NHC(O)H | H | $CH_3$ | 9.56[3)] | — |
| P13.8 | $CH_3$ | $OCH_3$ | $NHC(O)CH_3$ | H | $CH_3$ | 9.39[3)] | — |
| P13.9 | $CH_3$ | $OCH_3$ | $NHC(O)CH_2OCH_3$ | H | $CH_3$ | 10.40[3)] | — |
| P13.10 | $CH_3$ | $OCH_3$ | $NHC(O)OCH_3$ | H | $CH_3$ | 9.72[3)] | — |
| P13.11 | $CH_3$ | $OCH_3$ | $N(CH_3)C(O)H$ | H | $CH_3$ | 11.84[2)] | 11.09[2)] |
| P13.12 | $CH_3$ | $OCH_3$ | $N(CH_3)C(O)CH_3$ | H | $CH_3$ | 10.74[3)] | — |
| P13.13 | $CH_3$ | $OCH_3$ | $N(CH_3)C(O)CH_2OCH_3$ | H | $CH_3$ | 10.90[3)] | — |
| P13.14 | $CH_3$ | $OCH_3$ | $N(CH_3)O(O)OCH_3$ | H | $CH_3$ | 12.65[3)] | — |
| P13.15 | $CH_3$ | $OCH_3$ | $N(CH_3)CH_2CN$ | H | $CH_3$ | 13.38[2)] | 13.00[2)] |
| P13.16 | $CH_2CH_3$ | $OCH_3$ | OH | H | $CH_3$ | 12.25[5)] | — |
| P13.17 | $CH_3$ | $OCH_3$ | =N—OH | | $CH_3$ | 11.33[3)] | — |
| P13.18 | $OCH_3$ | $OCH_3$ | $OCH_3$ | H | H | 10.89[2)] | — |

TABLE P14

A compound of formula (I-27a)

[Structure diagram]

wherein $R_1$ is sec-butyl or isopropyl, and

| | | | | | Retention time (min) | |
|---|---|---|---|---|---|---|
| $R_2$ | $R_3$ | $R_4$ | $R_5$ | $R_6$ | B1a | B1b |
| P14.1 OCH$_3$ | OCH$_3$ | OCH$_3$ | H | H | 11.57[2)] | 10.74 |

TABLE P15

A compound of formula (I-27b)

[Structure diagram]

wherein $R_1$ is sec-butyl or isopropyl, and

| | | | | | Retention time (min) | |
|---|---|---|---|---|---|---|
| $R_2$ | $R_3$ | $R_4$ | $R_5$ | $R_6$ | B1a | B1b |
| P15.1 OCH$_3$ | OCH$_3$ | OCH$_3$ | H | H | 8.86[1)] | — |
| P15.2 CH$_3$ | OCH$_3$ | OH | H | CH$_3$ | 11.42[2)] | — |
| P15.3 CH$_3$ | OCH$_3$ | OH | CH$_3$ | CH$_3$ | 11.88[5)] | — |

TABLE P16

A compound of formula (I-53b)

[Structure diagram]

wherein $R_1$ is sec-butyl or isopropyl, and

| | | | | | Retention time (min) | |
|---|---|---|---|---|---|---|
| $R_2$ | $R_3$ | $R_4$ | $R_5$ | $R_6$ | B1a | B1b |
| P16.1 OCH$_3$ | OCH$_3$ | OCH$_3$ | H | H | 10.30[5)] | — |

TABLE P17

A compound of formula

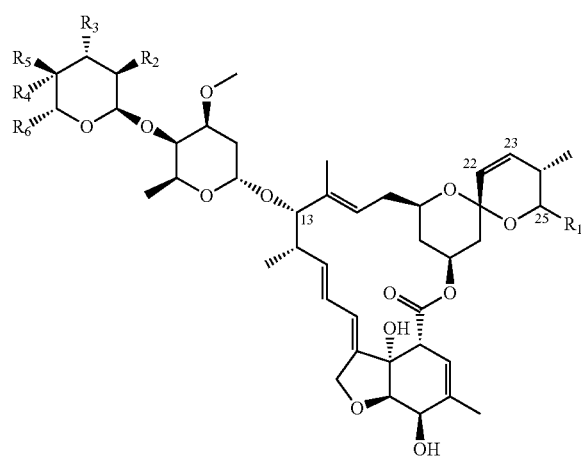

(I-89a)

wherein $R_1$ is sec-butyl or isopropyl, and

| | $R_2$ | $R_3$ | $R_4$ | $R_5$ | $R_6$ | Retention time (min) B1a | B1b |
|---|---|---|---|---|---|---|---|
| P17.1 | $OCH_3$ | $OCH_3$ | $OCH_3$ | H | H | 9.79[2)] | 9.02 |

TABLE P18

A compound of formula

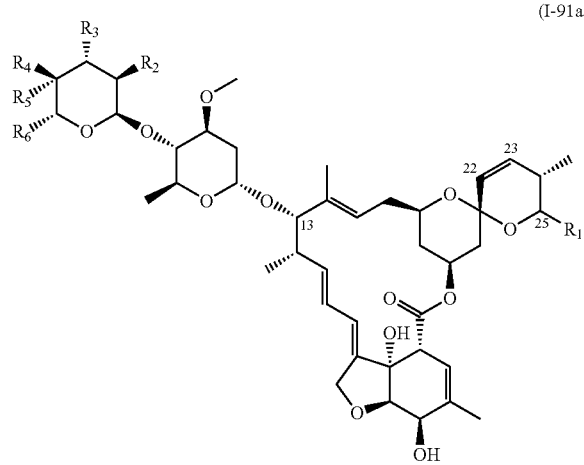

(I-91a)

wherein $R_1$ is sec-butyl or isopropyl, and

| | $R_2$ | $R_3$ | $R_4$ | $R_5$ | $R_6$ | Retention time (min) B1a | B1b |
|---|---|---|---|---|---|---|---|
| P18.1 | $OCH_3$ | $OCH_3$ | $OCH_3$ | H | $CH_2OCH_3$ | 11.79[2)] | 11.03 |

TABLE P19

A compound of formula

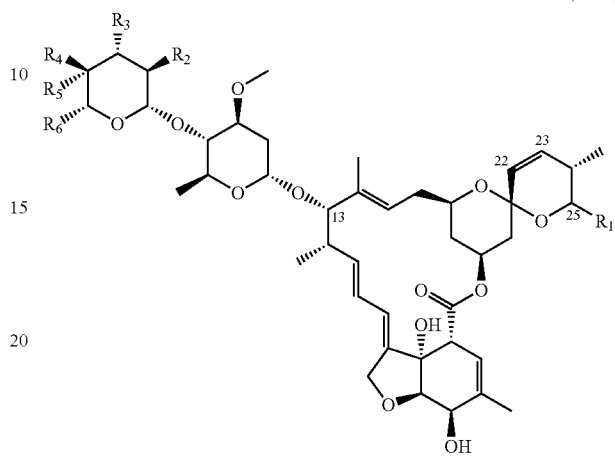

(I-91b)

wherein $R_1$ is sec-butyl or isopropyl, and

| | $R_2$ | $R_3$ | $R_4$ | $R_5$ | $R_6$ | Retention time (min) B1a | B1b |
|---|---|---|---|---|---|---|---|
| P19.1 | $OCH_3$ | $OCH_3$ | $OCH_3$ | H | $CH_2OCH_3$ | 12.53[2)] | |

TABLE P20

A compound of formula

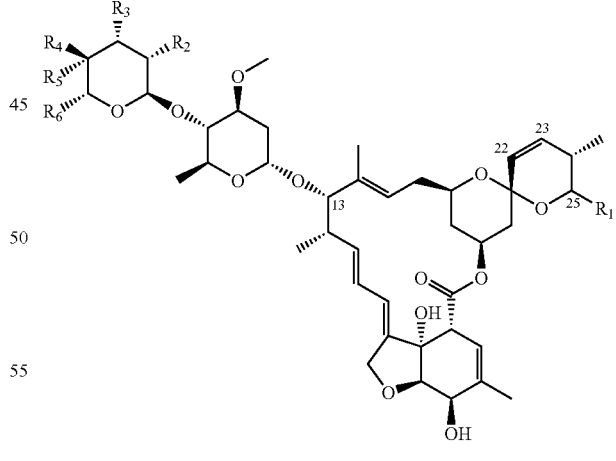

(I-105a)

wherein $R_1$ is sec-butyl or isopropyl, and

| | $R_2$ | $R_3$ | $R_4$ | $R_5$ | $R_6$ | Retention time (min) B1a | B1b |
|---|---|---|---|---|---|---|---|
| P20.1 | $OCH_3$ | $OCH_3$ | $OCH_3$ | H | H | 10.76[2)] | — |
| P20.2 | $OCH_3$ | $OCH_3$ | $OCH_3$ | H | $CH_2OCH_3$ | 7.93[1)] | |

TABLE P21

A compound of formula

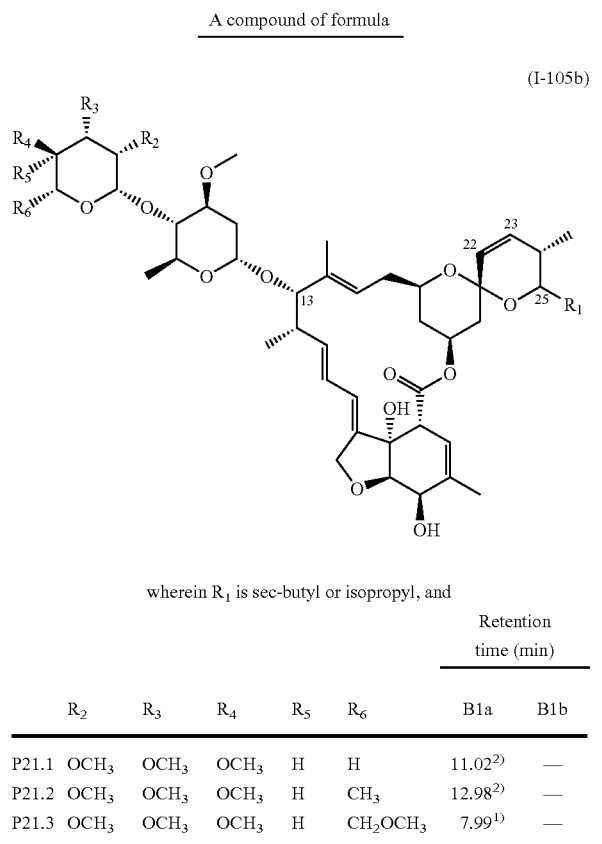

(I-105b)

wherein $R_1$ is sec-butyl or isopropyl, and

| | $R_2$ | $R_3$ | $R_4$ | $R_5$ | $R_6$ | Retention time (min) B1a | B1b |
|---|---|---|---|---|---|---|---|
| P21.1 | OCH$_3$ | OCH$_3$ | OCH$_3$ | H | H | 11.02[2) | — |
| P21.2 | OCH$_3$ | OCH$_3$ | OCH$_3$ | H | CH$_3$ | 12.98[2) | — |
| P21.3 | OCH$_3$ | OCH$_3$ | OCH$_3$ | H | CH$_2$OCH$_3$ | 7.99[1) | — |

TABLE P22

A compound of formula

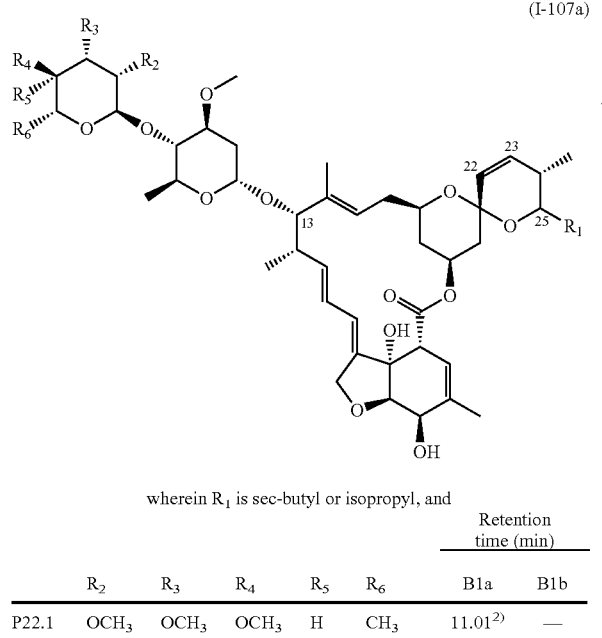

(I-107a)

wherein $R_1$ is sec-butyl or isopropyl, and

| | $R_2$ | $R_3$ | $R_4$ | $R_5$ | $R_6$ | Retention time (min) B1a | B1b |
|---|---|---|---|---|---|---|---|
| P22.1 | OCH$_3$ | OCH$_3$ | OCH$_3$ | H | CH$_3$ | 11.01[2) | — |

TABLE P23

A compound of formula

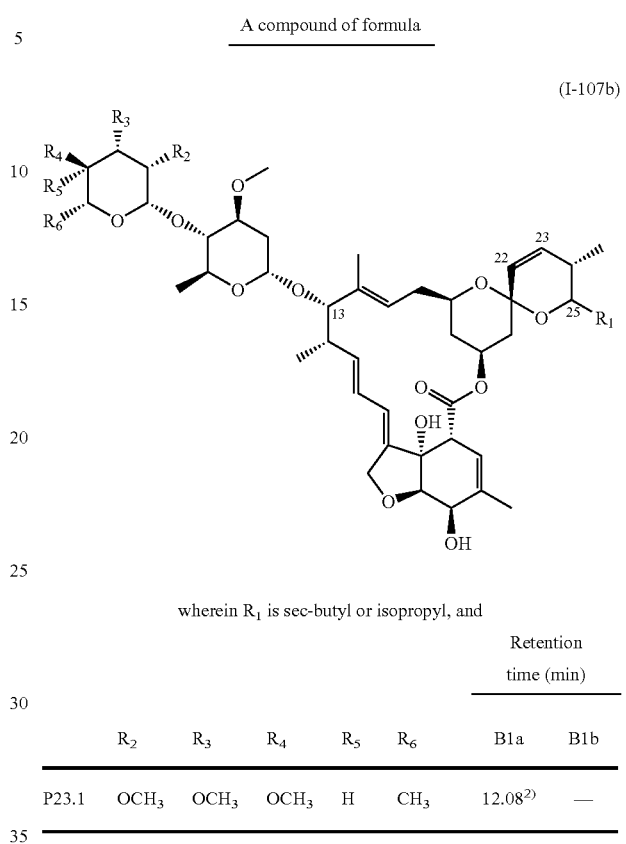

(I-107b)

wherein $R_1$ is sec-butyl or isopropyl, and

| | $R_2$ | $R_3$ | $R_4$ | $R_5$ | $R_6$ | Retention time (min) B1a | B1b |
|---|---|---|---|---|---|---|---|
| P23.1 | OCH$_3$ | OCH$_3$ | OCH$_3$ | H | CH$_3$ | 12.08[2) | — |

TABLE P24

A compound of formula

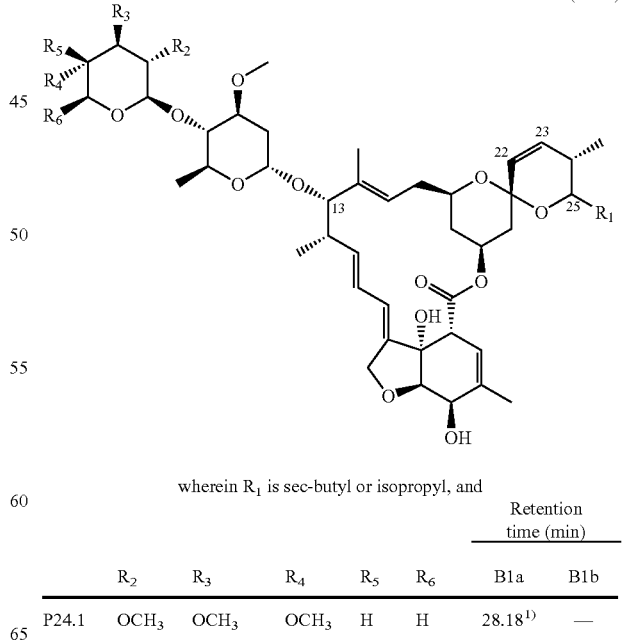

(I-45a)

wherein $R_1$ is sec-butyl or isopropyl, and

| | $R_2$ | $R_3$ | $R_4$ | $R_5$ | $R_6$ | Retention time (min) B1a | B1b |
|---|---|---|---|---|---|---|---|
| P24.1 | OCH$_3$ | OCH$_3$ | OCH$_3$ | H | H | 28.18[1) | — |

TABLE P25
A compound of formula
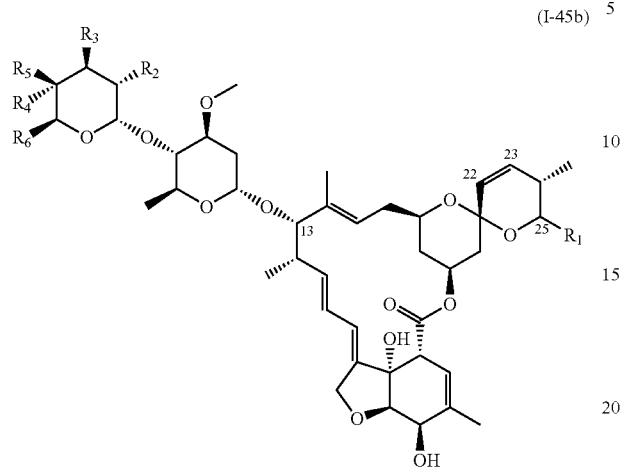
(I-45b)
wherein $R_1$ is sec-butyl or isopropyl, and
| | $R_2$ | $R_3$ | $R_4$ | $R_5$ | $R_6$ | Retention time (min) B1a | B1b |
|---|---|---|---|---|---|---|---|
| P25.1 | OCH$_3$ | OCH$_3$ | OCH$_3$ | H | H | 8.43[1) | — |
TABLE P26
A compound of formula
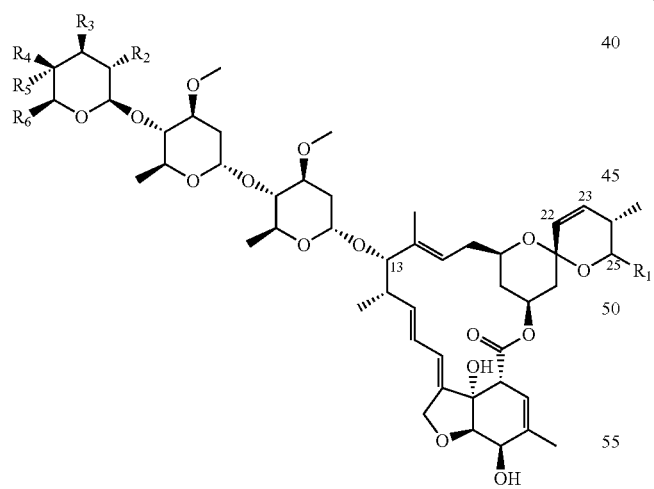
(I-55a)
wherein $R_1$ is sec-butyl or isopropyl, and
| | $R_2$ | $R_3$ | $R_4$ | $R_5$ | $R_6$ | Retention time (min) B1a | B1b |
|---|---|---|---|---|---|---|---|
| P26.1 | OCH$_3$ | OCH$_3$ | OCH$_3$ | H | H | 11.95[2) | 11.22 |

TABLE P27

A compound of formula (I-55b)

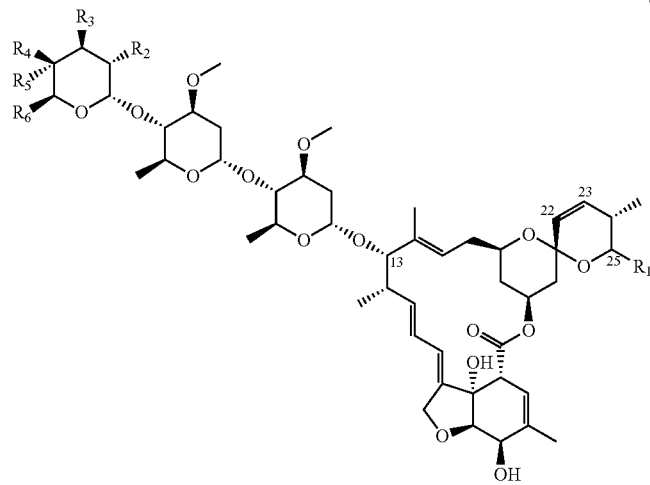

wherein $R_1$ is sec-butyl or isopropyl, and

| | $R_2$ | $R_3$ | $R_4$ | $R_5$ | $R_6$ | Retention time (min) B1a | B1b |
|---|---|---|---|---|---|---|---|
| P27.1 | $OCH_3$ | $OCH_3$ | $OCH_3$ | H | H | $12.10^{2)}$ | — |

Biological Examples

Example B1

Activity Against *Spodoptera littoralis*

Young soya bean plants are sprayed with an aqueous emulsion spray liquor which comprises 12.5 ppm of active compound, and, after the spray coating has dried on, populated with 10 caterpillars of the first stage of *Spodoptera littoralis* and introduced into a plastic container. 3 days later, the reduction in the population in percent and the reduction in the feeding damage in percent (% activity) are determined by comparing the number of dead caterpillars and the feeding damage between the treated and the untreated plants.

In this test, the compounds of formulae (I) show good activity. In particular, the compounds P3.3, P4.3, P7.1, P8.1, P10.9, P10.10, P12.1, P13.2, P13.4, P13.6, P13.7, P13.9, P13.11, P13.12, P13.13, P13.14, P13.15, P13.16, and P15.3 effect a reduction in the pest population by more than 80%.

Example B2

Activity Against *Spodoptera littoralis*, Systemic

Maize seedlings are placed into the test solution which comprises 12.5 ppm of active compound. After 6 days, the leaves are cut off, placed onto moist filter paper in a Petri dish and populated with 12 to 15 *Spodoptera littoralis* larvae of the L, stage. 4 days later, the reduction of the population in percent (% activity) is determined by comparing the number of dead caterpillars between the treated and the untreated plants. In this test, the compounds of formulae (I) show good activity. In particular, the compounds P2.3, P8.1, P10.9, P13.4, P13.6, P13.7, P13.9, and P13.16 effect a reduction in the pest population by more than 80%.

Example B3

Activity Against *Heliothis virescens*

0- to 24-hour-old eggs of *Heliothis virescens* are placed onto filter paper in a Petri dish on a layer of synthetic feed. 0.8 ml of the test solution which comprises 12.5 ppm of active compound, is then pipetted onto the filter papers. Evaluation is carried out after 6 days. The reduction in the population in percent (% activity) is determined by comparing the number of dead eggs and larvae on the treated and the untreated filter papers.

In this test, the compounds of formulae (I) show good activity. In particular, the compounds P2.2, P3.3, P3.5, P4.3, P4.5, P7.1, P8.1, P10.9, P10.10, P11.2, P12.1, P13.2, P13.4, P13.6, P13.7, P13.9, P13.11, P13.12, P13.13, P13.14, P13.15, P13.16, and P15.3 effect a reduction in the pest population by more than 80%.

Example B4

Activity Against *Plutella xylostella* Caterpillars

Young cabbage plants are sprayed with an aqueous emulsion spray liquor which comprises 12.5 ppm of the active compound. After the spray coating has dried on, the cabbage plants are populated with 10 caterpillars of the third stage of *Plutella xylostella* and introduced into a plastic container. Evaluation is carried out after 3 days. The reduction in the population in percent and the reduction in the feeding damage in percent (% activity) are determined by comparing the number of dead caterpillars and the feeding damage on the treated and the untreated plants.

In this test, the compounds of formulae (I) show good activity. In particular, the compounds P3.3, P3.5, P4.3, P4.5, P7.1, P8.1, P10.9, P10.10, P11.2, P12.1, P13.2, P13.4, P13.6, P13.7, P13.9, P13.11, P13.12, P13.13, P13.14, P13.15, P13.16, and P15.3 effect a reduction in the pest population by more than 80%.

Example B5

Activity Against *Frankliniella occidentalis*

In Petri dishes, discs of the leaves of beans are placed onto agar and sprayed with test solution which comprises 12.5 ppm of active compound, in a spraying chamber. The leaves are then populated with a mixed population of *Frankliniella occidentalis*. Evaluation is carried out after 10 days. The reduction in percent (% activity) is determined by comparing the population on the treated leaves with that of the untreated leaves.

In this test, the compounds of formulae (I) show good activity. In particular, the compounds P2.2, P3.3, P3.5, P4.3, P4.5, P7.1, P8.1, P10.9, P10.10, P11.2, P12.1, P13.2, P13.4, P13.6, P13.7P13.9, P13.11, P13.12, P13.13, P13.14, P13.15, P13.16, and P15.3 effect a reduction in the pest population by more than 80%.

Example B6

Activity Against *Diabrotica balteata*

Maize seedlings are sprayed with an aqueous emulsion spray liquor which comprises 12.5 ppm of active compound and, after the spray coating has dried on, populated with 10 larvae of the second stage of *Diabrotica balteata* and then introduced into a plastic container. After 6 days, the reduction in the population in percent (% activity) is determined by comparing the dead larvae between the treated and the untreated plants.

In this test, compounds of formula (I) show good activity, in particular, the compounds P3.3, P10.9, P10.10, P1.2, P13.2, P13.6, P13.9, P13.11, P1312, P13.16, and P15.3 effect a reduction in the pest population by more than 80%.

Example B7

Activity Against *Tetranychus urticae*

Young bean plants are populated with a mixed population of *Tetranychus urticae* and, after 1 day, sprayed with an aqueous emulsion spray liquor which comprises 12.5 ppm of active compound, incubated at 25° C. for 6 days and then evaluated. The reduction in the population in percent (% activity) is determined by comparing the number of dead eggs, larvae and adults on the treated and on the untreated plants.

In this test, the compounds of formulae (I) show good activity. In particular, the compounds P1.1, P1.4, P2.1, P2.2, P2.3, P3.3, P3.5, P4.3, P4.5, P7.1, P8.1, P10.9, P10.10, P11.2, P12.1, P13.2, P13.4, P13.6, P13.7, P13.9, P13.11, P13.12, P13.13, P13.14, P13.15, P13.16, and P15.3 effect a reduction in the pest population by more than 80%.

The invention claimed is:
1. A compound of the formula (I)

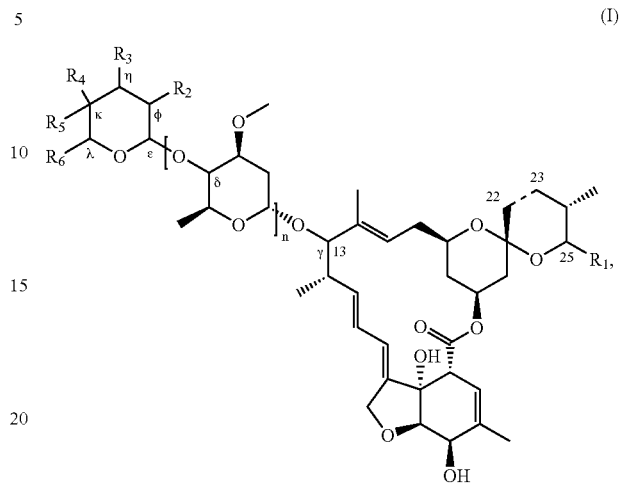

(I)

wherein the bond between carbon atoms 22 and 23 indicated with a broken line is a single or double bond, the symbols δ, ε, φ, η, κ, λ and γ represent that the configuration of the corresponding carbon atom can be (S) or (R), n is 0, 1 or 2, $R_1$ represents a $C_1$-$C_{12}$alkyl, $C_3$-$C_8$cycloalkyl or $C_2$-$C_{12}$alkenyl group, $R_2$ represents $R_{15}$, $R_{16}O$, $R_{16}C(=O)O$, $R_{15}OC(=O)O$, $R_{16}S$, $R_{16}C(=O)S$, $R_{16}R_{17}N$, $R_{16}(CN)N$, $R_{16}C(=O)R_{17}N$, $R_{15}OC(=O)R_{17}N$, $R_{15}SO_2R_{17}N$, $R_{18}R_{19}N$—C(=O)—O, $R_{18}R_{19}N$—C(=O)$R_{17}N$, or a $R_{18}R_{19}N$—$SO_2R_{17}N$ group, $R_3$ represents hydrogen or a $R_2$ group, or $R_2$ and $R_3$ together represent —$OCR_7R_8O$—$OC(O)O$—, or —$OC(S)O$—, $R_4$ represents a halogen, hydrogen, $R_{16}$, $R_{16}O$, $R_{16}C(=O)O$, $R_{16}OC(=O)O$, $R_{16}C(=S)O$, $R_{16}S$, $R_{16}C(=O)S$, $R_{16}C(=S)S$, $R_{16}R_{17}N$, $R_{16}(NC)N$, $R_{16}(R_{17}O)N$, $R_{16}C(=O)R_{17}N$, $R_{16}C(=O)(OR_{17})N$, $R_{15}OC(=O)R_{17}N$, $R_{15}OC(=O)(OR_{17})N$, $R_{15}SO_2R_{17}N$, $R_{16}R_{17}NO$, $R_{16}(NC)NO$, $(R_{16}R_{17}C=)NO$, $R_{16}C(=O)R_{17}NO$, $R_{18}R_{19}N$—$R_{17}N$, $R_{18}(NC)N$—$R_{17}N$, $R_{18}(R_{19}O)N$—$R_{17}N$, $R_{18}R_{19}N$—C(=O)—O, $R_{18}R_{19}N$—C(=O)$R_{17}N$, or a $R_{18}R_{19}N$—$SO_2R_{17}N$ group, $R_5$ represents hydrogen, a $C_1$-$C_{15}$ hydrocarbyl or $C_1$-$C_{15}$ substituted hydrocarbyl group, or $R_4$ and $R_5$ together represent =O, =$NR_9$ or =$CR_{10}R_{11}$, and $R_6$ represents $R_{16}$, $R_{16}OCH_2$, $R_{16}C(=O)OCH_2$, $R_{15}OC(=O)OCH_2$, $R_{16}C(=S)OCH_2$, $R_{16}SCH_2$, $R_{16}C(=O)SCH_2$, $R_{16}C(=S)SCH_2$, $R_{16}R_{17}NCH_2$, $R_{16}(NC)NCH_2$, $R_{16}(R_{17}O)NCH_2$, $R_{16}C(=O)NR_{17}CH_2$, $R_{16}C(=O)N(OR_{17})CH_2$, $R_{15}OC(=O)NR_{17}CH_2$, $R_{15}OC(=O)N(OR_{17})CH_2$, $R_{15}SO_2NR_{17}CH_2$, $R_{16}R_{17}NOCH_2$, $R_{16}(NC)NOCH_2$, $R_{16}(R_{17}O)NOCH_2$, $R_{16}C(=O)NR_{17}OCH_2$, $R_{18}R_{19}N$—$NR_{17}CH_2$, $R_{18}(NC)N$—$NR_{17}CH_2$, $R_{18}(R_{19}O)N$—$NR_{17}CH_2$, $R_{18}R_{19}N$—C(=O)—$OCH_2$, $R_{18}R_{19}N$—C(=O)$NR_{17}CH_2$, or a $R_{18}R_{19}N$—$SO_2NR_{17}CH_2$ group;

wherein $R_7$ and $R_8$ represent, independently of each other, hydrogen, or a $C_1$-$C_6$alkyl group, $R_9$ represents a hydrogen, or a $R_2$ group, $R_{10}$ and $R_{11}$ represent, independently of each other, hydrogen, halogen, cyano, formyl, $C(O)OR_{12}$, $C(O)$ NR$_{13}$R$_{14}$, unsubstituted or mono- to pentasubstituted C$_1$-C$_6$alkyl, unsubstituted or mono- to pentasubstituted C$_2$-C$_6$alkenyl, unsubstituted or mono- to pentasubstituted C$_2$-C$_6$alkynyl, unsubstituted or mono- to pentasubstituted C$_3$-C$_6$cycloalkyl, unsubstituted or mono- to pentasubstituted C$_6$-C$_{20}$ aryl, or unsubstituted or mono- to pentasubstituted C$_3$-C$_{14}$ heteroaryl group, R$_{15}$ represents unsubstituted or mono- to pentasubstituted C$_1$-C$_6$alkyl, unsubstituted or mono- to pentasubstituted C$_2$-C$_6$alkenyl, unsubstituted or mono- to pentasubstituted C$_2$-C$_6$alkynyl, unsubstituted or mono- to pentasubstituted C$_3$-C$_6$cycloalkyl, unsubstituted or mono- to pentasubstituted C$_6$-C$_{20}$ aryl, or unsubstituted or mono- to pentasubstituted C$_3$-C$_{14}$ heteroaryl group, and R$_{12}$, R$_{13}$, R$_{14}$, R$_{16}$, R$_{17}$, R$_{18}$ and R$_{19}$ represent, independently of each other, hydrogen or R$_{15}$, or R$_{16}$ and R$_{17}$, or R$_{18}$ and R$_{19}$, together represent, independently of each other, a three- to ten-membered ring, optionally containing heteroatoms;

with the proviso that (i) the substituent R$_4$ is not a hydroxy, if R$_2$ and R$_3$ are hydroxy groups, R$_5$ is a hydrogen, and R$_6$ is a CH$_3$ or CH$_2$OH group, or (ii) the substituent R$_4$ is not a OCH$_2$C$_6$H$_5$ or OC(=O)C$_6$H$_5$ group, if R$_2$ and R$_3$ are OCH$_2$C$_6$H$_5$ or OC(=O)C$_6$H$_5$ groups, R$_5$ is a hydrogen, and R$_6$ is a CH$_2$OCH$_2$C$_6$H$_5$ or CH$_2$C(=O)C$_6$H$_5$ group, or (iii) R$_4$ is not OCH$_3$, if R$_2$ and R$_3$ are OCH$_3$ groups, R$_5$ is a hydrogen, R$_6$ is CH$_2$OCH$_3$, and the carbon configurations of the cyclic acetal at 2-position ($\phi$) is (R), at 3-position ($\eta$) is (S), at 4-position ($\kappa$) is (S), and at 5-position ($\lambda$) is (R), or (iv) R$_4$ is not OCH$_3$, if R$_2$ and R$_3$ are OCH$_3$ groups, R$_5$ and R$_6$ are hydrogens, and the carbon configurations of the cyclic acetal at 2-position ($\phi$) is (S), at 3-position ($\eta$) is (R), and at 4-position ($\kappa$) is (R), and n is 1, or (v) R$_4$ is not OCH$_3$, if R$_2$ and R$_3$ are OCH$_3$ groups, R$_5$ is a hydrogen, R$_6$ is CH$_3$, and the carbon configurations of the cyclic acetal at 2-position ($\phi$) is (S), at 3-position ($\eta$) is (R), at 4-position ($\kappa$) is (R), and at 5-position ($\lambda$) is (S), and n is 1, or (vi) the substituent R$_4$ is not an unsubstituted acetyloxy group, if (a) R$_2$ and R$_3$ are an unsubstituted acetyloxy, or (b) R$_2$ is an unsubstituted acetylamino group and R$_3$ is an unsubstituted acetyloxy, and, for either (a) or (b), R$_5$ is hydrogen and R$_6$ is H, CH$_3$, CH$_2$C(=O)CH$_3$, or CO$_2$H group;

and if appropriate, an E/Z isomer and/or diastereoisomer and/or tautomer of the compound of formula (I), in each case in free form or in salt form.

2. A process for preparing a compound of formula (I)

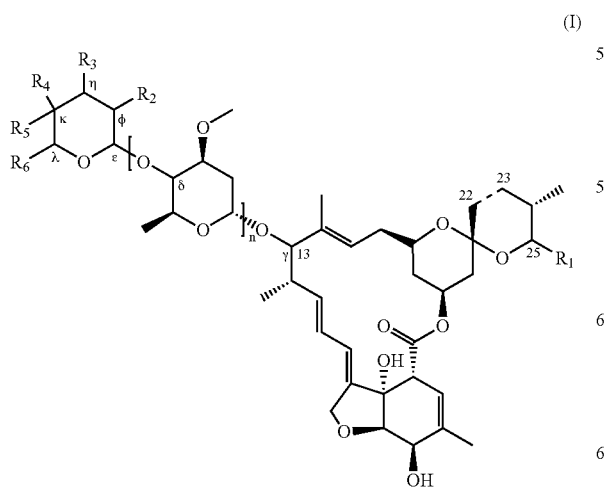

(I)

wherein R$_1$, R$_2$, R$_3$, R$_4$, R$_5$, R$_6$, the bond between the carbon atoms 22 and 23 and n are as defined in claim 1, comprising the steps of:

(i) carrying out a glycosylation reaction at the hydroxy group at the 13-, 4'-, or 4"-position (n is 0, 1 or 2 respectively) of a compound of formula (V)

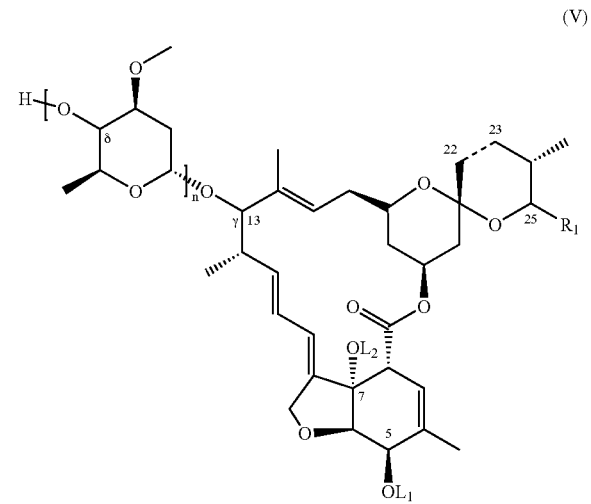

(V)

wherein R1, n and the bond between carbon atoms 22 and 23 are as defined for a compound of formula (I) and L1 and L2 are protecting groups, with an activated tetrahydropyran of formula ($\alpha$)

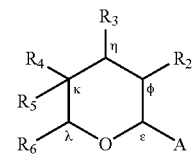

($\alpha$)

with R$_2$, R$_3$, R$_4$, R$_5$ and R$_6$ substituents to yield a compound of formula (II)

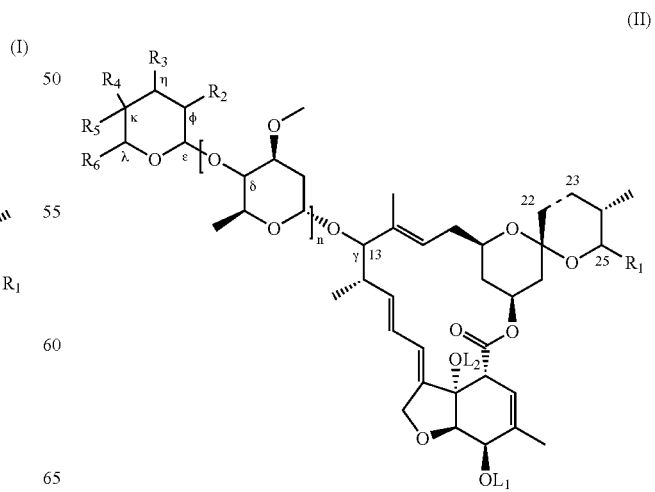

(II)

wherein $R_1$, $R_2$, $R_3$, $R_4$, $R_5$, $R_6$, the bond between the carbon atoms 22 and 23 and n are as defined in claim 1, $L_1$ is a protecting group and $L_2$ is a protecting group; and
either
(ii) removing the protecting group $L_1$ and $L_2$, if applicable, to yield a compound of formula (I), or
(iii) carrying out reactions on one or more of $R_2$, $R_3$, $R_4$, $R_5$, $R_6$ groups to modify the group and then removing the protecting group $L_1$ and $L_2$, if applicable, to yield a compound of formula (I).

3. A process for preparing a compound of formula (I)

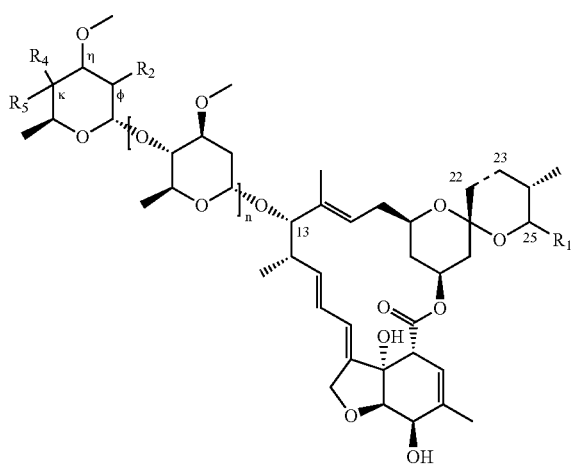

(I)

wherein $R_1$, $R_4$, $R_5$ and the bond between the carbon atoms 22 and 23 are as defined in claim 1, n is 0 or 1, and $R_2$ is $R_{15}$ as defined in claim 1, comprising the steps of:
(i) oxidising the hydroxy group at the 4'- or 4"-position to yield a oxo-compound of formula (III),

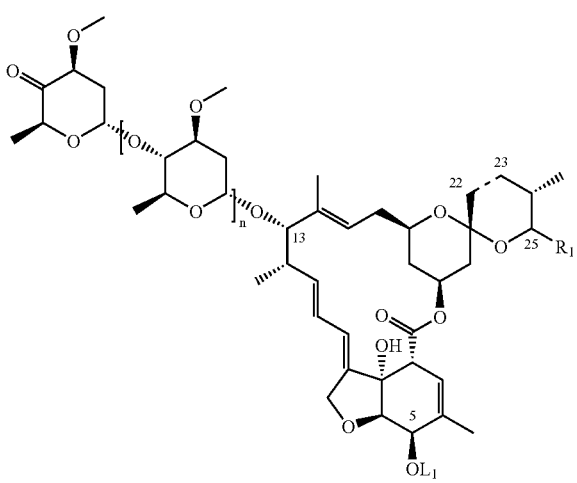

(III)

wherein $R_1$ and the bond between the carbon atoms 22 and 23 are as defined in claim 1, n is 0 or 1, and $L_1$ is a protecting group, and
(iii) reacting the compound of formula (III) with a base and a trialkylsilyl compound to form an enolate, (iv) oxidizing the enolate to an enone of the formula (IV),

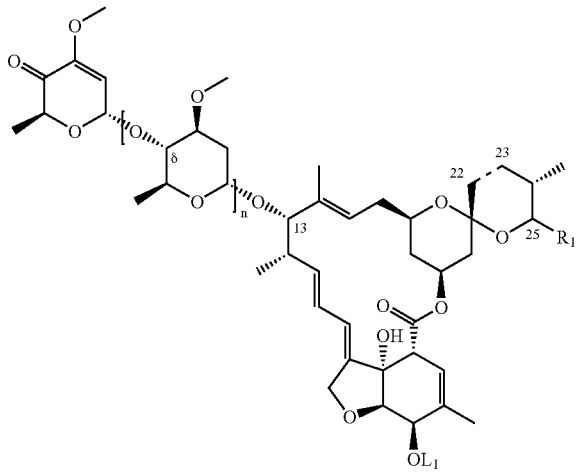

(IV)

wherein $R_1$ and the bond between the carbon atoms 22 and 23 are as defined in claim 1, n is 0 or 1, and $L_1$ is a protecting group
(v) adding an organometallic reagent having a substituent $R_2$ to the enone, and
(vi) carrying out reactions on one or more of $R_2$, $R_4$, $R_5$ groups to modify the group and then removing the protecting group $L_1$ to yield a compound of formula (I).

4. A compound of the formula (II)

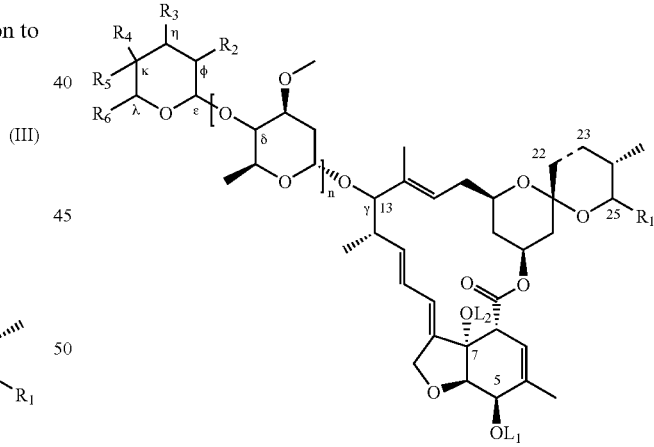

(II)

wherein $R_1$, $R_2$, $R_3$, $R_4$, $R_5$, $R_6$, the bond between the carbon atoms 22 and 23 and n are as defined in claim 1, $L_1$ is a protecting group, and $L_2$ is hydrogen or a protecting group.

5. A compound according to claim 1 wherein the bond between carbon atoms 22 and 23 is a double bond, n is 1 or 2, $R_1$ represents a $C_1$-$C_4$alkyl group (preferably isopropyl, or sec-butyl), $R_2$ represents $C_1$-$C_4$alkyl or $C_1$-$C_4$alkoxy, $R_3$ represents $C_1$-$C_4$alkoxy, $R_4$ represents H, OH, $C_1$-$C_4$alkoxy, $C_1$-$C_4$alkoxy $C_1$-$C_4$alkoxy, $C_1$-$C_4$alkanoyloxy, $C_1$-$C_4$alkoxycarbonyloxy, $C_2$-$C_4$alkenyloxycarbonyloxy, $C_1$-$C_4$alkylamino, di$C_1$-$C_4$alkylamino, $C_1$-$C_4$alkanoylamino, di$C_1$-$C_4$alkanoylamino, $C_1$-$C_4$alkanoyl-$C_1$-$C_4$alkyl-amino,
$C_1$-$C_4$alkoxycarbonylamino, di $C_1$-$C_4$alkoxycarbonylamino,
$C_1$-$C_4$alkoxycarbonyl-$C_1$-$C_4$alkyl-amino, or
$C_2$-$C_4$alkenyloxycarbonyl-$C_1$-$C_4$alkyl-amino, $R_5$ represents H, $C_1$-$C_4$alkyl, $C_2$-$C_3$alkenyl, $C_2$-$C_3$alkynyl or CN, or $R_4$ and $R_5$ together represent =O, =NOH, =$NOC_1$-$C_4$alkyl, or =$NOC_1$-$C_4$alkanoyl, and $R_6$ represents H, methyl, $C_1$-$C_4$alkoxy$CH_2$, or $C_1$-$C_4$alkanoyloxy$CH_2$, wherein (a) the carbon configurations of the cyclic acetal at 3-position (η) and 4-position (κ) are opposite to each other, (b) the carbon configurations of the cyclic acetal at 2-position (Φ) and 3-position (η) are the same, preferably (R), or (c) the carbon configurations of the cyclic acetal at 2-position (Φ), 3-position (η) and 4-position (κ) are the same, and in any one of (a), (b) or (c) the carbon configurations at any one of the other carbons atoms, independently of each other, is (R) or (S).

6. A pesticidal composition comprising at least one compound of the formula (I) as defined in claim 1, as active compound, and at least one auxiliary.

7. A method for controlling pests comprising applying a composition defined in claim 6 to the pests or their habitat.

8. A process for preparing a composition defined in claim 6 comprising mixing intimately and/or grinding at least one compound of formula (I)

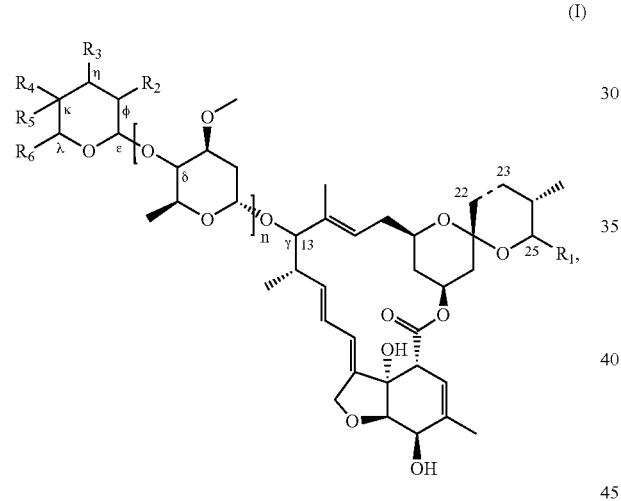

(I)

wherein the bond between carbon atoms 22 and 23 indicated with a broken line is a single or double bond, the symbols δ, ε, φ, η, κ, λ and γ represent that the configuration of the corresponding carbon atom can be (S) or (R), n is 0, 1 or 2, $R_1$ represents a $C_1$-$C_{12}$alkyl, $C_3$-$C_8$cycloalkyl or $C_2$-$C_{12}$alkenyl group, $R_2$ represents $R_{15}$, $R_{16}$O, $R_{16}$C(=O)O, $R_{15}$OC(=O)O, $R_{16}$S, $R_{16}$C(=O)S, $R_{16}R_{17}$N, $R_{16}$(CN)N, $R_{16}$C(=O)$R_{17}$N, $R_{15}$OC(=O)$R_{17}$N, $R_{15}SO_2R_{17}$N, $R_{18}R_{19}$N—C(=O)—O, $R_{18}R_{19}$N—C(=O)$R_{17}$N or a $R_{18}R_{19}$N—$SO_2R_{17}$N group, $R_3$ represents hydrogen or a $R_2$ group, or $R_2$ and $R_3$ together represent —$OCR_7R_8$O—OC(O)O—, or —OC(S)O—, $R_4$ represents a halogen, hydrogen, $R_{16}$, $R_{16}$C(=O)O, $R_{15}$OC(=O)O, $R_{16}$C(=s)O, $R_{16}$S, $R_{16}$C(=O)S, $R_{16}$C(=Os)S, $R_{16}R_{17}$N, $R_{16}$(NC)N, $R_{16}(R_{17}$O)N, $R_{16}$C(=O)$R_{17}$N, $R_{16}$C(=O)($OR_{17}$)N, $R_{15}$OC(=O)$R_{17}$N, $R_{15}$OC(=O)($OR_{17}$)N, $R_{15}SO_2R_{17}$N, $R_{16}R_{17}$NO, $R_{16}$(NC)NO, $(R_{16}R_{17}$C=)NO, C(=O)$R_{17}$N, or $R_{18}R_{19}$N—$SO_2R_{17}$N group, $R_5$ represents hydrogen, a $C_1$-$C_{15}$ hydrocarbyl or $C_1$-$C_{15}$ substituted hydrocarbyl group, or $R_4$ and $R_5$ to ether represent =O, =$NR_9$ or =$CR_{10}R_{11}$, and $R_6$ represents $R_{16}$, $R_{16}OCH_2$, $R_{16}$C(=O)$OCH_2$, $R_{16}$OC(=O)$OCH_2$, $R_{16}$C(=S)$OCH_2$, $R_{16}SCH_2$, $R_{16}$C(=O)$SCH_2$, $R_{16}$C(=S)$SCH_2$, $R_{16}R_{17}NCH_2$, $R_{16}$(NC)$NCH_2$, $R_{16}(R_{17}$O)$NCH_2$, $R_{16}$C(=O)$NR_{17}CH_2$, $R_{16}$C(=O)N($OR_{17}$)$CH_2$, $R_{15}$OC(=O)$NR_{17}CH_2$, $R_{15}$OC(=O)N($OR_{17}$)$CH_2$, $R_{15}SO_2NR_{17}CH_2$, $R_{16}R_{17}NOCH_2$, $R_{16}$(NC)$NOCH_2$, $R_{16}$(NC)$NOCH_2$, $R_{16}$C(=O)$NR_{17}OCH_2$, $R_{18}R_{19}$N—$NR_{17}CH_2$, $R_{18}$(NC)N—$NR_{17}CH_2$, $R_{18}(R_{19}$O)N—$NR_{17}CH_2$, $R_{18}R_{19}$N—C(=O)—$OCH_2$, $R_{18}R_{19}$N—C(=O)$NR_{17}CH_2$, or a $R_{18}R_{19}$N—$SO_2NR_{17}CH_2$ group;

wherein $R_7$ and $R_8$ represent, independently of each other, hydrogen, or a $C_1$-$C_6$alkyl group, $R_9$ represents a hydrogen, or a $R_2$ group, $R_{10}$ and $R_{11}$ represent independently of each other, hydrogen, halogen, cyano, formyl, C(O)$OR_{12}$, C(O)$NR_{13}R_{14}$, unsubstituted or mono- to pentasubstituted $C_1$-$C_6$alkyl, unsubstituted or mono- to pentasubstituted $C_2$-$C_6$alkenyl, unsubstituted or mono- to pentasubstituted $C_2$-$C_6$alkynyl, unsubstituted or mono- to pentasubstituted $C_3$-$C_6$cycloalkyl, unsubstituted or mono- to pentasubstituted $C_6$-$C_{20}$ aryl, or unsubstituted or mono- to pentasubstituted $C_3$-$C_{14}$ heteroaryl group, $R_{15}$ represents unsubstituted or mono- to pentasubstituted $C_1$-$C_6$alkyl, unsubstituted or mono- to pentasubstituted $C_2$-$C_6$alkenyl, unsubstituted or mono- to pentasubstituted $C_2$-$C_6$alkynyl, unsubstituted or mono- to pentasubstituted $C_3$-$C_6$cycloalkyl, unsubstituted or mono- to pentasubstituted $C_6$-$C_{20}$ aryl, or unsubstituted or mono- to pentasubstituted $C_3$-$C_{14}$ heteroaryl group, and $R_{12}$, $R_{13}$, $R_{14}$, $R_{16}$, $R_{17}$, $R_{18}$ and $R_{19}$ represent, independently of each other, hydrogen or $R_{15}$, or $R_{16}$ and $R_{17}$, or $R_{18}$ and $R_{19}$, together represent independently of each other, a three- to ten-membered ring, optionally containing heteroatoms;

with the proviso that (i) the substituent $R_4$ is not a hydroxy, if $R_2$ and $R_3$ are hydroxy groups, $R_5$ is a hydrogen, and $R_6$ is a $CH_3$ or $CH_2$OH group, or (ii) the substituent $R_4$ is not a $OCH_2C_6H_5$ or OC(=O)$C_6H_5$ group, if $R_2$ and $R_3$ are $OCH_2C_6H_5$ or OC(=O)$C_6H_5$ groups, $R_5$ is a hydrogen, $R_6$ is a $CH_2OCH_2C_6H_5$ or $CH_2$OC(=O)$C_6H_5$, or (iii) $R_4$ is not $OCH_3$, if $R_2$ and $R_3$ are $OCH_3$ groups, $R_5$ is a hydrogen, $R_6$ is $CH_2OCH_3$ and the carbon configurations of the cyclic acetal at 2-position (φ) is (R), at 3-position (η) is (S), at 4-position (κ) is (S), and at 5-position (λ) is (R), or (iv) $R_4$ is not $OCH_3$, if $R_2$ and $R_3$ are $OCH_3$ groups, $R_5$ and $R_6$ are hydrogens, and the carbon configurations of the cyclic acetal at 2-position (φ) is (S), at 3-position (η) is (R), and at 4-position (κ) is (R), and n is 1, or (v) $R_4$ is not $OCH_3$, if $R_2$ and $R_3$ are $OCH_3$ groups, $R_5$ is a hydrogen, $R_6$ is $CH_3$, and the carbon configurations of the cyclic acetal at 2-position (φ) is (S), at 3-position (η) is (R), at 4-position (κ) is (R), and at 5-position (λ) is (S), and n is 1, or (vi) the substituent $R_4$ is not an unsubstituted acetyloxy group, if (a) $R_2$ and $R_3$ are an unsubstituted acetyloxy, or (b) $R_2$ is an unsubstituted acetylamino group and $R_3$ is an unsubstituted acetyloxy, and, for either (a) or (b), $R_5$ is hydrogen and $R_6$ is H, $CH_3$, $CH_2$C(=O)$CH_3$, or $CO_2$H group;

and if appropriate, an E/Z isomer and/or diastereoisomer and/or tautomer of the compound of formula (I), in each case in free form or in salt form, as active compound, with at least one auxiliary.

9. A method for protecting plant propagation material comprising treating the propagation material, or the location where the propagation material is planted, with a composition defined in claim 6.

10. A pest resistant plant propagation material having adhered thereto at least one compound of the formula (I) as defined claim 1.

11. A pest resistant plant propagation material having adhered thereto at least one compound of the formula (II) as defined claim 4.

12. A pesticidal composition comprising at least one compound of the formula (II) as defined in claim 4, as active compound, and at least one auxiliary.

* * * * *